US007183298B2

(12) United States Patent
Watkins et al.

(10) Patent No.: US 7,183,298 B2
(45) Date of Patent: Feb. 27, 2007

(54) CARBAMIC ACID COMPOUNDS COMPRISING A SULFONAMIDE LINKAGE AS HDAC INHIBITORS

(75) Inventors: Clare J Watkins, Abingdon (GB); Maria Rosario Romero-Martin, Didcot (GB); Kathryn G Moore, Abingdon (GB); James Ritchie, Abingdon (GB); Paul W Finn, Abingdon (GB); Ivars Kalvinsh, Riga (LV); Einars Loza, Riga (LV); Klara Dikovska, Riga (LV); Vija Gailite, Riga (LV); Maxim Vorona, Riga (LV); Irina Piskunova, Riga (LV); Igor Starchenkov, Riga (LV); Victor Andrianov, Riga (LV); C. John Harris, Sittingbourne (GB); James E. S. Duffy, Sittingbourne (GB)

(73) Assignee: Topotarget UK Limited, Abingdon (GB)

( * ) Notice: Subject to any disclaimer, the term of this patent is extended or adjusted under 35 U.S.C. 154(b) by 247 days.

(21) Appl. No.: 10/953,106

(22) Filed: Sep. 30, 2004

(65) Prior Publication Data
US 2005/0085515 A1   Apr. 21, 2005

Related U.S. Application Data

(63) Continuation of application No. 10/381,790, filed as application No. PCT/GB01/04326 on Sep. 27, 2001, now Pat. No. 6,888,027.

(60) Provisional application No. 60/308,136, filed on Jul. 30, 2001, provisional application No. 60/297,784, filed on Jun. 14, 2001.

(30) Foreign Application Priority Data
Sep. 29, 2000 (GB) ................... 0023986.3

(51) Int. Cl.
 A01N 43/40 (2006.01)
 A61K 31/44 (2006.01)
(52) U.S. Cl. .................. 514/352; 514/426; 514/575; 546/304; 548/557; 562/623
(58) Field of Classification Search ................ 514/352, 514/426, 575; 546/304; 548/557; 562/623
See application file for complete search history.

(56) References Cited

U.S. PATENT DOCUMENTS

| 5,369,108 | A | 11/1994 | Breslow |
| 5,700,811 | A | 12/1997 | Breslow |
| 5,804,601 | A | 9/1998 | Kato |
| 5,834,249 | A | 11/1998 | Furukawa |
| 6,437,177 | B1 * | 8/2002 | Warpehoski et al. ........ 562/426 |
| 6,541,661 | B1 | 4/2003 | Delorme et al. |
| 6,696,456 | B1 * | 2/2004 | Pikul et al. .................. 514/274 |

FOREIGN PATENT DOCUMENTS

| EP | 0 301 861 A1 | 2/1989 |
| EP | 0 570 594 A | 11/1993 |
| EP | 0 827 742 A1 | 3/1998 |
| EP | 0 931 788 A | 7/1999 |
| GB | 2 312 674 A | 11/1997 |
| JP | 10-114681 A2 | 5/1998 |
| JP | 10-182583 | 7/1998 |
| WO | WO 93/12075 | 6/1993 |
| WO | WO 95/31977 | 11/1995 |
| WO | 98/38859 A | 9/1998 |
| WO | WO 98/55449 | 12/1998 |
| WO | 99/24399 A | 5/1999 |
| WO | 00/56704 A | 9/2000 |
| WO | 00/69819 A | 11/2000 |
| WO | WO 01/18171 | 3/2001 |
| WO | 01/38322 A | 5/2001 |
| WO | WO 01/38322 | 5/2001 |
| WO | WO 01/38322 A1 | 5/2001 |

OTHER PUBLICATIONS

Andrews et al., 2000, "Anti-malarial effect of histone deacetylation inhibitors and mammalian tumour cytodifferentiating agents" *Int. J. Parasitol.*, vol. 30, No. 6, pp. 761-768.

Bernhard, D. et al., 1999, "Apoptosis induced by the histone deacetylase inhibitor sodium butyrate in human leukemic lymphoblasts," *FASEB J.*, vol. 13, No. 14, pp. 1991-2001.

Bernstein et al., 2000,"Genomewide studies of histone deacetylase function in yeast" *Proc. Natl. Acad. Sci. USA*, vol. 97, No. 25, pp. 13708-13713.

Brehm, A., et al., 1998, "Retinoblastoma protein recruits histone deacetylase to repress transcription," *Nature*, 1998, vol. 391, pp. 597-601.

Chang et al., 2000,"Activation of the BRLF1 promoter and lytic cycle of Epstein-Barr virus by histone acetylation." *Nucleic Acids Res.*, vol. 28, No. 20, pp. 3918-3925.

Dangond et al., 1998, "Differential display cloning of a novel human histone deacetylase (HDAC3) cDNA from PHA-activated immune cells." *Biochem. Biophys. Res. Commun.*, vol. 242, No. 3, pp. 648-652.

(Continued)

*Primary Examiner*—Johann Richter
*Assistant Examiner*—Chukwuma Nwaonicha
(74) *Attorney, Agent, or Firm*—Nixon & Vanderhye P.C.

(57) ABSTRACT

This invention pertains to certain active carbamic acid compounds which inhibit HDAC activity and which have the following formula: (I) A is an aryl group; $Q^1$ is a covalent bond or an aryl leader group; J is a sulfonamide linkage selected from: —S(=O)$_2$NR$^1$— and —NR$^1$S(=O)$_2$—; $R^1$ is a sulfonamido substituent; and, $Q^2$ is an acid leader group; with the proviso that if J is —S(=O)$_2$NR$^1$—, then $Q^1$ is an aryl leader group; and pharmaceutically acceptable salts, solvates, amides, esters, ethers, chemically protected forms, and prodrugs thereof. The present invention also pertains to pharmaceutical compositions comprising such compounds, and the use of such compounds and compositions, both in vitro and in vivo, to inhibit HDAC, and, e.g., to inhibit proliferative conditions, such as cancer and psoriasis.

124 Claims, No Drawings

OTHER PUBLICATIONS

David, G., et al., 1998, "Histone deacetylase associated with mSin3A mediates repression by the acute promyelocytic leukaemia-associated PLZF protein." *Oncogene*, vol. 16(19), pp. 2549-2556.

Davie, J.R., 1998, "Covalent modifications of histones: expression from chromatic templates," *Curr. Opin. Genet. Dev.*, vol. 8, pp. 173-178.

Desai, D et al., 1999, "Chemopreventive efficacy of suberanilohydroxamic acid (SAHA), a cytodifferentiating agent, against tobacco-specific nitrosamine 4-(-methylnitros-amino)-1-(3-pyridyl)-1-butanone (NNK)-induced lung tumorigenesis in female A/J mice." *Proc. AACR*, vol. 40, abstract #2396.

Emiliani, S., et al., 1998, "Characterization of a human RPD3 ortholog, HDAC3," *Proc. Natl. Acad. Sci. USA*, vol. 95, p. 2795-2800.

Finnin et al., 1999, "Structures of a histone deacetylase homologue bound to the TSA and SAHA inhibitors" *Nature*, vol. 401, pp. 188-193.

Glick, R.D., et al., 1999, "Hybrid polar histone deacetylase inhibitor induces apoptosis and CD95/CD95 ligand expression in human neuroblastoma," *Cancer Research*, vol. 59, No. 17, pp. 4392-4399.

Grozinger et al., 1999,"Three proteins define a class of human histone deacetylases related to yeast Hda1p" *Proc. Natl. Acad. Sci. USA*, vol. 96, pp. 4868-4873.

Hoshikawa, Y., et al., 1994, "Trichostatin A induces morphological changes and gelsolin expression by inhibiting histone deacetylase in human carcinoma cell lines." *Exp. Cell. Res.*, vol. 214(1), pp. 189-197.

Howe, L., et al., 1999, "Histone acetyltransferase complexes and their link to transcription" *Crit. Rev. Eurkaryot. Gene Expr.*, vol. 9(3-4), pp. 231-243.

Iavarone et al., 1999, "E2F and histone deacetylase mediate trans-forming growth factor beta repression of cdc25A during keratinocyte cell cycle arrest". *Mol. Cell Biol.*, vol. 19, No. 1, pp. 916-922.

Jung et al., 1997, "Analogues of trichostatin A and trapoxin B as histone deacetylase inhibitors" *Bioorg.Med. Chem. Lett.*, vol. 7, No. 13, pp. 1655-1658.

Jung et al., 1999, "Amide analogues of trichostatin A as inhibitors of histone deacetylase and inducers of terminal cell differentiation" *J. Med. Chem.*, vol.42, pp. 4669-4679.

Kao et al., 2000, "Isolation of a novel histone deacetylase reveals that class I and class II deacetylases promote SMRT-mediated repression" *Genes Dev.*, vol. 14, p. 55-66.

Kijima et al., 1993, Trapoxin, an antitumor cyclic tetrapeptide, is an irreversible inhibitor of mammalian histone deacetylase *J. Biol. Chem.*, vol. 268, pp. 22429-22435.

Kim et al., 1999, "Oxamflatin is a novel antitumor compound that inhibits mammalian histone deacetylase" *Oncogene*, vol. 18(15), pp. 2461-2470.

Kim, M.S., et al., 2001 "Histone deacetylases induce angiogenesis by negative regulation of tumour suppressor genes," *Nature Medicine*, vol. 7, No. 4 pp. 437-443.

Kimura et al., 1994, "Dual modes of action of platelet-derived growth factor and its inhibition by trichostatin-A for DNA synthesis in primary cultured smooth muscle cells of rat aorta". *Biol. Pharm. Bull.*, vol. 17, No. 3, pp. 399-402.

Kitamura, K., et al., 2000, "Histone deacetylase inhibitor but not arsenic trioxide differentiates acute promyelocytic leukaemia cells with t(11;17) in combination with all-trans retinoic acid" *Br. J. Haematol.*, vol. 108(4), pp. 696-702.

Kouzarides, T., 1999, "Histone acetylases and deacetylases in cell proliferation," *Curr. Opin. Genet. Dev.*, vol. 9, No. 1, pp. 40-48.

Kuusisto et al., 2001, "Ubiquitin-binding protein p62 expression is induced during apoptosis and proteasomal inhibition in neuronal cells." *Biochem. Biophys. Res. Commun.*, vol. 280, No. 1, pp. 223-228.

Kwon et al., 1998,"Depudecin induces morphological reversion of transformed fibroblasts via the inhibition of histone deacetylase" *Proc. Natl. Acad. Sci. USA*, vol. 95, pp. 3356-3361.

Laherty, C.D., et al., 1997, Histone deacetylases associated with the mSin3 corepressor mediate mad transcriptional repression *Cell*, vol. 89(3), pp. 349-356.

Lea et al., 1999, "Increased acetylation of histones induced by diallyl disulfide and structurally related molecules" *Int. J. Oncol.*, vol. 2, pp. 347-352.

Lin, R.J., et al., 1998, "Role of the histone deacetylase complex in acute promyelocytic leukaemia" *Nature*, vol. 391(6669), pp. 811-814.

Massa et al., 2001, *J. Med. Chem.*, "3-(4-aroyl-1H-pyrrol-2-yl)-N-hydroxy-2-propenamides, a new class of synthetic histone deacetylase inhibitors" vol. 44, No. 13, pp. 2069-2072.

McCaffrey et al., 1997,"Induction of gamma-globin by histone deacetylase inhibitors." *Blood*, vol. 90, No. 5, pp. 2075-2083.

Mielnicki, L.M., et al. 1999, "Epigenetic regulation of gelsolin expression in human breast cancer cells" *Exp. Cell. Res.*, vol. 249(1), pp. 161-176.

Ng, H.H. and Bird, A., 2000, "Histone deacetylases: silencers for hire." *Trends Biochem. Sci.*, vol. 25(3), pp. 121-126.

Niki et al., 1999, "A histone deacetylase inhibitor, trichostatin A, suppresses myofibroblastic differentiation of rat hepatic stellate cells in primary culture" *Hepatology*, vol. 29, No. 3, pp. 858-867.

Nakajima et al., 1998, "FR901228, a potent antitumor antibiotic, is a novel histone deacetylase inhibitor" *Exp. Cell Res.*, vol. 241, pp. 126-133.

Ohtani et al., 1996, "(2E)-5-[3-[(Phenylsulfonyl)amino] phenyl]-pent-2-en-4-yno-hydroxamic acid and its derivatives as novel and potent inhibitors of ras transformation," *J. Med. Chem.*, vol. 39, No. 15, pp. 2871-2873.

Onishi et al., 1996., 1996, "Antibacterial agents that inhibit lipid A biosynthesis" *Science*, vol. 274, pp. 980-982.

Pazin, M.J., et al., 1997, "What's up and down with histone deacetylation and transcription?," *Cell*, vol. 89, No. 3, pp. 325-328.

Richon et al, 1996, "Second generation hybrid polar compounds are potent inducers of transformed cell differentiation" *Proc. Natl. Acad. Sci. USA*, vol. 93, pp. 5705-5708.

Lea Ma et al, 1995, "Discordant effects of butyrate analogues on erythroleukemia cell proliferation, differentiation and histone deacetylase" *Anticancer Res.*, vol. 15, pp. 879-883.

Richon et al., 1998, "A class of hybrid polar inducers of transformed cell differentiation inhibits histone deacetylases," *Proc. Natl. Acad. Sci. USA*, vol. 95, pp. 3003-3007.

Saito et al., 1999, "A synthetic inhibitor of histone deacetylase, MS-27-275, with marked in vivo antitumor activity against human tumors". *Proc. Natl. Acad. Sci. USA*, vol. 96, pp. 4592-4597.

Saunders, N. et al, 1999 "Histone deacetylase inhibitors as potential anti-skin cancer agents," *Cancer Res.*, vol. 59, No. 2 pp. 399-404.

Sonoda, H. et al., 1996, "Oxamflatin: a novel compound which reverses malignant phenotype to normal one via induction of JunD" *Oncogene*, vol. 13, pp. 143-149.

Spencer, V.A. et al., 1999, "Role of covalent modifications of histones in regulating gene expression." *Gene*, vol. 240(1), pp. 1-12.

Suzuki et al., 1999, "Synthesis and histone deactylase inhibitory activity of new benzamide derivatives," *J. Med. Chem.*, vol. 42, pp. 3001-3003.

Takahashi, I., et al, 1996, "Selective inhibition of IL-2 gene expression by trichostatin A, a potent inhibitor of mammalian histone deacetylase," *J. Antibiot.(Tokyo)*, vol. 49, No. 5, pp. 453-457.

Taunton, J., et al., 1996,"A mammalian histone deacetylase related to the yeast transcriptional regulator Rpd3p," *Science*, vol. 272, pp. 408-411.

Tsuji et al., 1976, "A new antifungal antibiotic, trichostatin" *J. Antibiot.(Tokyo)*, vol. 29, No. 1, pp. 1-6.

Ueda, H., et al., 1994, "FR901228, a novel antitumor bicyclic depsipeptide produced by Chromobacterium violaceum No. 968. III. Antitumor activities on experimental tumors in mice" *J. Antibiot.(Tokyo)*, vol. 47(3), pp. 315-323.

Van den Wyngaert et al., 2000, "Cloning and characterization of human histone deacetylase 8" *FEBS Lett*, vol. 478, pp. 77-83.

Vigushin et al., 2001, "Trichostatin A is a histone deacetylase inhibitor with potent antitumor activity against breast cancer in vivo" *Clin. Cancer Res.*, vol. 7, No. 4, pp. 971-976.

Wong, J., et al., 1998, "Distinct requirements for chromatin assembly in transcriptional repression by thyroid hormone receptor and histone deacetylase" *EMBO J.*, vol. 17(2), pp. 520-534.

Yang, W.M., et al., 1996, "Transcriptional repression of YY1 is mediated by interaction with a mammalian homolog of the yeast global regulator RPD3," *Proc. Natl. Acad. Sci. USA*, vol. 93, pp. 12845-12850.

Yang, W.M., et al., 1997, "Isolation and characterization of cDNAs corresponding to an additional member of the human histone deacetylase gene family," *J. Biol. Chem.*, vol. 272, pp. 28001-28007.

Yoshida et al., 1995, "Trichostatin A and trapoxin: novel chemical probes for the role of histone acetylation in chromatin structure and function" *Bioessays*, vol. 17, pp. 423-430.

Yoshida, M. et al 1999, "Trichostatin and leptomycin: inhibition of histone deacetylation and signal-dependent nuclear export" *Ann. N. Y. Acad. Sci.*, vol. 886, pp. 23-36.

Yoshida, M., et al 1988, "Reversible arrest of proliferation of rat 3Y1 fibroblasts in both G1 and G2 phases by trichostatin A," *Exp. Cell. Res.*, vol. 177, pp. 122-131.

Yoshida, M., et al., 1990, Potent and specific inhibition of mammalian histone deacetylase both in vivo and in vitro by trichostatin A *J. Biol. Chem.*, vol. 265(28), pp. 17174-17179.

Yoshida, M., et al., 1990, "Structural specificity for biological activity of trichostatin A, a specific inhibitor of mammalian cell cycle with potent differentiation-inducing activity in Friend leukemia cells." *J. Antibiot.(Tokyo)*, vol. 43(9), pp. 1101-1106.

\* cited by examiner

CARBAMIC ACID COMPOUNDS COMPRISING A SULFONAMIDE LINKAGE AS HDAC INHIBITORS

RELATED APPLICATIONS

This application is a continuation of U.S. Ser. No. 10/381,790, filed Aug. 20, 2003, now U.S. Pat. No. 6,88,027 which is a 371 U.S. national phase of PCT/GB01/04326, filed 27 Sep. 2001, which designated the U.S. and This application claims priority to United Kingdom Patent Application Number GB 0023986.3 filed 29 Sep. 2000; U.S. Provisional Patent Application No. 60/297,784 filed 14 Jun. 2001; and, U.S. Provisional Patent Application No. 60/308,136 filed 30 Jul. 2001; the contents of each of which are incorporated herein by reference in their entirety.

TECHNICAL FIELD

This invention pertains generally to the field of biologically active compounds, and more specifically to certain active carbamic acid compounds which inhibit HDAC (histone deacetylase) activity. The present invention also pertains to pharmaceutical compositions comprising such compounds, and the use of such compounds and compositions, both in vitro and in vivo, to inhibit HDAC, and, e.g., to inhibit proliferative conditions, such as cancer and psoriasis.

BACKGROUND

DNA in eukaryotic cells is tightly complexed with proteins (histones) to form chromatin. Histones are small, positively charged proteins which are rich in basic amino acids (positively charged at physiological pH), which contact the phosphate groups (negatively charged at physiological pH) of DNA. There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

The majority of histones are synthesised during the S phase of the cell cycle, and newly synthesised histones quickly enter the nucleus to become associated with DNA. Within minutes of its synthesis, new DNA becomes associated with histones in nucleosomal structures.

A small fraction of histones, more specifically, the amino side chains thereof, are enzymatically modified by post-translational addition of methyl, acetyl, or phosphate groups, neutralising the positive charge of the side chain, or converting it to a negative charge. For example, lysine and arginine groups may be methylated, lysine groups may be acetylated, and serine groups may be phosphorylated. For lysine, the —$(CH_2)_4$—$NH_2$ sidechain may be acetylated, for example by an acetyltransferase enzyme, to give the amide —$(CH_2)_4$—$NHC(=O)CH_3$. Methylation, acetylation, and phosphorylation of amino termini of histones which extend from the nucleosomal core affects chromatin structure and gene expression. (See, for example, Spencer and Davie, 1999).

Acetylation and deacetylation of histones is associated with transcriptional events leading to cell proliferation and/or differentiation. Regulation of the function of transcription factors is also mediated through acetylation. Recent reviews of histone deacetylation include Kouzarides, 1999 and Pazin et al., 1997.

The correlation between the acetylation status of histones and the transcription of genes has been known for over 30 years (see, for example, Howe et al., 1999). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, 1998. In general, histone acetylation correlates with transcriptional activation, whereas histone deacetylation is associated with gene repression.

A growing number of histone deacetylases (HDACs) have been identified (see, for example, Ng and Bird, 2000). The first-deacetylase, HDAC1, was identified in 1996 (see, for example, Tauton et al., 1996). Subsequently, two other nuclear mammalian deacetylases has been found, HDAC2 and HDAC3 (see, for example, Yang et al., 1996, 1997, and Emiliani et al., 1998). See also, Grozinger et al., 1999; Kao et al., 2000; and Van den Wyngaert et al., 2000.

Eight human HDACs have been cloned so far:
HDAC1 (Genbank Accession No. NP_004955)
HDAC2 (Genbank Accession No. NP_001518)
HDAC3 (Genbank Accession No. O15739)
HDAC4 (Genbank Accession No. AAD29046)
HDAC5 (Genbank Accession No. NP_005465)
HDAC6 (Genbank Accession No. NP_006035)
HDAC7 (Genbank Accession No. AAF63491)
HDAC8 (Genbank Accession No. AAF73428).

These eight human HDACs fall in two distinct classes: HDACs 1,2,3 and 8 are in class I, and HDACs 4,5,6 and 7 are in class II.

There are a number of histone deacetylases in yeast, including the following:
RPD3 (Genbank Accession No. NP_014069)
HDA1 (Genbank Accession No. P53973)
HOS1 (Genbank Accession No. Q12214)
HOS2 (Genbank Accession No. P53096)
HOS3 (Genbank Accession No. Q02959).

There are also numerous plant deacetylases, for example, HD2, in *Zea mays* (Genbank Accession No. AF254073_1).

HDACs function as part of large multiprotein complexes, which are tethered to the promoter and repress transcription. Well characterised transcriptional repressors such as Mad (Laherty et al., 1997), pRb (Brehm et al., 1998), nuclear receptors (Wong et al., 1998) and YY1 (Yang et al., 1997) associate with HDAC complexes to exert their repressor function.

The study of inhibitors of histone deacetylases indicates that these enzymes play an important role in cell proliferation and differentiation. The inhibitor Trichostatin A (TSA) (Yoshida et al., 1990a) causes cell cycle arrest at both G1 and G2 phases (Yoshida and Beppu, 1988), reverts the transformed phenotype of different cell lines, and induces differentiation of Friend leukaemia cells and others (Yoshida et al., 1990b). TSA (and SAHA) have been reported to inhibit cell growth, induce terminal differentiation, and prevent the formation of tumours in mice (Finnin et al., 1999).

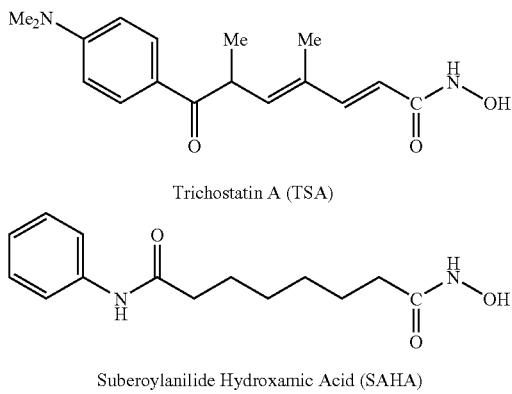

Trichostatin A (TSA)

Suberoylanilide Hydroxamic Acid (SAHA)

Cell cycle arrest by TSA correlates with an increased expression of gelsolin (Hoshikawa et al., 1994), an actin regulatory protein that is down regulated in malignant breast cancer (Mielnicki et al., 1999). Similar effects on cell cycle and differentiation have been observed with a number of deacetylase inhibitors (Kim et al., 1999).

Trichostatin A has also been reported to be useful in the treatment of fibrosis, e.g., liver fibrosis and liver cirrhosis. See, e.g., Geerts et al., 1998.

Recently, certain compounds that induce differentiation have been reported to inhibit histone deacetylases. Several experimental antitumour compounds, such as trichostatin A (TSA), trapoxin, suberoylanilide hydroxamic acid (SAHA), and phenylbutyrate have been reported to act, at least in part, by inhibiting histone deacetylase (see, e.g., Yoshida et al., 1990; Richon et al., 1998; Kijima et al., 1993). Additionally, diallyl sulfide and related molecules (see, e.g., Lea et al., 1999), oxamflatin (see, e.g., Kim et al., 1999), MS-27–275, a synthetic benzamide derivative (see, e.g., Saito et al., 1999; Suzuki et al., 1999; note that MS-27-275 was later re-named as MS-275), butyrate derivatives (see, e.g., Lea and Tulsyan, 1995), FR901228 (see, e.g., Nokajima et al., 1998), depudecin (see, e.g., Kwon et al., 1998), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al, 1996; Kim et al., 1999; Yoshida et al., 1995; Yoshida & Beppu, 1988). In vivo, phenybutyrate is reported to be effective in the treatment of acute promyelocytic leukemia in conjunction with retinoic acid (see, e.g., Warrell et al., 1998). SAHA is reported to be effective in preventing the formation of mammary tumours in rats, and lung tumours in mice (see, e.g., Desai et al., 1999).

The clear involvement of HDACs in the control of cell proliferation and differentiation suggest that aberrant HDAC activity may play a role in cancer. The most direct demonstration that deacetylases contribute to cancer development comes from the analysis of different acute promyelocytic leukaemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL patients are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., 2000; David et al., 1998; Lin et al., 1998).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, 1999). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda et al., 1994; Kim et al., 1999).

Psoriasis is a common chronic disfiguring skin disease which is characterised by well-demarcated, red, hardened scaly plaques: these may be limited or widespread. The prevalence rate of psoriasis is approximately 2%, i.e., 12.5 million sufferers in the triad countries (US/Europe/Japan). While the disease is rarely fatal, it clearly has serious detrimental effects upon the quality of life of the patient: this is further compounded by the lack of effective therapies. Present treatments are either ineffective, cosmetically unacceptable, or possess undesired side effects. There is therefore a large unmet clinical need for effective and safe drugs for this condition.

Psoriasis is a disease of complex etiology. Whilst there is clearly a genetic component, with a number of gene loci being involved, there are also undefined environmental triggers. Whatever the ultimate cause of psoriasis, at the cellular level, it is characterised by local T-cell mediated inflammation, by keratinocyte hyperproliferation, and by localised angiogenesis. These are all processes in which histone deacetylases have been implicated (see, e.g., Saunders et al., 1999; Bernhard et al, 1999; Takahashi et al, 1996; Kim et al, 2001). Therefore HDAC inhibitors may be of use in therapy for psoriasis. Candidate drugs may be screened, for example, using proliferation assays with T-cells and/or keratinocytes.

Thus, one aim of the present invention is the provision of compounds which are potent inhibitors of histone deacetylases (HDACs). There is a pressing need for such compounds, particularly for use as antiproliferatives, for example, anti-cancer agents, agents for the treatment of psoriasis, etc.

Such molecules desirably have one or more of the following properties and/or effects:
(a) easily gain access to and act upon tumour cells;
(b) down-regulate HDAC activity;
(c) inhibit the formation of HDAC complexes;
(d) inhibit the interactions of HDAC complexes;
(e) inhibit tumour cell proliferation;
(e) promote tumour cell apoptosis;

(f) inhibit tumour growth; and,
(g) complement the activity of traditional chemotherapeutic agents.

A number of carbamic acid compounds have been described.

Amides

Hashimoto et al., 1989 describe hydroxamic acid compounds which are claimed to inhibit cell proliferation. Some of the compounds are carbamic acid compounds having a substituted phenyl-dione group linked to a carbamic acid group (—CONHOH) via an aryl-substituted alkylene group.

Ohtani et al., 1993 describe a number of hydroxamic acid compounds which are claimed to be inhibitors of ras transformation. A few of the compounds are carbamic acid compounds having a phenylacylamido group (—NHCOPh) linked to a carbamic acid group (—CONHOH) via a phenylene-meta-alkylene group having a carbon-carbon triple bond. See, for example, compounds 1–29 (page 69), 1–39 (page 87), and 1–41 (page 90). Compound 1–41, shown below, employs an aryl leader.

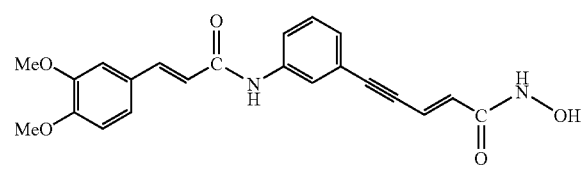

Onishi et al., 1996, describe several hydroxamic acid compounds which have a phenyl (or substituted phenyl) group linked via an oxazole group to a carbamic acid group. These compounds were reported to inhibit a deacetylase enzyme critical in the biosynthesis of lipid A (a component of the outer membrane of Gram-negative bacteria).

Parsons et al., 1998 describe a number of hydroxamic acid compounds which are claimed to selectively prevent the growth of a variety of human tumour cell lines.

Some of the compounds are carbamic acid compounds having an arylamide group linked to a carbamic acid group via a methylene or substituted methylene group (see, for example, pages 16 and 17).

Some of the compounds are carbamic acid compounds having a phenylamido group (—CONHPh) linked to a carbamic acid group (—CONHOH) via a long alkylene chain, —(CH$_2$)$_n$—, wherein n is from 4 to 7 (see, for example, pages 47, 48, and 58 therein).

Some of the compounds are carbamic acid compounds having an aryl group linked via a short chain to an amide group (—CONH—), which in turn is linked via a short chain (e.g., 3 atoms or less) to a carbamic acid group (—CONHOH). See, for example, page 16, 2nd formula; page 46, 4th formula; page 51, compound 7; and page 61, 2nd formula.

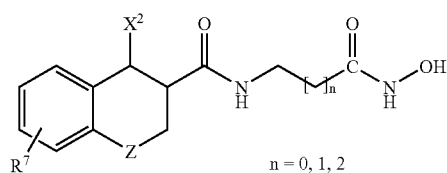

n = 0, 1, 2

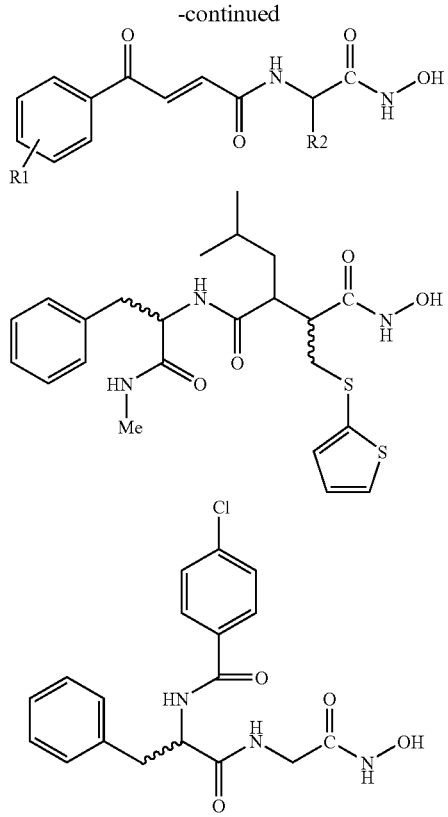

Richon et al., 1998 describe several hydroxamic acid compounds, including SAHA, which apparently inhibit HDAC activity, and induce terminal differentiation and/or apoptosis in various transformed cells (see, for example, Table 1 therein).

Suzuki et al., 1998 describe a number of hydroxamic acid compounds which are claimed to have antitumour activity. Some of the compounds are carbamic acid compounds having a substituted phenylamido group (—CONHPh) linked to a carbamic acid (—CONHOH) group via a phenylene-meta-ethenylene or phenylene-para-ethylene group (see, for example, pages 8 and 9, compounds 31–50).

Breslow et al., 1994, 1995, 1997 describe a number of hydroxamic acid compounds which are claimed to selectively induce terminal differentiation of neoplastic cells.

Some of the compounds are carbamic acid compounds having a substituted phenylacylamido group (—NHCOPh) linked to a carbamic acid (—CONHOH) group via a long alkylene chain, —(CH$_2$)$_n$—, wherein n is from 4 to 8

Some of the compounds are carbamic acid compounds having a substituted phenylamido group (—CONHPh) or phenylacylamido group (—NHCOPh) linked to a carbamic acid (—CONHOH) group via a long alkylene chain, —(CH$_2$)$_n$—, wherein n is from 4 to 8 (see, for example, columns 7 and 13 of Breslow et al., 1997), or via a phenylene group (see, for example, columns 24, 30–31 and compounds 20–55 in Table 1 of Breslow et al., 1997).

One of the compounds is a carbamic acid compound having benzylamido group (—CONHCH$_2$Ph) linked to a carbamic acid group (—CONHOH) via a —(CH$_2$)$_6$— group (see, for example, compound 19 in Table 1, at column 37 of Breslow et al., 1997).

Jung et al., 1997, 1999, describe several aromatic hydroxamic acid compounds which apparently inhibit HDAC. Some of the compounds have a phenylamido group (Ph-CONH—). One compound, a peptide analog, is shown below (see, e.g., compound 6 in Jung et al., 1997; compound 4 in Jung et al., 1999).

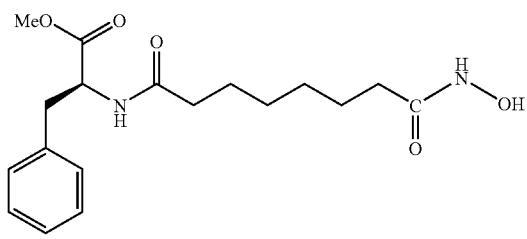

Kato et al., 1998, describe a number of aromatic hydroxamic acid compounds, comprising an aryl group linked via an alkylene group to a carbamic acid group, which are apparently active in the treatment of neurodegenerative conditions. One compound, 4-1 at columns 63–64, has a phenylamido group (PhCONH—) linked via a —(CH$_2$)$_5$— group to a carbamic acid group.

Glick et al., 1999, describe the apparent apoptotic and differentiating effects of m-carboxy-cinnamic acid bishydroxamide (CBHA) on various tumour cell lines.

Massa et al., 2001, describe various hydroxamic acid compounds which have a benzoyl (or substituted benzoyl) group linked via a pyrrolyl group and an C$_2$alkylene group (—CH=CH— or —CH$_2$CH$_2$—) to a carbamic acid group. The compounds apparently showed HDAC inhibitory activity in the micromolar range.

Sulfonamides

Oxamflatin, also known as (2E)-5-[3-[(phenylsulfonyl)amino]phenyl]-pent-2-en-4-ynohydroxamic acid, shown below, has been reported to have in vitro antiproliferative activity against various mouse and human tumour cell lines, and in vivo antitumour activity against B16 melanoma (see, e.g., Sonoda et al., 1996; Kim et al., 1999).

Oxamflatin

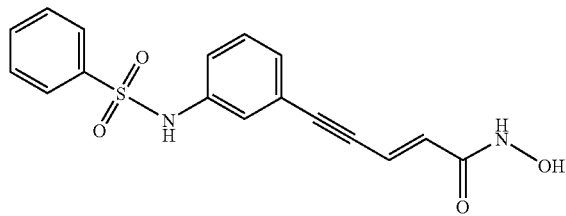

Ohtani et al., 1993, describe a number of hydroxamic acid compounds which are claimed to be inhibitors of ras transformation. Many of the compounds are hydroxmic acid compounds which have a sulfonamide group, and which employ an acid leader which is: a phenylene-ortho-alkylene (e.g., I-10); phenylene-meta-alkylene (e.g., I-24); phenylene-para-alkylene (e.g., I-12); or napthylen-1,2-diyl (e.g., I-20). However, in every case, the sulfonamide group is —SO$_2$NR—, as opposed to —NRSO$_2$—. Also, in every case, the terminal aryl group is linked directly to the —SO$_2$NR— sulfonamide group, without an intervening aryl leader. Ohtani et al., 1996, describe similar compounds.

Richon et al., 2001, describe various branched compounds which apparently inhibit histone deacetylase. See the table at pages 96–101 therein. Some of the compounds are carbamic acid compounds having a carbamic acid group (—CONHOH) linked to a branch point, from which two aryl groups are appended. A few linear carbamic acid compounds are also described, including a single —SO$_2$NH— sulfonamide carbamic acid with a —(CH$_2$)$_5$— acid leader (compound 671).

Delorme et al., 2001, describe various carbamic acid compounds, including compounds having, inter alia, a sulfonamide group. Of the 108 compounds in the table at pages 114–123 therein, 88 are carbamic acids (—CONHOH), and the remainder are terminal amides, —CONHR. Of the 88 carbamic acid compounds, 54 have a sulfonamide linkage.

Of the 54 sulfonamide carbamic acids, 51 are indicated to have a —SO$_2$NR-sulfonamide group, and 3 (compounds 98, 161, and 162) are indicated to have a —NRSO$_2$— sulfonamide group.

All of the 54 sulfonamide carbamic acids employ a phenylene-alkylene acid leader group (analogous to Q$^2$ herein). Of the 54 compounds, 52 employ a phenylene-para-alkylene group, and only 2 (compounds 41 and 26) employ a phenylene-meta-alkylene group (-Ph-CH$_2$ and -Ph-(CH$_2$)$_4$—, respectively). Compounds 41 and 26 both have a —SO$_2$NR— sulfonamide group, as opposed to a —NRSO$_2$— sulfonamide group; the former has a benzothiophenyl group, and the latter has a phenyl group.

All but one of the 54 sulfonamide carbamic acids have an aryl group linked directly to the sulfonamide; compound 100 has a benzyl group (Ph-CH$_2$—) linked a —SO$_2$NR— sulfonamide group linked to phenylene-para-ethylene.

SUMMARY OF THE INVENTION

One aspect of the invention pertains to active carbamic acid compounds, as described herein, which inhibit HDAC activity.

Another aspect of the invention pertains to active compounds, as described herein, which treat a proliferative condition, such as cancer or psoriasis.

Another aspect of the invention pertains to active compounds, as described herein, which treat conditions which are known to be mediated by HDAC, or which are known to be treated by HDAC inhibitors (such as, e.g., trichostatin A).

Another aspect of the present invention pertains to a composition comprising a compound as described herein and a pharmaceutically acceptable carrier.

Another aspect of the present invention pertains to methods of inhibiting HDAC in a cell, comprising contacting said cell with an effective amount of an active compound, as described herein.

Another aspect of the present invention pertains to methods of inhibiting cell proliferation, comprising contacting a cell with an effective amount of an active compound, as described herein, whether in vitro or in vivo.

Another aspect of the present invention pertains to methods of treating a proliferative condition in a patient comprising administering to said patient a therapeutically-effective amount of an active compound, as described herein.

In one preferred embodiment, the proliferative condition is cancer. In one preferred embodiment, the proliferative condition is psoriasis.

Another aspect of the present invention pertains to methods of treating a condition in a patient which is known to be mediated by HDAC, or which is known to be treated by HDAC inhibitors (such as, e.g., trichostatin A), comprising administering to said patient a therapeutically-effective amount of an active compound, as described herein.

Another aspect of the present invention pertains to an active compound, as described herein, for use in a method of treatment of the human or animal body.

Another aspect of the present invention pertains to use of an active compound, as described herein, for the manufacture of a medicament for use in the treatment of a proliferative condition. In one preferred embodiment, the proliferative condition is cancer. In one preferred embodiment, the proliferative condition is psoriasis.

Another aspect of the present invention pertains to use of an active compound for the manufacture of a medicament, for example, for the treatment of conditions which are known to be mediated by HDAC, or which are known to be treated by HDAC inhibitors (such, as, e.g., trichostatin A), as discussed herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

In one embodiment, the present invention pertains to carbamic acid compounds of the formula:

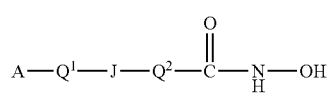
(1)

wherein:
A is an aryl group;
$Q^1$ is a covalent bond or an aryl leader group;
J is a sulfonamide linkage selected from:

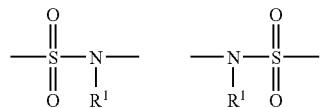

$R^1$ is a sulfonamido substituent; and,
$Q^2$ is an acid leader group;
with the proviso that if J is:

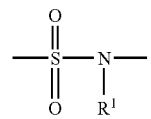

then $Q^1$ is an aryl leader group;

and pharmaceutically acceptable salts, solvates, amides, esters, ethers, chemically protected forms, and prodrugs thereof.

In preferred embodiments, the carbamic acid group, —C(=O)NHOH, is unmodified (e.g., is not an ester).

In one preferred embodiment, the present invention pertains to carbamic acid compounds of the formula:

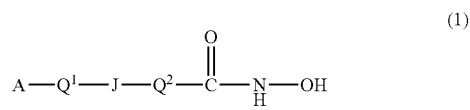
(1)

wherein:
A is an aryl group;
$Q^1$ is an aryl leader group;
J is a sulfonamide linkage selected from:

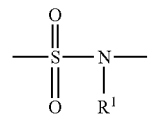

$R^1$ is an sulfonamido substituent; and,
$Q^2$ is an acid leader group.

In one preferred embodiment, the present invention pertains to carbamic acid compounds of the formula:

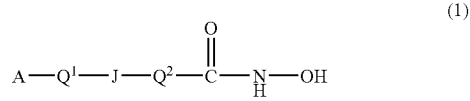
(1)

wherein:
A is an aryl group;
$Q^1$ is a covalent bond or an aryl leader group;
J is a sulfonamide linkage selected from:

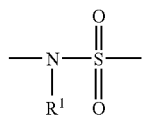

$R^1$ is an sulfonamido substituent; and, $Q^2$ is an acid leader group.

In one preferred embodiment, $Q^1$ is an aryl leader group, J is —SO$_2$NR$^1$—, and the compounds have the following formula:

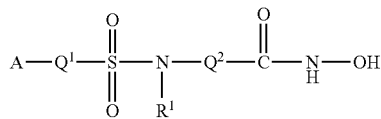

(2)

In one preferred embodiment, $Q^1$ is a covalent bond or an aryl leader group, J is —NR$^1$SO$_2$—, and the compounds have the following formula:

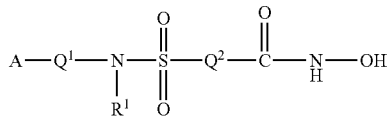

(3)

In one preferred embodiment, $Q^1$ is an aryl leader group, J is —NR$^1$SO$_2$—, and the compounds have the following formula:

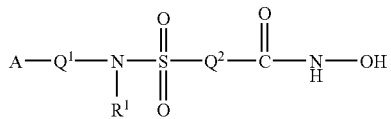

(3)

In one preferred embodiment, $Q^1$ is a covalent bond, J is —NR$^1$SO$_2$—, and the compounds have the following formula:

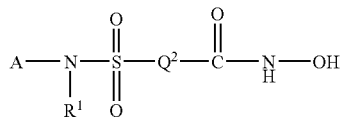

(4)

In one embodiment, where $Q^1$ is an aryl leader, the aryl group, A, is linked to $Q^1$ via a covalent single bond.

In one embodiment, where $Q^1$ is a cyclic aryl leader, the aryl group, A, may be fused to $Q^1$ and so the moiety A-$Q^1$- forms a fused polycyclic structure. For example, the moiety 2,3-dihydro-1H-inden-2-yl, derived from indan (2,3-dihydro-1H-indene), is considered to be a phenyl group (A) fused to a C$_5$cycloalkyl group ($Q^1$):

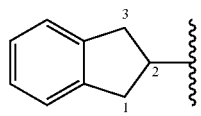

In such cases, the tridentate aryl leader, $Q^1$, may be denoted as:

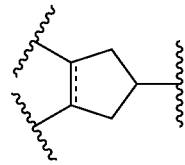

In a similar example, the moiety 9H-fluorene-9-yl, derived from fluorene, is considered to be two phenyl groups (either of which is A), fused to a C$_5$cycloalkyl group, which forms part of $Q^1$:

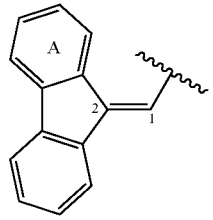

In such cases, the pentadentate aryl leader, $Q^1$, may be denoted as:

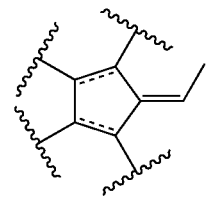

The Aryl Group, A

The aryl group, A, is a C$_{5-20}$aryl group, and is optionally substituted.

In one preferred embodiment, A is a C$_{5-20}$heteroaryl group, and is optionally substituted. In one preferred embodiment, A is a monocyclic C$_{5-20}$heteroaryl group, and is optionally substituted. In one preferred embodiment, A is a monocyclic C$_{5-6}$heteroaryl group, and is optionally substituted.

In one preferred embodiment, A is a C$_{5-20}$carboaryl group, and is optionally substituted. In one preferred embodiment, A is a monocyclic C$_{5-20}$carboaryl group, and is optionally substituted. In one preferred embodiment, A is a monocyclic C$_{5-6}$carboaryl group, and is optionally substituted. In one preferred embodiment, A is a phenyl group, and is optionally substituted.

In one preferred embodiment, A is a C$_{5-20}$aryl group derived from one of the following: benzene, pyridine, furan, indole, pyrrole, imidazole, naphthalene, quinoline, benzimidazole, benzothiofuran, fluorene, acridine, and carbazole.

In one preferred embodiment, A is an optionally substituted phenyl group of the formula:

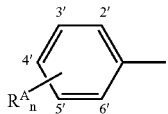

wherein n is an integer from 0 to 5, and each $R^A$ is independently a substituent as defined herein.

Thus, in one preferred embodiment, A is an optionally substituted phenyl group, $Q^1$ is an aryl leader group, J is —$SO_2NR^1$—, and the compounds have the following formula:

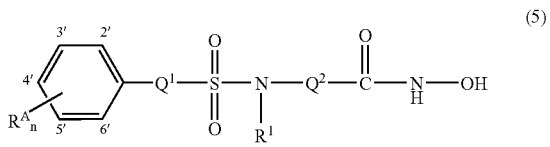
(5)

In one preferred embodiment, A is an optionally substituted phenyl group, $Q^1$ is a covalent bond or an aryl leader group, J is —$NR^1SO_2$—, and the compounds have the following formula:

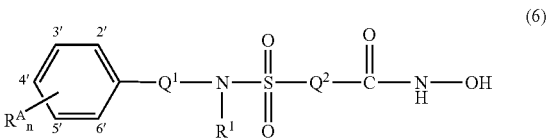
(6)

In one preferred embodiment, A is an optionally substituted phenyl group, $Q^1$ is an aryl leader group, J is —$NR^1SO_2$—, and the compounds have the following formula:

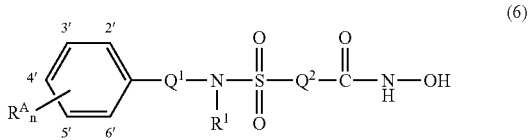
(6)

In one preferred embodiment, A is an optionally substituted phenyl group, $Q^1$ is a covalent bond, J is —$NR^1SO_2$—, and the compounds have the following formula:

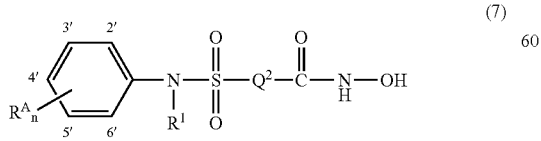
(7)

In one preferred embodiment, n is an integer from 0 to 5.
In one preferred embodiment, n is an integer from 0 to 4. In one preferred embodiment, n is an integer from 0 to 3. In one preferred embodiment, n is an integer from 0 to 2. In one preferred embodiment, n is 0 or 1.

In one preferred embodiment, n is an integer from 1 to 5.
In one preferred embodiment, n is an integer from 1 to 4.
In one preferred embodiment, n is an integer from 1 to 3.
In one preferred embodiment, n is 1 or 2.
In one preferred embodiment, n is 5.
In one preferred embodiment, n is 4.
In one preferred embodiment, n is 3.
In one preferred embodiment, n is 2.
In one preferred embodiment, n is 1.
In one preferred embodiment, n is 0.

If the phenyl group has less than the full complement of ring substituents, $R^A$, they may be arranged in any combination. For example, if n is 1, $R^A$ may be in the 2'-, 3'-, 4'-, 5'-, or 6'-position. Similarly, if n is 2, the two $R^A$ groups may be in, for example, the 2',3'-, 2',4'-, 2',5'-, 2',6'-, 3',4'-, or 3',5'-positions. If n is 3, the three $R^A$ groups may be in, for example, the 2',3',4'-, 2',3',5'-, 2',3',6'-, or 3',4',5'-positions.

In one preferred embodiment, n is 1, and the $R^A$ group is in the 4'-position.

In one preferred embodiment, n is 2, and one $R^A$ group is in the 4'-position, and the other $R^A$ group is in the 2'-position.

In one preferred embodiment, n is 2, and one $R^A$ group is in the 4'-position, and the other $R^A$ group is in the 3'-position.

Each aryl substituent, $R^A$, is a substituent as defined herein.

Examples of preferred aryl substituents, $R^A$, include, but are not limited to, the following: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido (unsubstituted, i.e., —$CONH_2$), acetamido, acetyl, nitro, sulfonamido (unsubstituted, i.e., —$SO_2NH_2$), and phenyl.

In one preferred embodiment, A is a substituted phenyl group selected from:

para-(fluoro)phenyl; ortho-(fluoro)phenyl; meta-(fluoro)phenyl;
para-(chloro)phenyl; ortho-(chloro)phenyl; meta-(chloro)phenyl;
para-(bromo)phenyl; ortho-(bromo)phenyl; meta-(bromo)phenyl;
para-(iodo)phenyl; ortho-(iodo)phenyl; meta-(iodo)phenyl;
para-(methyl)phenyl; ortho-(methyl)phenyl; meta-(methyl)phenyl;
para-(ethyl)phenyl; ortho-(ethyl)phenyl; meta-(ethyl)phenyl;
para-(isopropyl)phenyl; ortho-(isopropyl)phenyl; meta-(isopropyl)phenyl;
para-(t-butyl)phenyl; ortho-(t-butyl)phenyl; meta-(t-butyl)phenyl;
para-(cyano)phenyl; ortho-(cyano)phenyl; meta-(cyano)phenyl;
para-(trifluoromethyl)phenyl; ortho-(trifluoromethyl)phenyl; meta-(trifluoromethyl)phenyl;
para-(hydroxy)phenyl; ortho-(hydroxy)phenyl; meta-(hydroxy)phenyl;
para-(methoxy)phenyl; ortho-(methoxy)phenyl; meta-(methoxy)phenyl;
para-(ethoxy)phenyl; ortho-(ethoxy)phenyl; meta-(ethoxy)phenyl;
para-(isopropoxy)phenyl; ortho-(isopropoxy)phenyl; meta-(isopropoxy)phenyl;

para-(trifluoromethoxy)phenyl; ortho-(trifluoromethoxy)phenyl; meta-(trifluoromethoxy)phenyl;
para-(phenoxy)phenyl; ortho-(phenoxy)phenyl; meta-(phenoxy)phenyl;
para-(methylthio)phenyl; ortho-(methylthio)phenyl; meta-(methylthio)phenyl;
para-(trifluoromethylthio)phenyl; ortho-(trifluoromethylthio)phenyl; meta-(trifluoromethylthio)phenyl;
para-(hydroxymethyl)phenyl; ortho-(hydroxymethyl)phenyl; meta-(hydroxymethyl)phenyl;
para-(amino)phenyl; ortho-(amino)phenyl; meta-(amino)phenyl;
para-(dimethylamino)phenyl; ortho-(dimethylamino)phenyl; meta-(dimethylamino)phenyl;
para-(diethylamino)phenyl; ortho-(diethylamino)phenyl; meta-(diethylamino)phenyl;
para-(morpholino)phenyl; ortho-(morpholino)phenyl; meta-(morpholino)phenyl;
para-(amido)phenyl; ortho-(amido)phenyl; meta-(amido)phenyl;
para-(acetamido)phenyl; ortho-(acetamido)phenyl; meta-(acetamido)phenyl;
para-(acetyl)phenyl; ortho-(acetyl)phenyl; meta-(acetyl)phenyl;
para-(nitro)phenyl; ortho-(nitro)phenyl; meta-(nitro)phenyl;
para-(sulfonamido)phenyl; ortho-(sulfonamido)phenyl; meta-(sulfonamido)phenyl; and,
para-(phenyl)phenyl; ortho-(phenyl)phenyl; meta-(phenyl)phenyl.

In one preferred embodiment, A is a substituted phenyl group selected from:
para-(fluoro)phenyl;
para-(chloro)phenyl;
para-(bromo)phenyl;
para-(iodo)phenyl;
para-(methyl)phenyl;
para-(ethyl)phenyl;
para-(isopropyl)phenyl;
para-(t-butyl)phenyl;
para-(cyano)phenyl;
para-(trifluoromethyl)phenyl;
para-(hydroxy)phenyl;
para-(methoxy)phenyl;
para-(ethoxy)phenyl;
para-(isopropoxy)phenyl;
para-(trifluoromethoxy)phenyl;
para-(phenoxy)phenyl;
para-(methylthio)phenyl;
para-(trifluoromethylthio)phenyl;
para-(hydroxymethyl)phenyl;
para-(amino)phenyl;
para-(dimethylamino)phenyl;
para-(diethylamino)phenyl;
para-(morpholino)phenyl;
para-(amido)phenyl;
para-(acetamido)phenyl;
para-(acetyl)phenyl;
para-(nitro)phenyl;
para-(sulfonamido)phenyl; and,
para-(phenyl)phenyl.

In one preferred embodiment, A is a substituted phenyl group selected from:
ortho,para-di(methoxy)phenyl;
ortho,para-di(halo)phenyl;
ortho,para-di(fluoro)phenyl;
ortho-(methoxy),para-(methyl)phenyl;
ortho-(methoxy),para-(trifluoromethyl)phenyl;
ortho-(trifluoromethyl),para-(halo)phenyl;
ortho,meta-di(trifluoromethyl)phenyl;
ortho-(halo),meta-(trifluoromethyl)phenyl;
meta,para-di(halo)phenyl;
meta,para-di(hydroxy)phenyl;
meta,para-di(methyl)phenyl;
meta,para-di(methoxy)phenyl;
meta-(halo),para-(nitro)phenyl;
3',5'-di(trifluoromethyl)phenyl;
3'-(trifluoromethyl),5'-(methoxy)phenyl;
3'-(trifluoromethyl),5'-(halo)phenyl;
2'-(halo),5'-(methyl)phenyl;
2',6'-di(methyl)phenyl;
2',6'-di(halo)phenyl;
2',6'-di(isopropyl)phenyl;
2',4',6'-tri(halo)phenyl;
3',4',5'-tri(halo)phenyl;
3',4',5'-tri(methoxy)phenyl;
2',5'-di(halo)$_4$'-(hydroxy)phenyl; and
3'-(trifluoromethyl),5',6'-di(halo)phenyl.

The Aryl Leader Group, $Q^1$

As mentioned above, in some embodiments, $Q^1$ is a covalent bond or an aryl leader group; in some embodiments, $Q^1$ is a covalent bond; in some embodiments, $Q^1$ is an aryl leader group.

In one preferred embodiment, $Q^1$ is a covalent bond.

In one preferred embodiment, $Q^1$ is a $C_{1-7}$alkylene group and is optionally substituted.

In one preferred embodiment, $Q^1$ is a covalent bond or a $C_{1-7}$alkylene group and is optionally substituted.

In one preferred embodiment, $Q^1$ is a covalent bond or a saturated $C_{1-7}$alkylene group. In one preferred embodiment, $Q^1$ is a saturated $C_{1-7}$alkylene group.

In one preferred embodiment, $Q^1$ is a covalent bond or a partially unsaturated $C_{1-7}$alkylene group. In one preferred embodiment, $Q^1$ is a partially unsaturated $C_{1-7}$alkylene group.

In one preferred embodiment, $Q^1$ is a covalent bond or an aliphatic $C_{1-7}$alkylene group. In one preferred embodiment, $Q^1$ is an aliphatic $C_{1-7}$alkylene group.

In one preferred embodiment, $Q^1$ is a covalent bond or a linear $C_{1-7}$alkylene group.

In one preferred embodiment, $Q^1$ is a linear $C_{1-7}$alkylene group.

In one preferred embodiment, $Q^1$ is a covalent bond or a branched $C_{1-7}$alkylene group. In one preferred embodiment, $Q^1$ is a branched $C_{1-7}$alkylene group.

In one preferred embodiment, $Q^1$ is a covalent bond or an alicyclic $C_{1-7}$alkylene group. In one preferred embodiment, $Q^1$ is an alicyclic $C_{1-7}$alkylene group.

In one preferred embodiment, $Q^1$ is a covalent bond or a saturated aliphatic $C_{1-7}$alkylene group. In one preferred embodiment, $Q^1$ is a saturated aliphatic $C_{1-7}$alkylene group.

In one preferred embodiment, $Q^1$ is a covalent bond or a saturated linear $C_{1-7}$alkylene group. In one preferred embodiment, $Q^1$ is a saturated linear $C_{1-7}$alkylene group.

In one preferred embodiment, $Q^1$ is a covalent bond or a saturated branched $C_{1-7}$alkylene group. In one preferred embodiment, $Q^1$ is a saturated branched $C_{1-7}$alkylene group.

In one preferred embodiment, $Q^1$ is a covalent bond or a saturated alicyclic $C_{1-7}$alkylene group. In one preferred embodiment, $Q^1$ is a saturated alicyclic $C_{1-7}$alkylene group.

In one preferred embodiment, $Q^1$ is a covalent bond or a partially unsaturated aliphatic $C_{1-7}$alkylene group. In one preferred embodiment, $Q^1$ is a partially unsaturated aliphatic $C_{1-7}$alkylene group.

In one preferred embodiment, $Q^1$ is a covalent bond or a partially unsaturated linear $C_{1-7}$alkylene group. In one preferred embodiment, $Q^1$ is a partially unsaturated linear $C_{1-7}$alkylene group.

In one preferred embodiment, $Q^1$ is a covalent bond or a partially unsaturated branched $C_{1-7}$alkylene group. In one preferred embodiment, $Q^1$ is a partially unsaturated branched $C_{1-7}$alkylene group.

In one preferred embodiment, $Q^1$ is a covalent bond or a partially unsaturated alicyclic $C_{1-7}$alkylene group. In one preferred embodiment, $Q^1$ is a partially unsaturated alicyclic $C_{1-7}$alkylene group.

The Aryl Leader Group, $Q^1$: Backbone Length

In one embodiment, the aryl leader group, $Q^1$, has a backbone of at least 2 carbon atoms; that is, the shortest chain of atoms linking the aryl group, A, and the sulfonamide group, J, has 2 or more atoms, more specifically, 2 or more carbon atoms. In this way, groups such as methylene (—CH$_2$—) and substituted methylene (—CR$_2$— and —CHR—) are excluded.

If there are two or more paths linking the aryl group, A, and the sulfonamide group, J, then the shortest path is relevant. For example, in the embodiments shown below, where the moiety A-Q$^1$- is derived from indan (2,3-dihydro-1H-indene), A is considered to be a phenyl group fused to $Q^1$, a $C_5$cycloalkyl group:

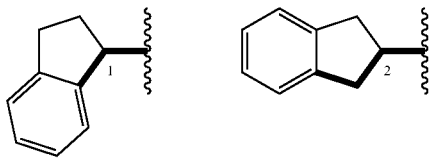

In each case, there are two paths to the aryl group. In the first case, one path has 1 carbon atom, and the other path has 3 carbon atoms, and so the relevant backbone length is 1. In the second case, both paths have 2 carbon atoms, and so the relevant backbone length is 2.

If the group A-Q$^1$- has two or more aryl groups, the aryl group furthest from the sulfonamide group, J, as measured by counting chain atoms, is identified as A; the relevant backbone is then the shortest chain of atoms linking that aryl group and the sulfonamide group, J. For example, where the group A-Q$^1$- is as shown below, the phenyl group marked "1" is identified as the A, Q$^1$ is —CH$_2$CH(Ph)- (i.e., substituted ethylene), and the backbone length is 2.

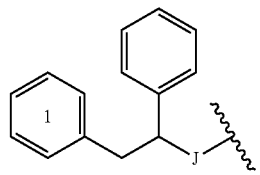

If the sulfonamide group is —NR$^1$SO$_2$— (as opposed to —SO$_2$NR$^1$—), and substituent, R$^1$, discussed below, is or comprises an aryl group (or two or more aryl groups), then the aryl group furthest from the sulfonamide group nitrogen atom, as measured by counting chain atoms, is identified as A. For example, where the group A-Q$^1$-NR$^1$SO$_2$— is as shown below, the phenyl group marked "1" is identified as the A, Q$^1$ is —CH$_2$—, and the backbone length is 1.

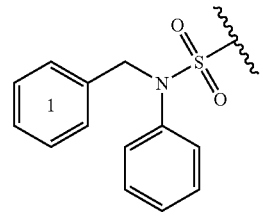

In one preferred embodiment, the aryl leader group, $Q^1$, has a backbone of at least 3 carbon atoms.

In one preferred embodiment, the aryl leader group, $Q^1$, has a backbone of at least 4 carbon atoms.

In one preferred embodiment, the aryl leader group, $Q^1$, has a backbone of at least 5 carbon atoms.

In one embodiment, the aryl leader group, $Q^1$, has a backbone of:
from 2 to 7 carbon atoms;
from 2 to 6 carbon atoms; or,
from 2 to 5 carbon atoms.

In one embodiment, the aryl leader group, $Q^1$, has a backbone of:
from 3 to 7 carbon atoms;
from 3 to 6 carbon atoms; or,
from 3 to 5 carbon atoms.

In one embodiment, the aryl leader group, $Q^1$, has a backbone of:
from 4 to 7 carbon atoms;
from 4 to 6 carbon atoms; or,
from 4 to 5 carbon atoms.

In one embodiment, the aryl leader group, $Q^1$, has a backbone of 2 carbon atoms.

In one embodiment, the aryl leader group, $Q^1$, has a backbone of 3 carbon atoms.

In one embodiment, the aryl leader group, $Q^1$, has a backbone of 4 carbon atoms.

In one embodiment, the aryl leader group, $Q^1$, has a backbone of 5 carbon atoms.

The Aryl Leader Group, $Q^1$: Alkylene

In one embodiment, the aryl leader group, $Q^1$, is an alkylene group, and has a backbone of at least 2 carbon atoms.

In one preferred embodiment, the aryl leader group, $Q^1$, has a backbone of at least 2 carbon atoms, and is a $C_{2-7}$alkylene group.

In one preferred embodiment, the aryl leader group, $Q^1$, has a backbone of at least 3 carbon atoms, and is a $C_{3-7}$alkylene group.

In one preferred embodiment, $Q^1$ has a backbone of at least 2 carbon atoms, and is a saturated $C_{2-7}$alkylene group.

In one preferred embodiment, $Q^1$ has a backbone of at least 3 carbon atoms, and is a saturated $C_{3-7}$alkylene group.

In one preferred embodiment, $Q^1$ has a backbone of at least 2 carbon atoms, and is a partially unsaturated $C_{2-7}$alkylene group.

In one preferred embodiment, $Q^1$ has a backbone of at least 3 carbon atoms, and is a partially unsaturated $C_{3-7}$alkylene group.

In one preferred embodiment, $Q^1$ has a backbone of at least 2 carbon atoms, and is an aliphatic $C_{2-7}$alkylene group.

In one preferred embodiment, $Q^1$ has a backbone of at least 3 carbon atoms, and is an aliphatic $C_{3-7}$alkylene group.

In one preferred embodiment, $Q^1$ has a backbone of at least 2 carbon atoms, and is a linear $C_{2-7}$alkylene group.

In one preferred embodiment, $Q^1$ has a backbone of at least 3 carbon atoms, and is a linear $C_{3-7}$alkylene group.

In one preferred embodiment, $Q^1$ has a backbone of at least 2 carbon atoms, and is a branched $C_{2-7}$alkylene group.

In one preferred embodiment, $Q^1$ has a backbone of at least 3 carbon atoms, and is a branched $C_{3-7}$alkylene group.

In one preferred embodiment, $Q^1$ has a backbone of at least 2 carbon atoms, and is an alicyclic $C_{2-7}$alkylene group.

In one preferred embodiment, $Q^1$ has a backbone of at least 3 carbon atoms, and is an alicyclic $C_{3-7}$alkylene group.

In one preferred embodiment, $Q^1$ has a backbone of at least 2 carbon atoms, and is a saturated aliphatic $C_{2-7}$alkylene group.

In one preferred embodiment, $Q^1$ has a backbone of at least 3 carbon atoms, and is a saturated aliphatic $C_{3-7}$alkylene group.

In one preferred embodiment, $Q^1$ has a backbone of at least 2 carbon atoms, and is a saturated linear $C_{2-7}$alkylene group.

In one preferred embodiment, $Q^1$ has a backbone of at least 3 carbon atoms, and is a saturated linear $C_{3-7}$alkylene group.

In one preferred embodiment, $Q^1$ has a backbone of at least 2 carbon atoms, and is a saturated branched $C_{2-7}$alkylene group.

In one preferred embodiment, $Q^1$ has a backbone of at least 3 carbon atoms, and is a saturated branched $C_{3-7}$alkylene group.

In one preferred embodiment, $Q^1$ has a backbone of at least 2 carbon atoms, and is a saturated alicyclic $C_{2-7}$alkylene group.

In one preferred embodiment, $Q^1$ has a backbone of at least 3 carbon atoms, and is a saturated alicyclic $C_{3-7}$alkylene group.

In one preferred embodiment, $Q^1$ has a backbone of at least 2 carbon atoms, and is a partially unsaturated aliphatic $C_{2-7}$alkylene group.

In one preferred embodiment, $Q^1$ has a backbone of at least 3 carbon atoms, and is a partially unsaturated aliphatic $C_{3-7}$alkylene group.

In one preferred embodiment, $Q^1$ has a backbone of at least 2 carbon atoms, and is a partially unsaturated linear $C_{2-7}$alkylene group.

In one preferred embodiment, $Q^1$ has a backbone of at least 3 carbon atoms, and is a partially unsaturated linear $C_{3-7}$alkylene group.

In one preferred embodiment, $Q^1$ has a backbone of at least 2 carbon atoms, and is a partially unsaturated branched $C_{2-7}$alkylene group.

In one preferred embodiment, $Q^1$ has a backbone of at least 3 carbon atoms, and is a partially unsaturated branched $C_{3-7}$alkylene group.

In one preferred embodiment, $Q^1$ has a backbone of at least 2 carbon atoms, and is a partially unsaturated alicyclic $C_{2-7}$alkylene group.

In one preferred embodiment, $Q^1$ has a backbone of at least 3 carbon atoms, and is a partially unsaturated alicyclic $C_{3-7}$alkylene group.

The Aryl Leader Group, $Q^1$: Backbone Length of 0 or 2 or more

In one preferred embodiment, the aryl leader group, $Q^1$, is either: a covalent bond, or: has a backbone of at least 2 carbon atoms.

In one preferred embodiment, $Q^1$ is either: a covalent bond, or: has a backbone of at least 2 carbon atoms and is a $C_{2-7}$alkylene group.

In one preferred embodiment, $Q^1$ is either: a covalent bond, or: has a backbone of at least 2 carbon atoms and is a saturated $C_{2-7}$alkylene group.

In one preferred embodiment, $Q^1$ is either: a covalent bond, or: has a backbone of at least 2 carbon atoms and is a partially unsaturated $C_{2-7}$alkylene group.

In one preferred embodiment, $Q^1$ is either: a covalent bond, or: has a backbone of at least 2 carbon atoms and is an aliphatic $C_{2-7}$alkylene group.

In one preferred embodiment, $Q^1$ is either: a covalent bond, or: has a backbone of at least 2 carbon atoms and is a linear $C_{2-7}$alkylene group.

In one preferred embodiment, $Q^1$ is either: a covalent bond, or: has a backbone of at least 2 carbon atoms and is a branched $C_{2-7}$alkylene group.

In one preferred embodiment, $Q^1$ is either: a covalent bond, or: has a backbone of at least 2 carbon atoms and is an alicyclic $C_{2-7}$alkylene group.

In one preferred embodiment, $Q^1$ is either: a covalent bond, or: has a backbone of at least 2 carbon atoms and is a saturated aliphatic $C_{2-7}$alkylene group.

In one preferred embodiment, $Q^1$ is either: a covalent bond, or: has a backbone of at least 2 carbon atoms and is a saturated linear $C_{2-7}$alkylene group.

In one preferred embodiment, $Q^1$ is either: a covalent bond, or: has a backbone of at least 2 carbon atoms and is a saturated branched $C_{2-7}$alkylene group.

In one preferred embodiment, $Q^1$ is either: a covalent bond, or: has a backbone of at least 2 carbon atoms and is a saturated alicyclic $C_{2-7}$alkylene group.

In one preferred embodiment, $Q^1$ is either: a covalent bond, or: has a backbone of at least 2 carbon atoms and is a partially unsaturated aliphatic $C_{2-7}$alkylene group.

In one preferred embodiment, $Q^1$ is either: a covalent bond, or: has a backbone of at least 2 carbon atoms and is a partially unsaturated linear $C_{2-7}$alkylene group.

In one preferred embodiment, $Q^1$ is either: a covalent bond, or: has a backbone of at least 2 carbon atoms and is a partially unsaturated branched $C_{2-7}$alkylene group.

In one preferred embodiment, $Q^1$ is either: a covalent bond, or: has a backbone of at least 2 carbon atoms and is a partially unsaturated alicyclic $C_{2-7}$alkylene group.

Note that, as discussed below in the context of isomers, where unsaturation permits isomers, e.g., cis- and trans-, E- and Z-, etc., and combinations thereof, a reference to one isomer is to be considered a reference to all such isomers, unless otherwise specified.

The Aryl Leader Grout, $Q^1$: Substituents

In one embodiment, $Q^1$ is unsubstituted.

In one embodiment, $Q^1$ is optionally substituted.

In one embodiment, $Q_1$ is substituted.

Examples of substituents on $Q_1$ include, but are not limited to, those described under the heading "Substituents" below.

In one preferred embodiment, substituents on $Q^1$, if present, are independently selected from: halo, hydroxy, ether (e.g., $C_{1-7}$alkoxy), $C_{5-20}$aryl, acyl, amido, and oxo.

In one preferred embodiment, substituents on $Q^1$, if present, are independently selected from —F, —Cl, —Br, —I, —OH, —OMe, —OEt, —OPr, -Ph, and =O.

In one preferred embodiment, substituents on $Q^1$, if present, are —OH or -Ph.

In one preferred embodiment, substituents on $Q^1$, if present, are -Ph.

For example, in one embodiment, $Q^1$ is unsubstituted ethylene, and is —CH$_2$—CH$_2$—; in one embodiment, $Q^1$ is oxo (=O) subsituted ethylene, and is —C(=O)—CH$_2$—; in one embodiment, $Q^1$ is hydroxy (—OH) subsituted ethylene, and is —CH(OH)—CH$_2$—; in one embodiment, $Q^1$ is phenyl (-Ph) substituted ethylene, and is —CH$_2$CH(Ph)-.

The Aryl Leader Group, $Q^1$: Certain Embodiments

Note that, for embodiments excluding, e.g., a covalent bond, certain backbone lengths, etc., it is to be understood that the corresponding species listed below are similarly excluded from the respective embodiments discussed below.

In one preferred embodiment, $Q^1$ is selected from the following:

a covalent bond;
—(CH$_2$)$_n$— where n is an integer from 1 to 7;
—CH(CH$_3$)—;
—CH(CH$_3$)CH$_2$— and —CH$_2$CH(CH$_3$)—;
—CH(CH$_3$)CH$_2$CH$_2$—, —CH$_2$CH(CH$_3$)CH$_2$—, and —CH$_2$CH$_2$CH(CH$_3$)—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$);
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$, and —CH$_2$CH$_2$CH$_2$CH$_2$CH(CH$_3$)—;
—CH(CH$_2$CH$_3$)—;
—CH(CH$_2$CH$_3$)CH$_2$— and —CH$_2$CH(CH$_2$CH$_3$)—;
—CH(CH$_2$CH$_3$)CH$_2$CH$_2$—, —CH$_2$CH(CH$_2$CH$_3$)CH$_2$—, and —CH$_2$CH$_2$CH(CH$_2$CH$_3$)—;
—CH(CH$_2$CH$_3$)CH$_2$CH$_2$CH$_2$—, —CH$_2$CH(CH$_2$CH$_3$)CH$_2$CH$_2$, —CH$_2$CH$_2$CH(CH$_2$CH$_3$)CH$_2$—, and —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, and —CH$_2$CH$_2$CH$_2$CH$_2$CH(CH$_2$CH$_3$)—;
—CH=CH—;
—CH=CHCH$_2$— and —CH$_2$CH=CH—;
—CH=CHCH$_2$CH$_2$—, —CH$_2$CH=CHCH$_2$—, and —CH$_2$CH$_2$CH=CH—;
—CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—;
—CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$—, and —CH$_2$CH$_2$CH$_2$CH$_2$CH=CH—;
—C(CH$_3$)=CH— and —CH=C(CH$_3$)—;
—C(CH$_3$)=CHCH$_2$—, —CH=C(CH$_3$)CH$_2$—, and —CH=CHCH(CH$_3$)—;
—CH(CH$_3$)CH=CH—, —CH$_2$C(CH$_3$)=CH—, and —CH$_2$CH=C(CH$_3$)—;
—CH=CHCH=CH—;
—CH=CHCH=CHCH$_2$—, —CH$_2$CH=CHCH=CH—, and —CH=CHCH$_2$CH=CH—;
—CH=CHCH=CHCH$_2$CH$_2$—, —CH=CHCH$_2$CH=CHCH$_2$—, —CH=CHCH$_2$CH$_2$CH=CH—, —CH$_2$CH=CHCH=CHCH$_2$—,
—CH$_2$CH=CHCH$_2$CH=CH—, and —CH$_2$CH$_2$CH=CHCH=CH—;
—C(CH$_3$)=CHCH=CH—, —CH=C(CH$_3$)CH=CH—, —CH=CHC(CH$_3$)=CH—, and —CH=CHCH=C(CH$_3$)—;
—C≡C—;
—C≡CCH$_2$—, —CH$_2$C≡C—; —C≡CCH(CH$_3$)—, and —CH(CH$_3$)C≡C—;
—C≡CCH$_2$CH$_2$—, —CH$_2$C≡CCH$_2$—, and —CH$_2$CH$_2$C≡C—;
—C≡CCH(CH$_3$)CH$_2$— and —C≡CCH$_2$CH(CH$_3$)—;
—CH(CH$_3$)C≡CCH$_2$— and —CH$_2$C≡CCH(CH$_3$)—;
—CH(CH$_3$)CH$_2$C≡C— and —CH$_2$CH(CH$_3$)C≡C—;
—C≡CCH=CH—, —CH=CHC≡C—, and —C≡CC≡C—;
—C≡CCH$_2$CH$_2$CH$_2$— and —CH$_2$CH$_2$CH$_2$C≡C—;
—C≡CCH$_2$CH$_2$CH$_2$CH$_2$— and —CH$_2$CH$_2$CH$_2$CH$_2$C≡C—;
—C≡CCH=CHCH=CH—, —CH=CHC≡CCH=CH—, and —CH=CHCH=CHC≡C—;
—C(CH$_3$)=CHC≡C—, —CH=C(CH$_3$)C≡C—, —C≡CC(CH$_3$)=CH—, and —C≡CCH=C(CH$_3$);

cyclopentylene and cyclopentenylene; and, cyclohexylene, cyclohexenylene, and cyclohexadienylene.

In one preferred embodiment, $Q^1$ is selected from:

a covalent bond;
—CH$_2$—, —(CH$_2$)$_2$—, —(CH$_2$)$_3$—, —(CH$_2$)$_4$—, —(CH$_2$)$_5$—, and —(CH$_2$)$_6$—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH$_2$CH(CH$_3$)CH$_2$—, and —CH$_2$CH$_2$CH$_2$CH$_2$CH(CH$_3$)—;
—CH=CH—;
—CH=CH—CH=CH—;
—CH=CHCH$_2$CH$_2$CH$_2$— and —CH$_2$CH$_2$CH$_2$CH=CH—;
—CH=CHCH$_2$CH$_2$CH$_2$CH$_2$— and —CH$_2$CH$_2$CH$_2$CH$_2$CH=CH—;
—C(CH$_3$)=CHCH=CH—, —CH=C(CH$_3$)CH=CH—, —CH=CHC(CH$_3$)=CH—, and —CH=CHCH=C(CH$_3$)—;

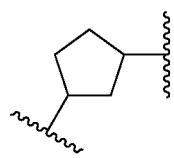

(cyclopent-1,3-ylene)

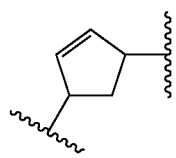

(4-cyclopenten-1,3-ylene)

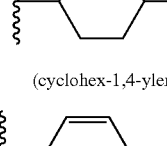

(cyclohex-1,4-ylene)

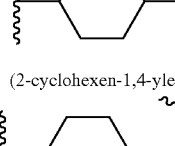

(2-cyclohexen-1,4-ylene)

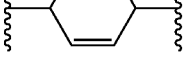

(2,5-cyclohexadien-1,4-ylene)

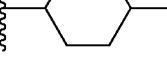

(cyclohex-1,4-ylene-methylene)

-continued

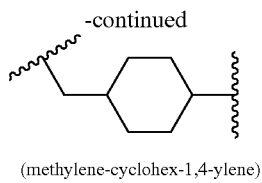

(methylene-cyclohex-1,4-ylene)

In one preferred embodiment, $Q^1$ is selected from:
a covalent bond;
—$CH_2$—, —$(CH_2)_2$—$(CH_2)_3$—, —$(CH_2)_4$—, —$(CH_2)_5$—,
—CH=CH—;
—CH=CH—CH=CH—;
—C($CH_3$)=CHCH=CH—, —CH=C($CH_3$)CH=CH—, —CH=CHC($CH_3$)=CH—, and —CH=CHCH=C($CH_3$)—;
—CH=CHCH$_2$CH$_2$CH$_2$— and —CH$_2$CH$_2$CH$_2$CH=CH—; and,

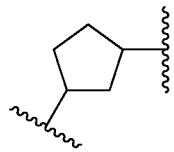   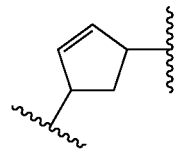

(cyclopent-1,3-ylene)   (4-cyclopenten-1,3-ylene)

In one preferred embodiment, $Q^1$ is selected from: a covalent bond, —$CH_2$—, —$CH_2CH_2$—, —$CH_2CH_2CH_2$—, —CH=CH—, and —CH=CH—CH=CH—.

In one preferred embodiment, $Q^1$ is selected from: a covalent bond, —$CH_2$—, —$CH_2CH_2$—, —$CH_2CH_2CH_2$—, —CH=CH—, —CH=CH—CH=CH—, and $C_5$cycloalkyl (e.g., cyclopentylene and cyclopentenylene, e.g., as in indan, fluorene, etc.).

The Sulfonamido Substituent, $R^1$

The sulfonamido substituent, $R^1$, is hydrogen, $C_{1-7}$alkyl (including, e.g., $C_{5-20}$aryl-$C_{1-7}$alkyl), $C_{3-20}$heterocyclyl, or $C_{5-20}$aryl.

Note that $R^1$ is a monodentate species. It is not intended that $R^1$ be additionally linked to A, $Q^1$, and/or $Q^2$, thereby forming a cyclic group.

In one preferred embodiment, $R^1$ is hydrogen, $C_{1-7}$alkyl, or $C_{5-20}$aryl.

In one preferred embodiment, $R^1$ is hydrogen or $C_{1-7}$alkyl.

In one preferred embodiment, $R^1$ is hydrogen, saturated $C_{1-7}$alkyl, or $C_{5-20}$aryl.

In one preferred embodiment, $R^1$ is hydrogen or saturated $C_{1-7}$alkyl.

In one preferred embodiment, $R^1$ is hydrogen, saturated aliphatic $C_{1-7}$alkyl, or $C_{5-20}$aryl.

In one preferred embodiment, $R^1$ is hydrogen or saturated aliphatic $C_{1-7}$alkyl.

In one preferred embodiment, $R^1$ is —H, -Me, -Et, -nPr, -iPr, -nBu, -sBu, -tBu, -Ph, or -Bn.

In one-preferred embodiment, $R^1$ is —H, -Me, -Et, -nPr, -iPr, -nBu, -sBu, or -tBu.

In one preferred embodiment, $R^1$ is —H, -Me, -Et, -Ph, or -Bn.

In one preferred embodiment, $R^1$ is —H, -Me, or -Et.
In one preferred embodiment, $R^1$ is —H.

The Acid Leader Group, $Q^2$

The acid leader group, $Q^2$, is $C_{1-7}$alkylene; $C_{5-20}$arylene; $C_{2-0}$arylene-$C_{1-7}$alkylene; $C_{1-7}$alkylene-$C_{5-20}$arylene; or an ether linkage (i.e. —$R^2$—X—$R^3$—); and is optionally substituted.

In one preferred embodiment, $Q^7$ is $C_{1-7}$alkylene; $C_{5-20}$arylene; $C_{5-20}$arylene-$C_{1-7}$alkylene; or $C_{1-7}$alkylene-$C_{5-20}$arylene; and is optionally substituted.

In one embodiment, $Q^2$ is unsubstituted.
In one embodiment, $Q^2$ is optionally substituted.
In one embodiment, $Q^2$ is substituted.

The Acid Leader Group, $Q^2$: Alkylene

In one preferred embodiment, the acid leader group, $Q^2$, is $C_{1-7}$alkylene and is optionally substituted.

In one preferred embodiment, $Q^2$ is a $C_{1-7}$alkylene group.
In one preferred embodiment, $Q^2$ is a saturated $C_{1-7}$alkylene group.
In one preferred embodiment, $Q^2$ is a partially unsaturated $C_{1-7}$alkylene group.
In one preferred embodiment, $Q^2$ is an aliphatic $C_{1-7}$alkylene group.
In one preferred embodiment, $Q^2$ is a linear $C_{1-7}$ alkylene group.
In one preferred embodiment, $Q^2$ is a branched $C_{1-7}$alkylene group.
In one preferred embodiment, $Q^2$ is a alicyclic $C_{1-7}$alkylene group.
In one preferred embodiment, $Q^2$ is a saturated aliphatic $C_{1-7}$alkylene group.
In one preferred embodiment, $Q^2$ is a saturated linear $C_{1-7}$alkylene group.
In one preferred embodiment, $Q^2$ is a saturated branched $C_{1-7}$alkylene group.
In one preferred embodiment, $Q^2$ is a saturated alicyclic $C_{1-7}$alkylene group.
In one preferred embodiment, $Q^2$ is a partially unsaturated aliphatic $C_{1-7}$alkylene group.
In one preferred embodiment, $Q^2$ is a partially unsaturated linear $C_{1-7}$alkylene group.
In one preferred embodiment, $Q^2$ is a partially unsaturated branched $C_{1-7}$alkylene group.
In one preferred embodiment, $Q^2$ is a partially unsaturated alicyclic $C_{1-7}$alkylene group.

Note that, for embodiments excluding, e.g., unsaturation, etc., it is to be understood that the corresponding species listed below are similarly excluded from the respective embodiments discussed below.

In one preferred embodiment, $Q^2$ is selected from:
—$(CH_2)_n$— where n is an integer from 1 to 7;
—CH($CH_3$)—;
—CH($CH_3$)$CH_2$— and —$CH_2$CH($CH_3$)—;
—CH($CH_3$)$CH_2CH_2$—, —$CH_2$CH($CH_3$)$CH_2$—, and —$CH_2CH_2$CH($CH_3$)—;
—CH($CH_3$)$CH_2CH_2CH_2$—, —$CH_2$CH($CH_3$)$CH_2CH_2$—, —$CH_2CH_2$CH($CH_3$)$CH_2$—, and —$CH_2CH_2CH_2$CH($CH_3$)—;
—CH($CH_3$)$CH_2CH_2CH_2CH_2$—, —$CH_2$CH($CH_3$)$CH_2CH_2CH_2$—, —$CH_2CH_2$CH($CH_3$)$CH_2CH_2$—, —$CH_2CH_2CH_2$CH($CH_3$)$CH_2$—, and —$CH_2CH_2CH_2CH_2$CH($CH_3$)—;
—CH($CH_2CH_3$)—;
—CH($CH_2CH_3$)$CH_2$— and —$CH_2$CH($CH_2CH_3$)—;
—CH($CH_2CH_3$)$CH_2CH_2$—, —$CH_2$CH($CH_2CH_3$)$CH_2$—, and —$CH_2CH_2$CH($CH_2CH_3$)—;

—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, and —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, and —CH$_2$CH$_2$CH$_2$CH$_2$CH(CH$_2$CH$_3$)—;
—CH=CH—;
—CH=CHCH$_2$— and —CH$_2$CH=CH—;
—CH=CHCH$_2$CH$_2$—, —CH$_2$CH=CHCH$_2$—, and —CH$_2$CH$_2$CH=CH—;
—CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—;
—CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$—, and —CH$_2$CH$_2$CH$_2$CH$_2$CH=CH—;
—C(CH$_3$)=CH— and —CH=C(CH$_3$)—;
—C(CH$_3$)=CHCH$_2$—, —CH=C(CH$_3$)CH$_2$—, and —CH=CHCH(CH$_3$)—;
—CH(CH$_3$)CH=CH—, —CH$_2$C(CH$_3$)=CH—, and —CH$_2$CH=C(CH$_3$)—;
—CH=CHCH=CH—;
—CH=CHCH=CHCH$_2$—, —CH$_2$CH=CHCH=CH—, and —CH=CHCH$_2$CH=CH—;
—CH=CHCH=CHCH$_2$CH$_2$—, —CH=CHCH$_2$CH=CHCH$_2$—, —CH=CHCH$_2$CH$_2$CH=CH—, —CH$_2$CH=CHCH=CHCH$_2$—, —CH$_2$CH=CHCH$_2$CH=CH—, and —CH$_2$CH$_2$CH=CHCH=CH—;
—C(CH$_3$)=CHCH=CH—, —CH=C(CH$_3$)CH=CH—, —CH=CHC(CH$_3$)=CH—, and —CH=CHCH=C(CH$_3$)—;
—C≡C—;
—C≡CCH$_2$—, —CH$_2$C≡C—; —C≡CCH(CH$_3$)—, and —CH(CH$_3$)C≡C—;
—C≡CCH$_2$CH$_2$—, —CH$_2$C≡CCH$_2$—, and —CH$_2$CH$_2$C≡C—;
—C≡CCH(CH$_3$)CH$_2$— and —C≡CCH$_2$CH(CH$_3$);
—CH(CH$_3$)C≡CCH$_2$— and —CH$_2$C≡CCH(CH$_3$)—;
—CH(CH$_3$)CH$_2$C≡C— and —CH$_2$CH(CH$_3$)C≡C—;
—C≡CCH=CH—, —CH=CHC≡C—, —C≡CC≡C—;
—C≡CCH$_2$CH$_2$CH$_2$ and —CH$_2$CH$_2$CH$_2$C≡C—;
—C≡CCH$_2$CH$_2$CH$_2$CH$_2$— and —CH$_2$CH$_2$CH$_2$CH$_2$C≡C—;
—C≡CCH=CHCH=CH—, —CH=CHC≡CCH=CH—, and —CH=CHCH=CHC≡C—;
—C(CH$_3$)=CHC≡C—, —CH=C(CH$_3$)C≡C—, —C≡CC(CH$_3$)=CH—, and —C≡CCH=C(CH$_3$)—;
cyclopentylene and cyclopentenylene; and,
cyclohexylene, cyclohexenylene, and cyclohexadienylene.

In one preferred embodiment, Q$^2$ is selected from:
—CH$_2$—, —(CH$_2$)$_2$—, —(CH$_2$)$_3$—, —(CH$_2$)$_4$—, —(CH$_2$)$_5$—, and —(CH$_2$)$_6$—;
—CH$_2$CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—;
—CH=CHCH$_2$CH$_2$CH$_2$— and —CH$_2$CH$_2$CH$_2$CH=CH—;
—CH=CHCH$_2$CH$_2$CH$_2$CH$_2$— and —CH$_2$CH$_2$CH$_2$CH$_2$CH=CH—;

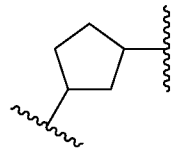

(cyclopent-1,3-ylene)  (4-cyclopenten-1,3-ylene)

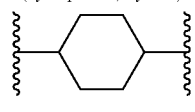

(cyclohex-1,4-ylene)  (2-cyclohexen-1,4-ylene)

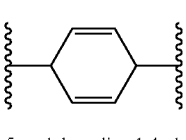

(2,5-cyclohexadien-1,4-ylene)  (cyclohex-1,4-ylene-methylene)

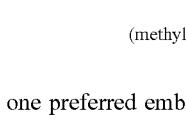

(methylene-cyclohex-1,4-ylene)

In one preferred embodiment, Q$^2$ is selected from:
—CH(CH$_3$)CH$_2$CH$_2$CH$_2$CH$_2$— and —CH$_2$CH$_2$CH$_2$CH$_2$CH(CH$_3$)—;
—CH$_2$CH$_2$CH$_2$CH=CH—; and,
—CH$_2$CH$_2$CH$_2$CH$_2$CH=CH—.

The Acid Leader Group, Q$^2$: Arylene

In one preferred embodiment, the acid leader group, Q$^2$, is C$_{5-20}$arylene, and is optionally substituted.

In one preferred embodiment, Q$^2$ is C$_{5-20}$arylene. In one preferred embodiment, Q$^2$ is C$_{5-6}$arylene. In one preferred embodiment, Q$^2$ is phenylene.

The Acid Leader Group, O$_2$:

Alkylene-Arylene and Arylene-Alkylene

In one preferred embodiment, the acid leader group, Q$^2$, is C$_{5-20}$arylene-C$_{1-7}$alkylene or C$_{1-7}$alkylene-C$_{5-20}$arylene, and is optionally substituted.

In one preferred embodiment, Q$^2$ is C$_{5-6}$arylene-C$_{1-7}$alkylene or C$_{1-7}$alkylene-C$_{5-6}$arylene, and is optionally substituted.

In one preferred embodiment, Q$^2$ is C$_{1-7}$alkylene-C$_{5-20}$arylene. In one preferred embodiment, Q$^2$ is C$_{1-7}$alkylene-C$_{5-6}$arylene.

In one preferred embodiment, Q$^2$ is C$_{5-20}$arylene-C$_{1-7}$alkylene. In one preferred embodiment, Q$^2$ is C$_{5-6}$arylene-C$_{1-7}$alkylene.

In one preferred embodiment, Q$^2$ is C$_{1-7}$alkylene-phenylene. In one preferred embodiment, Q$^2$ is methylene-phenylene, ethylene-phenylene, propylene-phenylene, and ethenylene-phenylene (also known as vinylene-phenylene).

In one preferred embodiment, Q$^2$ is phenylene-C$_{1-7}$alkylene. In one preferred embodiment, Q$^2$ is phenylene-methylene, phenylene-ethylene, phenylene-propylene, or phenylene-ethenylene (also known as phenylene-vinylene).

In the above alkylene-phenylene and phenylene-alkylene groups, the phenylene linkage may be ortho, meta, or para, and the phenylene group is optionally substituted with from 1 to 4 aryl substituents, $R^B$:

ortho    meta para

In one preferred embodiment, the phenylene linkage is meta or para. In one preferred embodiment, the phenylene linkage is para. In one preferred embodiment, the phenylene linkage is meta.

In one preferred embodiment, m is an integer from 0 to 4.
In one preferred embodiment, m is an integer from 0 to 3.
In one preferred embodiment, m is an integer from 0 to 2.
In one preferred embodiment, m is 0 or 1.
In one preferred embodiment, m is an integer from 1 to 4.
In one preferred embodiment, m is an integer from 1 to 3.
In one preferred embodiment, m is 1 or 2.
In one preferred embodiment, m is 4.
In one preferred embodiment, m is 3.
In one preferred embodiment, m is 2.
In one preferred embodiment, m is 1.
In one preferred embodiment, m is 0.

Each aryl substituent, $R^B$, is a substituent as defined herein.

Examples of preferred aryl substituents, $R^B$, include, but are not limited to, the following: fluoro, chloro, methyl, ethyl, isopropyl, t-butyl, trifluoromethyl, hydroxy, methoxy, ethoxy, isopropoxy, methylthio, amino, dimethylamino, diethylamino, morpholino, acetamido, nitro, and phenyl.

In one preferred embodiment, the phenylene linkage is meta, and $Q^2$ has the following formula, wherein $R^{Q2}$ is $C_{1-7}$alkylene and is optionally substitued (referred to herein as "phenylene-meta-$C_{1-7}$alkylene"):

In one preferred embodiment, $R^{Q2}$ is a saturated $C_{1-7}$alkylene group.

In one preferred embodiment, $R^{Q2}$ is a partially unsaturated $C_{1-7}$alkylene group.

In one preferred embodiment, $R^{Q2}$ is an aliphatic $C_{1-7}$alkylene group.

In one preferred embodiment, $R^{Q2}$ is a linear $C_{1-7}$alkylene group.

In one preferred embodiment, $R^{Q2}$ is a branched $C_{1-7}$alkylene group.

In one preferred embodiment, $R^{Q2}$ is an alicyclic $C_{1-7}$alkylene group.

In one preferred embodiment, $R^{Q2}$ is a saturated aliphatic $C_{1-7}$alkylene group.

In one preferred embodiment, $R^{Q2}$ is a saturated linear $C_{1-7}$alkylene group.

In one preferred embodiment, $R^{Q2}$ is a saturated branched $C_{1-7}$alkylene group.

In one preferred embodiment, $R^{Q2}$ is a saturated alicyclic $C_{1-7}$alkylene group.

In one preferred embodiment, $R^{Q2}$ is a partially unsaturated aliphatic $C_{1-7}$alkylene group.

In one preferred embodiment, $R^{Q2}$ is a partially unsaturated linear $C_{1-7}$alkylene group.

In one preferred embodiment, $R^{Q2}$ is a partially unsaturated branched $C_{1-7}$alkylene group.

In one preferred embodiment, $R^{Q2}$ is a partially unsaturated alicyclic $C_{1-7}$alkylene group.

In one preferred embodiment, $R^{Q2}$ is selected from:
—$(CH_2)_n$— where n is an integer from 1 to 7;
—$CH(CH_3)$—;
—$CH(CH_3)CH_2$— and —$CH_2CH(CH_3)$—;
—$CH(CH_3)CH_2CH_2$—, —$CH_2CH(CH_3)CH_2$—, and —$CH_2CH_2CH(CH_3)$—;
—$CH(CH_3)CH_2CH_2CH_2$—, —$CH_2CH(CH_3)CH_2CH_2$—, —$CH_2CH_2CH(CH_3)CH_2$—, and —$CH_2CH_2CH_2CH(CH_3)$—;
—$CH(CH_3)CH_2CH_2CH_2CH_2$—, —$CH_2CH(CH_3)CH_2CH_2CH_2$, —$CH_2CH_2CH(CH_3)CH_2CH_2$—, —$CH_2CH_2CH_2CH(CH_3)CH_2$—, and —$CH_2CH_2CH_2CH_2CH(CH_3)$—;
—$CH(CH_2CH_3)$—;
—$CH(CH_2CH_3)CH_2$— and —$CH_2CH(CH_2CH_3)$—;
—$CH(CH_2CH_3)CH_2CH_2$—, —$CH_2CH(CH_2CH_3)CH_2$—, and —$CH_2CH_2CH(CH_2CH_3)$—;
—$CH(CH_2CH_3)CH_2CH_2CH_2$, —$CH_2CH(CH_2CH_3)CH_2CH_2$—, —$CH_2CH_2CH(CH_2CH_3)CH_2$—, and —$CH_2CH_2CH_2CH(CH_2CH_3)$—;
—$CH(CH_2CH_3)CH_2CH_2CH_2CH_2$—, —$CH_2CH(CH_2CH_3)CH_2CH_2CH_2$—, —$CH_2CH_2CH(CH_2CH_3)CH_2CH_2$—, —$CH_2CH_2CH_2CH(CH_2CH_3)CH_2$—, and —$CH_2CH_2CH_2CH_2CH(CH_2CH_3)$—;
—$CH=CH$—;
—$CH=CHCH_2$— and —$CH_2CH=CH$—;
—$CH=CHCH_2CH_2$—, —$CH_2CH=CHCH_2$—, and —$CH_2CH_2CH=CH$—;
—$CH=CHCH_2CH_2CH_2$—, —$CH_2CH=CHCH_2CH_2$—, —$CH_2CH_2CH=CHCH_2$—, and —$CH_2CH_2CH_2CH=CH$—;
—$CH=CHCH_2CH_2CH_2CH_2$—, —$CH_2CH=CHCH_2CH_2CH_2$—, —$CH_2CH_2CH=CHCH_2CH_2$—, —$CH_2CH_2CH_2CH=CHCH_2$—, and —$CH_2CH_2CH_2CH_2CH=CH$—;
—$C(CH_3)=CH$— and —$CH=C(CH_3)$—;
—$C(CH_3)=CHCH_2$—, —$CH=C(CH_3)CH_2$—, and —$CH=CHCH(CH_3)$—;
—$CH(CH_3)CH=CH$—, —$CH_2C(CH_3)=CH$—, and —$CH_2CH=C(CH_3)$—;
—$CH=CHCH=CH$—;
—$CH=CHCH=CHCH_2$—, —$CH_2CH=CHCH=CH$—, and —$CH=CHCH_2CH=CH$—;

—CH=CHCH=CHCH$_2$CH$_2$—,
—CH=CHCH$_2$CH=CHCH$_2$—, and
—CH=CHCH$_2$CH$_2$CH=CH—,
—CH$_2$CH=CHCH=CHCH$_2$—,
—CH$_2$CH=CHCH$_2$CH=CH—, and
—CH$_2$CH$_2$CH=CHCH=CH—;
—C(CH$_3$)=CHCH=CH—, —CH=C(CH$_3$)CH=CH—, —CH=CHC(CH$_3$)=CH—, and —CH=CHCH=C(CH$_3$)—;
—C≡C—;
—C≡CCH$_2$—, —CH$_2$C≡C—; —C≡CCH(CH$_3$)—, and —CH(CH$_3$)C≡C—;
—C≡CCH$_2$CH$_2$—, —CH$_2$C≡CCH$_2$—, and —CH$_2$CH$_2$C≡C—;
—C≡CCH(CH$_3$)CH$_2$— and —C≡CCH$_2$CH(CH$_3$);
—CH(CH$_3$)C≡CCH$_2$— and —CH$_2$C≡CCH(CH$_3$)—;
—CH(CH$_3$)CH$_2$C≡C— and —CH$_2$CH(CH$_3$)C≡C—;
—C≡CCH=CH—, —CH=CHC≡C—, and —C≡CC≡C—;
—C≡CCH$_2$CH$_2$CH$_2$— and —CH$_2$CH$_2$CH$_2$C≡C—;
—C≡CCH$_2$CH$_2$CH$_2$CH$_2$— and —CH$_2$CH$_2$CH$_2$CH$_2$C≡C—;
—C≡CCH=CHCH=CH—, —CH=CHC≡CCH=CH—, and —CH=CHCH=CHC≡C—;
—C(CH$_3$)=CHC≡C—, —CH=C(CH$_3$)C≡C—, —C≡CC(CH$_3$)=CH—, and —C≡CCH=C(CH$_3$)—;
cyclopentylene and cyclopentenylene; and,
cyclohexylene, cyclohexenylene, and cyclohexadienylene.

In one preferred embodiment, $R^{Q2}$ is selected from:
—CH$_2$, —(CH$_2$)$_2$—, —(CH$_2$)$_3$—, —(CH$_2$)$_4$—, —(CH$_2$)$_5$—, and —(CH$_2$)$_6$;
—CH=CH—, —CH=CH—CH=CH—;

In one preferred embodiment, $R^{Q2}$ is cis or trans —CH=CH—.
In one preferred embodiment, $R^{Q2}$ is cis —CH=CH—.
In one preferred embodiment, $R^{Q2}$ is trans —CH=CH—.
In one preferred embodiment, $R^{Q2}$ is —CH=CH—, and $Q^2$ is (referred to herein as "phenylene-meta-trans-ethylene"):

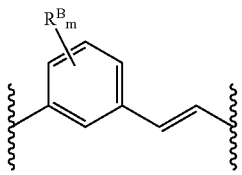

In one preferred embodiment, m is 0, and $Q^2$ is (referred to herein as "unsubstituted phenylene-meta-trans-ethylene"):

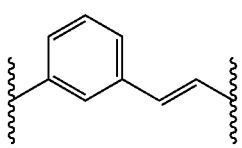

The Acid Leader Group, $Q^2$: Ether

In one embodiment, $Q^2$ is an ether linkage, —R$^2$—X—R$^3$—, wherein X is an ether heteroatom, and is —O— or —S— and each of R$^2$ and R$^3$ is independently an ether group.

Each of the ether groups, R$^2$ and R$^3$, is independently a C$_{1-7}$alkylene group, and is optionally substituted.

In one embodiment, each of R$^2$ and R$^3$ is unsubstituted. In one embodiment, each of R$^2$ and R$^3$ is optionally substituted. In one embodiment, each of R$^2$ and R$^3$ is substituted.

In one preferred embodiment, R$^2$ and/or R$^3$ is a saturated C$_{1-7}$alkylene group.
In one preferred embodiment, R$^2$ and/or R$^3$ is a partially unsaturated C$_{1-7}$alkylene group.
In one preferred embodiment, R$^2$ and/or R$^3$ is an aliphatic C$_{1-7}$alkylene group.
In one preferred embodiment, R$^2$ and/or R$^3$ is a linear C$_{1-7}$alkylene group.
In one preferred embodiment, R$^2$ and/or R$^3$ is a branched C$_{1-7}$alkylene group.
In one preferred embodiment, R$^2$ and/or R$^3$ is an alicyclic C$_{1-7}$alkylene group.
In one preferred embodiment, R$^2$ and/or R$^3$ is a saturated aliphatic C$_{1-7}$alkylene group.
In one preferred embodiment, R$^2$ and/or R$^3$ is a saturated linear C$_{1-7}$alkylene group.
In one preferred embodiment, R$^2$ and/or R$^3$ is a saturated branched C$_{1-7}$alkylene group.
In one preferred embodiment, R$^2$ and/or R$^3$ is a saturated alicyclic C$_{1-7}$alkylene group.
In one preferred embodiment, R$^2$ and/or R$^3$ is a partially unsaturated aliphatic C$_{1-7}$alkylene group.
In one preferred embodiment, R$^2$ and/or R$^3$ is a partially unsaturated linear C$_{1-7}$alkylene group.
In one preferred embodiment, R$^2$ and/or R$^3$ is a partially unsaturated branched C$_{1-7}$alkylene group.
In one preferred embodiment, R$^2$ and/or R$^3$ is a partially unsaturated alicyclic C$_{1-7}$alkylene group.

In one preferred embodiment, R$^2$ and/or R$^3$ is selected from:
—(CH$_2$)$_n$— where n is an integer from 1 to 7;
—CH(CH$_3$)—;
—CH(CH$_3$)CH$_2$— and —CH$_2$CH(CH$_3$)—;
—CH(CH$_3$)CH$_2$CH$_2$—, —CH$_2$CH(CH$_3$)CH$_2$—, and —CH$_2$CH$_2$CH(CH$_3$)—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, and —CH$_2$CH$_2$CH$_2$CH$_2$CH(CH$_3$)—;
—CH(CH$_2$CH$_3$)—;
—CH(CH$_2$CH$_3$)CH$_2$— and —CH$_2$CH(CH$_2$CH$_3$)—;
—CH(CH$_2$CH$_3$)CH$_2$CH$_2$—, —CH$_2$CH(CH$_2$CH$_3$)CH$_2$—, and —CH$_2$CH$_2$CH(CH$_2$CH$_3$)—;
—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, and —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, and —CH$_2$CH$_2$CH$_2$CH$_2$CH(CH$_2$CH$_3$)—;
—CH=CH—;
—CH=CHCH$_2$— and —CH$_2$CH=CH—;
—CH=CHCH$_2$CH$_2$—, —CH$_2$CH=CHCH$_2$—, and —CH$_2$CH$_2$CH=CH—;

—CH═CHCH₂CH₂CH₂—, —CH₂CH═CHCH₂CH₂—,
—CH₂CH₂CH═CHCH₂—, and
—CH₂CH₂CH₂CH═CH—;

—CH═CHCH₂CH₂CH₂CH₂—,
—CH₂CH═CHCH₂CH₂CH₂—,
—CH₂CH₂CH═CHCH₂CH₂—,
—CH₂CH₂CH₂CH═CHCH₂—, and
—CH₂CH₂CH₂CH₂CH═CH—;

—C(CH₃)═CH— and —CH═C(CH₃)—;

—C(CH₃)═CHCH₂—, —CH═C(CH₃)CH₂—, and
—CH═CHCH(CH₃)—;

—CH(CH₃)CH═CH—, —CH₂C(CH₃)═CH—, and
—CH₂CH═C(CH₃)—;

—CH═CHCH═CH—;

—CH═CHCH═CHCH₂—,
—CH₂CH═CHCH═CH—, and
—CH═CHCH₂CH═CH—;

—CH═CHCH═CHCH₂CH₂—,
—CH═CHCH₂CH═CHCH₂—, and
—CH═CHCH₂CH₂CH═CH—,
—CH₂CH═CHCH═CHCH₂—,
—CH₂CH═CHCH₂CH═CH—, and
—CH₂CH₂CH═CHCH═CH—;

—C(CH₃)═CHCH═CH—, —CH═C(CH₃)CH═CH—, —CH═CHC(CH₃)═CH—, and —CH═CHCH═C(CH₃)—;

—C≡C—;

—C≡CCH₂—, —CH₂C≡C—; —C≡CCH(CH₃), and —CH(CH₃)C≡C—;

—C≡CCH₂CH₂—, —CH₂C≡CCH₂—, and —CH₂CH₂C≡C—;

—C≡CCH(CH₃)CH₂— and —C≡CCH₂CH(CH₃)—;

—CH(CH₃)C≡CCH₂— and —CH₂C≡CCH(CH₃)—;

—CH(CH₃)CH₂C≡C— and —CH₂CH(CH₃)C≡C—;

—C≡CCH═CH—, —CH═CHC≡C—, and —C≡CC≡C—;

—C≡CCH₂CH₂CH₂ and —CH₂CH₂CH₂C≡C—;

—C≡CCH₂CH₂CH₂CH₂— and —CH₂CH₂CH₂CH₂C≡C—;

—C≡CCH═CHCH═CH—, —CH═CHC≡C—CH═CH—, and —CH═CHCH═CHC≡C—;

—C(CH₃)═CHC≡C—, —CH═C(CH₃)C≡C—, —C≡CC(CH₃)═CH—, and —C≡CCH═C(CH₃)—;

cyclopentylene and cyclopentenylene; and, cyclohexylene, cyclohexenylene, and cyclohexadienylene.

In one preferred embodiment, R² and/or R³ is selected from:

—CH₂—, —(CH₂)₂—, —(CH₂)₃—, —(CH₂)₄—, —(CH₂)₅—, and —(CH₂)₆—;

—CH(CH₃)CH₂CH₂CH₂CH₂—, —CH₂CH(CH₃)CH₂CH₂CH₂—, —CH₂CH₂CH(CH₃)CH₂CH₂—, and —CH₂CH₂CH₂CH₂CH(CH₃)—;

—CH═CHCH₂CH₂CH₂— and
—CH₂CH₂CH₂CH═CH—;

—CH═CHCH₂CH₂CH₂CH₂— and
—CH₂CH₂CH₂CH₂CH═CH—;

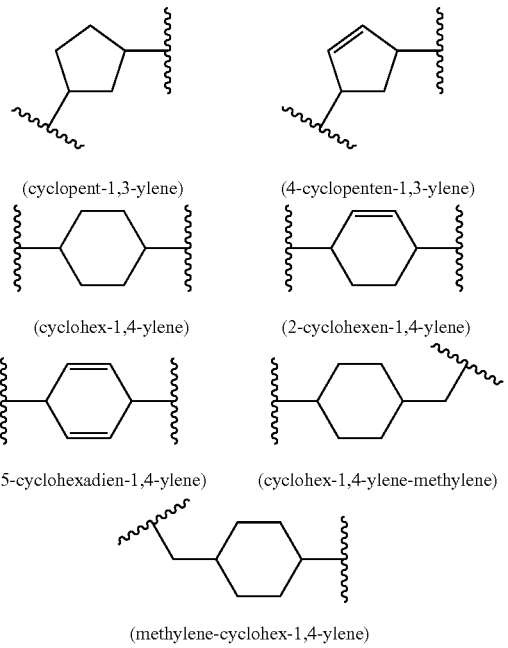

(cyclopent-1,3-ylene) (4-cyclopenten-1,3-ylene)

(cyclohex-1,4-ylene) (2-cyclohexen-1,4-ylene)

(2,5-cyclohexadien-1,4-ylene) (cyclohex-1,4-ylene-methylene)

(methylene-cyclohex-1,4-ylene)

In one preferred embodiment, each of R² and R³ is a saturated $C_{1-7}$alkylene group.

In one preferred embodiment, each of R² and R³ is selected from —(CH₂)ₙ—, wherein n is an integer from 1 to 5.

In one preferred embodiment, the group R²—X—R³ is selected from the following:
—CH₂—O—CH₂— and —CH₂—S—CH₂—;
—CH₂—O—CH₂CH₂— and —CH₂—S—CH₂CH₂—;
—CH₂CH₂—O—CH₂— and —CH₂CH₂—S—CH₂—;
—CH₂—O—CH₂CH₂CH₂— and —CH₂—S—CH₂CH₂CH₂—;
—CH₂CH₂—O—CH₂CH₂— and —CH₂CH₂—S—CH₂CH₂—;
—CH₂CH₂CH₂—O—CH₂— and —CH₂CH₂CH₂—S—CH₂—;
—CH₂—O—CH₂CH₂CH₂CH₂— and —CH₂—S—CH₂CH₂CH₂CH₂—;
—CH₂CH₂—O—CH₂CH₂CH₂— and —CH₂CH₂—S—CH₂CH₂CH₂—;
—CH₂CH₂CH₂—O—CH₂CH₂— and —CH₂CH₂CH₂—S—CH₂CH₂—;
—CH₂CH₂CH₂CH₂—O—CH₂— and —CH₂CH₂CH₂CH₂—S—CH₂—;
—CH₂—O—CH₂CH₂CH₂CH₂CH₂— and —CH₂—S—CH₂CH₂CH₂CH₂CH₂—;
—CH₂CH₂—O—CH₂CH₂CH₂CH₂— and —CH₂CH₂—S—CH₂CH₂CH₂CH₂—;
—CH₂CH₂CH₂—O—CH₂CH₂CH₂— and —CH₂CH₂CH₂—S—CH₂CH₂CH₂—;
—CH₂CH₂CH₂CH₂—O—CH₂CH₂— and —CH₂CH₂CH₂CH₂—S—CH₂CH₂—;
—CH₂CH₂CH₂CH₂CH₂—O—CH₂— and —CH₂CH₂CH₂CH₂CH₂—S—CH₂—;

In one preferred embodiment, the group R²—X—R³ is selected from the following:
—CH₂—O—CH₂— and —CH₂—S—CH₂—.

In one preferred embodiment, the group R²—X—R³ is selected from the following:

—CH$_2$—O—CH$_2$CH$_2$— and —CH$_2$—S—CH$_2$CH$_2$—;
—CH$_2$CH$_2$—O—CH$_2$— and —CH$_2$CH$_2$—S—CH$_2$—.

In one preferred embodiment, the group R$^2$—X—R$^3$ is selected from the following:
—CH$_2$—O—CH$_2$CH$_2$CH$_2$— and —CH$_2$—S—CH$_2$CH$_2$CH$_2$—;
—CH$_2$CH$_2$—O—CH$_2$CH$_2$— and —CH$_2$CH$_2$—S—CH$_2$CH$_2$—;
—CH$_2$CH$_2$CH$_2$—O—CH$_2$— and —CH$_2$CH$_2$CH$_2$—S—CH$_2$—.

In one preferred embodiment, the group R$^2$—X—R$^3$ is selected from the following:
—CH$_2$—O—CH$_2$CH$_2$CH$_2$CH$_2$— and —CH$_2$—S—CH$_2$CH$_2$CH$_2$CH$_2$—;
—CH$_2$CH$_2$—O—CH$_2$CH$_2$CH$_2$— and —CH$_2$CH$_2$—S—CH$_2$CH$_2$CH$_2$—;
—CH$_2$CH$_2$CH$_2$—O—CH$_2$CH$_2$— and —CH$_2$CH$_2$CH$_2$—S—CH$_2$CH$_2$—;
—CH$_2$CH$_2$CH$_2$CH$_2$—O—CH$_2$— and —CH$_2$CH$_2$CH$_2$CH$_2$—S—CH$_2$—.

In one preferred embodiment, the group R$^2$—X—R$^3$ is selected from the following:
—CH$_2$—O—CH$_2$CH$_2$CH$_2$CH$_2$CH$_2$— and —CH$_2$—S—CH$_2$CH$_2$CH$_2$CH$_2$CH$_2$—;
—CH$_2$CH$_2$—O—CH$_2$CH$_2$CH$_2$CH$_2$— and —CH$_2$CH$_2$—S—CH$_2$CH$_2$CH$_2$CH$_2$—;
—CH$_2$CH$_2$CH$_2$—O—CH$_2$CH$_2$CH$_2$— and —CH$_2$CH$_2$CH$_2$—S—CH$_2$CH$_2$CH$_2$—;
—CH$_2$CH$_2$CH$_2$CH$_2$—O—CH$_2$CH$_2$— and —CH$_2$CH$_2$CH$_2$CH$_2$—S—CH$_2$CH$_2$—;
—CH$_2$CH$_2$CH$_2$CH$_2$CH$_2$—O—CH$_2$ and —CH$_2$CH$_2$CH$_2$CH$_2$CH$_2$—S—CH$_2$—.

Certain Embodiments

In one preferred embodiment, Q$^1$ is a covalent bond or an aryl leader group, J is —NR$^1$SO$_2$—, Q$^2$ is meta-phenylene-C$_{1-7}$alkylene, and the compounds have the following formula:

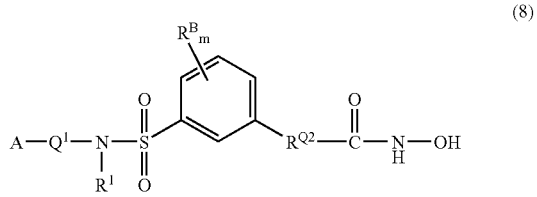
(8)

In one preferred embodiment, Q$^1$ is a covalent bond, J is —NR$^1$SO$_2$—, Q$^2$ is meta-phenylene-C$_{1-7}$alkylene, and the compounds have the following formula:

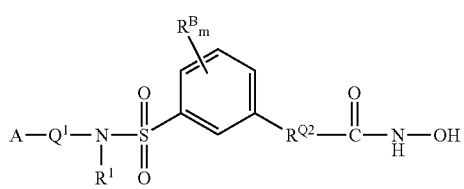
(9)

In one preferred embodiment, Q$^1$ is an aryl leader group, J is —NR$^1$SO$_2$—, Q$^2$ is meta-phenylene-C$_{1-7}$alkylene, and the compounds have the following formula:

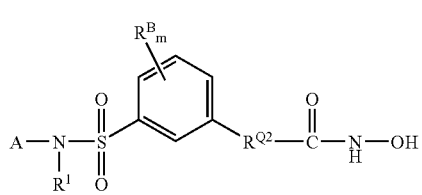
(8)

In one preferred embodiment, the aryl leader group, Q$^1$, has a backbone of at least 2 carbon atoms.

In one preferred embodiment, the aryl leader group, Q$^1$, has a backbone of at least 3 carbon atoms.

In one preferred embodiment, the aryl leader group, Q$^1$, has a backbone of at least 4 carbon atoms.

In one preferred embodiment, the aryl leader group, Q$^1$, has a backbone of at least 5 carbon atoms.

In one preferred embodiment, Q$^1$ is —CH$_2$CH$_2$—, J is —NR$^1$SO$_2$—, Q$^2$ is meta-phenylene-C$_{1-7}$alkylene, and the compounds have the following formula:

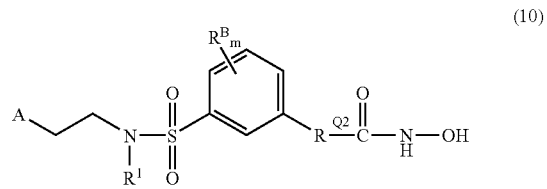
(10)

In one preferred embodiment, Q$^1$ is a covalent bond or an aryl leader group, J is —NR$^1$SO$_2$—, Q$^2$ is phenylene-meta-trans-ethylene, and the compounds have the following formula:

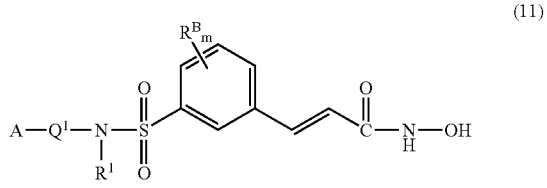
(11)

In one preferred embodiment, Q$^1$ is a covalent bond, J is —NR$^1$SO$_2$—, Q$^2$ is phenylene-meta-trans-ethylene, and the compounds have the following formula:

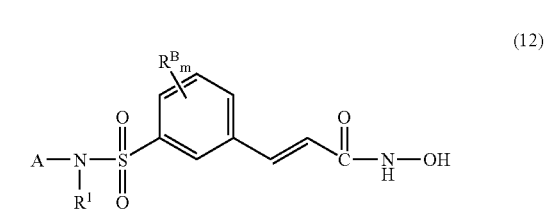
(12)

In one preferred embodiment, Q$^1$ is an aryl leader group, J is —NR$^1$SO$_2$—, Q$^2$ is phenylene-meta-trans-ethylene, and the compounds have the following formula:

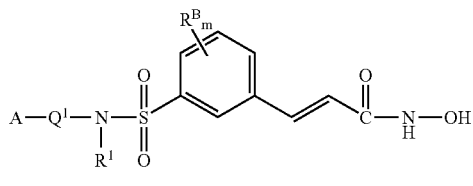

(11)

In one preferred embodiment, the aryl leader group, $Q^1$, has a backbone of at least 2 carbon atoms.

In one preferred embodiment, the aryl leader group, $Q^1$, has a backbone of at least 3 carbon atoms.

In one preferred embodiment, the aryl leader group, $Q^1$, has a backbone of at least 4 carbon atoms.

In one preferred embodiment, the aryl leader group, $Q^1$, has a backbone of at least 5 carbon atoms.

In one preferred embodiment, $Q^1$ is —CH$_2$CH$_2$—, J is —NR$^1$SO$_2$—, $Q^2$ is phenylene-meta-trans-ethylene, and the compounds have the following formula:

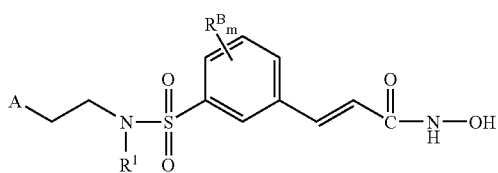

(13)

In one preferred embodiment, A is an optionally substituted phenyl group, $Q^1$ is a covalent bond or an aryl leader group, J is —NR$^1$SO$_2$—, $Q^2$ is phenylene-meta-trans-ethylene, and the compounds have the following formula:

(14)

In one preferred embodiment, A is an optionally substituted phenyl group, $Q^1$ is a covalent bond, J is —NR$^1$SO$_2$—, $Q^2$ is phenylene-meta-trans-ethylene, and the compounds have the following formula:

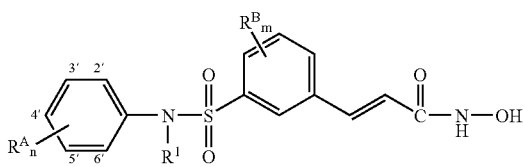

(15)

In one preferred embodiment, A is an optionally substituted phenyl group, $Q^1$ is an aryl leader group, J is —NR$^1$SO$_2$—, $Q^2$ is phenylene-meta-trans-ethylene, and the compounds have the following formula:

(14)

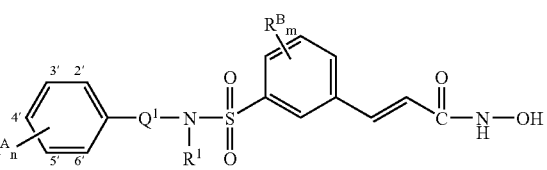

In one preferred embodiment, the aryl leader group, $Q^1$, has a backbone of at least 2 carbon atoms.

In one preferred embodiment, the aryl leader group, $Q^1$, has a backbone of at least 3 carbon atoms.

In one preferred embodiment, the aryl leader group, $Q^1$, has a backbone of at least 4 carbon atoms.

In one preferred embodiment, the aryl leader group, $Q^1$, has a backbone of at least 5 carbon atoms.

In one preferred embodiment, A is an optionally substituted phenyl group, $Q^1$ is —CH$_2$CH$_2$—, J is —NR$^1$SO$_2$—, $Q^2$ is phenylene-meta-trans-ethylene, and the compounds have the following formula:

(16)

Examples of Specific Embodiments

Examples of compounds with J as —SO$_2$NR$^1$— and no $Q^1$ group (i.e., where $Q^1$ is a covalent bond) are shown below, for comparison purposes.

-continued
| | | |
|---|---|---|
| 2 | 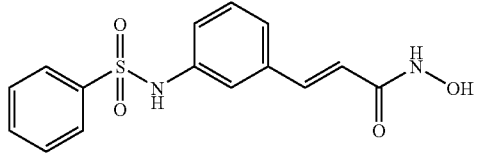 | PX089344 |
| 3 | 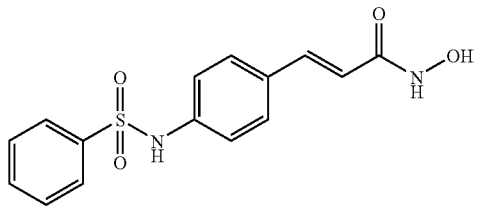 | PX106499 |
| 4 | 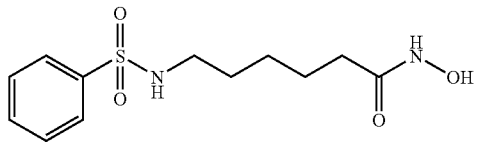 | PX106522 |
| 5 | 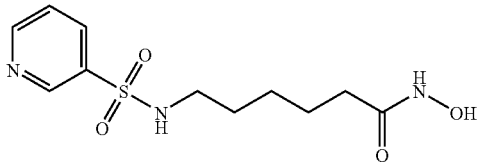 | PX117432 |
| 6 | 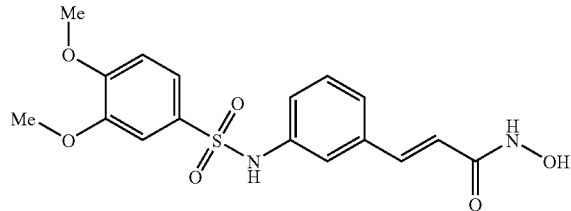 | PX117780 |
| 7 | 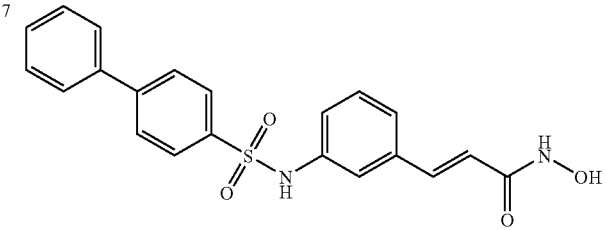 | PX117781 |
| 8 | 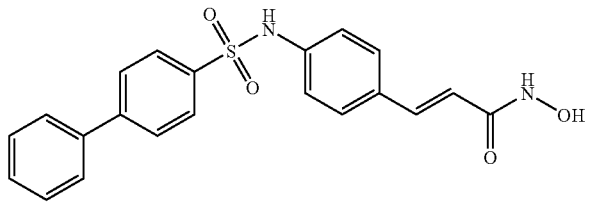 | PX117793 |

-continued
9 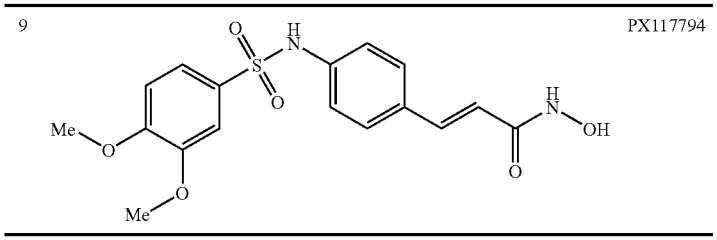 PX117794
Some individual embodiments of the present invention include the following compounds.
10  PX089343
11 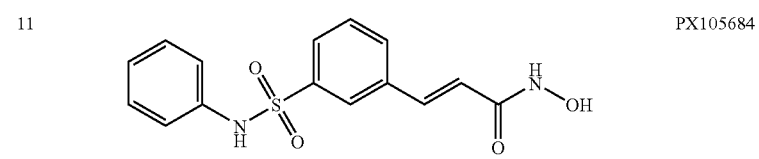 PX105684
12 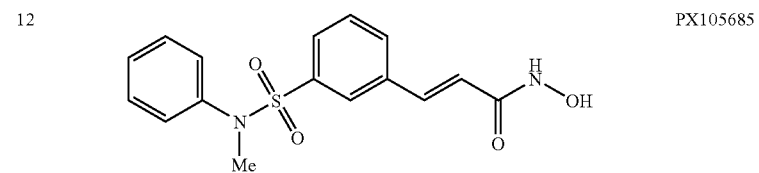 PX105685
13 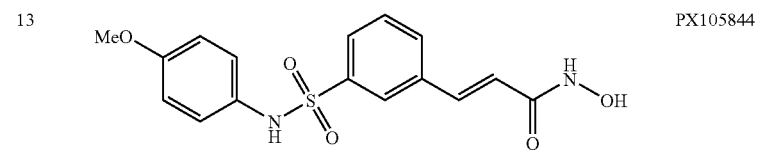 PX105844
14 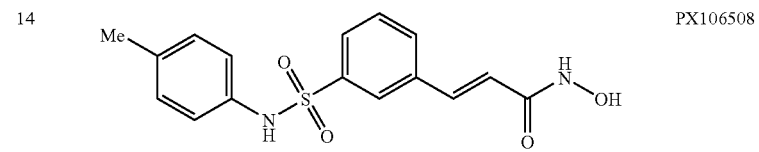 PX106508
15 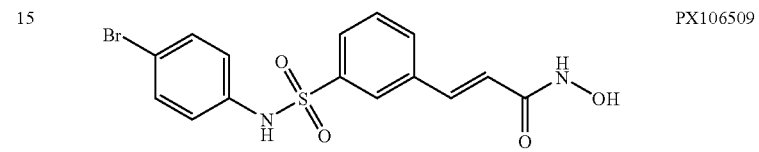 PX106509
16 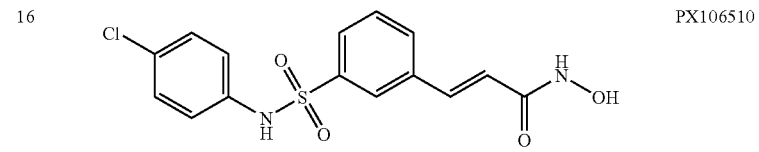 PX106510

-continued
| | | |
|---|---|---|
| 17 | 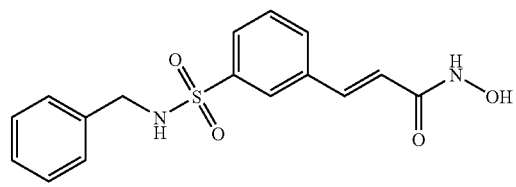 | PX106511 |
| 18 | 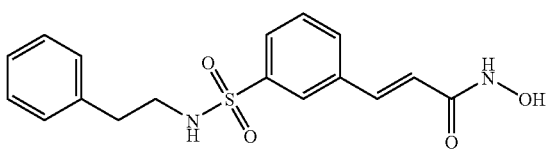 | PX106512 |
| 19 | 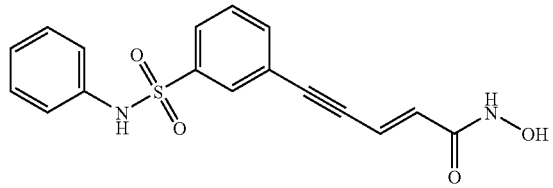 | PX116238 |
| 20 | 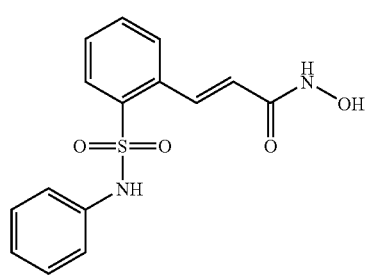 | PX116242 |
| 21 | 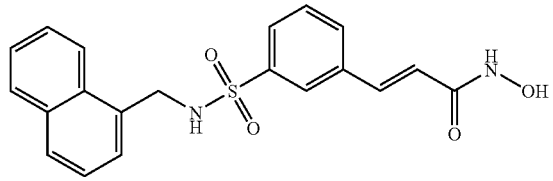 | PX117225 |
| 22 | 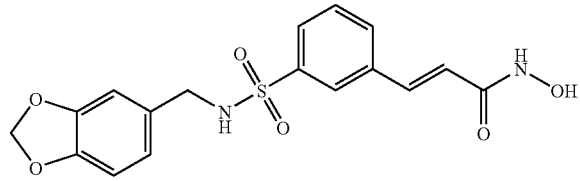 | PX117226 |
| 23 | 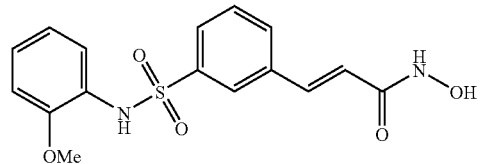 | PX117227 |
| 24 | 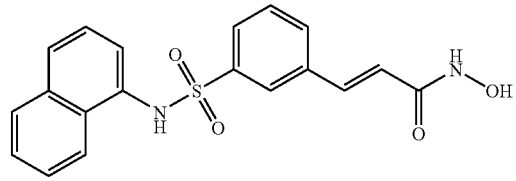 | PX117228 |

| | | |
|---|---|---|
| 25 | 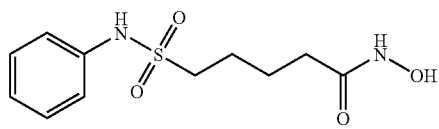 | PX117233 |
| 26 | 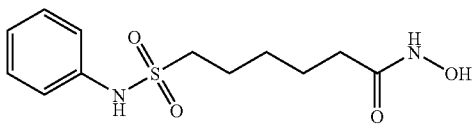 | PX117234 |
| 27 | 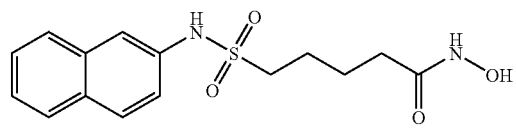 | PX117235 |
| 28 | 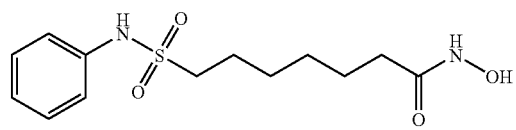 | PX117236 |
| 29 | 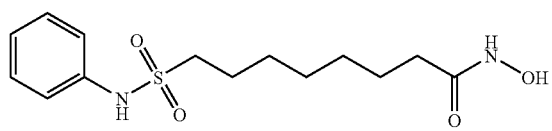 | PX117245 |
| 30 | 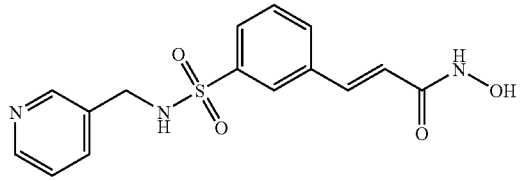 | PX117250 |
| 31 | 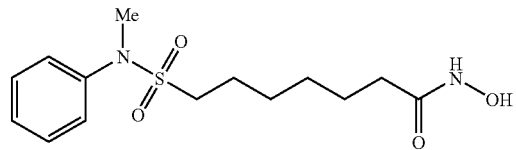 | PX117260 |
| 32 | 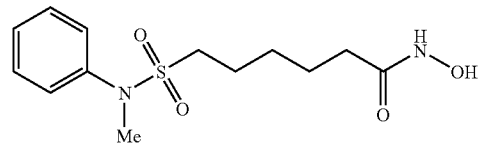 | PX117410 |
| 33 | 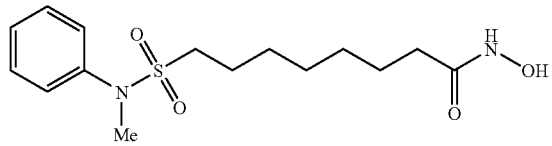 | PX117411 |
| 34 | 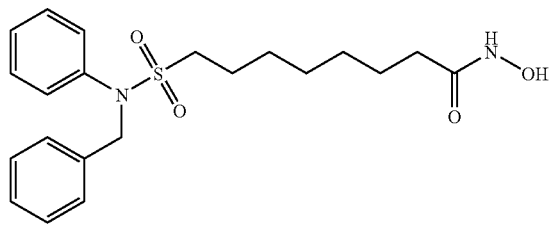 | PX117412 |

| | | |
|---|---|---|
| 35 | 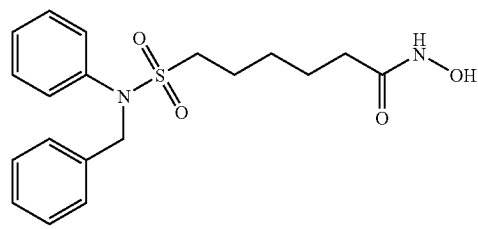 | PX117414 |
| 36 | 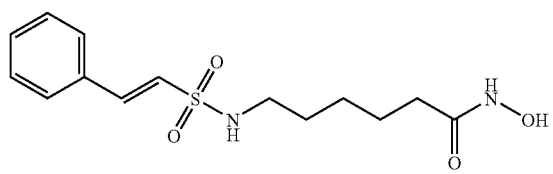 | PX117429 |
| 37 | 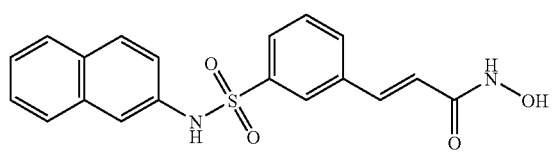 | PX117445 |
| 38 | 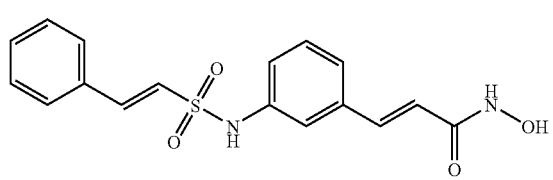 | PX117446 |
| 39 | 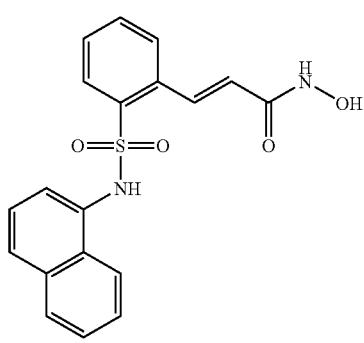 | PX117447 |
| 40 | 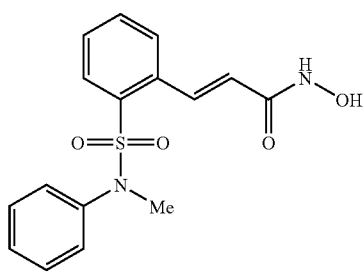 | PX117446 |

-continued
| | | |
|---|---|---|
| 41 | 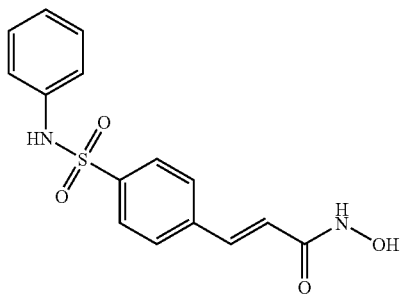 | PX117450 |
| 42 | 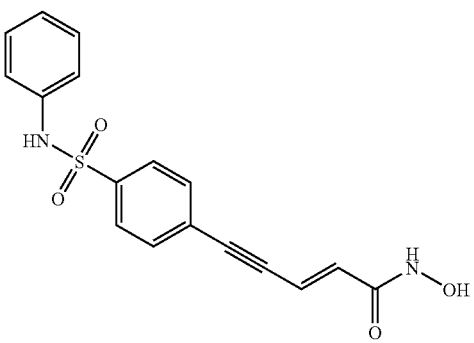 | PX117453 |
| 43 | 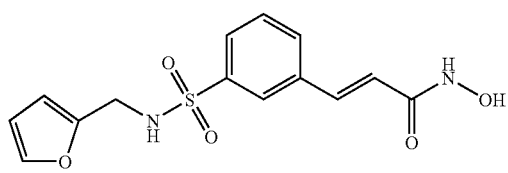 | PX117710 |
| 44 | 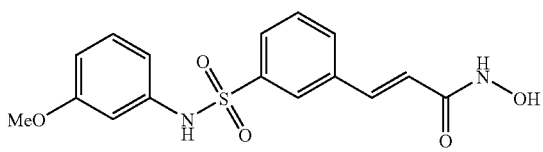 | PX117712 |
| 45 | 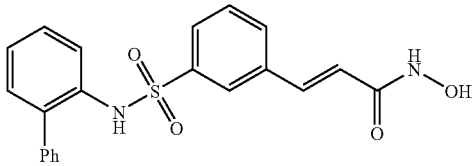 | PX117713 |
| 46 | 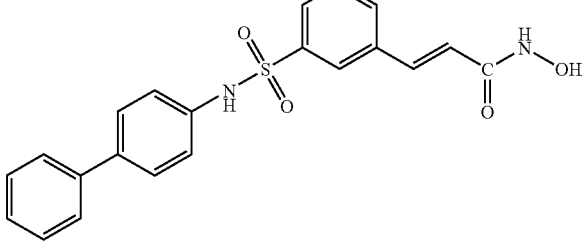 | PX117715 |
| 47 | 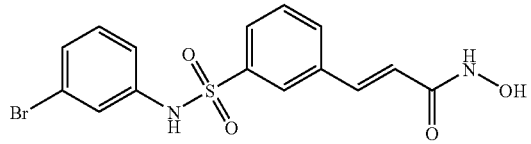 | PX117734 |

-continued
| | | |
|---|---|---|
| 48 | 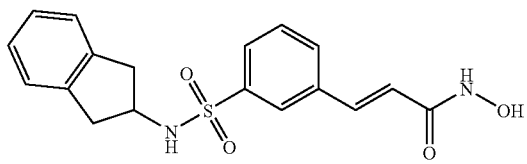 | PX117735 |
| 49 | 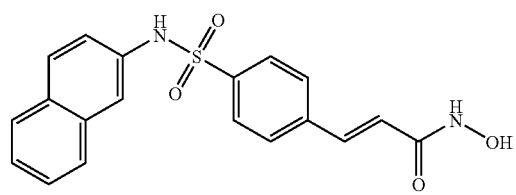 | PX117736 |
| 50 | 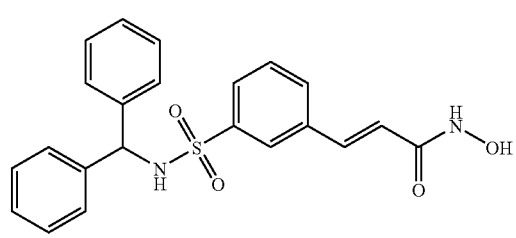 | PX117773 |
| 51 | 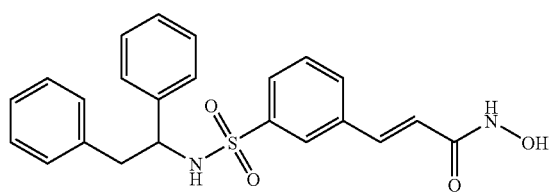 | PX117774 |
| 52 | 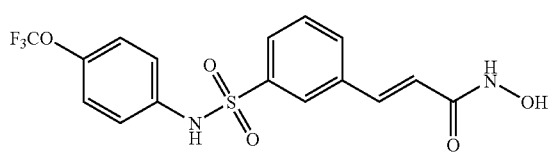 | PX117775 |
| 53 | 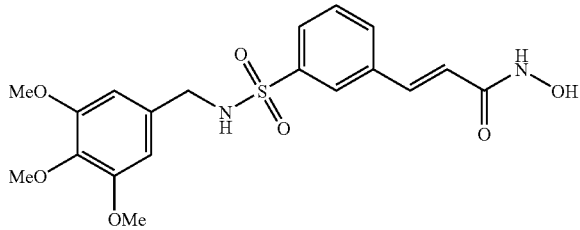 | PX117778 |
| 54 | 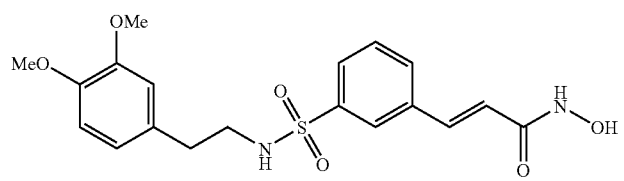 | PX117779 |
| 55 | 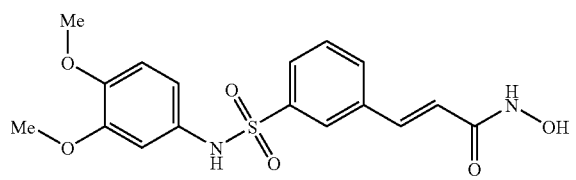 | PX117782 |

-continued
| | | |
|---|---|---|
| 56 | 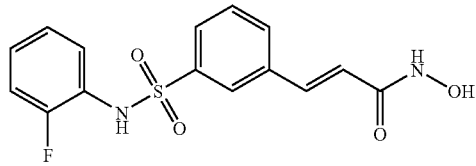 | PX117787 |
| 57 | 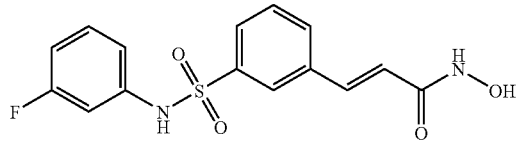 | PX117788 |
| 58 | 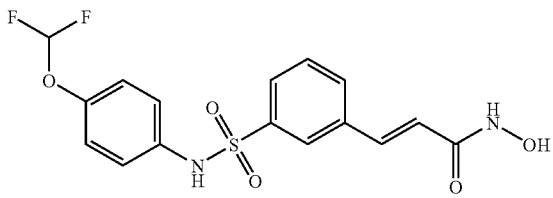 | PX117789 |
| 59 | 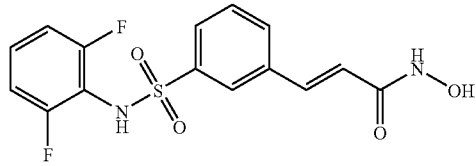 | PX117790 |
| 60 | 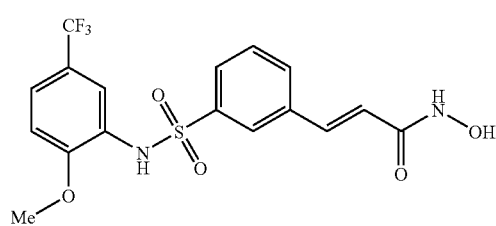 | PX117791 |
| 61 | 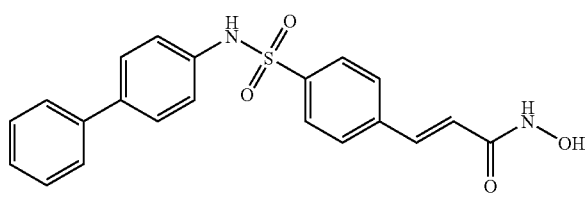 | PX117792 |
| 62 | 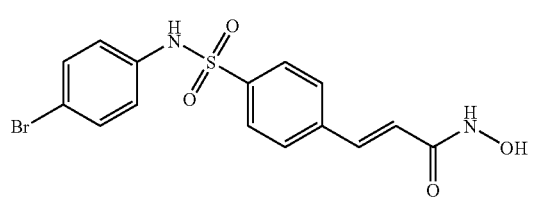 | PX117795 |
| 63 | 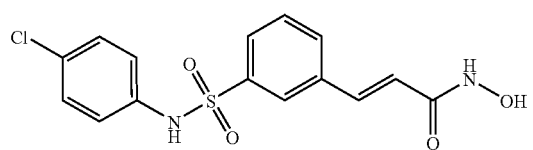 | PX117796 |

-continued
64 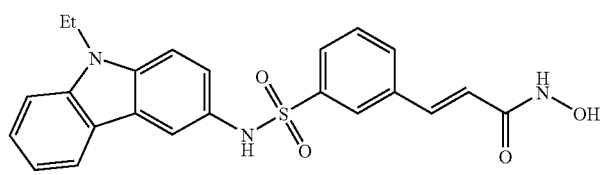
65 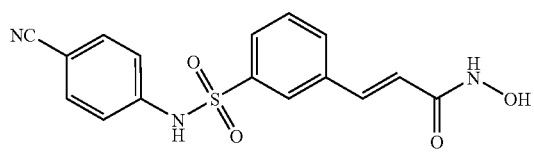
66 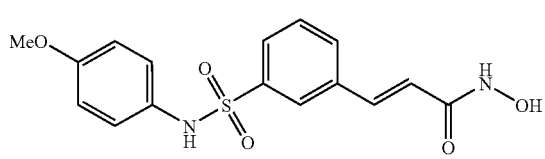
67 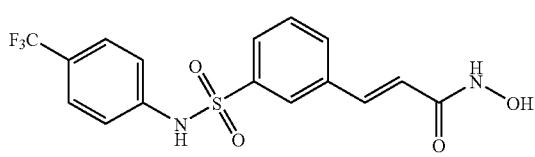
68 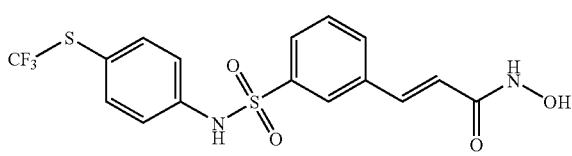
69 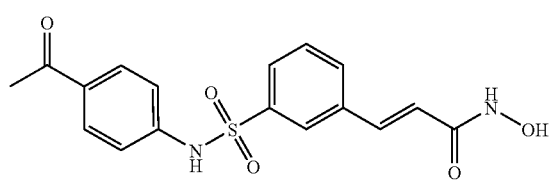
70 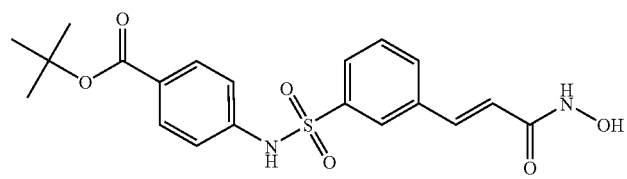
71 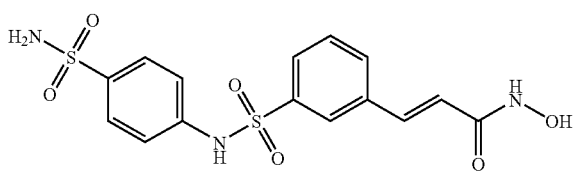
72 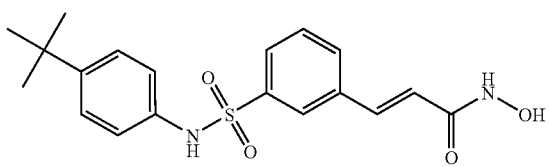

-continued
73 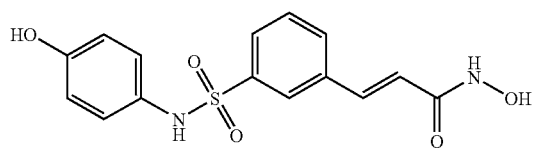
74 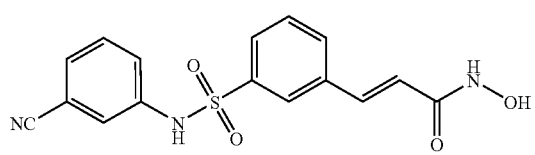
75 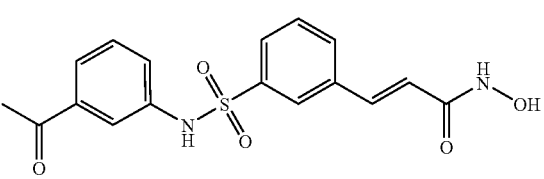
76 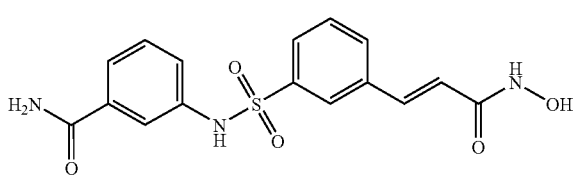
77 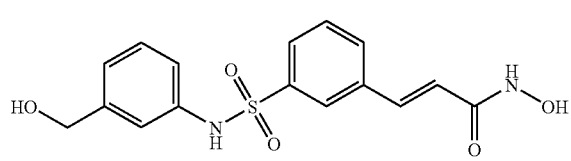
78 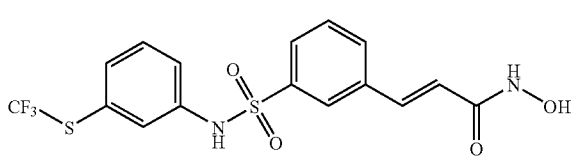
79 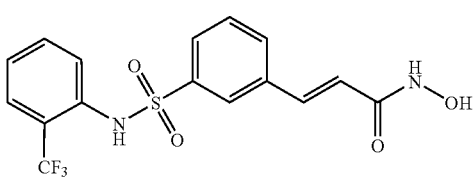
80 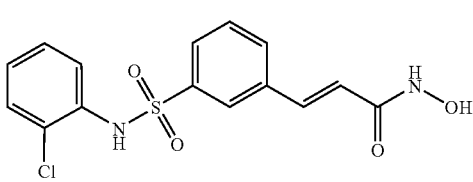
81 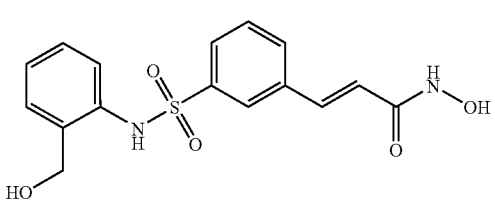

-continued
| | |
|---|---|
| 82 | 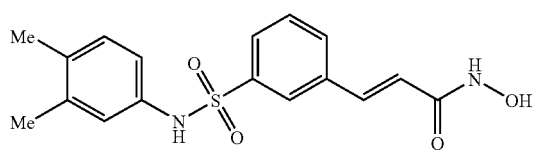 |
| 83 | 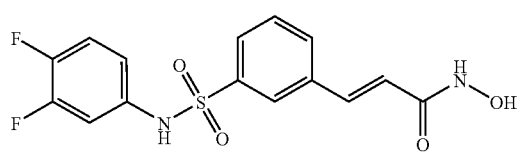 |
| 84 | 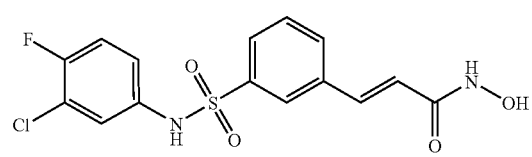 |
| 85 | 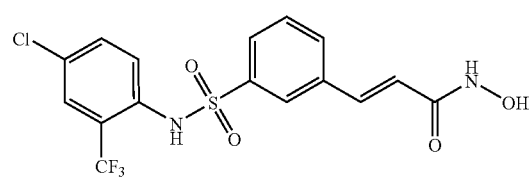 |
| 86 | 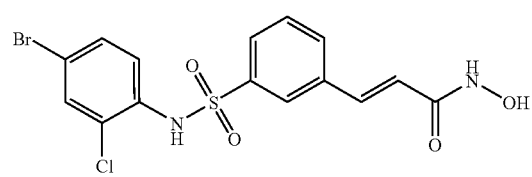 |
| 87 | 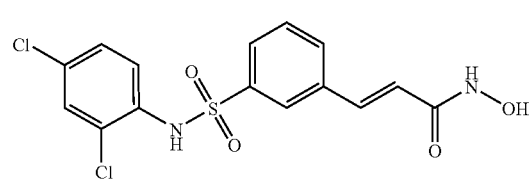 |
| 88 | 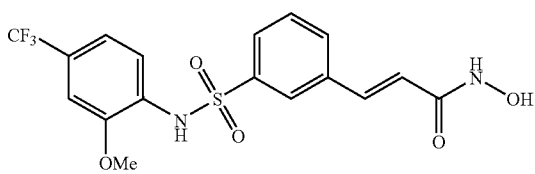 |
| 89 | 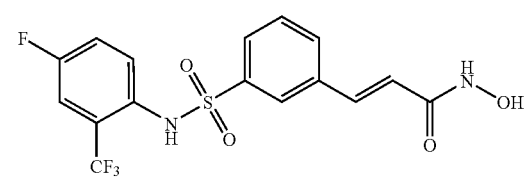 |
| 90 | 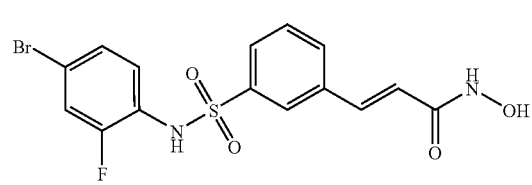 |

-continued
91 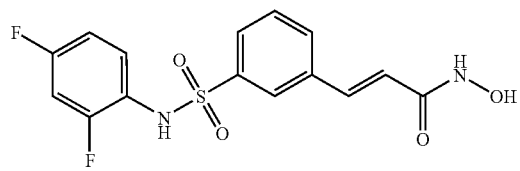
92 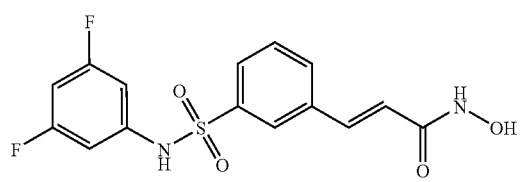
93 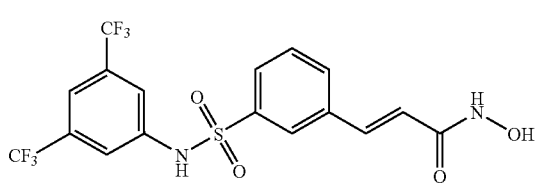
94 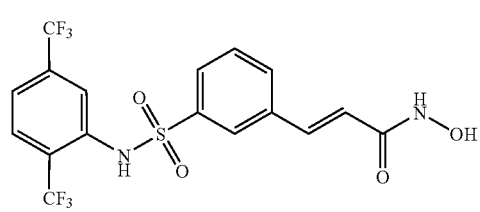
95 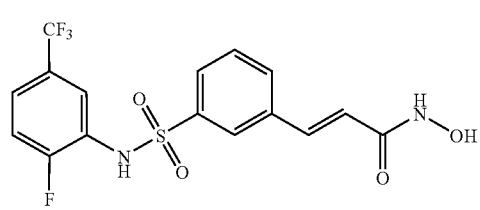
96 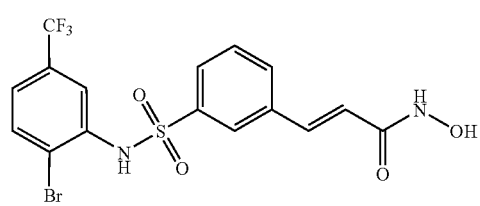
97 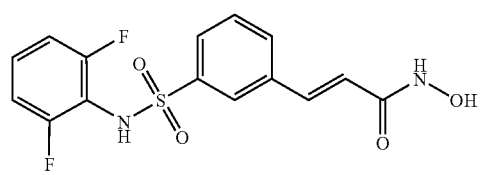
98 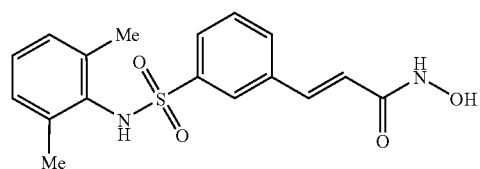

-continued
| | |
|---|---|
| 99 | 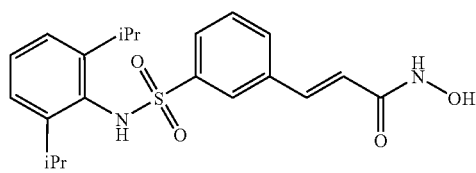 |
| 100 | 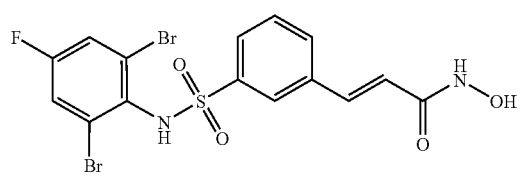 |
| 101 | 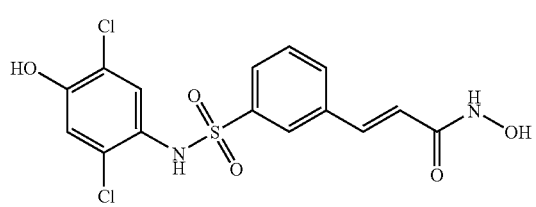 |
| 102 | 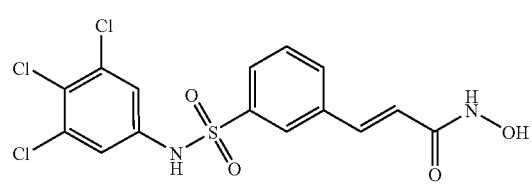 |
| 103 | 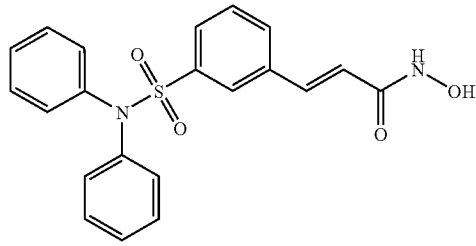 |
| 104 | 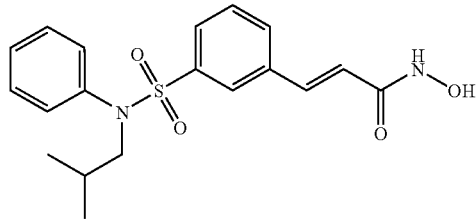 |
| 105 | 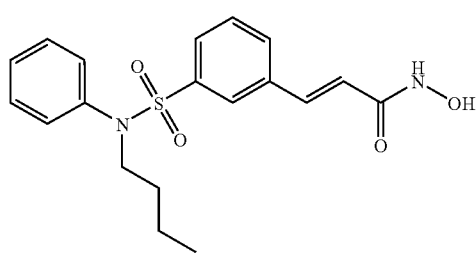 |

-continued
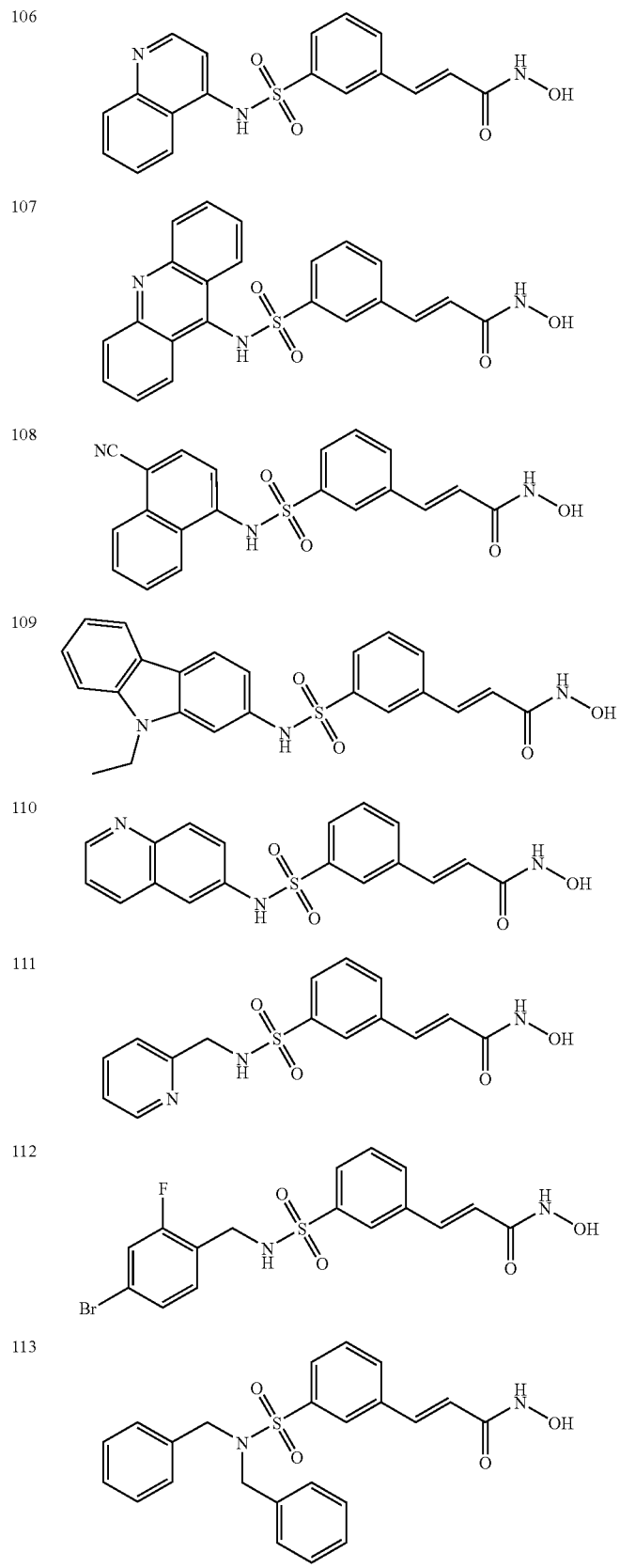

-continued
114
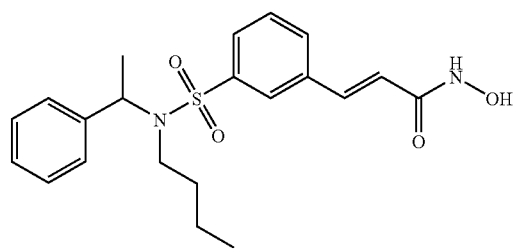
115
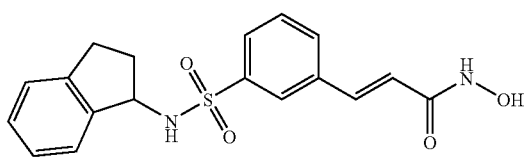
116
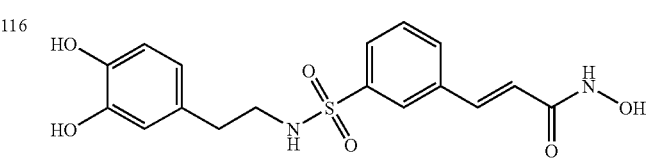
117
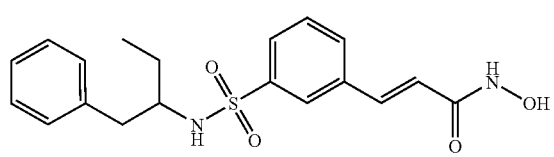
118
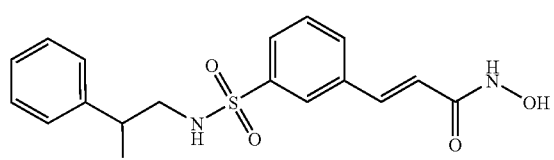
119
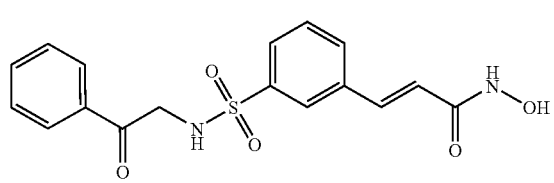
120
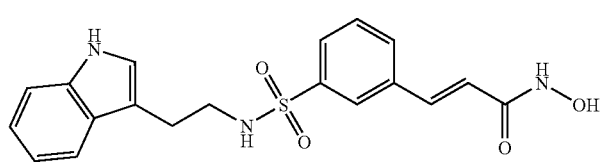
121
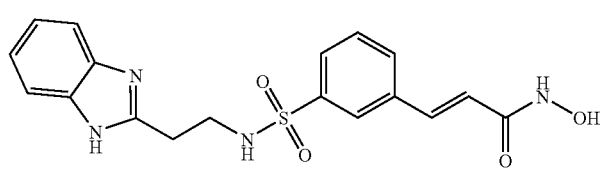
122
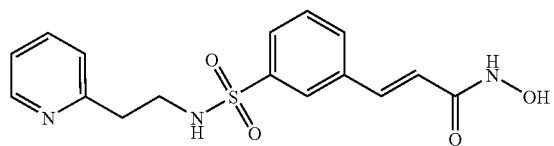

-continued

123

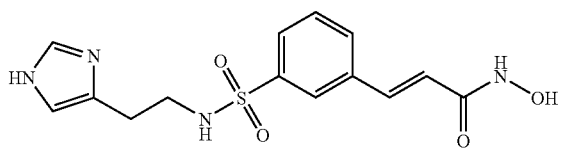

124

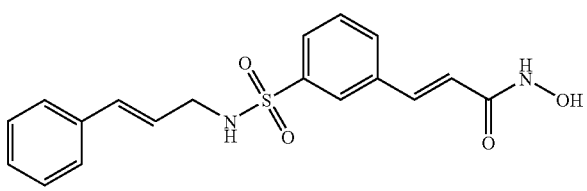

125

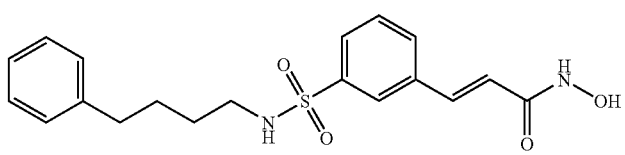

Chemical Terms

The term "carbo," "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein at least one of said ring(s) is aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one preferred embodiment, the substituent(s), often referred to herein as R, are independently selected from: halo; hydroxy; ether (e.g., $C_{1-7}$alkoxy); formyl; acyl (e.g., C: 7alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s), often referred to herein as R, are independently selected from:

—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NMe$_2$; and, optionally substituted phenyl.

In one preferred embodiment, the substituent(s), often referred to herein as R, are independently selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

In one preferred embodiment, the substituent(s), often referred to herein as R, are independently selected from: hydroxy; ether (e.g., C$_{1-7}$alkoxy); ester; amido; amino; and, C$_{1-7}$alkyl (including, e.g., C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl).

In one preferred embodiment, the substituent(s), often referred to herein as R, are independently selected from:
—OH;
—OMe, —OEt, —O(tBu), and —OCH$_2$Ph;
—C(=O)OMe, —C(=O)OEt, and —C(=O)O(tBu);
—C(=O)NH$_2$, —C(=O)NHMe, —C(=O)NMe$_2$, and —C(=O)NHEt;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$CH$_2$OH, and —CH(OH)CH$_2$OH; and,
—CH$_2$NH$_2$, —CH$_2$CH$_2$NH$_2$, and —CH$_2$CH$_2$NMe$_2$.

The substituents are described in more detail below.

C$_{1-7}$alkyl: The term "C$_{1-7}$alkyl," as used herein, pertains to a monovalent moiety obtained by removing a hydrogen atom from a C$_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear C$_{1-7}$alkyl groups include, but are not limited to, methyl, ethyl, n-propyl, n-butyl, and n-pentyl (amyl).

Examples of (unsubstituted) saturated branched C$_{1-7}$alkyl groups include, but are not limited to, iso-propyl, iso-butyl, sec-butyl, tert-butyl, and neo-pentyl.

Examples of saturated alicyclic (also carbocyclic) C$_{1-7}$alkyl groups (also referred to as "C$_{3-7}$cycloalkyl" groups) include, but are not limited to, unsubstituted groups such as cyclopropyl, cyclobutyl, cyclopentyl, cyclohexyl, and norbornane, as well as substituted groups (e.g., groups which comprise such groups), such as meathylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated C$_{1-7}$alkyl groups which have one or more carbon-carbon double bonds (also referred to as "C$_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated C$_{1-7}$alkyl groups which have one or more carbon-carbon triple bonds (also referred to as "C$_{2-7}$alkynyl" groups) include, but are not limited to, ethynyl (ethinyl) and 2-propynyl (propargyl).

Examples of unsaturated alicyclic (also carbocyclic) C$_{1-7}$alkyl groups which have one or more carbon-carbon double bonds (also referred to as "C$_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Additional examples of substituted C$_{3-7}$cycloalkyl groups include, but are not limited to, those with one or more other rings fused thereto, for example, those derived from: indene (C$_9$), indan (2,3-dihydro-1H-indene) (C$_9$), tetraline (1,2,3,4-tetrahydronaphthalene (C$_{10}$), adamantane (C$_{10}$), decalin (decahydronaphthalene) (C$_{12}$), fluorene (C$_{13}$), phenalene (C$_{13}$). For example, 2H-inden-2-yl is a C$_5$cycloalkyl group with a substituent (phenyl) fused thereto.

C$_{3-20}$heterocyclyl: The term "C$_{3-20}$heterocyclyl," as used herein, pertains to a monovalent moiety obtained by removing a hydrogen atom from a ring atom of a C$_{3-20}$heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms.

In this context, the prefixes (e.g., C$_{3-20}$, C$_{3-7}$, C$_{5-6}$, etc.) denote the number of ring atoms, or range of number of ring atoms, whether carbon atoms or heteroatoms. For example, the term "C$_{5-6}$heterocyclyl," as used herein, pertains to a heterocyclyl group having 5 or 6 ring atoms. Examples of groups of heterocyclyl groups include C$_{3-20}$heterocyclyl, C$_{3-7}$heterocyclyl, C$_{5-7}$heterocyclyl.

Examples of (non-aromatic) monocyclic heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);

S$_1$: thiirane (C$_3$), thietane (C$_4$), thiolane (tetrahydrothiophene) (C$_5$), thiane (tetrahydrothiopyran) (C$_6$), thiepane (C$_7$);

O$_2$: dioxolane (C$_5$), dioxane (C$_6$), and dioxepane (C$_7$);

O$_3$: trioxane (C$_6$);

N$_2$: imidazolidine (C$_5$), pyrazolidine (diazolidine) (C$_5$), imidazoline (C$_5$), pyrazoline dihydropyrazole) (C$_5$), piperazine (C$_6$);

N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);

N$_1$S$_1$: thiazoline (C$_5$), thiazolidine (C$_5$), thiomorpholine (C$_6$);

N$_2$O$_1$: oxadiazine (C$_6$);

O$_1$S$_1$: oxathiole (C$_5$) and oxathiane (thioxane) (C$_6$); and,

N$_1$O$_1$S$_1$: oxathiazine (C$_6$).

Examples of substituted (non-aromatic) monocyclic heterocyclyl groups include saccharides, in cyclic form, for example, furanoses (C$_5$), such as arabinofuranose, lyxofuranose, ribofuranose, and xylofuranse, and pyranoses (C$_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

C$_{5-20}$aryl: The term "C$_{5-20}$aryl," as used herein, pertains to a monovalent moiety obtained by removing a hydrogen atom from an aromatic ring atom of a C$_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms. In this context, the prefixes (e.g., C$_{3-20}$, C$_{5-7}$, C$_{5-6}$, etc.) denote the number of ring atoms, or range of number of ring atoms, whether carbon atoms or heteroatoms. For example, the term "C$_{5-6}$aryl," as used herein, pertains to an aryl group having 5 or 6 ring atoms. Examples of groups of aryl groups include C$_{3-20}$aryl, C$_{5-7}$aryl, C$_{5-6}$aryl.

The ring atoms may be all carbon atoms, as in "carboaryl groups" (e.g., C$_{5-20}$carboaryl).

Examples of carboaryl groups include, but are not limited to, those derived from benzene (i.e., phenyl) (C$_6$), naphthalene (C$_{10}$), azulene (C$_{10}$), anthracene (C$_{14}$), phenanthrene (C$_{14}$), naphthacene (C$_{18}$), and pyrene (C$_{16}$).

Examples of aryl groups which comprise fused rings, at least one of which is an aromatic ring, include, but are not limited to, groups derived from indene (C$_9$), isoindene (C$_9$), and fluorene (C$_{13}$).

Alternatively, the ring atoms may include one or more heteroatoms, including but not limited to oxygen, nitrogen, and sulfur, as in "heteroaryl groups." In this case, the group may conveniently be referred to as a "C$_{5-20}$heteroaryl" group, wherein "C$_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

N$_1$: pyrrole (azole) (C$_5$), pyridine (azine) (C$_6$);

O$_1$: furan (oxole) (C$_5$);

S$_1$: thiophene (thiole) (C$_5$);

N$_1$O$_1$: oxazole (C$_5$), isoxazole (C$_5$), isoxazine (C$_6$);

N$_2$O$_1$: oxadiazole (furazan) (C$_5$);

N$_3$O$_1$: oxatriazole (C$_5$);

N$_1$S$_1$: thiazole (C$_5$), isothiazole (C$_5$);

N$_2$: imidazole (1,3-diazole) (C$_5$), pyrazole (1,2-diazole) (C$_5$), pyridazine (1,2-diazine) (C$_6$), pyrimidine (1,3-diazine) (C$_6$) (e.g., cytosine, thymine, uracil), pyrazine (1,4-diazine) (C$_6$);

N$_3$: triazole (C$_5$), triazine (C$_6$); and,

N$_4$: tetrazole (C$_5$).

Examples of heterocyclic groups (some of which are also heteroaryl groups) which comprise fused rings, include, but are not limited to:

C$_9$heterocyclic groups (with 2 fused rings) derived from benzofuran (O$_1$), isobenzofuran (O$_1$), indole (N$_1$), isoindole (N$_1$), purine (N$_4$) (e.g., adenine, guanine), benzimidazole (N$_2$), benzoxazole (N$_1$O$_1$), benzisoxazole (N$_1$O$_1$), benzodioxole (O$_2$), benzofurazan (N$_2$O$_1$), benzotriazole (N$_3$), benzothiofuran (S$_1$), benzothiazole (N$_1$S$_1$), benzothiadiazole (N$_2$S);

C$_{10}$heterocyclic groups (with 2 fused rings) derived from benzodioxan (O$_2$), quinoline (N$_1$), isoquinoline (N$_1$), benzoxazine (N$_1$O$_1$), benzodiazine (N$_2$), pyridopyridine (N$_2$), quinoxaline (N$_2$), quinazoline (N$_2$);

C$_{13}$heterocyclic groups (with 3 fused rings) derived from carbazole (N$_1$), dibenzofuran (O$_1$), dibenzothiophene (S$_1$); and, C$_{14}$heterocyclic groups (with 3 fused rings) derived from acridine (N$_1$), xanthene (O$_1$), phenoxathiin (O$_1$S$_1$), phenazine (N$_2$), phenoxazine (N$_1$O$_1$), phenothiazine (N$_1$S$_1$), thianthrene (S$_2$), phenanthridine (N$_1$), phenanthroline (N$_2$), phenazine (N$_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to C$_{1-7}$alkyl, C$_{3-20}$heterocyclyl, C$_{5-20}$aryl, and acyl groups.

Heterocyclic groups (including heteroaryl groups) which have a nitrogen ring atom in the form of an —N═ group may be substituted in the form of an N-oxide, that is, as —N(→O)═ (also denoted —N$^+$(→O$^-$)═). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (═O) groups on ring carbon atoms. Monocyclic examples of such groups include, but are not limited to, those derived from:

C$_5$: cyclopentanone, cyclopentenone, cyclopentadienone;

C$_6$: cyclohexanone, cyclohexenone, cyclohexadienone;

O$_1$: furanone (C$_5$), pyrone (C$_6$);

N$_1$: pyrrolidone (pyrrolidinone) (C$_5$), piperidinone (piperidone) (C$_6$), piperidinedione (C$_6$);

N$_2$: imidazolidone (imidazolidinone) (C$_5$), pyrazolone (pyrazolinone) (C$_5$), piperazinone (C$_6$), piperazinedione (C$_6$), pyridazinone (C$_6$), pyrimidinone (C$_6$) (e.g., cytosine), pyrimidinedione (C$_6$) (e.g., thymine, uracil), barbituric acid (C$_6$);

N$_1$S$_1$: thiazolone (C$_5$), isothiazolone (C$_5$);

N$_1$O$_1$: oxazolinone (C$_5$).

Polycyclic examples of such groups include, but are not limited to, those derived from:

C$_9$: indenedione;

N$_1$: oxindole (C$_9$);

O$_1$: benzopyrone (e.g., coumarin, isocoumarin, chromone) (C$_{10}$);

N$_1$O$_1$: benzoxazolinone (C$_9$), benzoxazolinone (C$_{10}$);

N$_2$: quinazolinedione (C$_{10}$);

N$_4$: purinone (C$_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$hetercyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O) in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam, δ-valerolactam, and ε-caprolactam.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or —I.

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, preferably a $C_{1-7}$alkyl group, and R$^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamido groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, for example, succinimidyl, maleimidyl, and phthalimidyl:

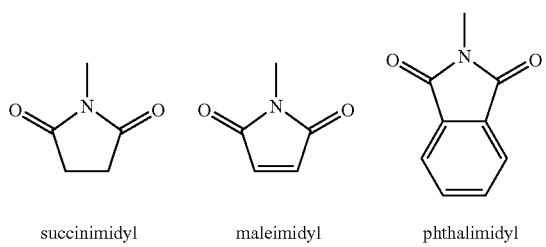

succinimidyl  maleimidyl  phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

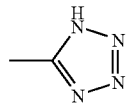

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, piperidino, piperazino, morpholino, and thiomorpholino.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Sulfonic acid (sulfo): —S(=O)$_2$OH.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group. Examples of sulfone groups include, but are not limited to, —S(O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=b)$_2$NHPh.

As mentioned above, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted groups are also discussed below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$perhaloalkyl group." Examples of C$_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

C$_{1-7}$hydroxyalkyl: The term "C$_{1-7}$hydroxyalkyl group," as used herein, pertains to a C$_{1-7}$alkyl group in which at least one hydrogen atom has been replaced with a hydroxy group. Examples of C$_{1-7}$hydroxyalkyl groups include, but are not limited to, —CH$_2$OH, —CH$_2$CH$_2$OH, and —CH(OH)CH$_2$OH.

C$_{1-7}$carboxyalkyl: The term "C$_{1-7}$carboxyalkyl group," as used herein, pertains to a C$_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "C$_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, and triphenylmethyl (trityl).

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

Some substituents are bidentate, that is, have two points for covalent attachment. For example, a bidentate group may be covalently bound to two different atoms on two different groups, thereby acting as a linker therebetween. Alternatively, a bidentate group may be covalently bound to two different atoms on the same group, thereby forming, together with the two atoms to which it is attached (and any intervening atoms, if present) a cyclic or ring structure. In this way, the bidentate substituent may give rise to a heterocyclic group/compound and/or an aromatic group/compound. Typically, the ring has from 3 to 8 ring atoms, which ring atoms are carbon or divalent heteroatoms (e.g., boron, silicon, nitrogen, phosphorus, oxygen, and sulfur, typically nitrogen, oxygen, and sulfur), and wherein the bonds between said ring atoms are single or double bonds, as permitted by the valencies of the ring atoms. Typically, the bidentate group is covalently bound to vicinal atoms, that is, adjacent atoms, in the parent group.

$C_{1-7}$alkylene: The term "$C_{1-7}$alkylene," as used herein, pertains to a bidentate moiety obtained by removing two hydrogen atoms, either both from the same carbon atom, or one from each of two different carbon atoms, of a $C_{1-7}$hydrocarbon compound having from 1 to 7 carbon atoms, which may be aliphatic or alicyclic, or a combination thereof, and which may be saturated, partially unsaturated, or fully unsaturated.

Examples of linear saturated $C_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$-(butylene).

Examples of branched saturated $C_{1-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{1-7}$alkylene groups include, but are not limited to, —CH=CH— (vinylene), —CH=CH—CH$_2$—, —CH=CH—CH$_2$CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$CH=CH—, and —CH=CH—CH$_2$—CH$_2$—CH=CH—.

Examples of branched partially unsaturated $C_{1-7}$alkylene groups include, but are not limited to, —C(CH$_3$)=CH—, —C(CH$_3$)=CH—CH$_2$—, and —CH=CH—CH(CH$_3$)—.

Examples of alicyclic saturated $C_{1-7}$alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$alkylene groups include, but are not limited to, cyclopentenylene (e.g., 4-cyclopenten-1,3-ylene), cyclohexenylene (e.g., 2-cyclohexen-1,4-ylene, 3-cyclohexen-1,2-ylene, 2,5-cyclohexadien-1,4-ylene).

$C_{5-20}$arylene: The term "$C_{5-20}$arylene," as used herein, pertains to a bidentate moiety obtained by removing two hydrogen atoms, one from each of two different ring atoms of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboarylene groups," in which case the group may conveniently be referred to as a "$C_{5-20}$carboarylene" group.

Alternatively, the ring atoms may include one or more heteroatoms, including but not limited to oxygen, nitrogen, and sulfur, as in "heteroarylene groups." In this case, the group may conveniently be referred to as a "$C_{5-20}$heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$arylene groups which do not have ring heteroatoms (i.e., $C_{5-20}$carboarylene groups) include, but are not limited to, those derived from benzene (i.e., phenyl) ($C_6$), naphthalene ($C_{10}$), anthracene ($C_{14}$), phenanthrene ($C_{14}$), and pyrene ($C_{16}$).

Examples of $C_{5-20}$heteroarylene groups include, but are not limited to, $C_5$heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$heteroarylene groups derived from isoxazine, pyridine (azine),pyridazine (1,2-diazine), pyrimidine (1,3-diazine; e.g., cytosine, thymine, uracil), pyrazine (1,4-diazine), triazine, tetrazole, and oxadiazole (furazan).

$C_{5-20}$Arylene-$C_{1-7}$alkylene: The term "$C_{5-20}$arylene-$C_{1-7}$alkylene," as used herein, pertains to a bidentate moiety comprising a $C_{5-20}$arylene moiety, -Arylene-, linked to a $C_{1-7}$alkylene moiety, -Alkylene-, that is, -Arylene-Alkylene-.

Examples of $C_{5-20}$arylene-$C_{1-7}$alkylene groups include, but are not limited to, phenylene-methylene, phenylene-ethylene, phenylene-propylene, and phenylene-ethenylene (also known as phenylene-vinylene).

$C_{5-20}$Alkylene-$C_{1-7}$arylene: The term "$C_{5-20}$alkylene-$C_{1-7}$arylene," as used herein, pertains to a bidentate moiety comprising a $C_{5-20}$alkylene moiety, -Alkylene-, linked to a $C_{1-7}$arylene moiety, -Arylene-, that is, -Alkylene-Arylene-.

Examples of $C_{5-20}$alkylene-$C_{1-7}$arylene groups include, but are not limited to, methylene-phenylene, ethylene-phenylene, propylene-phenylene, and ethenylene-phenylene (also known as vinylene-phenylene).

Included in the above are the well known ionic, salt, solvate (e.g., hydrate), and protected forms of these substituents. For example, a reference to carboxylic acid (—COOH) also includes carboxylate (—COO). Similarly, a reference to an amino group includes a salt, for example, a hydrochloride salt, of the amino group. A reference to a hydroxyl group also includes conventional protected forms of a hydroxyl group. Similarly, a reference to an amino group also includes conventional protected forms of an amino group.

Acronyms

For convenience, many chemical moieties are represented herein using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented herein using well known abbreviations, including but not limited to, methanol (MeOH), ethanol (EtOH), iso-propanol (i-PrOH), methyl ethyl ketone (MEK), acetic acid (AcOH), dichloromethane (methylene chloride, DCM), tri-fluoroacetic acid (TFA), dimethylformamide (DMF), and tetrahydrofuran (THF).

Isomers, Salts, Solvates, Protected Forms, and Prodrugs

A certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exoforms; R—, S, and meso-forms; D- and L-forms; (+) and (−) forms; keto-, enol-, and enolate-forms; syn- and anti-forms; syn-clinal- and anticlinal-forms; α- and β-forms; axial and equatorial forms; boat-, chair-, twist-, envelope, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

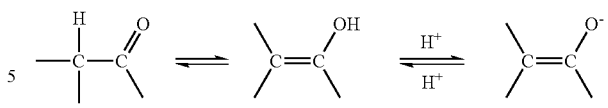

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1–19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: -ethylamine, diethylamine, ethylenediamine, ethanolamine, diethanolamine, piperazine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluene-sulfonic, methanesulfonic, ethanesulfonic, ethane disulfonic, oxalic, isethionic, and valeric.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyidimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; an acetamidomethyl ether (—SCH$_2$NHC(=O)CH$_3$).

It may be convenient or desirable to prepare, purify, and/or handle the active compound in the form of a prodrug. The term "prodrug," as used herein, pertains to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis

Several methods for the chemical synthesis of compounds of the present invention are described herein. These methods may be modified and/or adapted in known ways in order to facilitate the synthesis of additional compounds within the scope of the present invention.

The compounds of the present invention may be prepared, for example, by the methods described herein, or by adapting these or other well known methods in well known ways.

In one method, an arylaldehyde is reacted with oleum to form a sulfonyl-arylaldehyde product. The aldehyde group is then reacted with a phosphono ester, to form a pendant carboxylic acid ester. The sulfonyl group is then reacted with SOCl$_2$ to form a sulfonyl halide group. The product is then reacted with an amine (e.g., an aryl amine) to form the corresponding sulfonamide. The carboxylic acid ester is then deprotected by reaction with base, and subsequently converted to an acyl halide. The acyl halide is reacted with hydroxylamine to form the corresponding carbamic acid.

One example of this approach is illustrated below, in Scheme 1, wherein the reaction conditions are as follows: (i) H$_2$SO$_4$+SO$_3$, 30° C. at mixing, mixing 40° C. for 10 hours, mixing at room temperature overnight, add cold H$_2$O, add CaCO$_3$; (ii) K$_2$CO$_3$, (MeO)$_2$P(=O)CH$_2$COOMe, H$_2$O, room temperature, 30 min.; (iii) thionyl chloride, benzene, DMF, reflux, one hour; (iv) aniline, pyridine, DCM, 50° C., 1 hour; (v) NaOH, MeOH; (vi) oxalyl chloride, DMF, DCM, 40° C., 1 hour; (vii) hydroxylamine hydrochloride and NaHCO$_3$ in THF, room temperature, 1 hour.

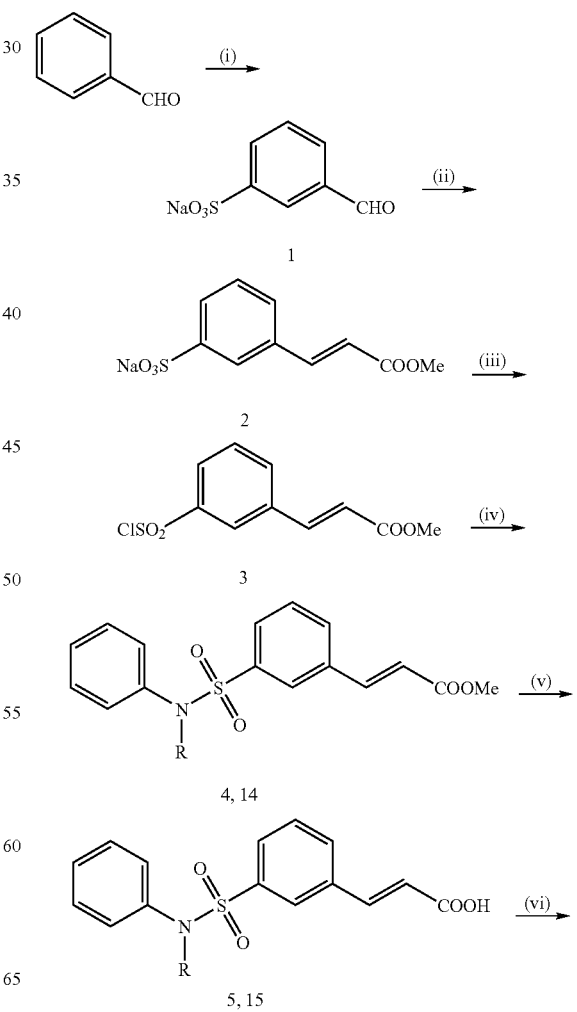

-continued

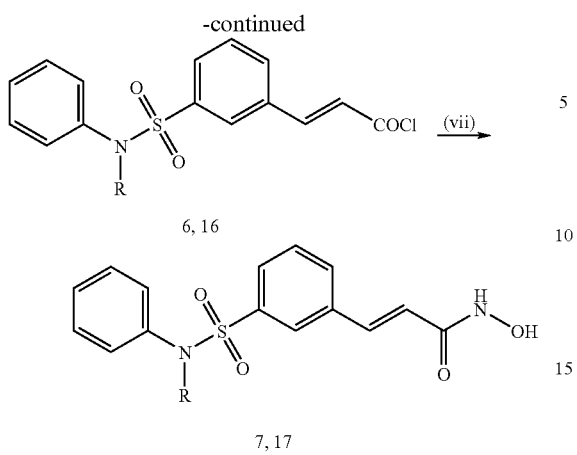

6, 16

7, 17

By using amines instead of aniline, the corresponding products may be obtained. The use of aniline, 4-methoxyaniline, 4-methylaniline, 4-bromoaniline, 4-chloroaniline, 4-benzylamine, and 4-phenethyamine, among others, is described in the Examples below.

In another method, a suitable amino acid (e.g., ω-amino acid) having a protected carboxylic acid (e.g., as an ester) and an unprotected amino group is reacted with a sulfonyl chloride compound (e.g., $RSO_2Cl$) to give the corresponding sulfonamide having a protected carboxylic acid. The protected carboxylic acid is then deprotected using base to give the free carboxylic acid, which is then reacted with, for example, hydroxylamine 2-chlorotrityl resin followed by acid (e.g., trifluoroacetic acid), to give the desired carbamic acid.

One example of this approach is illustrated below, in Scheme 2, wherein the reaction conditions are as follows: (i) $RSO_2Cl$, pyridine, DCM, room temperature, 12 hours; (ii) 1 M LiOH or 1 M NaOH, dioxane, room temperature, 3–48 hours; (iii) hydroxylamine 2-chlorotrityl resin, HOAt, HATU, DIPEA, DCM, room temperature, 16 hours; and (iv) TFA/DCM (5:95, v/v), room temperature, 1.5 hours.

Scheme 2

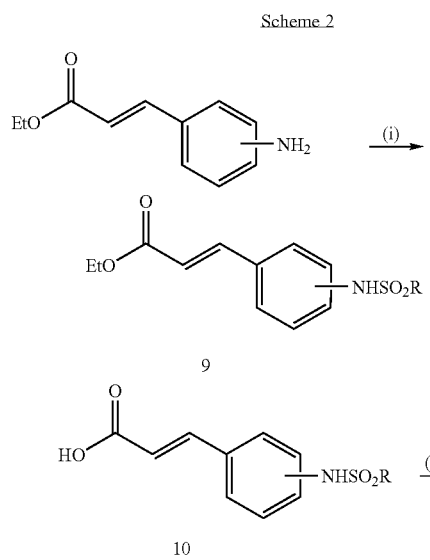

-continued

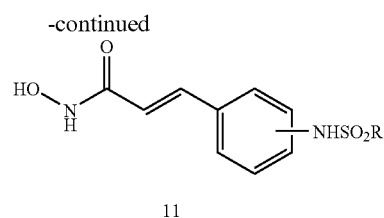

11

Additional methods for the synthesis of compounds of the present invention are illustrated below and are exemplified in the examples below.

Scheme 3A

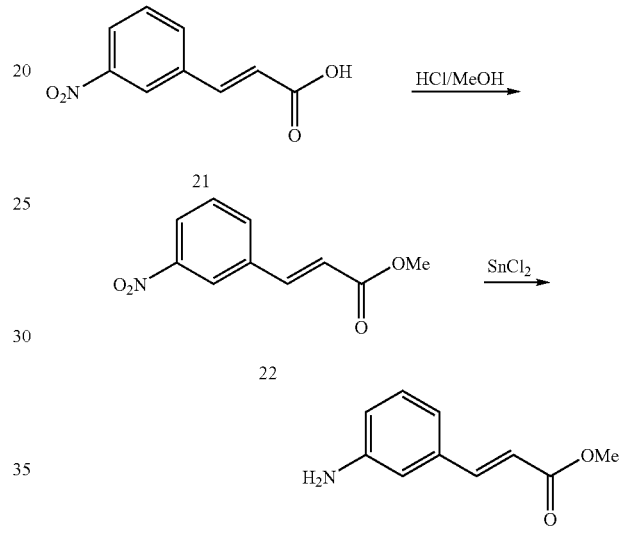

Scheme 3B

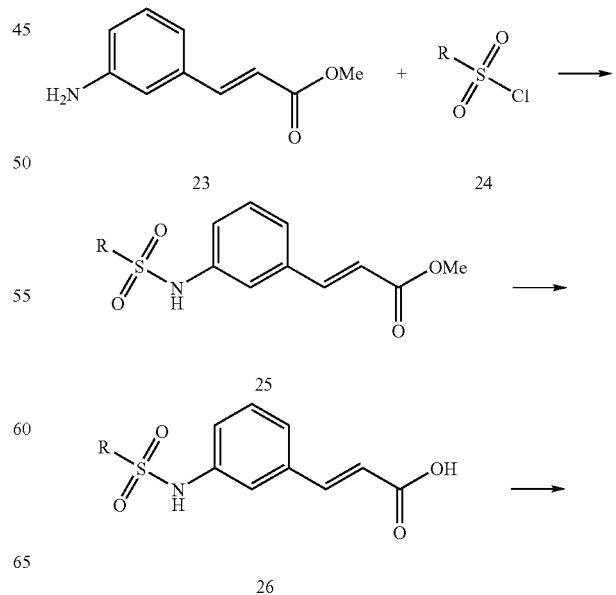

-continued
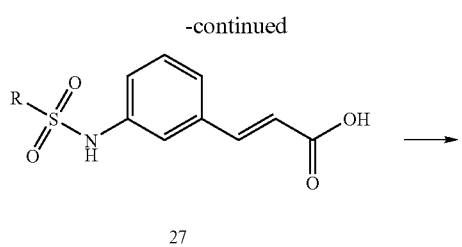
27
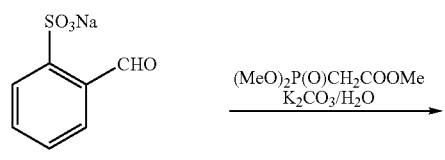
28
Scheme 4
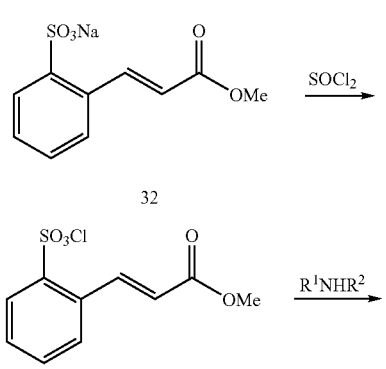
31
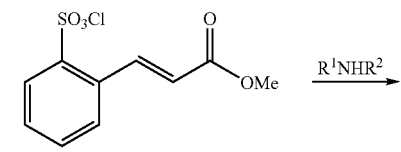
32
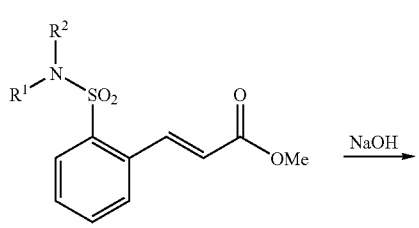
33
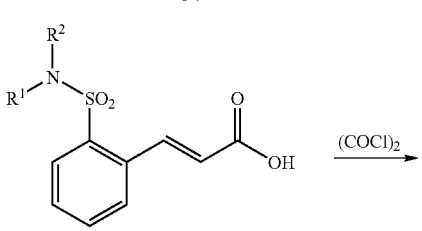
34
35
-continued
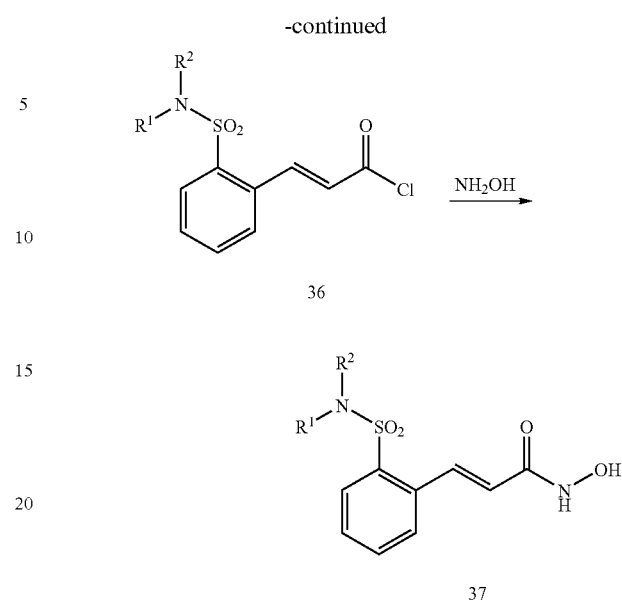
36
37
Scheme 5
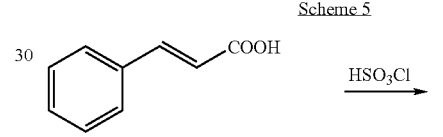
41
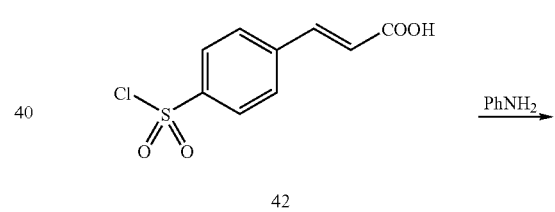
42
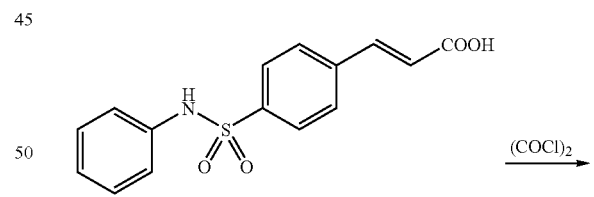
43
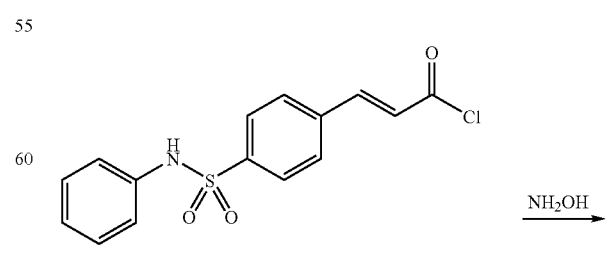
44

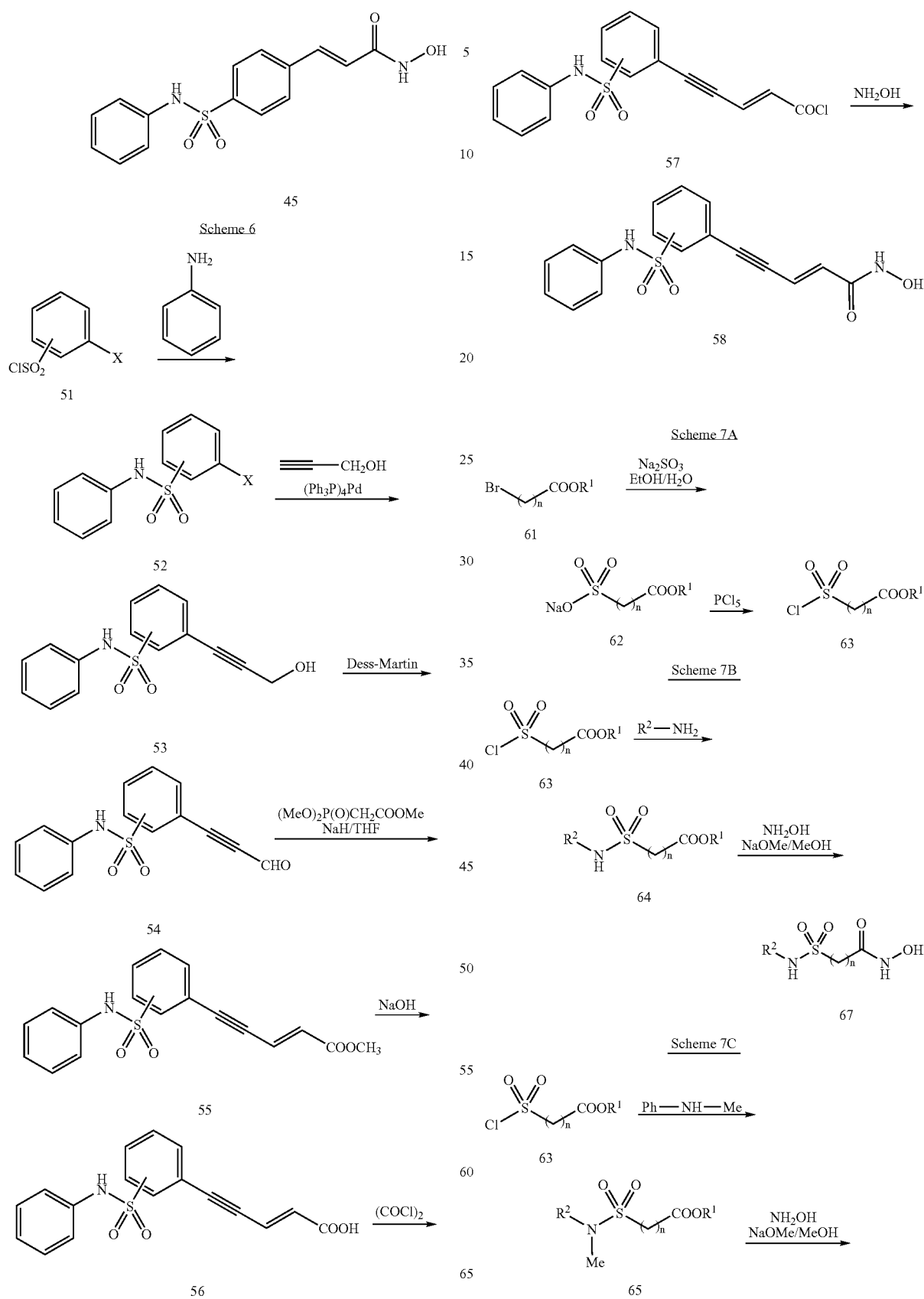

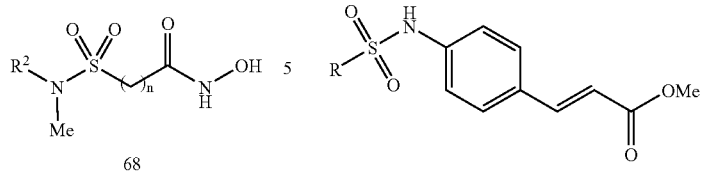
68
Scheme 7D
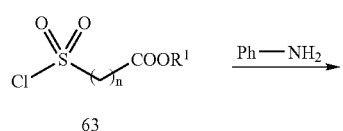
63
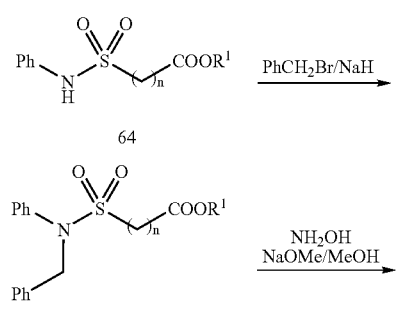
Scheme 8
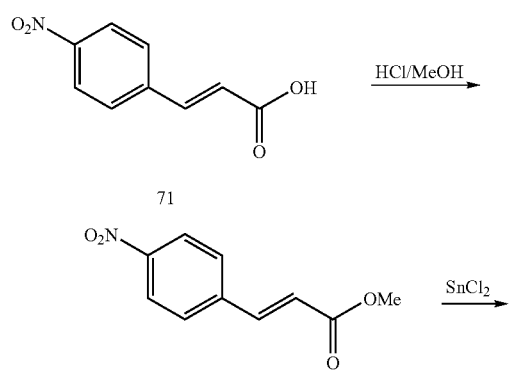
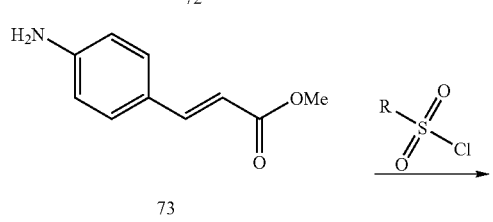
73
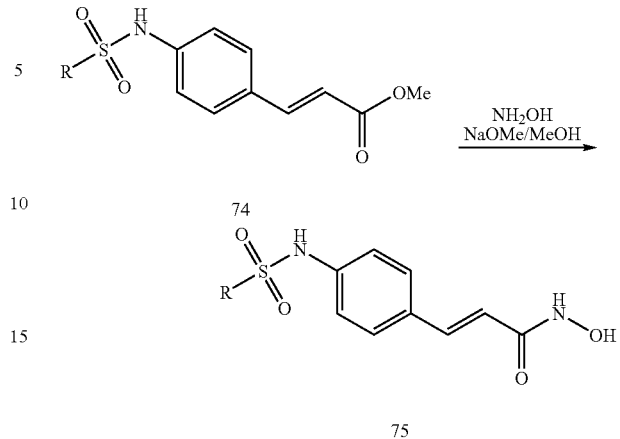
74
75
Scheme 9
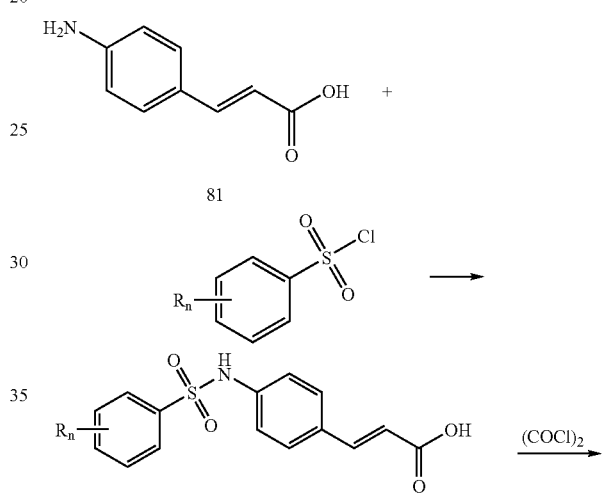
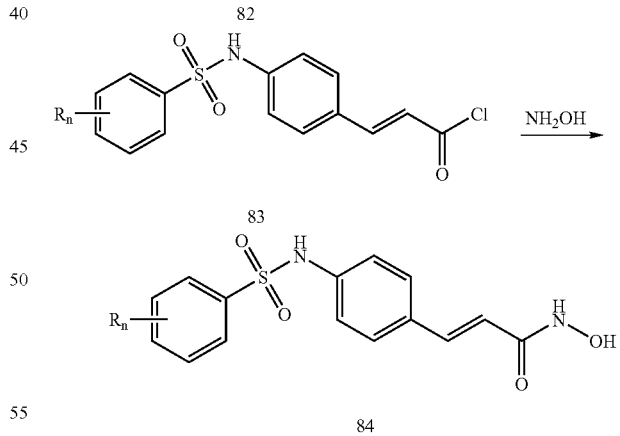
84
Scheme 10
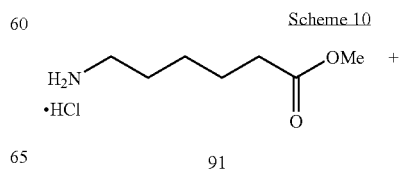
91

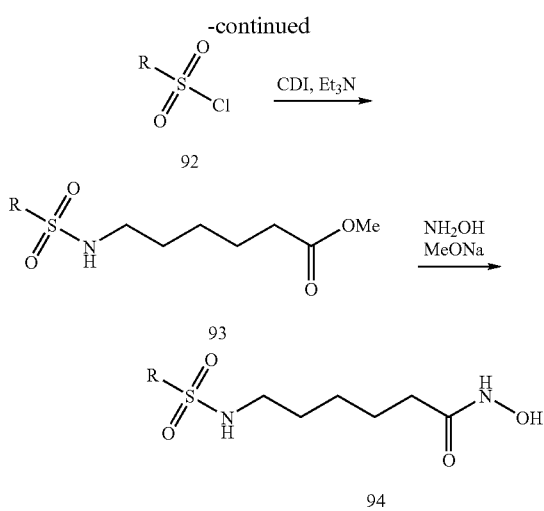

Uses

The present invention provides active compounds which are capable of inhibiting HDAC (for example, inhibiting HDAC activity, inhibiting formation of HDAC complexes, inhibiting activity of HDAC complexes), as well as methods of inhibiting HDAC activity, comprising contacting a cell with an effective amount of an active compound, whether in vitro or in vivo.

The term "active," as used herein, pertains to compounds which are capable of inhibiting HDAC activity, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active, that is, capable of inhibiting HDAC activity. For example, assays which may conveniently be used to assess the inhibition offered by a particular compound are described in the examples below.

For example, a sample of cells (e.g., from a tumour) may be grown in vitro and a candidate compound brought into contact with the cells, and the effect of the compound on those cells observed. As examples of "effect," the morphological status of the cells may be determined (e.g., alive or dead), or the expression levels of genes regulated by HDAC. Where the candidate compound is found to exert an influence on the cells, this may be used as a prognostic or diagnostic marker of the efficacy of the compound in methods of treating a patient carrying cells of the same type (e.g., the tumour or a tumour of the same cellular type).

In one aspect, the present invention provides antiproliferative agents. The term "antiproliferative agent" as used herein, pertains to a compound which treats a proliferative condition (i.e., a compound which is useful in the treatment of a proliferative condition).

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The compounds of the present invention may also be used in the treatment of conditions which are known to be mediated by HDAC, or which are known to be treated by HDAC inhibitors (such as, e.g., trichostatin A). Examples of such conditions include, but are not limited to, the following:

Cancer (see, e.g., Vigushin et al., 2001).
Psoriasis (see, e.g., Iavarone et al., 1999).
Fibroproliferative disorders (e.g., liver fibrosis) (see, e.g., Niki et al., 1999; Corneil et al., 1998).
Smooth muscle proliferative disorder (e.g., atherosclerosis, restenosis) (see, e.g., Kimura et al., 1994).
Neurodegenerative diseases (e.g., Alzheimer's, Parkinson's, Huntington's chorea, amyotropic lateral sclerosis, spinocerebellar degeneration) (see, e.g., Kuusisto et al., 2001).
Inflammatory disease (e.g., osteoarthritis, rheumatoid arthritis) (see, e.g., Dangond et al., 1998; Takahashi et al., 1996).
Diseases involving angiogenesis (e.g., cancer, rheumatoid arthritis, psoriasis, diabetic retinopathy) (see, e.g., Kim et al., 2001).
Haematopoietic disorders (e.g., anaemia, sickle cell anaemia, thalassaeimia) (see, e.g., McCaffrey et al., 1997).
Fungal infection (see, e.g., Bernstein et al., 2000; Tsuji et al., 1976).
Parasitic infection (e.g., malaria, trypanosomiasis, helminthiasis, protozoal infections (see, e.g., Andrews et al., 2000).
Bacterial infection (see, e.g., Onishi et al., 1996).
Viral infection (see, e.g., Chang et al., 2000).
Conditions treatable by immune modulation (e.g., multiple sclerosis, autoimmune diabetes, lupus, atopic dermatitis, allergies, asthma, allergic rhinitis, inflammatory bowel disease; and for improving grafting of transplants) (see, e.g., Dangond et al., 1998; Takahashi et al., 1996).

The invention further provides active compounds for use in a method of treatment of the human or animal body. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides the use of an active compound for the manufacture of a medicament, for example, for the treatment of a proliferative condition, as discussed above.

The invention further provides the use of an active compound for the manufacture of a medicament, for example, for the treatment of conditions which are known to be mediated by HDAC, or which are known to be treated by HDAC inhibitors (such as, e.g., trichostatin A), as discussed above.

The invention further provides a method for inhibiting HDAC in a cell comprising said cell with an effective amount of an active compound.

The invention further provides a method of treatment of the human or animal body, the method comprising administering to a subject in need of treatment a therapeutically-effective amount of an active compound, preferably in the form of a pharmaceutical composition.

Active compounds may also be used, as described above, in combination therapies, that is, in conjunction with other agents, for example, cytotoxic agents.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, etc.

The compounds of the present invention may also be used in methods of improving protein production by cultured cells (see, e.g., Furukawa et al., 1998).

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrastemal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fem, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active ingredient, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, losenges, granules, powders, capsules, cachets, pills, ampoules, suppositories, pessaries, ointments, gels, pastes, creams, sprays, foams, lotions, oils, boluses electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, paste, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freese-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound.

The written instructions may also include a list of indications for which the active ingredient is a suitable treatment.

EXAMPLES

The following are examples are provided solely to illustrate the present invention and are not intended to limit the scope of the invention, as described herein.

General $^1$H NMR spectra were recorded at ambient temperature with WH-90/DS or Mercury 200 (Varian) spectrometers. The HPLC measurements were performed on a Gilson Model 302 system equipped with a spectrophotometer. Elemental analyses were obtained with a Carlo Erba EA 1108 instrument. Melting points were measured on a "Boëtius" or "Fisher" micro melting point apparatus and are uncorrected. Silicagel, 0.035–0.070 mm, (Acros) was employed for column chromatography. All the solvents were purified before use by routine techniques. To isolate reaction products, the solvents were removed by evaporation using a vacuum rotary evaporator, the water bath temperature not exceeding 40° C.

Various reagents were purchased from Sigma-Aldrich (The Old Brickyard, New Road, Gillingham, Dorset, UK), Acros Organics (Janssens Pharmaceuticalaan 3A, 2440 Geel, Belgium), Lancaster Synthesis Ltd. (Eastgate, White Lund, Morecambe, Lancashire, LA3 3DY, UK), and Maybridge plc (Trevillett, Tingagel, Cornwall, PL34 0HW, UK).

Example 1

3-Formylbenzenesulfonic acid, sodium salt (1)

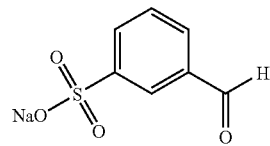

Oleum (5 ml) was placed in a reaction vessel and benzaldehyde (2.00 g, 18.84 mmol) was slowly added not exceeding the temperature of the reaction mixture more than 30° C. The obtained solution was stirred at 40° C. for ten hours and at ambient temperature overnight. The reaction mixture was poured into ice and extracted with ethyl acetate. The aqueous phase was treated with $CaCO_3$ until the evolution of $CO_2$ ceased (pH~6–7), then the precipitated $CaSO_4$ was filtered off and washed with water. The filtrate was treated with $Na_2CO_3$ until the pH of the reaction medium increased to pH 8, obtained $CaCO_3$ was filtered off and water solution was evaporated in vacuum. The residue was washed with methanol, the washings were evaporated and the residue was dried in desiccator over $P_2O_5$ affording the title compound (2.00 g, 51%). $^1$H NMR ($D_2O$), δ: 7.56–8.40 (4H, m); 10.04 ppm (1H, s).

Example 2

3-(3-Sulfophenyl)acrylic acid methyl ester, sodium salt (2)

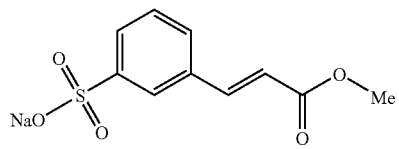

Sodium salt of 3-formylbenzenesulfonic acid (1) (1.00 g, 4.80 mmol), potassium carbonate (1.32 g, 9.56 mmol), trimethyl phosphonoacetate (1.05 g, 5.77 mmol) and water (2 ml) were stirred at ambient temperature for 30 min., precipitated solid was filtered and washed with methanol. The filtrate was evaporated and the title compound (2) was obtained as a white solid (0.70 g, 55%). $^1$H NMR (DMSO-$d_6$, HMDSO), δ: 3.68 (3H, s); 6.51 (1H, d, J=16.0 Hz); 7307.88 (5H, m).

Example 3

3-(3-Chlorosulfonylphenyl)acrylic acid methyl ester (3)

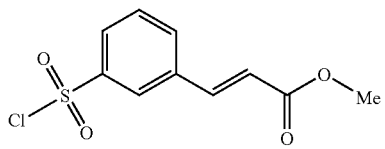

To the sodium salt of 3-(3-sulfophenyl)acrylic acid methyl ester (2) (0.670 g, 2.53 mmol) benzene (2 ml), thionyl chloride (1.508 g, 0.9 ml, 12.67 mmol) and 3 drops of dimethylformamide were added and the resultant suspension was stirred at reflux for one hour. The reaction mixture was evaporated, the residue was dissolved in benzene (3 ml), filtered and the filtrate was evaporated to give the title compound (0.640 g, 97%).

Example 4

3-(3-Phenylsulfamoylphenyl)acrylic acid methyl ester (4a)

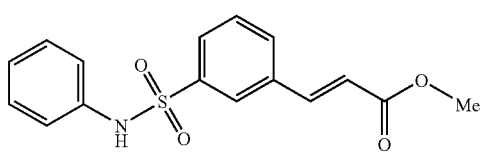

A solution of 3-(3-chlorosulfonylphenyl)acrylic acid methyl ester (3) (0.640 g, 2.45 mmol) in dichloromethane (2 ml) was added to a mixture of aniline (0.465 g, 4.99 mmol) and pyridine (1 ml), and the resultant solution was stirred at 50° C. for one hour. The reaction mixture was evaporated and the residue was partitioned between ethyl acetate and 10% HCl. The organic layer was washed successively with water, saturated NaCl, and dried ($Na_2SO_4$). The solvent was removed and the residue was chromatographed on silica gel with chloroform-ethyl acetate (7:1, v/v) as eluent. The obtained product was washed with diethyl ether to give the title compound (0.226 g, 29%). $^1$H NMR (CDCl$_3$, HMDSO), δ: 3.72 (3H, s); 6.34 (1H, d, J=16.0 Hz); 6.68 (1H, br s); 6.92–7.89 (10H, m).

Example 5

3-(3-Phenylsulfamoylphenyl)acrylic acid (5a)

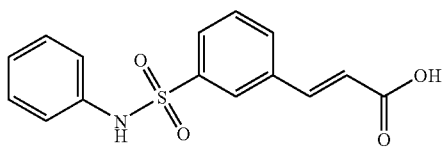

3-(3-Phenylsulfamoylphenyl)acrylic acid methyl ester (4a) (0.220 g, 0.69 mmol) was dissolved in methanol (3 ml), 1N NaOH (2.08 ml, 2.08 mmol) was added and the resultant solution was stirred at ambient temperature overnight. The reaction mixture was partitioned between ethyl acetate and water. The aqueous layer was acidified with 10% HCl and stirred for 30 min. The precipitated solid was filtered, washed with water and dried in desiccator over $P_2O_5$ to give the title compound as a white solid (0.173 g, 82%).

Example 6

3-(3-Phenylsulfamoylphenyl)acryloyl chloride (6a)

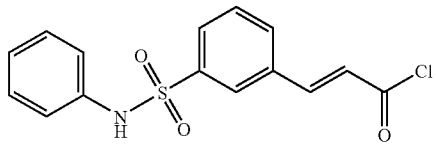

To a suspension of 3-(3-phenylsulfamoylphenyl)acrylic acid (5a) (0.173 g, 0.57 mmol) in dichloromethane (2.3 ml) oxalyl chloride (0.17 ml, 1.95 mmol) and one drop of dimethylformamide were added. The reaction mixture was stirred at 40° C. for one hour and concentrated under reduced pressure to give crude title compound (0.185 g).

Example 7

N-Hydroxy-3-(3-phenylsulfamoylphenyl)acrylamide (7a) (PX105684)

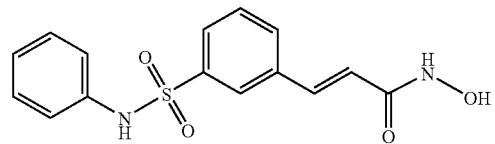

To a suspension of hydroxylamine hydrochloride (0.200 g, 2.87 mmol) in tetrahydrofuran (3.5 ml) a saturated NaHCO$_3$ solution (2.5 ml) was added and the resultant mixture was stirred at ambient temperature for 10 min. To the reaction mixture a 3-(3-phenylsulfamoylphenyl)acryloyl chloride (6a) (0.185 g) solution in tetrahydrofuran (2.3 ml) was added and stirred at ambient temperature for one hour. The reaction mixture was partitioned between ethyl acetate and 2N HCl. The organic layer was washed successively with water and saturated NaCl, the solvent was removed and the residue was washed with acetonitrile and diethyl ether.

The title compound was obtained as a white solid (0.066 g, 36%), m.p. 172° C. $^1$H NMR (DMSO-d$_6$, HMDSO), δ: 6.49 (1H, d, J=16.0 Hz); 7.188.05 (10H, m); 9.16 (1H, br s); 10.34 (1H, s); 10.85 ppm (1H, br s). HPLC analysis on Symmetry C$_{18}$ column: impurities 4% (column size 3.9×150 mm; mobile phase acetonitrile—0.1M phosphate buffer (pH 2.5), 40:60; sample concentration 1 mg/ml; flow rate 0.8 ml/min; detector UV 220 nm). Anal. Calcd for C$_{15}$H$_{14}$N$_2$O$_4$S, %: C, 56.59; H, 4.43; N, 8.80. Found, %: C, 56.28; H, 4.44; N, 8.56.

Example 8

3-[3-(Methylphenylsulfamoyl)phenyl]acrylic acid methyl ester (4b)

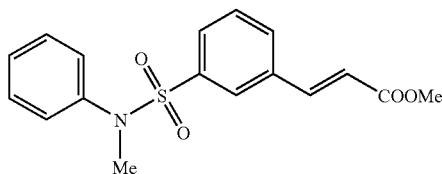

A solution of 3-(3-chlorosulfonylphenyl)acrylic acid methyl ester (3) (0.440 g, 1.68 mmol) in dichloromethane (2 ml) was added to a mixture of N-methylaniline (0.364 g, 3.40 mmol) and pyridine (0.5 ml), and the resultant solution was stirred at 50° C. for one hour. The reaction mixture was evaporated and the residue was partitioned between ethyl acetate and 10% HCl. The organic layer was washed successively with water, saturated NaCl, and dried (Na$_2$SO$_4$). The solvent was removed and the residue was chromatographed on silica gel with chloroform-ethyl acetate (15:1, v/v) as eluent. The obtained product was washed with diethyl ether to give the title compound (0.155 g, 28%). $^1$H NMR (CDCl$_3$, HMDSO), δ: 3.12 (3H, s); 3.74 (3H, s); 6.34 (1H, d, J=16.0 Hz); 6.97–7.74 (10H, m).

Example 9

3-[3-(Methylphenylsulfamoyl)phenyl]acrylic acid (5b)

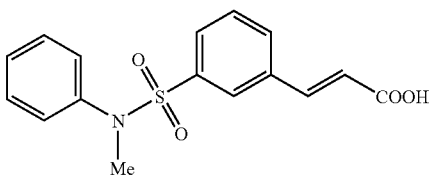

3-[3-(Methylphenylsulfamoyl)phenyl]acrylic acid methyl ester (4b) (0.150 g, 0.45 mmol) was suspended in methanol (2 ml), 1 N NaOH solution (1.35 ml, 1.35 mmol) was added and the resultant solution was stirred at ambient temperature overnight. The reaction mixture was partitioned between ethyl acetate and water. The aqueous layer was acidified with 10% HCl and extracted with ethyl acetate. The organic layer was washed successively with water, saturated NaCl, and dried (Na$_2$SO$_4$). The solvent was removed to give the title compound (0.135 g, 94%).

Example 10

3-[3-Methylphenylsulfamoyl)phenyl]acryloyl chloride (6b)

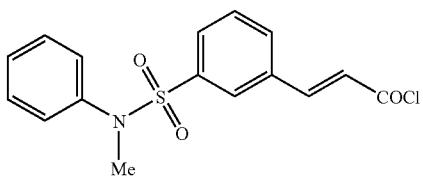

To a suspension of 3-[3-(methylphenylsulfamoyl)phenyl] acrylic acid (5b) (0.135 g, 0.42 mmol) in dichloromethane (2.3 ml) oxalyl chloride (0.17 ml, 1.95 mmol) and one drop of dimethylformamide were added. The reaction mixture was stirred at 40° C. for one hour and concentrated under reduced pressure to give crude title compound (0.142 g).

Example 11

N-Hydroxy-[3-(3-methylphenylsulfamoyl)phenyl] acrylamide (7b) (PX105685)

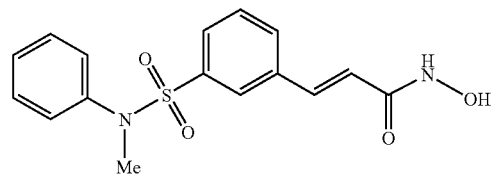

To a suspension of hydroxylamine hydrochloride (0.200 g, 2.87 mmol) in tetrahydrofuran (3.5 ml) a saturated NaHCO$_3$ solution (2.5 ml) was added and the resultant mixture was stirred at ambient temperature for 10 min. To the reaction mixture a 3-[3-(methylphenylsulfamoyl)phenyl]acryloyl chloride (6b) (0.142 g) solution in tetrahydrofuran (2.3 ml) was added and stirred at ambient temperature for one hour. The reaction mixture was partitioned between ethyl acetate and 2N HCl. The organic layer was washed successively with water and saturated NaCl, the solvent was removed and the residue was washed with diethyl ether.

The title compound was obtained as a white solid (0.062 mg, 42%), m.p. 152° C. $^1$H NMR (DMSO-d$_6$, HMDSO), δ: 3.16 (3H, s); 6.47 (1H, d, J=116.0 Hz); 7.03–7.96 (10H, m); 9.09 (1H, br s); 10.78 ppm (1H, br s). HPLC analysis on Symmetry C$_{18}$ column: impurities 1.7% (column size 3.9× 150 mm; mobile phase acetonitrile −0.1M phosphate buffer (pH 2.5), 40:60; sample concentration 1 mg/ml; flow rate 1.0 ml/min; detector UV 220 nm). Anal. Calcd for C$_{16}$H$_{16}$N$_2$O$_4$S, %: C, 57.82; H, 4.85; N, 8.43. Found, %: C, 57.82; H, 4.83; N, 8.35.

Example 12

3-[3-(4-Methoxyphenylsulfamoyl)-phenyl)]acrylic acid methyl ester (4c)

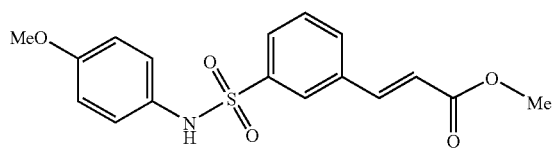

A solution of 3-(3-chlorosulfonylphenyl)acrylic acid methyl ester (3) (2.0 g, 7.23 mmol) in dioxane (10 ml) was added to a mixture of 4-methoxyaniline (0.89 g, 7.23 mmol) in dioxane (15 ml) and NaHCO$_3$ (1.29, 14.5 mmol) in water (20 ml), and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with dichloromethane-ethyl acetate (20:1, v/v) as eluent. The obtained product was washed with diethyl ether to the title compound (2.0 g, 80%). $^1$H NMR (DMSO-d$_6$, HMDSO), δ: 3.65 (3H, s); 3.74 (3H, s); 6.65 (1H, d, J=16.0 Hz); 6.72–7.20 (4H, m); 7.56–8.18 (5H, m); 9.96 (1H, br s).

Example 13

3-[3-(4-Methoxyphenylsulfamoyl)-phenyl)]-acrylic acid (5c)

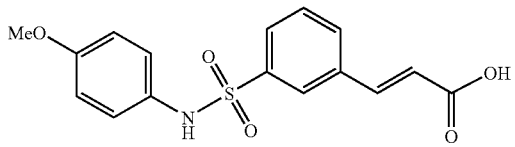

To a suspension of 3-[3-(4-methoxyphenylsulfamoyl)-phenyl)]-acrylic acid methyl ester (4c) (1.09, 2.88 mmol) in methanol (15 ml) 1N NaOH solution (8.63 ml, 8.63 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over P$_2$O$_5$ to give the title compound as a white solid (0.95 g, 99%).

Example 14

3-[3-(4-Methoxyphenylsulfamoyl)-phenyl)]-acryloyl chloride (6c)

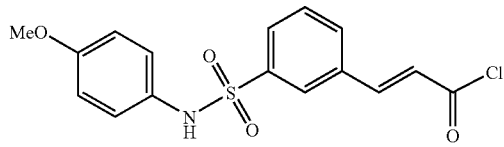

To a suspension of 3-[3-(4-methoxyphenylsulfamoyl)-phenyl)]-acrylic acid (5c) (0.95 g, 2.85 mmol) in dichloromethane (12.0 ml) oxalyl chloride (0.88 ml, 10.07 mmol) and one drop of dimethylformamide were added. The reaction mixture was stirred at 40° C. for one hour and concentrated under reduced pressure to give crude title compound (1.01 g).

Example 15

N-Hydroxy-3-[3-(4-methoxyphenylsulfamoyl)-phenyl)]-acrylamide (7c) (PX105844)

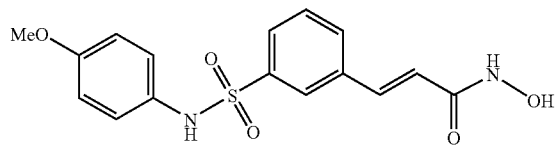

To a suspension of hydroxylamine hydrochloride (0.99 g, 14.38 mmol) in tetrahydrofuran (17.0 ml) a saturated NaHCO$_3$ solution (12.0 ml) was added and the resultant mixture was stirred at ambient temperature for 10 min. To the reaction mixture a solution of 3-[3-(4-methoxyphenyl-sulfamoyl)-phenyl)-acryloyl chloride (6c) (1.01 g) in tetrahydrofuran (12.0 ml) was added and the mixture was stirred at ambient temperature for one hour. The reaction mixture was partitioned between ethyl acetate and 2N HCl. The organic layer was washed successively with water and saturated NaCl, then the solvent was removed.

The residue was crystallised from ethyl acetate-methanol affording the title compound (0.77 g, 77%), m.p. 186° C. $^1$H NMR (DMSO-d$_6$, HMDSO), 6:3.67 (s, 3H); 6.49 (d, J=16.0 Hz, 1H); 6.72–8.03 (m, 9H); 9.14 (br s, 1H); 9.91 (s, 1H); 10.85 (br s, 1H). HPLC analysis on Symmetry C$_{18}$ column: impurities 2.5% (column size 3.9×150 mm; mobile phase acetonitrile—0.1M phosphate buffer (pH 2.5), 30:70; sample concentration 0.25 mg/ml; flow rate 1.0 ml/min; detector UV 220 nm). Anal. Calcd for C$_{16}$H$_{16}$N$_2$O$_5$S, %: C, 55.16; H, 4.63; N, 8.04; S, 9.20. Found, %: C, 55.07; H, 4.60; N, 7.94; S, 9.01.

Example 16

3-(3-p-Tolylsulfamoyl-phenyl)-acrylic acid methyl ester (4d)

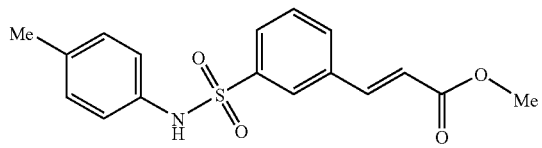

A solution of 3-(3-chlorosulfonylphenyl)acrylic acid methyl ester (3) (2.0 g, 7.23 mmol) in dioxane (10 ml) was added to a mixture of 4-methylaniline (0.77 g, 7.23 mmol) in dioxane (20 ml) and NaHCO$_3$ (1.2 g, 14.5 mmol) in water (20 ml), and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with dichloromethane-ethyl acetate (20:1, v/v) as eluent. The obtained product was washed with diethyl ether to give the title compound (1.9 g, 79%). $^1$H NMR (DMSO-d$_6$, HMDSO), δ: 2.16 (3H, s); 3.69 (3H, s); 6.65 (1H, d, J=16.0 Hz); 7.00 (4H, s); 7.49–8.11 (5H, m); 10.14 (1H, br s).

Example 17

3-(3-p-Tolylsulfamoyl-phenyl)-acrylic acid (5d)

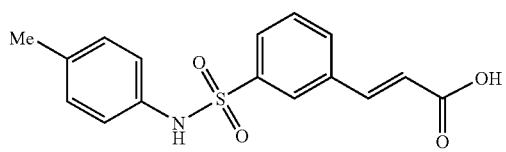

To a suspension of 3-(3-p-tolylsulfamoyl-phenyl)-acrylic acid methyl ester (4d) (0.89 g, 2.70 mmol) in methanol (12 ml) 1N NaOH solution (8.10 ml, 8.10 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over $P_2O_5$ to give the title compound as a white solid (0.75 g, 87%).

Example 18

3-(3-p-Tolylsulfamoyl-phenyl)-acryloyl chloride (6d)

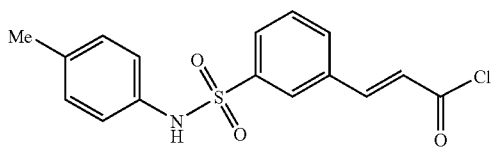

To a suspension of 3-(3-p-tolylsulfamoyl-phenyl)-acrylic acid (5d) (0.75 g, 2.36 mmol) in dichloromethane (10.0 ml) oxalyl chloride (0.62 ml, 7.08 mmol) and one drop of dimethylformamide were added. The reaction mixture was stirred at 40° C. for one hour and concentrated under reduced pressure to give crude title compound (0.79 g).

Example 19

N-Hydroxy-3-(3-p-tolylsulfamoyl)-phenyl)-acrylamide (7d) (PX106508)

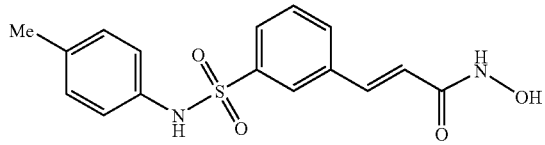

To a suspension of hydroxylamine hydrochloride (0.82 g, 11.80 mmol) in tetrahydrofuran (10.0 ml) a saturated $NaHCO_3$ solution (12.0 ml) was added and the resultant mixture was stirred at ambient temperature for 10 min. To the reaction mixture a solution of 3-(3-p-tolylsulfamoyl)-phenyl)acryloyl chloride (6d) (0.79 g) in tetrahydrofuran (12.0 ml) was added and the mixture was stirred at ambient temperature for one hour. The reaction mixture was partitioned between ethyl acetate and 2N HCl. The organic layer was washed successively with water and saturated NaCl, and the solvent was removed.

The residue was crystallised from ethyl acetate giving the title compound (0.67 g, 85%), m.p. 200° C. $^1$H NMR (DMSO-$d_6$, HMDSO) δ: 2.16 (s, 3H); 6.47 (d, 1H, J=16.0 Hz); 6.98 (s, 4H); 7.29–7.98 (m, 5H); 9.09 (br s, 1H); 10.09 (s, 1H); 10.76 (br s, 1H). HPLC analysis on Zorbax SB—$C_{18}$ column: impurities 4% (column size 4.6×150 mm; mobile phase acetonitrile—0.1% $H_3PO_4$, gradient from 40 to 100%; sample concentration 0.6 mg/ml; flow rate 1.5 ml/min; detector UV 270 nm). Anal. Calcd for $C_{16}H_{16}N_2O_4S$, %: C, 57.82; H, 4.85; N, 8.43. Found, %: C, 57.61; H, 4.93; N, 8.16.

Example 20

3-[3-(4-Bromo-phenylsulfamoyl-phenyl)]-acrylic acid methyl ester (4e)

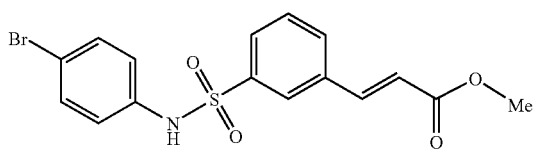

A solution of 3-(3-chlorosulfonylphenyl)-acrylic acid methyl ester (3) (1.85 g, 6.50 mmol) in dioxane (10 ml) was added to a mixture of 4-bromoaniline (1.12 g, 6.50 mmol) in dioxane (20 ml) and $NaHCO_3$ (1.10 g, 13.09 mmol) in water (15 ml), and the resultant solution was stirred at room temperature for one hour. The reaction mixture was evaporated and the residue was partitioned between ethyl acetate and 2N HCl. The organic layer was washed successively with water, saturated NaCl, and dried ($Na_2SO_4$). The solvent was removed and the residue was chromatographed on silica gel with dichloromethane-ethyl acetate (20:1, v/v) as eluent. The obtained product was washed with diethyl ether to give the title compound (1.62 g, 63%). $^1$H NMR (DMSO-$d_6$, HMDSO), δ: 3.76 (3H, s); 6.69 (1H, d, J=16.0 Hz); 6.98–7.23 (2H, m); 7.32–8.07 (7H, m); 10.47 (1H, br s).

Example 21

3-[(3-(4-Bromo-phenylsulfamoyl-phenyl))]-acrylic acid (5e)

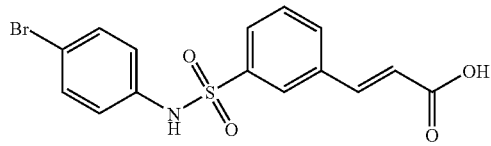

To a suspension of 3-[3-(4-bromo-phenylsulfamoyl-phenyl)]-acrylic acid methyl ester (4e) (0.80 g, 2.02 mmol) in methanol (10 ml) 1N NaOH solution (6.00 ml, 6.00 mmol) was added and the resultant mixture was stirred at ambient temperature overnight. The reaction mixture was partitioned between ethyl acetate and water. The aqueous layer was acidified with 2N HCl and stirred for 30 min. The precipitated solid was filtered, washed with water and dried in desiccator over $P_2O_5$ to give the title compound as a white solid (0.64 g, 84%).

Example 22

3-[3-(4-Bromo-phenylsulfamoyl-phenyl))]-acryloyl chloride (6e)

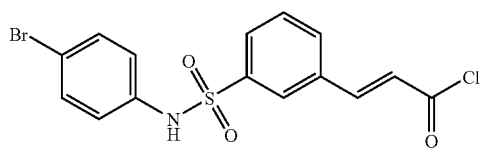

To a suspension of 3-[3-(4-bromo-phenylsulfamoyl-phenyl)]-acrylic acid (5e) (0.64 g, 1.67 mmol) in dichloromethane (8.0 ml) oxalyl chloride (0.44 ml, 5.02 mmol) and one drop of dimethylformamide were added. The reaction mixture was stirred at 40° C. for one hour and concentrated under reduced pressure to give crude title compound (0.67 g).

Example 23

N-Hydroxy-3-[3-(4-bromo-phenylsulfamoyl)-phenyl)]-acrylamide (7e) (PX106509)

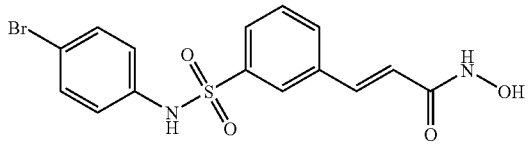

To a suspension of hydroxylamine hydrochloride (0.58 g, 8.35 mmol) in tetrahydrofuran (8.0 ml) a saturated NaHCO₃ solution (8.0 ml) was added and the resultant mixture was stirred at ambient temperature for 10 min. To the reaction mixture a 3-[3-(4-bromo-phenylsulfamoyl)-phenyl)]-acryloyl chloride (6e) (0.67 g) solution in tetrahydrofuran (8.0 ml) was added and stirred at ambient temperature for one hour. The reaction mixture was partitioned between ethyl acetate and 2N HCl. The organic layer was washed successively with water and saturated NaCl, and the solvent was removed.

The residue was crystallised from ethyl acetate giving the title compound (0.52 g, 78%), m.p. 204° C. $^1$H NMR (DMSO-d₆, HMDSO), δ: 6.49 (d, 1H, J=16.0 Hz); 7.05 (d, 2H, J=9.0 Hz); 7.34–7.98 (m, 7H); 9.09 (br s, 1H); 10.47 (s, 1H); 10.80 (br s, 1H). HPLC analysis on Zorbax SB—C₁₈ column: impurities 5% (column size 4.6×150 mm; mobile phase acetonitrile—0.1% H₃PO₄, gradient from 40 to 100%; sample concentration 0.9 mg/ml; flow rate 1.5 ml/min; detector UV 270 nm). Anal. Calcd for $C_{15}H_{13}BrN_2O_4S$, %: C, 45.35; H, 3.30; N, 7.05. Found, %: C, 45.73; H, 3.33; N, 6.81.

Example 24

3-[3-(4-Chloro-phenylsulfamoyl-phenyl)]-acrylic acid methyl ester (4f)

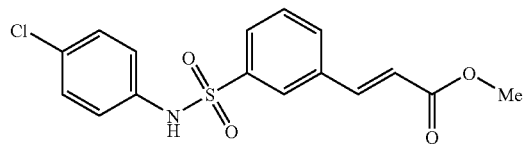

A solution of 3-(3-chlorosulfonylphenyl)acrylic acid methyl ester (3) (1.10 g, 4.22 mmol) in dioxane (10 ml) was added to a mixture of 4-chloroaniline (0.53 g, 4.22 mmol) in dioxane (10 ml) and NaHCO₃ (0.50 g, 5.95 mmol) in water (10 ml), and the resultant solution was stirred at room temperature for one hour. The reaction mixture was evaporated and the residue was partitioned between ethyl acetate and 2N HCl. The organic layer was washed successively with water, saturated NaCl, and dried (Na₂SO₄). The solvent was removed and the residue was chromatographed on silica gel with dichloromethane-ethyl acetate (20:1, v/v) as eluent. The obtained product was washed with diethyl ether to give the title compound (1.01 g, 71%).

Example 25

3[(3-(4-Chloro-phenylsulfamoyl-phenyl)]-acrylic acid (5f)

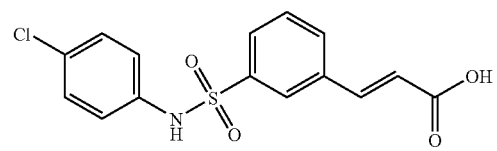

To a suspension of 3-[3-(4-chloro-phenylsulfamoyl-phenyl)]-acrylic acid methyl ester (4f) (0.77 g, 2.12 mmol) in methanol (10 ml) 1N NaOH solution (6.57 ml, 6.57 mmol) was added and the resultant solution was stirred at ambient temperature overnight. The reaction mixture was partitioned between ethyl acetate and water. The aqueous layer was acidified with 2N HCl and stirred for 30 min. The precipitated solid was filtered, washed with water and dried in desiccator over P₂O₅ to give the title compound as a white solid (0.64 g, 86%).

Example 26

3-[3-(4-Chloro-phenylsulfamoyl-phenyl)]-acryloyl chloride (6f)

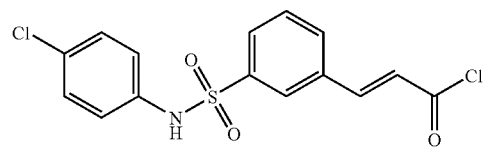

To a suspension of 3-[3-(4-chloro-phenylsulfamoyl-phenyl)]-acrylic acid (5f) (0.64 g, 1.89 mmol) in dichloromethane (8.0 ml) oxalyl chloride (0.50 ml, 5.68 mmol) and one drop of dimethylformamide were added. The reaction mixture was stirred at 40° C. for one hour and concentrated under reduced pressure to give crude title compound (0.65 g).

Example 27

N-Hydroxy-3-[3-(4-chloro-phenylsulfamoyl)-phenyl)]-acrylamide (7f) (PX106510)

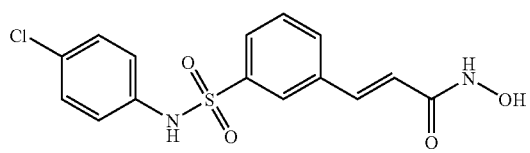

To a suspension of hydroxylamine hydrochloride (0.66 g, 9.45 mmol) in tetrahydrofuran (12.0 ml) a saturated NaHCO$_3$ solution (8.0 ml) was added and the resultant mixture was stirred at ambient temperature for 10 min. To the reaction mixture a 3-[3-(4-chloro-phenylsulfamoyl)-phenyl)]-acryloyl chloride (6f) (0.65 g) solution in tetrahydrofuran (8.0 ml) was added and the mixture was stirred at ambient temperature for one hour. The reaction mixture was partitioned between ethyl acetate and 2N HCl. The organic layer was washed successively with water and saturated NaCl, and the solvent was removed.

The residue was crystallised from acetonitrile giving the title compound (0.47 g, 75%), m.p. 198° C. $^1$H NMR (DMSO-d$_6$, HMDSO), δ: 6.49 (d, 1H, J=16.0 Hz); 6.98–8.05 (m, 9H); 9.16 (br s, 1H); 10.49 (s, 1H); 10.85 (s, 1H). HPLC analysis on Zorbax SB—C$_{18}$ column: impurities 5% (column size 4.6×150 mm; mobile phase acetonitrile—0.1% H$_3$PO$_4$, gradient from 30 to 100%; sample concentration 0.2 mg/ml; flow rate 1.5 ml/min; detector UV 270 nm). Anal. Calcd for C$_{15}$H$_{13}$ClN$_2$O$_4$S, %: C, 51.07; H, 3.71; N, 7.94; S, 9.09. Found, %: C, 50.96; H, 3.62; N, 7.76; S, 9.00.

Example 28

3-(3-Benzylsulfamoyl-phenyl)-acrylic acid methyl ester (4g)

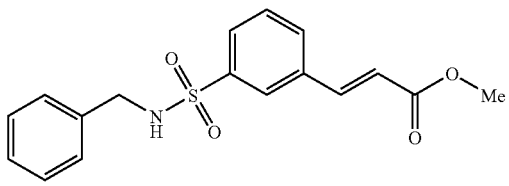

A solution of 3-(3-chlorosulfonylphenyl)acrylic acid methyl ester (3) (0.40 g, 1.53 mmol) in dioxane (5.0 ml) was added to a mixture of 4-benzylamine (0.17 ml, 1.53 mmol) in dioxane (1.0 ml) and NaHCO$_3$ (0.26 g, 3.06 mmol) in water (3.0 ml), and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (2:1, v/v) as eluent. The obtained product was washed with diethyl ether to give the title compound (0.29 g, 57%).

Example 29

3-(3-Benzylsulfamoyl-phenyl)acrylic acid (5g)

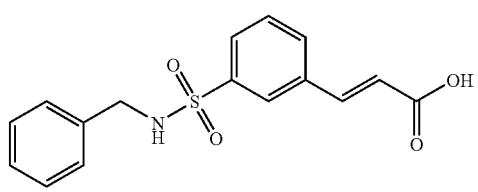

To a suspension of 3-(3-benzylsulfamoyl-phenyl)-acrylic acid methyl ester (4g) (0.29 g, 0.87 mmol) in methanol (4.5 ml) 1N NaOH solution (2.60 ml, 2.60 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over P$_2$O$_5$ to give the title compound as a white solid (0.22 g, 81%). $^1$H NMR (DMSO-d$_6$, HMDSO), δ: 4.05 (2H, d, J=6.4 Hz); 6.60 (1H, d, J=16.0 Hz); 7.27 (4H, s), 7.52–8.09 (6H, m); 8.20 (1H, t, J=6.4 Hz); 12.58 (1H, br s).

Example 30

3-(3-Benzylsulfamoyl-phenyl)-acryloyl chloride (6g)

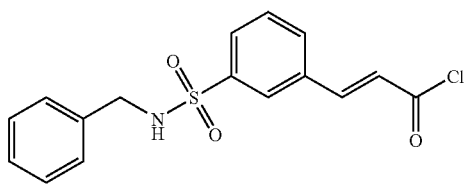

To a suspension of 3-(3-(benzylsulfamoyl-phenyl)-acrylic acid (5g) (0.16 g, 0.52 mmol) in dichloromethane (2.0 ml) oxalyl chloride (0.16 ml, 1.79 mmol) and one drop of dimethylformamide were added. The reaction mixture was stirred at 40° C. for one hour and concentrated under reduced pressure to give crude title compound (0.17 g).

Example 31

N-Hydroxy-3-(3-benzylsulfamoyl)phenyl)-acrylamide (7g) (PX106511)

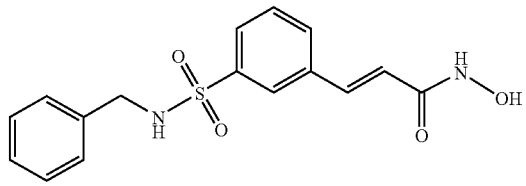

To a suspension of hydroxylamine hydrochloride (0.18 g, 2.60 mmol) in tetrahydrofuran (3.0 ml) a saturated NaHCO$_3$ solution (2.5 ml) was added and the resultant mixture was stirred at ambient temperature for 10 min. To the reaction mixture a 3-(3-benzylsulfamoyl)-phenyl)-acryloyl chloride (6g) (0.17 g) solution in tetrahydrofuran (2.0 ml) was added and stirred at ambient temperature for one hour. The reaction mixture was partitioned between ethyl acetate and 2N HCl. The organic layer was washed successively with water and saturated NaCl, and the solvent was removed.

The residue was crystallised from ethyl acetate giving the title compound (0.12 g, 68%), m.p. 179° C. $^1$H NMR (DMSO-d$_6$, HMDSO), δ: 4.02 (d, 2H, J=6.4 Hz); 6.53 (d, 1H, J=16.0 Hz); 7.25 (s, 5H); 7.39–8.03 (m, 5H); 8.20 (t, 1H, J=6.4 Hz); 9.12 (br s, 1H); 10.80 (br s, 1H). HPLC analysis on Zorbax SB—C$_{18}$ column: impurities 5% (column size 4.6×150 mm; mobile phase acetonitrile—0.1% H$_3$PO$_4$, gradient from 30 to 100%; sample concentration 0.5 mg/ml; flow rate 1.5 ml/min; detector UV 230 nm). Anal. Calcd for C$_{16}$H$_{16}$N$_2$O$_4$S, %: C, 57.82; H, 4.85; N, 8.43; S, 9.6. Found, %: C, 57.59; H, 4.82; N, 8.14; S, 9.6.

Example 32

3-(3-Phenethylsulfamoyl-phenyl)-acrylic acid methyl ester (4h)

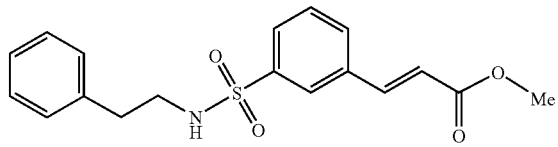

A solution of 3-(3-chlorosulfonylphenyl)acrylic acid methyl ester (3) (0.40 g, 1.53 mmol) in dioxane (5.0 ml) was added to a mixture of 4-phenethylamine (0.19 ml, 1.53 mmol) in dioxane (1.0 ml) and NaHCO$_3$ (0.26 g, 3.06 mmol) in water (3.0 ml) and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographel on silica gel with petroleum ether-ethyl acetate (2:1, v/v) as eluent. The obtained product was washed with diethyl ether to give the title compound (0.43 g, 82%). $^1$H NMR (DMSO-d$_6$, HMDSO), δ: 2.69 (2H, m); 2.98 (2H, m); 3.72 (3H, s); 6.72 (1H, d, J=16.0 Hz); 7.05–7.43 (5H, m); 7.54–8.14 (6H, m).

Example 33

3-(3-Phenethylsulfamoyl-phenyl)-acrylic acid (5h)

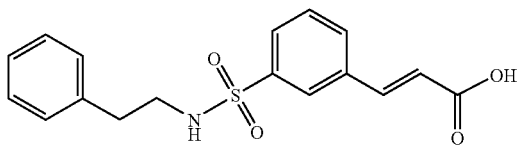

To a suspension of 3-(3-phenethylsulfamoyl-phenyl)-acrylic Acid Methyl Ester (4h) (0.20 g, 0.58 mmol) in methanol (3.0 ml) 1N NaOH solution (1.75 ml, 1.75 mmol) was added and the resultant solution was stirred at ambient temperature overnight. The reaction mixture was partitioned between ethyl acetate and water. The aqueous layer was acidified with 2N HCl solution and extracted with ethyl acetate. The organic layer was washed successively with water, saturated NaCl, and dried (Na$_2$SO$_4$). The solvent was removed and the residue was washed with ether to give the title compound as a white solid (0.15 g, 77%).

Example 34

3-(3-Phenethylsulfamoyl-phenyl)-acryloyl chloride (6h)

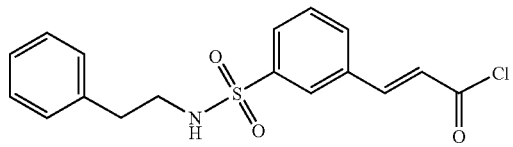

To a suspension of 3-(3-phenethylsulfamoyl-phenyl)-acrylic acid (5h) (0.15 g, 0.45 mmol) in dichloromethane (2.0 ml) oxalyl chloride (0.14 ml, 1.57 mmol) and one drop of dimethylformamide were added. The reaction mixture was stirred at 40° C. for one hour and concentrated under reduced pressure to give crude title compound (0.16 g).

Example 35

N-Hydroxy-3-(3-phenethylsulfamoyl)-phenyl)-acrylamide (7h) (PX106512.

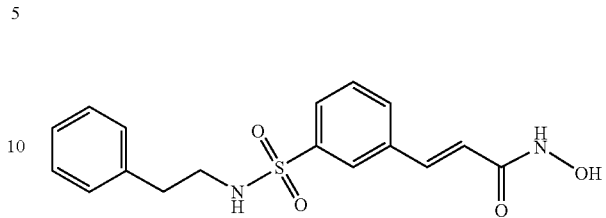

To a suspension of hydroxylamine hydrochloride (0.16 g, 2.25 mmol) in tetrahydrofuran (3.0 ml) a saturated NaHCO$_3$ solution (2.0 ml) was added and the resultant mixture was stirred at ambient temperature for 10 min. To the reaction mixture a 3-(3-phenethylsulfamoyl)-phenyl)-acryloyl chloride (6h) (0.16 g) solution in tetrahydrofuran (2.0 ml) was added and stirred at ambient temperature for one hour. The reaction mixture was partitioned between ethyl acetate and 2N HCl. The organic layer was washed successively with water and saturated NaCl, and the solvent was removed.

The residue was crystallised from dichloromethane-ether giving the title compound (0.10 g, 66%), m.p. 114° C. $^1$H NMR (DMSO-d$_6$, HMDSO), δ: 2.67 (m, 2H); 3.00 (m, 2H); 6.55 (d, 1H, J=16.0 Hz); 7.00–8.05 (m, 11H); 9.12 (br s, 1H); 10.78 (br s, 11H). HPLC analysis on Zorbax SB—C$_{18}$ column: impurities 5% (column size 4.6×150 mm; mobile phase acetonitrile—0.1% H$_3$PO$_4$, gradient from 30 to 100%; sample concentration 1.0 mg/ml; flow rate 1.5 ml/min; detector: UV 230 nm). Anal. Calcd for C$_{17}$H$_{18}$N$_2$C$_4$S, %: C, 58.94; H, 5.24; N, 8.09; S, 9.26. Found, %: C, 58.81; H, 5.16; N, 8.00; S, 9.05.

Example 36

3-[3-(3-Methoxy-phenylsulfamoyl)phenyl]-acrylic acid methyl ester (4i)

A solution of 3-(3-chlorosulfonylphenyl)-acrylic acid methyl ester (3) (0.4 g, 1.53 mmol) in dioxane (5 ml) was added to a mixture of 3-methoxyphenylamine (0.189 g, 1.53 mmol) in dioxane (1 ml) and NaHCO$_3$ (0.25 g, 3.06 mmol) in water (3 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (2:1, v/v) as eluent. The obtained product was washed with diethyl ether to give the title compound (0.44 g, 82%) as a white solid. $^1$H NMR (DMSO-d$_6$, HMDSO), δ: 3.60 (3H, s), 3.71 (3H, s); 6.52–6.74 (3H, m); 6.63 (1H, d, J=16.0 Hz); 7.07 (1H, m); 7.43–8.05 (5H, m); 10.27 ppm (1H, br s).

Example 37

3-[3-(3-Methoxy-phenylsulfamoyl)-phenyl]-acrylic acid (5i)

To a suspension of 3-[3-(3-methoxyphenyl-sulfamoyl)-phenyl]-acrylic acid methyl ester (4i) (0.42 g, 1.2 mmol) in methanol (5.5 ml) 1N NaOH solution (3.6 ml, 3.6 mmol)

was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over $P_2O_5$. The title compound was obtained as a white solid (0.38 g, 95%). $^1$H NMR DMSO-$d_6$, HMDSO), δ 3.65 (3H, s); 6.40–6.78 (4H, m); 7.16 (1H, m); 7.45–8.09 (5H, m); 10.32 (1H, br s).

Example 38

3-[3-(3-Methoxy-phenylsulfamoyl)-phenyl]-acryloyl chloride (6i)

To a suspension of 3-[3-(3-methoxyphenyl-sulfamoyl)-phenyl]-acrylic acid (5i) (0.38 g, 1.14 mmol) in dichloromethane (4 ml) oxalyl chloride (0.3 ml, 3.43 mmol) and one drop of dimethylformamide were added. The reaction mixture was stirred at 40° C. for one hour and concentrated under reduced pressure to give crude title compound (0.40 g, 100%).

Example 39

N-Hydroxy-3-[3-(3-methoxy-phenylsulfamoyl)-phenyl]-acrylamide (7i) (PX117712)

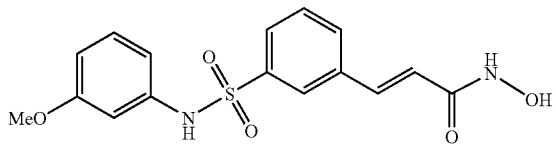

To a suspension of hydroxylamine hydrochloride (0.39 g, 5.7 mmol) in tetrahydrofuran (6 ml) a saturated $NaHCO_3$ solution (4.5 ml) was added and the resultant mixture was stirred at ambient temperature for 10 min. To the reaction mixture a solution of crude 3-[3-(3-methoxy-phenylsulfamoyl)-phenyl]-acryloyl chloride (6i) (0.40 g) in tetrahydrofuran (4 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from ethyl acetate-acetonitrile affording the title compound (0.15 g, 39%) as a lightly pink crystals. M.p. 137° C. $^1$H NMR (DMSO-$d_6$, HMDSO) δ: 3.65 (3H, s); 6.38–6.78 (4H, m); 6.98–7.27 (1H, m); 7.34–8.03 (5H, m); 9.14 (1H, br s); 10.30 (1H, s); 10.83 (1H, br s). HPLC analysis on Symmetry $C_8$ column: impurities 5% (column size 3.9×150 mm; mobile phase acetonitrile—0.1M phosphate buffer (pH 2.5), 40:60; sample concentration 0.5 mg/ml; flow rate 1.2 ml/min; detector UV 254 nm). Anal. Calcd for $C_{16}H_{16}N_2O_5S$ containing 1% of inorganic impurities, %: C, 54.67; H, 4.50; N, 8.09. Found, %: C, 54.61; H, 4.58; N, 7.96.

Example 40

3-[3-(Biphenyl-2-ylsulfamoyl)-phenyl]-acrylic acid methyl ester (4j)

Using an analogous method, the title compound was obtained from 3-(3-chlorosulfonylphenyl)acrylic acid methyl ester (3) and 2-aminobiphenyl, as a white solid, yield 48%, $^1$H NMR (DMSO-$d_6$, HMDSO), δ: 3.65 (3H, s); 6.56 (1H, d, J=16.0 Hz); 6.93–8.02 (14H, m); 9.54 (1H, br s).

Example 41

3-[3-(Biphenyl-2-ylsulfamoyl)phenyl]-acrylic acid (5j)

Using an analogous method, the title compound was obtained from 3-[3-(biphenyl-2-ylsulfamoyl)-phenyl]-acrylic acid methyl ester (4j) and sodium hydroxide, yield 89%. $^1$H NMR (DMSO-$d_6$, HMDSO), δ: 6.47 (1H, d, J=16.0 Hz); 6.98–8.03 (14H, m); 9.54 (1H, br s).

Example 42

3-[3-(Biphenyl-2-ylsulfamoyl)-phenyl]-acryloyl chloride (6j)

Using an analogous method, the title compound was obtained from 3-[3-(biphenyl-2-ylsulfamoyl)-phenyl]-acrylic acid (5j) and oxalyl chloride in a form of a crude product, yield ca. 97%.

Example 43

3-[3-(Biphenyl-2-ylsulfamoyl)phenyl]-N-hydroxyacrylamide (7j) (PX117713)

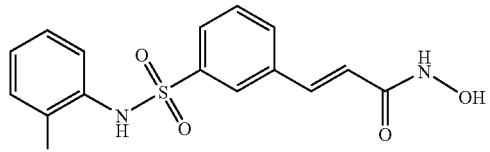

Using an analogous method, the title compound was obtained from 3-[3-(biphenyl-2-ylsulfamoyl)-phenyl]-acryloyl chloride (6j) and hydroxylamine hydrochloride, yield 47%, foam. $^1$H NMR (DMSO-$d_6$, HMDSO), δ: 6.43 (1H, d, J=16.0 Hz); 6.94–7.85 (14H, m); 9.07 (1H, br s); 9.58 (1H, br s); 10.78 (1H, br s). HPLC analysis on Symmetry $C_8$ column: impurities 6.4% (column size 3.9×150 mm; mobile phase acetonitrile-0.1M phosphate buffer, pH 2.5, 50:50; sample concentration 0.5 mg/ml; flow rate 1.0 ml/min; detector UV 254 nm). Anal. Calcd for $C_{21}H_{18}N_2O_4S*0.5H_2O$, %: 62.52; H, 4.75; N, 6.94. Found, %: C, 62.58; H, 4.66; N, 6.65.

Example 44

3-[3-(Biphenyl-4-ylsulfamoyl)-phenyl]-acrylic acid methyl ester (4k)

Using an analogous method, the title compound was obtained from 3-(3-chlorosulfonylphenyl)-acrylic acid methyl ester (3) and 4-aminobiphenyl as a white solid, yield 88%, $^1$H NMR (DMSO-$d_6$, HMDSO), δ: 3.71 (3H, s); 6.67 (1H, d, J=16.0 Hz); 7.07–8.09 (14H, m); 10.36 ppm (1H, br s).

Example 45

3-[3-(Biphenyl-4-ylsulfamoyl)-phenyl]-acrylic acid (5k)

Using an analogous method, the title compound was obtained from 3-[3-(biphenyl-4-ylsulfamoyl)-phenyl]-acrylic acid methyl ester (4k) and sodium hydroxide, yield 88%. $^1$H NMR (DMSO-$d_6$, HMDSO), δ: 6.56 (1H, d, J=16.0 Hz); 7.09–8.12 (14H, m); 10.38 ppm (1H, br s).

Example 46

3-[3-(Biphenyl-4-ylsulfamoyl)-phenyl]-acryloyl chloride (6k)

Using an analogous method, the title compound was obtained from 3-[3-(biphenyl-4-ylsulfamoyl)-phenyl]-acrylic acid (5k) and oxalyl chloride in a form of a crude product, yield ca. 98%.

Example 47

3-[3-(Biphenyl-4-ylsulfamoyl)-phenyl]-N-hydroxy-acrylamide (7k) (PX117715)

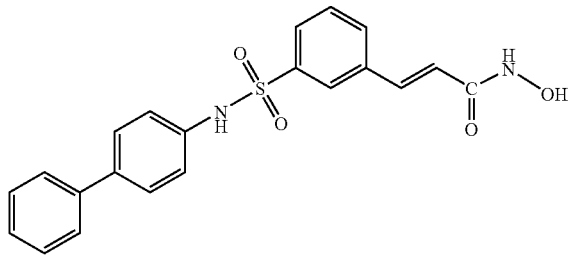

Using an analogous method, the title compound was obtained from 3-[3-(biphenyl-4-ylsulfamoyl)-phenyl]-acryloyl chloride (6k) and hydroxylamine hydrochloride, yield 78%. M.p. 188° C. $^1$H NMR (DMSO-$d_6$, HMDSO), δ: 6.49 (1H, d, J=16.0 Hz); 7.07–8.07 (14H, m); 9.09 (1H, br s); 10.35 (1H, br s); 10.80 (1H, br s). HPLC analysis on Symmetry $C_8$ column: impurities 2.2% (column size 3.9× 150 mm; mobile phase acetonitril-0.1 M phosphate buffer, pH 2.5, 40:60; sample concentration 0.5 mg/ml; flow rate 1.5 ml/min; detector UV 254 nm). Anal. Calcd for $C_{21}H_{18}N_2O_4S$*0.2$H_2O$, %: C, 63.37; H, 4.66; N, 7.04. Found, %: C, 63.42; H, 4.57; N, 6.95.

Example 48

3-[3-(3-Bromo-phenylsulfamoyl)phenyl]-acrylic acid methyl ester (4l)

Using an analogous method, the title compound was obtained from 3-(3-chlorosulfonylphenyl)-acrylic acid methyl ester (3) and 3-bromoaniline as a white solid, yield 79%, $^1$H NMR (DMSO-$d_6$, HMDSO), δ: 3.73 (3H, s); 6.65 (1H, d, J=16.0 Hz); 6.98–7.34 (4H, m); 7.49–8.07 (5H, m); 10.52 ppm (1H, br s).

Example 49

3-[3-(3-Bromo-phenylsulfamoyl)-phenyl]-acrylic acid (5l)

Using an analogous method, the title compound was obtained from 3-[3-(3-bromo-phenylsulfamoyl)-phenyl]-acrylic acid methyl ester (4l) and sodium hydroxide, yield 85%.

Example 50

3-[3-(3-Bromo-phenylsulfamoyl)phenyl]-acryloyl chloride (6l)

Using an analogous method, the title compound was obtained from 3-[3-(3-bromo-phenylsulfamoyl)-phenyl]-acrylic acid (5l) and oxalyl chloride in a form of a crude product, yield ca. 98%.

Example 51

3-[3-(3-Bromo-phenylsulfamoyl)phenyl]-N-hydroxy-acrylamide (7l) (PX117734)

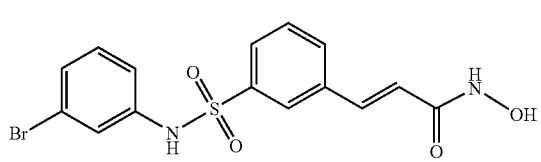

Using an analogous method, the title compound was obtained from 3-[3-(3-bromo-phenylsulfamoyl)-phenyl]-acryloyl chloride (6l) and hydroxylamine hydrochloride, yield 24%. M.p. 135.5–136.5° C. $^1$H NMR (DMSO-$d_6$, HMDSO), δ: 6.53 (1H, d, J=15.6 Hz); 7.07–7.28 (4H, m); 7.48 (1H, d, J=15.6 Hz); 7.60 (1H, t, J=7.6 Hz); 7.72 (1H, d, J=7.6 Hz); 7.81 (1H, d, J=7.6 Hz); 7.94 (1H, s); 9.15 (1H, br s); 10.60 (1H, br s); 10.84 (1H, br s). HPLC analysis on Symmetry $C_8$ column: impurities 2.5% (column size 3.9× 150 mm; mobile phase acetonitrile—0.1M phosphate buffer, pH 2.5, 50:50; sample concentration 0.5 mg/ml; flow rate 0.8 ml/min; detector UV 220 nm). Anal. Calcd for $C_{15}H_{13}BrN_2O_4S$, %: C, 45.35; H, 3.30; N, 7.05. Found, C, 45.38; H, 3.03; N, 6.96.

Example 52

3-[3-(Indan-2-ylsulfamoyl)-phenyl]-acrylic acid methyl ester (4m)

Using an analogous method, the title compound was obtained from 3-(3-chlorosulfonylphenyl)-acrylic acid methyl ester (3) and 2-aminoindane hydrochloride as a white solid, yield 80%, $^1$H NMR (DMSO-$d_6$, HMDSO), δ: 2.65–2.93 (4H, m); 3.71 (3H, s); 3.93 (1H, m); 6.71 (1H, d, J=16.0 Hz); 7.09 (4H, s); 7.49–8.27 ppm (6H, m).

Example 53

3-[3-(Indan-2-ylsulfamoyl)-phenyl]-acrylic acid (5m)

Using an analogous method, the title compound was obtained from 3-[3-(indan-2-ylsulfamoyl)phenyl]-acrylic acid methyl ester (4m) and sodium hydroxide, yield 86%.

Example 54

3-[3-(Indan-2-ylsulfamoyl)-phenyl]-acryloyl chloride (6m)

Using an analogous method, the title compound was obtained from 3-[3-(indan-2-ylsulfamoyl)-phenyl]-acrylic acid (5m) and oxalyl chloride in a form of a crude product, yield ca. 98%.

Example 55

N-Hydroxy-3-[3-(indan-2-ylsulfamoyl)-phenyl]-acrylamide (7m) (PX117735)

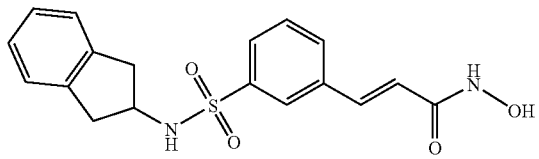

Using an analogous method, the title compound was obtained from 3-[3-(indan-2-ylsulfamoyl)-phenyl]-acryloyl chloride (6m) and hydroxylamine hydrochloride, yield 63%. M.p. 164° C. (from acetonitrile). $^1$H NMR (DMSO-$d_6$, HMDSO), δ: 2.72 (2H, dd, J=15.8 and 7.0 Hz); 2.94 (2H, dd, J=15.8 and 7.4 Hz); 3.83–4.03 (1H, m); 6.59 (1H, d, J=15.9 Hz); 7.04–7.19 (4H, m); 7.55 (1H, d, J=15.9 Hz); 7.66 (1H, t, J=7.7 Hz); 7.84 (1H, d, J=7.2 Hz); 7.84 (1H, d, J=8.2 Hz); 8.02 (1H, s); 8.11 (1H, br d, J=6.6 Hz); 9.15 (1H, br s); 10.84 (1H, br s). HPLC analysis on Symmetry $C_8$ column: impurities 1% (column size 3.9×150 mm; mobile phase acetonitrile—0.1M phosphate buffer, pH 2.5, 45:55; sample concentration 0.5 mg/ml; flow rate 1.0 ml/min; detector UV 254 nm). Anal. Calcd for $C_{18}H_{18}N_2O_4S*0.25H_2O$, %: C, 59.57; H, 5.14; N, 7.72. Found C, 59.51; H, 5.01; N, 7.54.

Example 56

3-[3-(Benzhydryl-sulfamoyl)-phenyl]-acrylic acid methyl ester (4n)

Using an analogous method, the title compound was obtained from 3-(3-chlorosulfonylphenyl)-acrylic acid methyl ester (3) and aminodiphenylmethane as a white solid, yield 73%, $^1$H NMR (DMSO-$d_6$, HMDSO), δ: 3.72 (3H, s); 5.60 (1H, d, J=9.0 Hz); 6.52 (1H, d, J=16.0 Hz); 7.00–7.83 (15H, m); 8.76 ppm (1H, d, J=9.0 Hz).

Example 57

3-[3-(Benzhydryl-sulfamoyl)-phenyl]-acrylic acid (5n)

Using an analogous method, the title compound was obtained from 3-[3-(benzhydryl-sulfamoyl)-phenyl]-acrylic acid methyl ester (4n) and sodium hydroxide, yield 78%. $^1$H NMR (DMSO-$d_6$, HMDSO), δ: 5.60 (1H, d, J=9.0 Hz); 6.43 (1H, d, J=16.0 Hz); 6.94–7.83 (15H, m); 8.80 ppm (1H, d, J=9.0 Hz).

Example 58

3-[3-(Benzhydryl-sulfamoyl)-phenyl]-acryloyl chloride (6n)

Using an analogous method, the title compound was obtained from 3-[3-(benzhydryl-sulfamoyl)-phenyl]-acrylic acid (5n) and oxalyl chloride in a form of a crude product, yield ca. 98%.

Example 59

3-[3-(Benzhydryl-sulfamoyl)-phenyl]-N-hydroxy-acrylamide (7n) (PX117773)

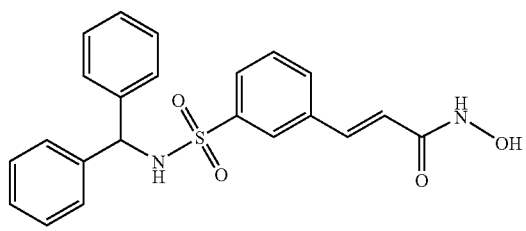

Using an analogous method, the title compound was obtained from 3-[3-(benzhydryl-sulfamoyl)-phenyl]-acryloyl chloride (6n) and hydroxylamine hydrochloride, yield 68%. M.p. 180° C. $^1$H NMR (DMSO-$d_6$, HMDSO), δ: 5.60 (1H, d, J=9.0 Hz); 6.43 (1H, d, J=16.0 Hz); 6.98–7.83 (15H, m); 8.85 (1H, d, J=9.0 Hz); 9.14 (1H, br s); 10.80 (1H, br s). HPLC analysis on Symmetry $C_8$ column: impurities <1% (column size 3.9×150 mm; mobile phase acetonitrile—0.1M phosphate buffer, pH 2.5, 45:55; sample concentration 0.5 mg/ml; flow rate 1.4 ml/min; detector UV 220 nm). Anal. Calcd for $C_{22}H_{20}N_2O_4S$, %: C, 64.69; H, 4.94; N, 6.86. Found C, 64.60; H, 4.94; N, 6.77.

Example 60

3-[3-(1,2-Diphenyl-ethylsulfamoyl)-phenyl]-acrylic acid methyl ester (4o)

Using an analogous method, the title compound was obtained from 3-(3-chlorosulfonylphenyl)-acrylic acid methyl ester (3) and 1,2-diphenylamine as a white solid, yield 96%, $^1$H NMR (DMSO-$d_6$, HMDSO), δ: 2.83 (2H, d, J=9.0 Hz); 3.78 (3H, s); 4.49 (1H, q, J=9.0 Hz); 6.54 (1H, d, J=16.0 Hz); 6.94–7.83 (15H, m); 8.38 ppm (1H, d, J=9.0 Hz).

Example 61

3-[3-(1,2-Diphenyl-ethylsulfamoyl)phenyl]-acrylic acid (5o)

Using an analogous method, the title compound was obtained from 3-[3-(1,2-diphenyl-ethylsulfamoyl)-phenyl]-acrylic acid methyl ester (4o) and sodium hydroxide, yield 70%. $^1$H NMR (DMSO-$d_6$, HMDSO), δ: 2.85 (2H, d, J=9.0

Hz); 4.49 (1H, q, J=9.0 Hz); 6.40 (1H, d, J=16.0 Hz); 6:85–7.78 (15H, m); 8.38 ppm (1H, d, J=9.0 Hz).

Example 62

3-[3-(1,2-Diphenyl-ethylsulfamoyl)-phenyl]-acryloyl chloride (6o)

Using an analogous method, the title compound was obtained from 3-[3-(1,2-diphenyl-ethylsulfamoyl)-phenyl]-acrylic acid (5o) and oxalyl chloride in a form of a crude product, yield ca. 98%.

Example 63

3-[3-(1,2-Diphenyl-ethylsulfamoyl)-phenyl]-N-hydroxy-acrylamide (7o) (PX117774)

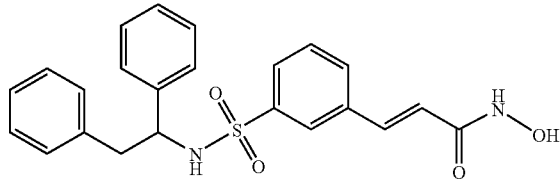

Using an analogous method, the title compound was obtained from 3-[3-(1,2-diphenyl-ethylsulfamoyl)-phenyl]-acryloyl chloride (6o) and hydroxylamine hydrochloride, yield 72%. M.p. 150° C. $^1$H NMR (DMSO-$d_6$, HMDSO), δ: 2.83 (2H, d, J=9.0 Hz); 4.47 (1H, q, J=9.0 Hz); 6.38 (1H, d, J=16.0 Hz); 6.92–7.65 (15H, m); 8.38 (1H, d, J=9.0 Hz); 9.12 (1H, br s); 10.80 (1H, br s). HPLC analysis on Symmetry $C_8$ column: impurities 1% (column size 3.9×150 mm; mobile phase acetonitrile—0.1M phosphate buffer, pH 2.5, 45:55; sample concentration 0.5 mg/ml; flow rate 1.4 ml/min; detector UV 220 nm). Anal. Calcd for $C_{23}H_{22}N_2O_4S$, %: C, 65.39; H, 5.25; N, 6.63. Found C, 64.97; H, 5.14; N, 6.57.

Example 64

3-[3-(4-Trifluoromethoxy-phenylsulfamoyl)-phenyl]-acrylic acid methyl ester (4p)

Using an analogous method, the title compound was obtained from 3-(3-chlorosulfonylphenyl)-acrylic acid methyl ester (3) and 4-trifluoromethoxyaniline as a white solid, yield 82%, $^1$H NMR (CDCl$_3$, TMS) δ: 3.82 (3H, s); 6.47 (1H, d, J=16.0 Hz); 6.89–7.98 ppm (10H, m).

Example 65

3-[3-(4-Trifluoromethoxy-phenylsulfamoyl)phenyl]-acrylic acid (5p)

Using an analogous method, the title compound was obtained from 3-[3-(4-trifluoromethoxy-phenylsulfamoyl)-phenyl]-acrylic acid methyl ester (4p) and sodium hydroxide, yield 94%. $^1$H NMR (DMSO-$d_6$, HMDSO), δ: 6.54 (1H, d, J=16.0 Hz); 7.23 (4H, s) 7.47–8.14 (6H, m); 10.54 ppm (1H, br s).

Example 66

3-[3-(4-trifluoromethoxy-phenylsulfamoyl)-phenyl]-acryloyl chloride (6p)

Using an analogous method, the title compound was obtained from 3-[3-(4-trifluoromethoxy-phenylsulfamoyl) phenyl]-acrylic acid (5p) and oxalyl chloride in a form of a crude product, yield ca. 98%.

Example 67

N-Hydroxy-3-[3-(4-trifluoromethoxy-phenylsulfamoyl)-phenyl]-acrylamide (7p) (PX117775)

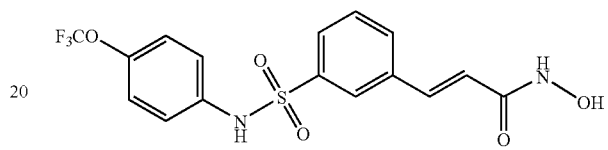

Using an analogous method, the title compound was obtained from 3-[3-(4-trifluoromethoxy-phenylsulfamoyl) phenyl]-acryloyl chloride (6p) and hydroxylamine hydrochloride, yield 46%. M.p. 131° C. $^1$H NMR (DMSO-$d_6$, HMDSO), δ: 6.49 (1H, d, J=16.0 Hz); 7.03–8.05 (9H, m); 8.98 (1H, br s); 10.54 (1H, br s); 10.78 (1H, br s). HPLC analysis on Symmetry $C_8$ column: impurities 3.5% (column size 3.9×150 mm; mobile phase acetonitrile—0.1M phosphate buffer, pH 2.5, 45:55; sample concentration 0.5 mg/ml; flow rate 1.4 m/min; detector UV 220 nm). Anal. Calcd for $C_{16}H_{13}F_3N_2O_5S$, %: C, 47.76; H, 3.26; N, 6.96. Found C, 47.68; H, 3.15; N, 6.91.

Example 68

3-[3-(3,4,5-Trimethoxy-benzylsulfamoyl)-phenyl]-acrylic acid methyl ester (4q)

Using an analogous method, the title compound was obtained from 3-(3-chlorosulfonylphenyl)acrylic acid methyl ester (3) and 3,4,5-trimethoxybenzylamine as a white solid, yield 85%, $^1$H NMR (CDCl$_3$, TMS) δ: 3.72 (6H, s); 3.78 (3H, s); 3.83 (3H, s); 4.14 (2H, d, J=8.0 Hz); 5.07 (1H, t, J=8.0 Hz); 6.38 (2H, s); 6.49 (1H, d, J=16.0 Hz); 7.36–4.07 ppm (5H, m).

Example 69

3-[3-(3,4,5-Trimethoxy-benzylsulfamoyl)-phenyl]-acrylic acid (5q)

Using an analogous method, the title compound was obtained from 3-[3-(3,4,5-trimethoxy-benzylsulfamoyl)-phenyl]-acrylic acid methyl ester (4q) and sodium hydroxide, yield 90%. $^1$H NMR (DMSO-$d_6$, HMDSO), δ: 3.52 (3H, s); 3.65 (6H, s); 3.98 (2H, d, J=8.0 Hz); 6.43 (2H, s); 6.49 (1H, d; J=16.0 Hz); 7.38–8.27 ppm (6H, m).

Example 70

3-[3-(3,4,5-Trimethoxy-benzylsulfamoyl)-phenyl]-acryloyl chloride (6q)

Using an analogous method, the title compound was obtained from 3-[3-(3,4,5-trimethoxy-benzylsulfamoyl)-phenyl]-acrylic acid (5q) and oxalyl chloride in a form of a crude product, yield ca. 100%.

Example 71

N-Hydroxy-3-[3-(3,4,5-trimethoxy-benzylsulfamoyl)-phenyl]-acrylamide (7q) (PX117778)

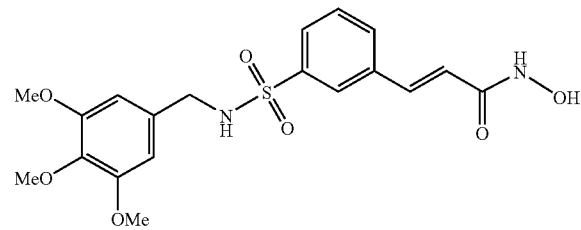

Using an analogous method, the title compound was obtained from 3-[3-(3,4,5-trimethoxy-benzylsulfamoyl)phenyl]-acryloyl chloride (6q) and hydroxylamine hydrochloride, yield 19%, foam. $^1$H NMR (DMSO-$d_6$, HMDSO), δ: 3.54 (3H, s); 3.65 (6H, s); 3.98 (2H, m); 6.46 (2H, s); 6.56 (1H, d, J=15.0 Hz); 7.32–7.98 (5H, m); 8.18 (1H, br t, J=5.5 Hz); 9.12 (1H, br s); 10.78 (1H, br s). HPLC analysis on Symmetry $C_8$ column: impurities 7% (column size 3.9×150 mm; mobile phase acetonitrile—0.1M phosphate buffer, pH 2.5, 30:70; sample concentration 0.5 mg/ml; flow rate 1.4 ml/min; detector UV 220 nm). Anal. Calcd for $C_{19}H_{22}N_2O_7S$* 0.25 EtOAc, containing 1.6% of inorganic impurities, %: C, 53.18; H, 5.36; N, 6.20.
Found C, 53.13; H, 5.31; N, 6.02.

Example 72

3-{3-[2-(3,4-Dimethoxy-phenyl)-ethylsulfamoyl]-phenyl}-acrylic acid methyl ester (4r)

Using an analogous method, the title compound was obtained from 3-(3-chlorosulfonylphenyl)acrylic acid methyl ester (3) and 2-(3,4-dimethoxyphenyl)ethylamine as a white solid, yield 81%, $^1$H NMR (CDCl$_3$, TMS) δ: 2.72 (2H, t, J=7.0 Hz); 3.20 (2H, q, J=7.0 Hz); 3.80 (9H, s); 4.49 (1H, t, J=7.0 Hz); 6.36–6.87 (4H, m); 7.38–8.00 ppm (5H, m).

Example 73

3-{3-[2-(3,4-Dimethoxy-phenyl)-ethylsulfamoyl]-phenyl}-acrylic acid (5r)

Using an analogous method, the title compound was obtained from 3-{3-[2-(3,4-dimethoxy-phenyl)-ethylsulfamoyl]-phenyl}-acrylic acid methyl ester (4r) and sodium hydroxide, yield 87%. $^1$H NMR (DMSO-$d_6$, HMDSO), δ: 2.58 (2H, t, partially overlapped with a signal of DMSO); 2.83–3.20 (2H, m, partially overlapped with a water signal of DMSO); 3.72 (6H, s); 6.43–0.89 (4H, m); 7.49–8.09 ppm (6H, m).

Example 74

3-{3-[2-(3,4-Dimethoxy-phenyl)-ethylsulfamoyl]-phenyl}-acryloyl chloride (6r)

Using an analogous method, the title compound was obtained from 3-{3-[2-(3,4-dimethoxy-phenyl)ethylsulfamoyl]-phenyl}-acrylic acid (5r) and oxalyl chloride in a form of a crude product, yield ca. 100%.

Example 75

3-{3-[2-(3,4-Dimethoxy-phenyl)-ethylsulfamoyl]-phenyl}N-hydroxy-acrylamide (7r) (PX117779)

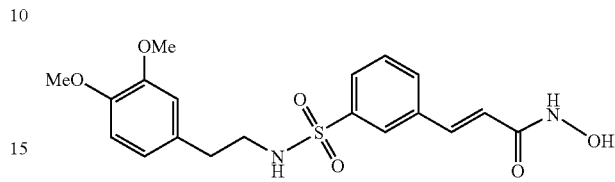

Using an analogous method, the title compound was obtained from 3-{3-[2-(3,4-dimethoxy-phenyl)-ethylsulfamoyl]-phenyl}-acryloyl chloride (6r) and hydroxylamine hydrochloride, yield 32%, foam. $^1$H NMR (DMSO-$d_6$, HMDSO), δ: 2.58 (2H, t, partially overlapped with a signal of DMSO, J=7.0 Hz); 2.85–3.16 (2H, m); 3.67 (6H, s); 6.38–6.94 (4H, m); 7.38–8.05 (6H, m); 9.16 (1H, br s); 10.76 (1H, br s). HPLC analysis on Symmetry $C_8$ column: impurities 3.6% (column size 3.9×150 mm; mobile phase acetonitrile-0.1 M phosphate buffer, pH 2.5, 30:70; sample concentration 0.5 mg/ml; flow rate 1.5 ml/min; detector UV 254 nm). Anal. Calcd for $C_{19}H_{22}N_2O_6S$ containing 4.3% of inorganic impurities, %: C, 53.73; H, 5.22; N, 6.60. Found C, 53.75; H, 5.24; N, 6.45.

Example 76

3-[3-(3,4-Dimethoxy-phenylsulfamoyl)-phenyl]-acrylic acid methyl ester (4s)

Using an analogous method, the title compound was obtained from 3-(3-chlorosulfonylphenyl)-acrylic acid methyl ester (3) and 3,4-dimethoxyaniline as a white solid, yield 90%, $^1$H NMR (DMSO-$d_6$, HMDSO), δ: 3.60 (3H, s); 3.65 (3H, s); 3.76 (3H, s); 6.45–6.85 (4H, m); 7.47–8.05 (5H, m); 9.92 ppm (1H, br s).

Example 77

3-[3-(3,4-Dimethoxy-phenylsulfamoyl)-phenyl]-acrylic acid (5s)

Using an analogous method, the title compound was obtained from 3-[(3,4-dimethoxy-phenylsulfamoyl)-phenyl]-acrylic acid methyl ester (4s) and sodium hydroxide, yield 90%. $^1$H NMR (DMSO-$d_6$, HMDSO), δ: 3.60 (3H, s); 3.65 (3H, s); 6.29–6.89 (4H, m); 7.47–8.09 (5H, m); 9.93 ppm (1H, br s).

Example 78

3-[3-(3,4-Dimethoxy-phenylsulfamoyl)-phenyl]-acryloyl chloride (6s)

Using an analogous method, the title compound was obtained from 3-[3-(3,4-dimethoxy-phenylsulfamoyl)-phenyl]-acrylic acid (5s) and oxalyl chloride in a form of a crude product, yield ca. 100%.

Example 79

3-[3-(3,4-Dimethoxy-phenylsulfamoyl)-phenyl]-N-hydroxy-acrylamide (7s) (PX117782)

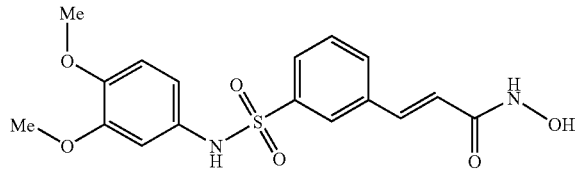

Using an analogous method, the title compound was obtained from 3-[3-(3,4-dimethoxy-phenylsulfamoyl)-phenyl]-acryloyl chloride (VI$_{12}$) and hydroxylamine hydrochloride, yield 45%. M.p. 191° C. $^1$H NMR (DMSO-d$_6$, HMDSO), δ: 3.60 (3H, s); 3.65 (3H, s); 6.34–6.87 (4H, m); 7.32–8.03 (5H, m); 9.09 (1H, br s); 9.92 (1H, br s); 10.80 (1H, br s). HPLC analysis on Symmetry C$_8$ column: impurities 6% (column size 3.9×150 mm; mobile phase acetonitrile—0.1M phosphate buffer, pH 2.5, 30:70; sample concentration 0.5 mg/ml; flow rate 1.3 ml/min; detector UV 220 nm). Anal. Calcd for C$_{17}$H$_{18}$N$_2$O$_6$S, %: C, 53.96; H, 4.79; N, 7.40. Found C, 53.84; H, 4.78; N, 7.25.

Example 80

3-[3-(4-Difluoromethoxy-phenylsulfamoyl)-phenyl]-acrylic acid methyl ester (4t)

Using an analogous method, the title compound was obtained from 3-(3-chlorosulfonylphenyl)acrylic acid methyl ester (3) and 4-difluoromethoxyphenylamine as a white solid, yield 79%.

Example 81

3-[3-(4-Difluoromethoxy-phenylsulfamoyl)-phenyl]-acrylic acid (5t)

Using an analogous method, the title compound was obtained from 3-[3-(4-difluoromethoxy-phenylsulfamoyl)-phenyl]-acrylic Acid Methyl Ester (4t) and sodium hydroxide, yield 71%. $^1$H NMR (DMSO-d$_6$, HMDSO), δ: 6.56 (1H, d, J=16.0 Hz); 7.11 (4H, s); 7.47–8.04 (6H, m).

Example 82

3-[3-(4-Difluoromethoxy-phenylsulfamoyl)-phenyl]-acryloyl chloride (6t)

Using an analogous method, the title compound was obtained from 3-[3-(4-difluoromethoxy-phenylsulfamoyl)-phenyl]-acrylic acid (5t) and oxalyl chloride, ca. yield of the crude product 98% (yellow oil).

Example 83

3-[3-(4-Difluoromethoxy-phenylsulfamoyl)-phenyl]-N-hydroxy-acrylamide (7t) (PX11789)

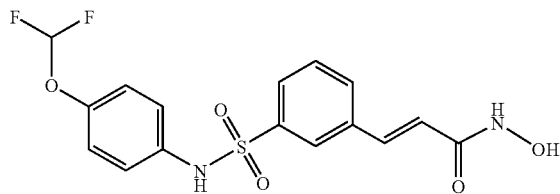

Using an analogous method, the title compound was obtained from 3-[3-(4-difluoromethoxy-phenylsulfamoyl)-phenyl]-acryloyl chloride (6t) and hydroxylamine hydrochloride, yield 65%. M.p. 91–93° C. $^1$H NMR (DMSO-d$_6$, HMDSO) δ: 6.47 (1H, d, J=16.0 Hz); 6.96 (4H, s); 7.31–7.93 (6H, m). HPLC analysis on Symmetry C$_8$ column: impurities 3.5% (column size 3.9×150 mm; mobile phase acetonitrile—0.1M phosphate buffer (pH 2.5), 40:60; detector UV 220 nm; flow rate 1.4 ml/min; sample concentration 0.5 mg/ml). Anal. Calcd for C$_{16}$H$_{14}$N$_2$O$_5$F$_2$S*0.2H$_2$O*0.5 EtOH, %: C, 49.68; H, 4.27; N, 6.82; S, 7.80. Found, %: C, 49.46; H, 3.95; N, 6.65; S, 7.39.

Example 84

3-[3-(9-Ethyl-9H-carbazol-3-ylsulfamoyl)phenyl]-acrylic acid methyl ester (4u)

Using an analogous method, the title compound was obtained from 3-(3-chlorosulfonylphenyl)-acrylic acid methyl ester (3) and 9-ethyl-9H-carbazol-3-ylamine in a form of yellow solid, yield 86%. $^1$H NMR (CDCl$_3$, HMDSO), δ: 1.38 (3H, t, J=7.0 Hz); 3.78 (3H, s); 4.33 (2H, q, J=7.0 Hz); 6.33 (1H, d, J=16.0 Hz); 6.58 (1H, s); 7.02–8.04 (12H, m).

Example 85

3-[3-(9-Ethyl-9H-carbazol-3-ylsulfamoyl)-phenyl]-acrylic acid (5u)

Using an analogous method, the title compound was obtained from 3-[3-(9-ethyl-9H-carbazol-3-ylsulfamoyl)-phenyl]-acrylic acid methyl ester (4u) and sodium hydroxide, yield 65%.

Example 86

3-[3-(9-Ethyl-9H-carbazol-3-ylsulfamoyl)phenyl]-acryloyl chloride (6u)

Using an analogous method, the title compound was obtained from 3-[3-(9-ethyl-9H-carbazol-3-ylsulfamoyl)-phenyl]-acrylic acid (5u) and oxalyl chloride, ca. yield of the crude product 98% (yellow oil).

Example 87

3-[3-(9-Ethyl-9H-carbazol-3-ylsulfamoyl)-phenyl]-N-hydroxy-acrylamide (7u) (PX117798)

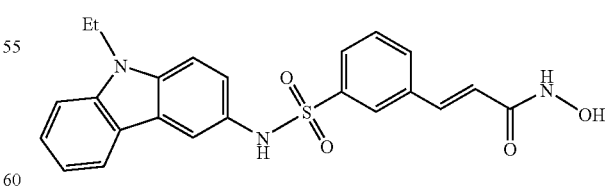

Using an analogous method, the title compound was obtained from 3-[3-(9-ethyl-9H-carbazol-3-ylsulfamoyl)-phenyl]-acryloyl chloride (6u) and hydroxylamine hydrochloride, yield 42%. M.p. 130–133° C. $^1$H NMR (DMSO-d$_6$, HMDSO) δ: 1.20 (3H, t, J=6.6 Hz); 4.34 (2H, q, J=6.6 Hz); 6.42 (11H, d, J=16 Hz); 6.93–8.07 (0.13H, m); 9.07 (1H, br.

s); 10.3 (1H, br. s). HPLC analysis on Symmetry $C_8$ column: impurities 10% (column size 3.9×150 mm; mobile phase acetonitrile—0.1M phosphate buffer (pH 2.5), 40:60; detector UV 254 nm; flow rate 1.0 ml/min; sample concentration 1 mg/ml). Anal. Calcd for $C_{23}H_{21}N_3O_4S*1H_2O$, %: C, 60.91; H, 5.11; N, 9.27; S, 7.07. Found, %: C, 61.01; H, 5.15; N, 8.75; S, 6.65.

Example 88

3-[3-(2,6-Difluoro-phenylsulfamoyl)-phenyl]-acrylic acid methyl ester (4v)

Using an analogous method, the title compound was obtained from 3-(3-chlorosulfonylphenyl)acrylic acid methyl ester (3) and 2,4-difluorophenylamine in a form of yellow crystals, yield 70%. $^1$H NMR (CDCl$_3$, HMDSO), δ: 3.82 (3H, s); 6.49 (1H, d, J=16.0 Hz); 7.00 (1H, t, J=8 Hz); 5.89–6.69 (7H, m).

Example 89

3-[3-(2,4-Difluoro-phenylsulfamoyl)phenyl]-acrylic acid (5v)

Using an analogous method, the title compound was obtained from 3-[3-(2,4-difluoro-phenylsulfamoyl)-phenyl]-acrylic acid methyl ester (4v) and sodium hydroxide in a form of white solid, yield 66%. $^1$H NMR (DMSO-d$_6$, HMDSO), δ: 6.56 (1H, d, J=16.0 Hz); 6.96–8.09 (9H, m); 10.13 (1H, br. s).

Example 90

3-[3-(2,4-Difluoro-phenylsulfamoyl)-phenyl]-acryloyl chloride (6v)

Using an analogous method, the title compound was obtained from 3-[3-(2,4-difluoro-phenylsulfamoyl)-phenyl]-acrylic acid (5v) and oxalyl chloride, ca. yield of the crude product 98% (yellow oil).

Example 91

3-[3-(2,4-Difluoro-phenylsulfamoyl)-phenyl]-N-hydroxy-acrylamide (7v) (PX117790)

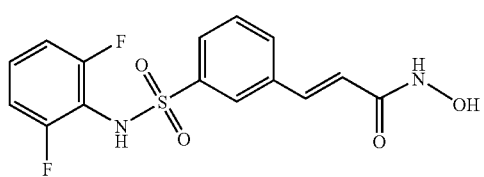

Using an analogous method, the title compound was obtained from 3-[3-(2,4-difluoro-phenylsulfamoyl)-phenyl]-acryloyl chloride (6v) and hydroxylamine hydrochloride, yield 26%. M.p. 79–82° C. $^1$H NMR (DMSO-d$_6$, HMDSO) δ: 6.47 (1H, d, J=16.0 Hz); 6.89–7.89 (8H, m); 9.07 (1H, br. s); 10.02 (1H, br. s); 10.73 (1H, br s). HPLC analysis on Symmetry $C_8$ column: impurities 7.5% (column size 3.9×150 mm; mobile phase acetonitrile—0.1M phosphate buffer (pH 2.5), 35:65; detector UV 220 nm; flow rate 1.4 ml/min; sample concentration 0.5 mg/ml). Anal. Calcd for $C_{15}H_{12}N_2O_4F_2S*1$ EtOH, %: C, 51.00; H, 4.53; N, 7.00; S, 8.01. Found, %: C, 50.84; H, 4.60; N, 6.78; S, 7.76.

Example 92

3-[3-(2-Fluoro-phenylsulfamoyl)-phenyl]-acrylic acid methyl ester (4w)

Using an analogous method, the title compound was obtained from 3-(3-chlorosulfonyl-phenyl)acrylic acid methyl ester (3) and 2-fluorophenylamine in a form of white crystals, yield 65%. $^1$H NMR (CDCl$_3$, HMDSO), δ: 3.80 (3H, s); 6.44 (1H, d, J=16.0 Hz); 6.71–7.22 (4H, m); 7.44–7.93 (6H, m).

Example 93

3-[3-(2-Fluoro-phenylsulfamoyl)-phenyl]-acrylic acid (5w)

Using an analogous method, the title compound was obtained from 3-[3-(2-fluoro-phenylsulfamoyl)-phenyl]-acrylic acid methyl ester (4w) and sodium hydroxide, yield 50%. $^1$H NMR (DMSO-d$_6$, HMDSO), δ: 6.58 (1H, d, J=16.0 Hz); 7.04–7.36 (4H, m); 7.51–8.09 (5H, m).

Example 94

3-[3-(2-Fluoro-phenylsulfamoyl)-phenyl]-acryloyl chloride (6w)

Using an analogous method, the title compound was obtained from 3-[3-(2-fluoro-phenylsulfamoyl)-phenyl]-acrylic acid (5w) and oxalyl chloride, ca. yield of the crude product 98% (yellow oil).

Example 95

3-[3-(2-Fluoro-phenylsulfamoyl)-phenyl]-N-hydroxy-acrylamide (7w) (PX117787)

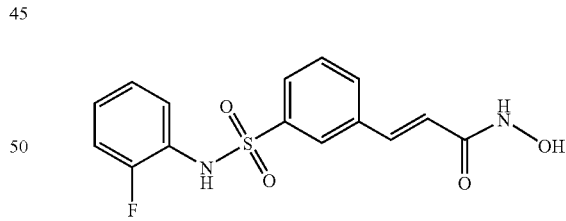

Using an analogous method, the title compound was obtained from 3-[3-(2-fluoro-phenylsulfamoyl)phenyl]-acryloyl chloride (6w) and hydroxylamine hydrochloride, yield 30%. M.p. 102–103° C. $^1$H NMR (DMSO-d$_6$, HMDSO), δ: 6.44 (1H, d, J=16.0 Hz); 6.96–7.24 (4H, m); 7.43 (1H, d, J=16.0 Hz); 7.49–7.91 (4H, m); 9.04 (1H, br s); 10.13 (1H, br s); 10.73 (1H, br s). HPLC analysis on Symmetry $C_8$ column: impurities 4.5% (column size 3.9× 150 mm; mobile phase acetonitrile—0.1M phosphate buffer (pH 2.5), 35:65; detector UV 220 nm; flow rate 1.4 ml/min; sample concentration 0.5 mg/ml). Anal. Calcd for $C_{15}H_{13}N_2O_4FS*0.9$ EtOH, %: C, 53.41; H, 4.91; N, 7.41. Found, %: C, 53.79; H, 4.62; N, 7.13.

Example 96

3-[3-(3-Fluoro-phenylsulfamoyl)-phenyl]-acrylic acid methyl ester (4x)

Using an analogous method, the title compound was obtained from 3-(3-chlorosulfonyl-phenyl)acrylic acid methyl ester (3) and 3-fluorophenylamine in a form of white crystals, yield 80%. $^1$H NMR (CDCl$_3$, HMDSO), δ: 3.78 (3H, s); 6.42 (1H, d, J=16.0 Hz); 6.64–8.02 (10H m).

Example 97

3-[3-(3-Fluoro-phenylsulfamoyl)-phenyl]-acrylic acid (5x)

Using an analogous method, the title compound was obtained from 3-[3-(3-fluoro-phenylsulfamoyl)-phenyl]-acrylic acid methyl ester (4x) and sodium hydroxide, yield 60%. $^1$H NMR (DMSO-d$_6$, HMDSO), δ: 6.56 (1H, d, J=16.0 Hz); 6.80–7.36 (4H, m); 7.49–8.09 (6H, m).

Example 98

3-[3-(3-Fluoro-phenylsulfamoyl)-phenyl]-acryloyl chloride (6x)

Using an analogous method, the title compound was obtained from 3-[3-(3-fluoro-phenylsulfamoyl)-phenyl]-acrylic acid (5x) and oxalyl dichloride, ca. yield of the crude product 99% (yellow oil).

Example 99

3-[3-(3-Fluoro-phenylsulfamoyl)-phenyl]-N-hydroxy-acrylamide (7x) (PX117788)

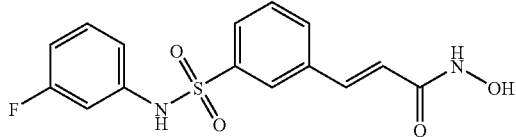

Using an analogous method, the title compound was obtained from 3-[3-(3-fluoro-phenylsulfamoyl)-phenyl]-acryloyl chloride (6x) and hydroxylamine hydrochloride, yield 65%. M.p. 130–133° C. $^1$H NMR (DMSO-d$_6$, HMDSO) δ: 6.52 (1H, d, J=15.8 Hz); 6.75–6.97 (4H, m); 7.17–7.32 (1H, m); 7.47 (1H, d, J=15.8 Hz); 7.58 (1H, t, J=7.8 Hz); 7.67–7.85 (2H, m); 7.94 (1H, s); 9.19 (1H, br s); 10.89 (1H, br s). HPLC analysis on Symmetry C$_8$ column: impurities 5.5% (column size 3.9×150 mm; mobile phase acetonitrile—0.1M phosphate buffer (pH 2.5), 40:60; detector UV 254 nm; flow rate 1.5 ml/min; sample concentration 0.5 mg/ml). Anal. Calcd for C$_{15}$H$_{13}$N$_2$O$_4$FS*0.65 EtOH, %: C, 53.45; H, 4.65; N, 7.65; S, 8.75. Found, %: C, 53.54; H, 4.32; N, 7.37; S, 8.50.

Example 100

3-[3-(2-Methoxy-5-trifluoromethyl-phenylsulfamoyl)-phenyl]-acrylic acid methyl Ester (4y)

Using an analogous method, the title compound was obtained from 3-(3-chlorosulfonylphenyl)-acrylic acid methyl ester (3) and 2-methoxy-5-(trifluoromethyl)aniline as a white solid, yield 55%. $^1$H NMR (CDCl$_3$, HMDSO), δ: 3.68 (3H, s), 3.80 (3H, s); 6.39 (1H, d, J=16.0 Hz); 6.77 (1H, d, J=8.4 Hz); 7.11 (1H, s); 7.20–7.95 ppm (7H, m).

Example 101

3-[3-(2-Methoxy-5-trifluoromethyl-phenylsulfamoyl)-phenyl]-acrylic acid (5y)

Using an analogous method, the title compound was obtained from 3-[3-(2-methoxy-5-trifluoromethyl-phenylsulfamoyl)phenyl]-acrylic acid methyl ester (4y) and sodium hydroxide, yield 80%. $^1$H NMR (DMSO-d$_6$, HMDSO), δ: 3.60 (3H, s); 6.54 (1H, d, J=16.0 Hz); 7.07 (1H, d, J=8.4 Hz); 7.45–7.97 (8H, m); 9.70 ppm (1H, br s).

Example 102

3-[3-(2-Methoxy-5-trifluoromethyl-phenylsulfamoyl)-phenyl]-acryloyl chloride (6y)

Using an analogous method, the title compound was obtained from 3-[3-(2-methoxy-5-trifluoromethyl-phenylsulfamoyl)-phenyl]-acrylic acid (5y) and oxalyl chloride, ca. yield of the crude product 98% (yellow oil).

Example 103

N-Hydroxy-3-[3-(2-methoxy-5-trifluoromethyl-phenylsulfamoyl)-phenyl]-acrylamide (7y) (PX117791)

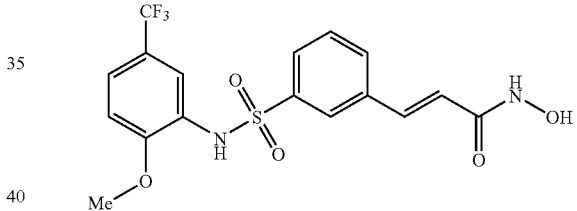

Using an analogous method, the title compound was obtained from 3-[3-(2-methoxy-5-trifluoromethyl-phenylsulfamoyl)-phenyl]-acryloyl chloride (6y) and hydroxylamine hydrochloride, yield 64%. M.p. 207° C. (dec.). $^1$H NMR (DMSO-d$_6$, HMDSO) δ: 3.57 (3H, s); 6.52 (1H, d, J=15.8 Hz); 7.12 (1H, d, J=8.4 Hz); 7.36–8.09 (7H, m); 9.11 (1H, br s); 9.98 (1H, s); 10.82 (1H, s). HPLC analysis on Symmetry C$_8$ column: impurities 1.8% (column size 3.9×150 mm; mobile phase acetonitrile—0.1M phosphate buffer (pH 2.5), 50:50; detector UV 254 nm; flow rate 0.9 ml/min; sample concentration 0.5 mg/ml). Anal. Calcd for C$_{17}$H$_{15}$F$_3$N$_2$O$_5$S, %: C, 49.04; H, 3.63; N, 6.78. Found, %: C, 49.39; H, 3.41; N, 6.66.

Example 104

3-{3-[(Furan-2-ylmethyl)-sulfamoyl]-phenyl)-acrylic acid methyl ester (4z)

Using an analogous method, the title compound was obtained from 3-(3-chlorosulfonylphenyl)-acrylic acid methyl ester (3) and furfurilamine as a white solid, yield 87%. $^1$H NMR (DMSO-d$_6$, HMDSO), δ: 3.73 (3H, s); 4.05 (2H, d, J=6.4 Hz); 6.20 (2H, m); 6.71 (1H, d, J=16.0 Hz); 7.38–8.38 (7H, m).

Example 105

3-{3-[(Furan-2-ylmethyl)-sulfamoyl]-phenyl}-acrylic acid (5z)

Using an analogous method, the title compound was obtained from 3-{3-[(furan-2-ylmethyl)sulfamoyl]-phenyl}-acrylic acid methyl ester (4z) and sodium hydroxide, yield 89%.

Example 106

3-{3-[(Furan-2-ylmethyl)-sulfamoyl]-phenyl}-N-hydroxyacrylamide (7z) (PX117710)

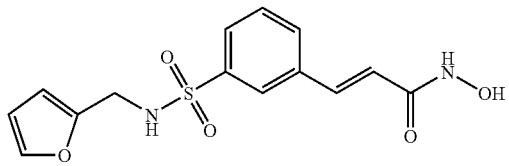

To a solution of 3-{3-[(furan-2-ylmethyl)-sulfamoyl]-phenyl}-acrylic acid (5z) (0.17 g, 0.55 mmol) in tetrahydrofuran (2.0 ml) at 0° C. temperature ethylchloroformate (0.072 g, 0.66 mmol) and triethylamine (0.1 ml, 0.72 mmol) were added and the resulting mixture was stirred for 15 min. To a stirred solution of KOH (0.058 g, 1.04 mmol) in methanol (0.25 ml) a solution of hydroxylamine hydrochloride (0.072 g, 1.04 mmol) in methanol (0.7 ml) was added at 0° C. The mixture was stirred for 15 min., the precipitated KCl was removed and the filtrate was added to the first solution. The reaction mixture was stirred at room temperature for 2 hours. Then the mixture was partitioned between 1N $KH_2PO_4$ solution and ethyl acetate. The organic layer was washed with water, saturated NaCl, and dried ($Na_2SO_4$). The solvent was evaporated and the residue was washed successively with dichloromathane and ethyl acetate affording the title compound (0.057 g, 32%). M.p. 165° C. $^1H$ NMR (DMSO-$d_6$, HMDSO) δ: 4.03 (2H, d, J=6.4 Hz); 6.23 (2H, m); 6.54 (1H, d, J=16.0 Hz); 7.38–8.05 (6H, m); 8.20 (1H, t, J=6.4 Hz); 9.09 (1H, br s); 10.83 (1H, br s). HPLC analysis on Zorbax SB—$C_{18}$ column: impurities 8% (column size 4.6×150 mm; mobile phase methanol—0.1% $H_3PO_4$, gradient from 30 to 90%; detector UV 270 nm; flow rate 1.5 ml/min; sample concentration 1.0 mg/ml). Anal. Calcd for $C_{14}H_{14}N_2O_5S$, %: C, 52.17; H, 4.38; N, 8.69. Found, %: C, 51.87; H, 4.39; N, 8.41.

Example 107

3-(4-(((Phenylmethyl)sulfonyl)amino)phenyl)acrylic acid ethyl ester (9)

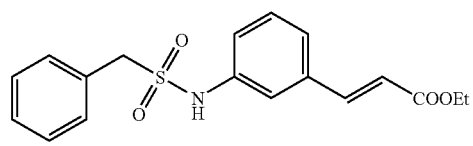

α-Toluenesulfonyl chloride (1.0 g, 5.2 mmol) was added to a mixture of 4-aminocinnamic acid ethyl ester (1.0 g, 5.2 mmol), pyridine (0.42 ml, 5.2 mmol) and dichloromethane (10 ml) and the resultant solution was stirred at ambient temperature for twelve hours. The solution was then heated at reflux for a further eight hours.

The mixture was allowed to cool to ambient temperature and was diluted with dichloromethane (100 ml) and was washed with 10% aqueous citric acid (20 ml), saturated aqueous sodium hydrogen carbonate (20 ml), and water (2×20 ml). The organic extract was dried ($MgSO_4$), filtered and the solvent was removed under reduced pressure.

The crude product was purified by column chromatography on silica gel using a gradient of ethyl acetate B hexane (1:10) to ethyl acetate as the eluent to afford the title compound as a yellow solid (0.80 g, 45%), $t_R$ 5.18 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 368 [M-Na]$^+$.

Example 108

3-(4-(((Phenylmethyl)sulfonyl)amino)phenyl)acrylic acid (10)

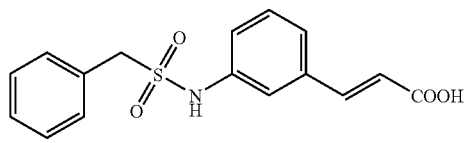

A 1 M aqueous solution of lithium hydroxide (2.9 ml, 2.9 mmol) was added to a solution of 3-(4-(((phenylmethyl)sulfonyl)amino)phenyl)acrylic acid ethyl ester (9) (500 mg, 1.45 mmol) in dioxane (4 ml). The resultant solution was stirred at ambient temperature for two hours. Additional 1 M aqueous lithium hydroxide (2.9 ml, 2.9 mmol) was added and the reaction mixture was stirred at ambient temperature for one hour. The solution was stored at +4° C. for sixteen hours.

The solvent was removed under reduced pressure and ethyl acetate (15 ml) was added to the residue. The resultant mixture was washed with water (2×10 ml). The aqueous extracts were combined and acidified to ~pH 4 with a 1 M aqueous solution of hydrochloric acid. The acidified solution was extracted with ethyl acetate (4×10 ml). The combined organic extracts were washed with water (10 ml), dried ($MgSO_4$) and the solvent was removed under reduced pressure.

The crude product was purified by column chromatography on silica gel using of ethyl acetate as the eluent to afford to afford the title compound as a yellow solid (320 mg, 70%), $t_R$ 4.56 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 316 [M+TFA]$^-$ and 430 [M+TFA]$^-$.

Example 109

3-(4-(((Phenylmethyl)sulfonyl)amino)phenyl)acrylic acid hydroxyamide (11) (PX089343)

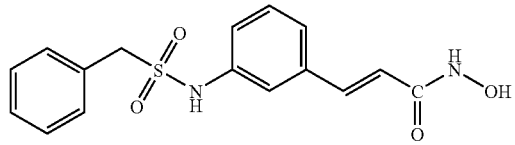

N-Fmoc-hydroxylamine 2-chlorotrityl resin (0.80 g, 0.57 mmol) (Calbiochem-Novabiochem Corp., Nottingham, UK)

was swollen with a solution of piperidine in dichloromethane (20/80, v/v) (5 ml) and then agitated at ambient temperature for two hours. The resin was filtered and was washed with 1-methylpyrrolidinone (5 ml), alternately with methanol (4×5 ml) and dichloromethane (4×5 ml) and finally with diethyl ether (5 ml).

The resin was placed in a reaction vessel and was swollen with dichloromethane (2 ml). The swollen resin was treated with 3-(4-(((Phenylmethyl)sulfonyl)amino)phenyl)acrylic acid (10) (90 mg, 0.28 mmol), 1-hydroxy-7-azabenzotriazole (HOAt) (Aldrich, Dorset, UK) (77 mg, 0.57 mmol), O-(7-azabenzotriazol-1-yl)-N,N,N',N'-tetramethyluronium hexafluorophosphate (HATU) (216 mg, 0.57 mmol) (Aldrich, Dorset, UK), N,N-diisopropylethylamine (198 μl, 1.14 mmol) and a mixture of dichloromethane and N,N-dimethylformamide (4:1, v/v) (5 ml). The resultant mixture was agitated at ambient temperature for sixteen hours.

The resin was filtered and was washed with 1-methylpyrrolidinone (5 ml), alternately with methanol (4×5 ml) and dichloromethane (4×5 ml) and finally with diethyl ether (5 ml). The resin was placed in a reaction vessel and was swollen with dichloromethane (2 ml). The swollen resin was treated with a solution of trifluoroacetic acid in dichloromethane (5/95, v/v) (3 ml) and the resultant mixture was agitated at ambient temperature for ninety minutes. The mixture was filtered and the resin was washed with methanol (2×5 ml). The solvent was removed from the combined filtrates under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water. The title compound was obtained as a white solid (1.2 mg, 14%), $t_R$ 4.11 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 317 [M−H]$^-$ and 311 [M+H]$^-$.

Example 110

3-{3-[(Naphthalen-1-ylmethyl)-sulfamoyl]-phenyl}-acrylic acid methyl ester (14a)

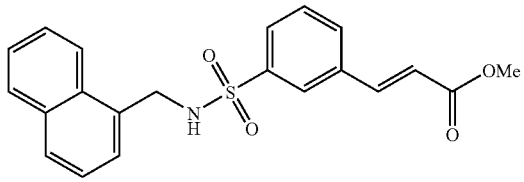

A solution of 3-(3-chlorosulfonylphenyl)acrylic acid methyl ester (3) (0.4 g, 1.53 mmol) in dioxane (5 ml) was added to a mixture of 1-naphthalenemethylamine (0.24 g, 1.53 mmol) in dioxane (1 ml) and NaHCO$_3$ (0.25 g, 3.06 mmol) in water (3 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (2:1, v/v) as eluent. The obtained product was washed with diethyl ether to give the title compound (0.44 g, 76%) as a white solid. $^1$H NMR (DMSO-d$_6$, HMDSO), δ: 3.74 (3H, s); 4.47 (2H, d, J=6.0 Hz); 6.69 (1H, d, J=16.0 Hz); 7.32–8.32 (13H, m).

Example 111

3-{3-[(Naphthalen-1-ylmethyl)-sulfamoyl]-phenyl}-acrylic acid (15a)

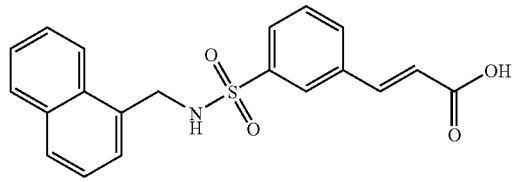

To a suspension of 3-{3-[(naphthalen-1-ylmethyl)-sulfamoyl]-phenyl}-acrylic acid methyl ester (14a) (0.44 g, 1.15 mmol) in methanol (5 ml) 1N NaOH solution (3.45 ml, 3.45 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over P$_2$O$_5$. The title compound was obtained as a white solid (0.32 g, 76%).

Example 112

3-{3-[(Naphthalen-1-ylmethyl)-sulfamoyl]-phenyl}-acryloyl chloride (16a)

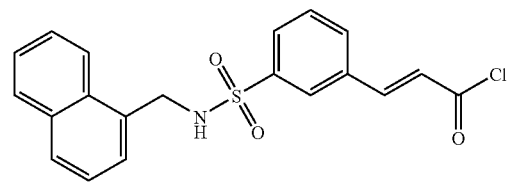

To a suspension of 3-{3-[(naphthalen-1-ylmethyl)-sulfamoyl]-phenyl}-acrylic acid (15a) (0.32 g, 0.87 mmol) in dichloromethane (4 ml) oxalyl chloride (0.22 ml, 2.61 mmol) and one drop of dimethylformamide were added. The reaction mixture was stirred at 40° C. for one hour and concentrated under reduced pressure to give the title compound (0.33 g, 98%).

Example 113

N-Hydroxy-3-{3-[(naphthalen-1-ylmethyl)-sulfamoyl]-phenyl}-acrylamide (17a) (PX117225)

To a suspension of hydroxylamine hydrochloride (0.30 g, 4.35 mmol) in tetrahydrofuran (6 ml) a saturated NaHCO$_3$ solution (4 ml) was added and the resultant mixture was stirred at ambient temperature for 10 min. To the reaction mixture a solution of crude 3-(3-[(naphthalen-1-ylmethyl)-sulfamoyl]-phenyl}-acryloyl chloride (16a) (0.33 g) in tetrahydrofuran (4 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from ethyl acetate-acetonitrile affording the title compound (0.13 g, 40%) as a lightly pink crystals. M.p. 177° C. $^1$H NMR (DMSO-$d_6$, HMDSO) δ: 4.45 (2H, d, J=6.0 Hz); 6.58 (1H, d, J=16.0 Hz); 7.29–8.38 (13H, m); 9.12 (1H, br s); 10.83 (1H, br s). HPLC analysis on Symmetry $C_8$ column: impurities 1.5% (column size 3.9× 150 mm; mobile phase acetonitrile—0.1M phosphate buffer (pH 2.5), 40:60; sample concentration 0.25 mg/ml; flow rate 1.2 ml/min; detector UV 220 nm). Anal. Calcd for $C_{20}H_{18}N_2O_4S$, %: C, 62.54; H, 4.70; N, 7.21. Found, %: C, 62.81; H, 4.74; N, 7.32.

Example 114

3-{3-[(Pyridin-3-ylmethyl)-sulfamoyl]-phenyl}-acrylic acid methyl ester (14b)

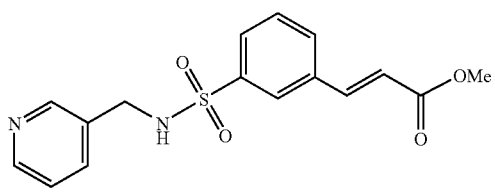

A solution of 3-(3-chlorosulfonylphenyl)acrylic acid methyl ester (3) (0.40 g, 1.53 mmol) in dioxane (5 ml) was added to a mixture of 3-(aminomethyl)pyridine (0.16 g, 1.48 mmol) in dioxane (1 ml) and $NaHCO_3$ (0.37 g, 4.49 mmol) in water (3 ml), and the resultant solution was stirred at room temperature until the completion of the reaction (control by TLC). The reaction mixture was evaporated and the residue was partitioned between ethyl acetate and water. The organic layer was washed successively with water, saturated NaCl, and dried ($Na_2SO_4$). The solvent was removed and the residue was chromatographed on silica gel with dichloromethane-methanol (20:1, v/v) as eluent. The obtained product was washed with diethyl ether to give the title compound (0.35 g, 71%) as a white solid. $^1$H NMR (DMSO-$d_6$, HMDSO), δ: 3.76 (3H, s); 4.09 (2H, d, J=6.0 Hz); 6.72 (1H, d, J=16.2 Hz); 7.29 (1H, dd, J=8.0 and 5.0 Hz); 7.51–8.12 (6H, m); 8.27 (1H, br t, J=6.0 Hz); 8.31–8.50 (2H, m).

Example 115

3-{3-[(Pyridin-3-ylmethyl)-sulfamoyl]-phenyl}-acrylic acid (15b)

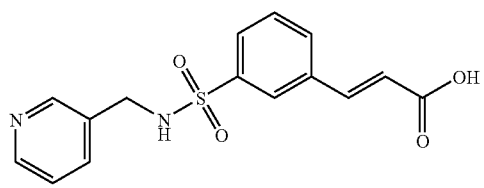

To a suspension of 3-{3-[(pyridin-3-ylmethyl)-sulfamoyl]-phenyl}-acrylic acid methyl ester (14b) (0.35 g, 1.05 mmol) in methanol (4.3 ml) 1N NaOH solution (3.15 ml, 3.15 mmol) was added and the resultant mixture was stirred at ambient temperature overnight. The reaction mixture was partitioned between ethyl acetate and water. The aqueous layer was acidified with 2N HCl solution to pH~5 of the reaction medium and stirred for 30 min. The precipitated solid was filtered, washed with water and dried in desiccator over $P_2O_5$. The title compound was obtained as a white solid (0.28 g, 84%).

Example 116

3-{3-[(Pyridin-3-ylmethyl)-sulfamoyl]-phenyl}-acryloyl chloride (16b)

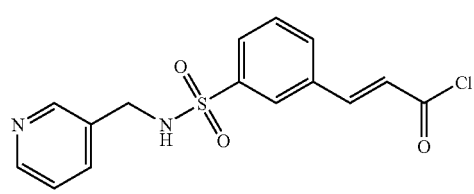

To a suspension of 3-{3-[(pyridin-3-ylmethyl)-sulfamoyl]-phenyl}-acrylic acid (15b) (0.28 g, 0.88 mmol) in dichloromethane (3.5 ml) oxalyl chloride (0.23 ml, 2.64 mmol) and one drop of dimethylformamide were added. The reaction mixture was stirred at 40° C. for one hour and concentrated under reduced pressure to give crude title compound (0.29 g, 98%).

Example 117

N-Hydroxy-3-{3-[(pyridin-3-ylmethyl)-sulfamoyl]-phenyl}-acrylamide (17b) (PX117250)

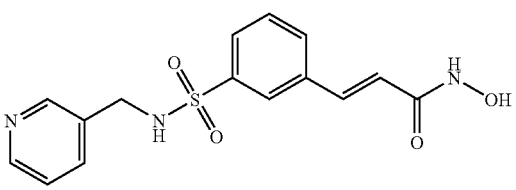

To a suspension of hydroxylamine hydrochloride (0.31 g, 4.40 mmol) in tetrahydrofuran (5 ml) a saturated $NaHCO_3$ solution (6.8 ml) was added and the resultant mixture was stirred at ambient temperature for 10 min. To the reaction mixture a solution of crude 3-{3-[(pyridin-3-ylmethyl)-sulfamoyl]-phenyl}-acryloyl chloride (16b) (0.29 g, 0.86 mmol) in tetrahydrofuran (5 ml) was added and the mixture was stirred at ambient temperature for one hour. The reaction mixture was poured into water, the obtained solution was acidified with 2N HCl to pH~5 of the reaction medium and extracted with ethyl acetate. The organic layer was washed successively with water and saturated NaCl, then the solvent was removed. The residue was washed with hot ethyl acetate and methanol affording the title compound (0.12 g, 37%). M.p. 191° C. $^1$H NMR (DMSO-$d_6$, HMDSO) δ: 4.05 (2H, d, J=6.4 Hz); 6.56 (1H, d, J=16.0 Hz); 7.16–8.05 (7H, m); 8.16–8.49 (3H, m); 9.12 (1H, br s); 10.80 (1H, br s). HPLC analysis on Symmetry $C_{18}$ column: impurities 8% (column size 3.9×150 mm; mobile phase acetonitrile—0.1M phosphate buffer (pH 2.5), 10:90; sample concentration 0.4 mg/ml; flow rate 1.3 ml/min; detector UV 270 nm). Anal. Calcd for $C_{15}H_{15}N_3O_4S$ containing 0.5% of inorganic impurities, %: C, 53.77; H, 4.51; N, 12.54. Found, %: C, 53.72; H, 4.33; N, 12.41.

Example 118

3-[3-(2-Methoxy-phenylsulfamoyl)-phenyl]-acrylic acid methyl ester (14c)

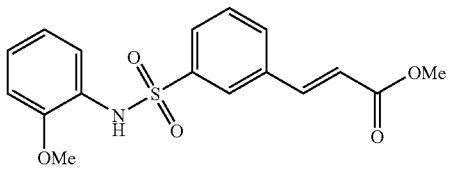

A solution of 3-(3-chlorosulfonylphenyl)acrylic acid methyl ester (3) (0.40 g, 1.53 mmol) in dioxane (5 ml) was added to a mixture of o-anisidine (0.19 g, 1.54 mmol) in dioxane (1 ml) and NaHCO$_3$ (0.26 g, 3.06 mmol) in water (3 ml), and the resultant solution was stirred at room temperature until the completion of the reaction (control by TLC). The reaction mixture was evaporated and the residue was partitioned between ethyl acetate and water. The organic layer was washed successively with water, saturated NaCl, and dried (Na$_2$SO$_4$). The solvent was removed and the residue was chromatographed on silica gel with petroleum ether-ethyl acetate (2:1, v/v) as eluent. The obtained product was washed with diethyl ether to give the title compound (0.42 g, 79%) as a white solid. $^1$H NMR (DMSO-d$_6$, HMDSO), δ: 3.43 (3H, s); 3.72 (3H, s); 6.60 (1H, d, J=16.0 Hz); 6.72–7.27 (4H, m); 7.45–8.12 (5H, m); 9.47 (1H, s).

Example 119

3-[3-(2-Methoxy-phenylsulfamoyl)-phenyl]-acrylic acid (15c)

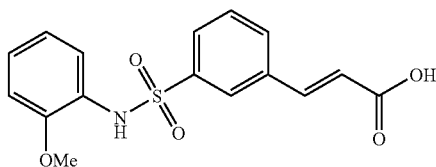

To a suspension of 3-[3-(2-methoxy-phenylsulfamoyl)phenyl]-acrylic acid methyl ester (14c) (0.42 g, 1.20 mmol) in methanol (5.5 ml) 1N NaOH solution (3.6 ml, 3.60 mmol) was added and the resultant mixture was stirred at ambient temperature overnight. The reaction mixture was partitioned between ethyl acetate and water. The aqueous layer was acidified with 2N HCl solution and extracted with ethyl acetate. The extract was washed with saturated NaCl and dried (Na$_2$SO$_4$). The solvent was removed and the residue was dried in desiccator over P$_2$O$_5$ to give the title compound as a white solid (0.37 g, 92%).

Example 120

3-[3-(2-Methoxy-phenylsulfamoyl)-phenyl]-acryloyl chloride (16c)

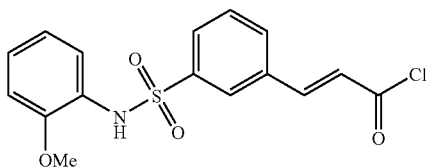

To a suspension of 3-[3-(2-methoxy-phenylsulfamoyl)phenyl]-acrylic acid (15c) (0.36 g, 1.04 mmol) in dichloromethane (4 ml) oxalyl chloride (0.27 ml, 3.12 mmol) and one drop of dimethylformamide were added. The reaction mixture was stirred at 40° C. for one hour and concentrated under reduced pressure to give crude title compound (0.37 g, 97%).

Example 121

N-Hydroxy-3-[3-(2-methoxy-phenylsulfamoyl phenyl]-acrylamide (17c) (PX117227)

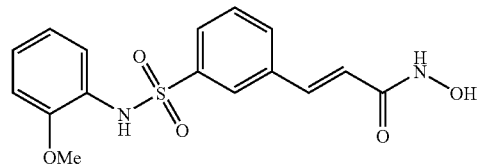

To a suspension of hydroxylamine hydrochloride (0.36 g, 5.20 mmol) in tetrahydrofuran (6 ml) a saturated NaHCO$_3$ solution (4.5 ml) was added and the resultant mixture was stirred at ambient temperature for 10 min. To the reaction mixture a solution of crude 3-[3-(2-methoxy-phenylsulfamoyl)phenyl]-acryloyl chloride (16c) (0.37 g, 1.05 mmol) in tetrahydrofuran (5 ml) was added and the mixture was stirred at ambient temperature for one hour. The reaction mixture was poured into water, the obtained solution was acidified with 2N HCl and extracted with ethyl acetate. The organic layer was washed successively with water and saturated NaCl, then the solvent was removed. The residue was crystallised from ethyl acetate and washed with diethyl ether affording the title compound (0.23 g, 64%). M.p. 181° C. $^1$H NMR (DMSO-d$_6$, HMDSO) δ: 3.45 (3H, s); 6.49 (1H, d, J=16.0 Hz); 6.76–7.96 (9H, m); 9.09 (1H, br s); 9.54 (1H, s); 10.78 (1H, br s). HPLC analysis on Symmetry C$_8$ column: impurities 1.3% (column size 3.9×150 mm; mobile phase acetonitrile—0.1M phosphate buffer (pH 2.5), 35:65; sample concentration 0.15 mg/ml; flow rate 1.2 ml/min; detector UV 230 nm). Anal. Calcd for C$_{16}$H$_{16}$N$_2$O$_5$S, %: C, 55.16; H, 4.63; N, 8.04. Found, %: C, 55.14; H, 4.52; N, 7.99.

Example 122

3-[3-(Naphthalen-1-ylsulfamoyl)-phenyl]-acrylic acid methyl ester (14d)

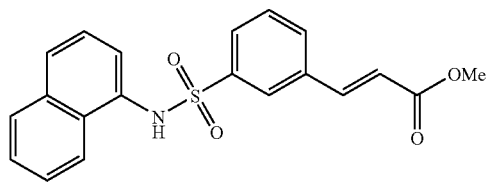

A solution of 3-(3-chlorosulfonylphenyl)acrylic acid methyl ester (3) (0.4 g, 1.53 mmol) in dioxane (5 ml) was added to a mixture of 1-aminonaphthalene (0.22 g, 1.53 mmol) in dioxane (1 ml) and NaHCO$_3$ (0.26 g, 3.09 mmol) in water (3 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (gradient from 2:1 to 1:1, v/v) as eluent.

The obtained product was washed with diethyl ether to give the title compound (0.29 g, 51%) as a white solid. $^1$H NMR (DMSO-d$_6$, HMDSO), δ: 3.69 (3H, s); 6.56 (1H, d, J=16.0 Hz); 7.16 (1H, dd, J=7.0 and 1.4 Hz); 7.27–8.14 (11H, m); 10.25 (1H, s).

Example 123

3-[3-(Naphthalen-1-ylsulfamoyl)-phenyl]-acrylic acid (15d)

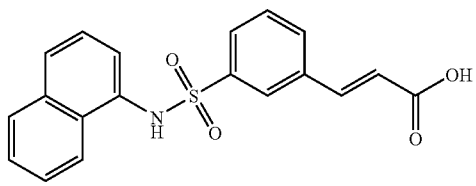

To a suspension of 3-[3-(naphthalen-1-ylsulfamoyl)phenyl]-acrylic Acid Methyl ester (14d) (0.29 g, 0.79 mmol) in methanol (3 ml) 1N NaOH solution (2.4 ml, 2.4 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over P$_2$O$_5$. The title compound was obtained as a white solid. (0.22 g, 79%).

Example 124

3-[3-(Naphthalen-1-ylsulfamoyl)phenyl]-acryloyl chloride (16d)

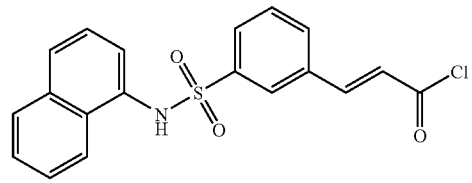

To a suspension of 3-[3-(naphthalen-1-ylsulfamoyl)-phenyl]-acrylic acid (15d) (0.22 g, 0.62 mmol) in dichloromethane (2.5 ml) oxalyl chloride (0.16 ml, 1.86 mmol) and one drop of dimethylformamide were added. The reaction mixture was stirred at 40° C. for one hour and concentrated under reduced pressure to give crude title compound (0.23 g, 99%).

Example 125

N-Hydroxy-3-[3-(naphthalen-1-ylsulfamoyl)-phenyl]-acrylamide (17d) (PX117228)

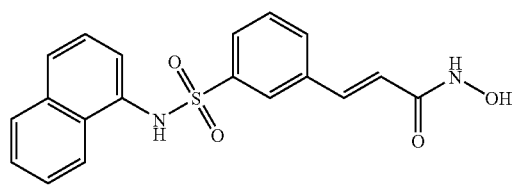

To a suspension of hydroxylamine hydrochloride (0.215 g, 3.1 mmol) in tetrahydrofuran (3.5 ml) a saturated NaHCO$_3$ solution (2.7 ml) was added and the resultant mixture was stirred at ambient temperature for 10 min. To the reaction mixture a solution of crude 3-[3-(naphthalen-1-ylsulfamoyl)phenyl]-acryloyl chloride (16d) (0.23 g) in tetrahydrofuran (2.5 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from ethyl acetate affording the title compound (0.054 g, 24%). M.p. 180° C. $^1$H NMR (DMSO-d$_6$, HMDSO) δ: 6.45 (1H, d, J=16.0 Hz); 7.14 (1H, dd, J=7.0 and 1.4 Hz); 7.31–8.14 (11H, m); 9.09 (1H, br s); 10.27 (1H, s); 10.76 (1H, br s). HPLC analysis on Symmetry C$_{18}$ column: impurities 4% (column size 3.9×150 mm; mobile phase acetonitrile—0.1M phosphate buffer (pH 2.5), 40:60; sample concentration 0.3 mg/ml; flow rate 1.2 ml/min; detector UV 220 nm). Anal. Calcd for C$_{19}$H$_{16}$N$_2$O$_4$S, %: C, 61.94; H, 4.38; N, 7.60. Found, %: C, 61.18; H, 4.32; N, 7.54.

Example 126

3-[3-(Naphthalen-2-ylsulfamoyl)-phenyl]-acrylic acid methyl ester (14e)

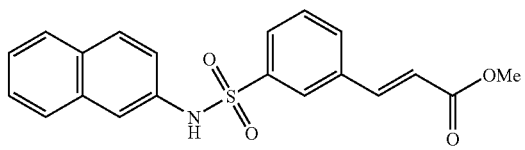

A solution of 3-(3-chlorosulfonylphenyl)acrylic acid methyl ester (3) (1.0 g, 3.83 mmol) in dioxane (10 ml) was added to a mixture of 2-aminonaphthalene (0.55 g, 3.83 mmol) and NaHCO$_3$ (0.48 g, 5.71 mmol) in water (6 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (3:2, v/v) as eluent. The obtained product was crystallised from petroleum ether-ethyl acetate to give the title compound (0.52 g, 34%) as a white solid. $^1$H NMR (DMSO-d$_6$, HMDSO), δ:3.73 (3H, s); 6.67 (1H, d, J=16.0 Hz); 7.21–8.07 (11H, m); 8.16 (1H, s); 10.55 (1H, s).

Example 127

3-[3-(Naphthalen-2-ylsulfamoyl)-phenyl]-acrylic acid (15e)

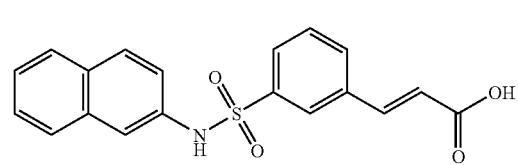

To a suspension of 3-[3-(naphthalen-2-ylsulfamoyl)phenyl]-acrylic acid methyl ester (14e) (0.25 g, 0.68 mmol) in methanol (3.5 ml) 2N NaOH solution (1.0 ml, 2.0 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over $P_2O_5$. The title compound was obtained as a white solid (0.21 g, 87%). $^1$H NMR (DMSO-$d_6$, HMDSO), δ: 6.56 (1H, d, J=16.0 Hz); 7.21–8.01 (11H, m); 8.12 (1H, s); 10.56 (1H, br s); 12.54 (1H, br s).

Example 128

3-[3-(Naphthalen-2-ylsulfamoyl)phenyl]-acryloyl chloride (16e)

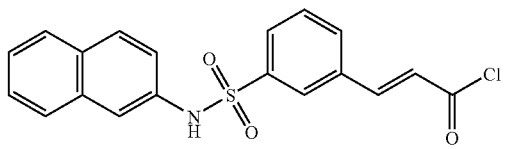

To a suspension of 3-[3-(naphthalen-2-ylsulfamoyl)-phenyl]-acrylic acid (15e) (0.21 g, 0.57 mmol) in dichloromethane (2.5 ml) oxalyl chloride (0.15 ml, 1.71 mmol) and one drop of dimethylformamide were added. The reaction mixture was stirred at 40° C. for one hour and concentrated under reduced pressure to give crude title compound (0.21 g, 95%).

Example 129

N-Hydroxy-3-[3-(naphthalen-2-ylsulfamoyl)-phenyl]-acrylamide (17e) (PX117445)

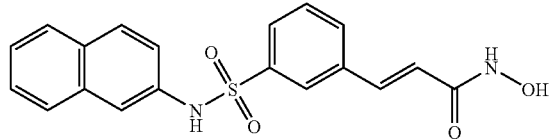

To a suspension of hydroxylamine hydrochloride (0.2 g, 2.85 mmol) in tetrahydrofuran (3.5 ml) a saturated NaHCO$_3$ solution (2.3 ml) was added and the resultant mixture was stirred at ambient temperature for 10 min. To the reaction mixture a solution of crude 3-[3-(naphthalen-2-ylsulfamoyl)-phenyl]-acryloyl chloride (16e) (0.21 g) in tetrahydrofuran (2.5 ml) was added and the mixture was stirred at ambient temperature for one hour. The reaction mixture was partitioned between ethyl acetate and 2N HCl. The organic layer was washed successively with water and saturated NaCl, then the solvent was removed. The residue was washed with diethyl ether and potroleum ether-ethyl acetate (3:1) affording the title compound (0.14 g, 68%). M.p. 164° C. $^1$H NMR (DMSO-$d_6$, HMDSO) δ: 6.49 (1H, d, J=16.0 Hz); 7.16–7.89 (12H, m); 7.98 (1H, br s); 10.52 (1H, s); 10.76 (1H, br s). HPLC analysis on Symmetry $C_{18}$ column: impurities 5% (column size 3.9×150 mm; mobile phase acetonitrile—0.1M phosphate buffer (pH 2.5), 50:50; sample concentration 0.5 mg/ml; flow rate 0.8 ml/min; detector UV 220 nm). Anal. Calcd for $C_{19}H_{16}N_2O_4S$, %: C, 61.94; H, 4.38; N, 7.60. Found, %: C, 61.44; H, 4.39; N, 7.48.

Example 130

3-(3-Nitro-phenyl)-acrylic acid methyl ester (22)

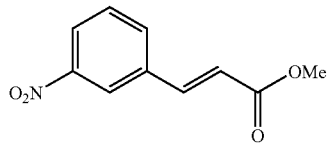

Acetyl chloride (6.5 ml, 0.09 mol) was added dropwise to methanol (130 ml) at −15° C. temperature. The reaction mixture was stirred for 30 min. simultaneously allowing to warm up to 0° C. 3-(3-Nitro-phenyl)-acrylic acid (21) (25 g, 0.13 mol) was added by small portions to the mixture at 0° C. and the resulting reaction mixture was stirred overnight at ambient temperature. The forming precipitate was filtered, washed with methanol and dried affording the title compound in a form of white crystals (26.58 g, 98%).

Example 131

3-(3-Amino-phenyl)-acrylic acid methyl ester (23)

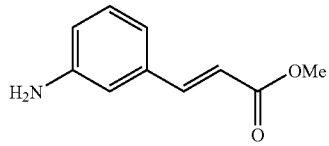

A mixture of 3-(3-nitro-phenyl)-acrylic acid methyl ester (22) (10.0 g, 48 mmol) and SnCl$_2$.2H$_2$O (54 g, 240 mmol) in anhydrous ethanol (200 ml) was heated at 80° C. for 1 hour. The reaction mixture was allowed to cool to room temperature, then the solvent was partially evaporated by vacuum rotary evaporator (up to ca. ½ volume). The residue was poured in ice water, neutralised (pH~7) with saturated Na$_2$CO$_3$ and the resulting mixture was extracted with ethyl acetate. The organic extract was washed with saturated NaCl and dried (Na$_2$SO$_4$). The extract was filtrated through a small amount of silica gel and evaporated to give pure title compound in a form of white crystals (8.5 g, 99%). $^1$H NMR (CDCl$_3$, HMDSO), δ: 3.69 (2H, br s), 3.79 (3H, s); 6.39 (1H, d, J=16.0 Hz); 6.61–7.03 (3H, m); 7.18 (1H, t, J=7.6 Hz); 7.62 (1H, d, J=16.0 Hz).

Example 132

3-{3-[(E2-Phenylethenesulfonylamino]phenyl}acrylic acid methyl ester (25a)

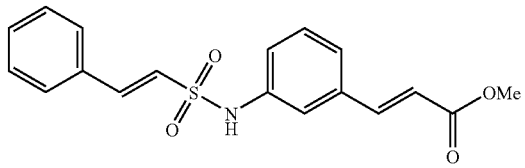

A solution of (E)-2-phenylethenesulfonyl chloride (24a) (0.59 g, 2.82 mmol) in dioxane (3 ml) was added to a mixture of 3-(3-aminophenyl)-acrylic acid methyl ester (23) (0.50 g, 2.82 mmol) in dioxane (12 ml) and NaHCO$_3$ (0.36 g, 4.28 mmol) in water (8 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with chloroform-ethyl acetate (100:2, v/v) as eluent to give the title compound (0.68 g, 70%) as a white solid. $^1$H NMR (CDCl$_3$, HMDSO), δ: 3.78 (3H, s); 6.39 (1H, d, J=16.0 Hz); 6.77 (1H, d, J=15.8 Hz); 6.78 (1H, s); 7.17–7.48 (9H, m); 7.49 (1H, d, J=15.8 Hz); 7.58 (1H, d, J=16.0 Hz).

Example 133

3-{3-[(E)-2-Phenylethenesulfonylamino] phenyl}acrylic acid (26a)

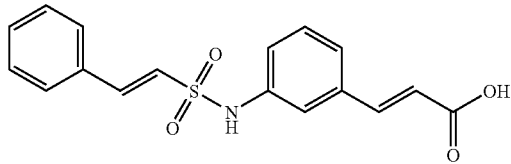

To a suspension of 3-{3-[(E)-2-phenylethenesulfonylamino]phenyl}acrylic acid methyl ester (25a) (0.30 g, 0.87 mmol) in methanol (4 ml) 1 N NaOH solution (2.62 ml, 2.62 mmol) was added and the resultant mixture was stirred at ambient temperature overnight. The reaction mixture was partitioned between ethyl acetate and water. The aqueous layer was acidified with 2N HCl solution and extracted with ethyl acetate. The extract was washed with saturated NaCl and dried (Na$_2$SO$_4$). The solvent was evaporated and the residue was dried in desiccator over P$_2$O$_5$. The title compound was obtained as a white solid (0.26 g, 90%). $^1$H NMR (DMSO-d$_6$, HMDSO) δ: 6.41 (1H, d, J=16.0 Hz); 7.12–7.51 (9H, m); 7.55–7.81 (3H, m); 10.16 (1H, br s), 12.32 (1H, br s).

Example 134

3-{3-[(E)-2-Phenylethenesulfonylamino] phenyl}acryloyl chloride (27a)

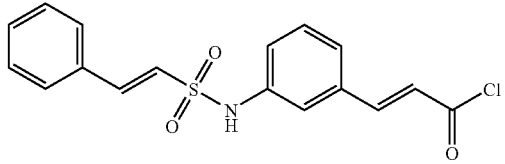

To a suspension of 3-{3-[(E)-2-phenylethenesulfonylamino]phenyl}acrylic acid (26a) (0.26 g, 0.79 mmol) in dichloromethane (3.5 ml) oxalyl chloride (0.21 ml, 2.37 mmol) and one drop of dimethylformamide were added. The reaction mixture was stirred at 40° C. for one hour and concentrated under reduced pressure to give crude title compound (0.27 g, 98%).

Example 135

N-Hydroxy-3-{3-[(E)-2-phenylethenesulfonylamino] phenyl}acrylamide (28a) (PX117446)

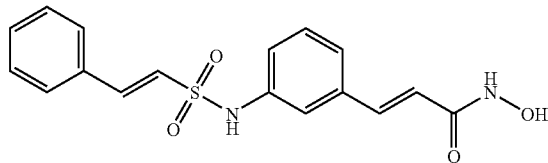

To a suspension of hydroxylamine hydrochloride (0.27 g, 3.88 mmol) in tetrahydrofuran (5 ml) a saturated NaHCO$_3$ solution (3 ml) was added and the resultant mixture was stirred at ambient temperature for 10 min. To the reaction mixture a solution of crude 3-{3-[(E)-2-phenylethenesulfonylamino]phenyl}acryloyl chloride (27a) (0.27 g, 0.77 mmol) in tetrahydrofuran (3.5 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from ethyl acetate and washed with diethyl ether affording the title compound (0.115 g, 42%) as white crystals. M.p. 171° C. $^1$H NMR (DMSO-d$_6$, HMDSO) δ: 6.38 (d, J=16.0 Hz, 1H); 7.07–7.80 (m, 12H); 9.03 (br s, 1H); 10.16 (s, 1H); 10.76 (br s, 1H). HPLC analysis on Symmetry C$_{18}$ column: impurities 1% (column size 3.9×150 mm; mobile phase acetonitrile—0.1M phosphate buffer (pH 2.5), 35:65; sample concentration 0.4 mg/ml; flow rate 1.2 ml/min; detector UV 254 nm). Anal. Calcd for C$_{17}$H$_{16}$N$_2$O$_4$S, %: C, 59.29; H, 4.68; N, 8.13. Found, %: C, 59.13; H, 4.70; N, 7.92.

Example 136

3-[3-(3,4-Dimethoxy-benzenesulfonylamino)-phenyl]-acrylic acid methyl ester (25b)

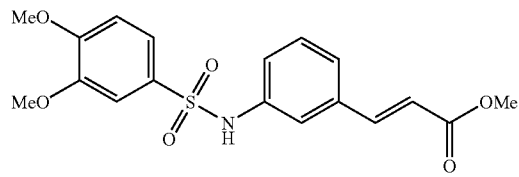

Using an analogous method, the title compound was obtained from 3,4-dimethoxybenzenesulphonyl chloride (24b) and 3-(3-aminophenyl)acrylic acid methyl ester (23) as a white solid, yield 77%. $^1$H NMR (DMSO-d$_6$, HMDSO), δ: 3.69(3H, s); 3.72 (3H, s); 3.78 (3H, s); 6.45 (1H, d, J=16.0 Hz); 6.94–7.67 (8H, m); 10.23 ppm (1H, br s).

Example 137

3-[3-(3,4-Dimethoxy-benzenesulfonylamino)-phenyl]-acrylic acid (26b)

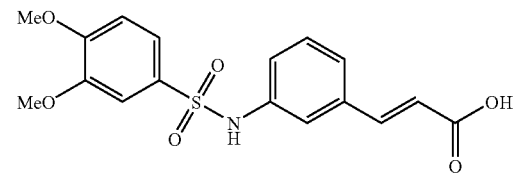

Using an analogous method, the title compound was obtained from 3-[3-(3,4-dimethoxy-benzenesulfonylamino)-phenyl]-acrylic acid methyl ester (25b) and sodium hydroxide, ca. yield of the crude product 95%.

Example 138

3-[3-(3,4-Dimethoxy-benzenesulfonylamino)-phenyl]-acryloyl chloride (27b)

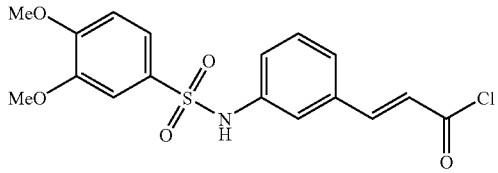

Using an analogous method, the title compound was obtained from 3-[3-(3,4-dimethoxy-benzenesulfonylamino)-phenyl]-acrylic acid (26b) and oxalyl chloride, ca. yield of the crude product 98% (yellow oil).

Example 139

3-[3-(3,4-Dimethoxy-benzenesulfonylamino)-phenyl]-N-hydroxy-acrylamide (28b) (PX117780)

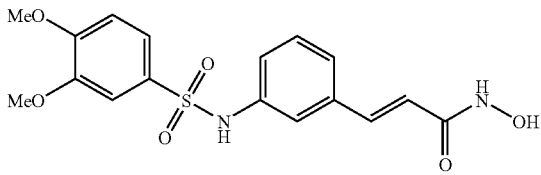

Using an analogous method, the title compound was obtained from 3-[3-(3,4-dimethoxy-benzenesulfonylamino)-phenyl]-acryloyl chloride (27b) and hydroxylamine hydrochloride, yield 32%. M.p. 158° C. $^1$H NMR (DMSO-$d_6$, HMDSO) δ: 3.72 (3H, s); 3.80 (3H, s); 6.36 (1H, d, J=16.0 Hz); 6.89–7.52 (8H, m); 9.03 (1H, br s); 10.16 (1H, br s); 10.78 (1H, br s). HPLC analysis on Symmetry $C_8$ column: impurities 2.5% (column size 3.9×150 mm; mobile phase acetonitrile—0.1M phosphate buffer (pH 2.5), 30:70; detector UV 254 nm; flow rate 1.3 ml/min; sample concentration 0.5 mg/ml). Anal. Calcd for $C_{17}H_{18}N_2O_6S$, %: C, 53.96; H, 4.79; N, 7.40. Found, %: C, 53.74; H, 4.71; N, 7.35.

Example 140

3-[3-(Biphenyl-4-sulfonylamino)-phenyl]-acrylic acid methyl ester (25c)

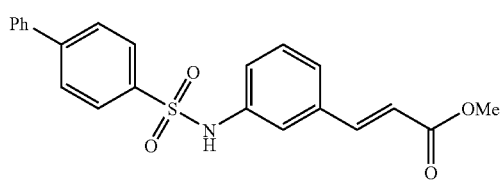

Using an analogous method, the title compound was obtained from biphenyl-4-sulfonyl chloride (24c) and 3-(3-aminophenyl)acrylic acid methyl ester (23) as a white solid, yield 78%. $^1$H NMR (DMSO-$d_6$, HMDSO), δ: 3.71 (3H, s); 6.43 (1H, d, J=16.0 Hz); 7.12–8.11 (14H, m); 10.49 ppm (1H, br s).

Example 141

3-[3-(Biphenyl-4-sulfonylamino)-phenyl]-acrylic acid (26c)

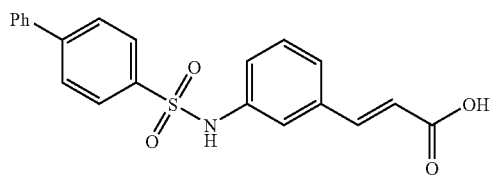

Using an analogous method, the title compound was obtained from 3-[3-(biphenyl-4-sulfonylamino)-phenyl]-acrylic acid methyl ester (25c) and sodium hydroxide, ca. yield of the crude product 87%.

Example 142

3-[3-(Biphenyl-4-sulfonylamino)-phenyl]-acryloyl chloride (27c)

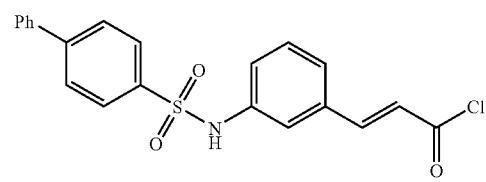

Using an analogous method, the title compound was obtained from 3-[3-(biphenyl-4-sulfonylamino)-phenyl]-acrylic acid (26c) and oxalyl chloride, ca. yield of the crude product 98% (yellow oil).

Example 143

3-[3-(Biphenyl-4-sulfonylamino)-phenyl]-N-hydroxy-acrylamide (28c) (PX117781)

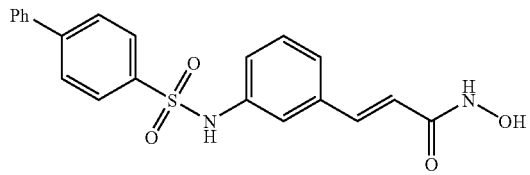

Using an analogous method, the title compound was obtained from 3-[3-(biphenyl-4-sulfonylamino)-phenyl]-acryloyl chloride (27c) and hydroxylamine hydrochloride, yield 20%. M.p. 115° C. $^1$H NMR (DMSO-$d_6$, HMDSO) δ: 6.38 (1H, d, J=16.0 Hz); 6.98–7.65 (10H, m); 7.87 (4H, s); 9.03 (1H, br s); 10.45 (1H, br s); 10.78 (1H, br s). HPLC analysis on Symmetry $C_8$ column: impurities 2.5% (column size 3.9×150 mm; mobile phase acetonitrile—0.1M phosphate buffer (pH 2.5), 50:50; detector UV 254 nm; flow rate 1.0 ml/min; sample concentration 0.5 mg/ml). Anal. Calcd for $C_{21}H_{18}N_2O_4S$ containing 1.3% of inorganic impurities, %: C, 63.11; H, 4.54; N, 7.01. Found, %: C, 63.16; H, 4.53; N, 6.93.

Example 144

3-[3-(Toluene-4-sulfonylamino)-phenyl]-acrylic acid methyl ester (25d)

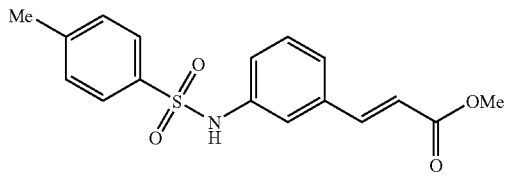

Using an analogous method, the title compound was obtained from tolylsulfonyl chloride (24d) and 3-(3-aminophenyl)acrylic acid methyl ester (23) as a white solid, yield 78%. ¹H NMR (CDCl₃, TMS), δ: 2.38 (3H, s); 3.78 (3H, s); 6.34 (1H, d, J=16.0 Hz); 6.80 (1H, br, s); 7.00–7.76 (9H, m).

Example 145

3-[3-(Toluene-4-sulfonylamino)-phenyl]-acrylic acid (26d)

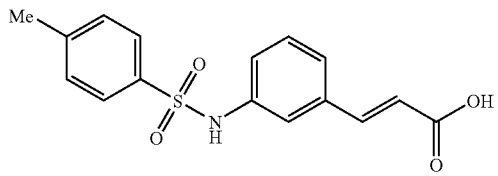

Using an analogous method, the title compound was obtained from 3-[3-(toluene-4-sulfonylamino)phenyl]-acrylic acid methyl ester (25d) and sodium hydroxide, ca. yield of the crude product 91%.

Example 146

3-[3-(Toluene-4-sulfonylamino)-phenyl]-acryloyl chloride (27d)

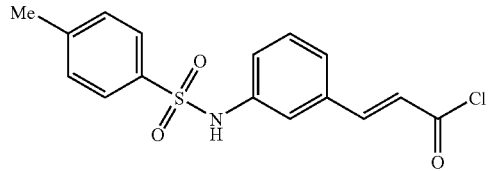

Using an analogous method, the title compound was obtained from 3-[3-(toluene-4-sulfonylamino)-phenyl]-acrylic acid (26d) and oxalyl chloride, ca. yield of the crude product 98% (yellow oil).

Example 147

N-Hydroxy-3-[3-(toluene-4-sulfonylamino)-phenyl]-acrylamide (28d) (PX089342)

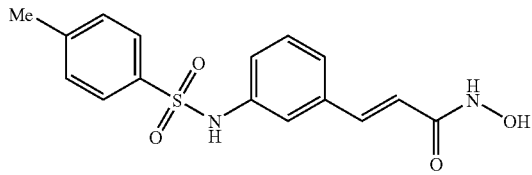

Using an analogous method, the title compound was obtained from 3-[3-(toluene-4-sulfonylamino)-phenyl]-acryloyl chloride (27d) and hydroxylamine hydrochloride, yield 82%. M.p. 147° C. ¹H NMR (DMSO-d₆, HMDSO) δ: 2.32 (s, 3H); 6.36 (d, J=16.0 Hz, 1H); 6.94–7.76 (m, 9H); 9.03 (br s, 1H); 10.32 (s, 1H); 10.78 ppm (br s, 1H). HPLC analysis on Symmetry C₁₈ column: impurities <1% (column size 3.9×150 mm; mobile phase acetonitrile—0.1M phosphate buffer (pH 2.5), 35:65; detector UV 220 nm; flow rate 1.0 ml/min; sample concentration 1.0 mg/ml). Anal. Calcd for C₁₆H₁₆N₂O₄S, %: C, 57.82; H, 4.85; N, 8.43. Found, %: C, 57.73; H, 4.86; N, 8.36.

Example 148

3-[3-(Benzene-4-sulfonylamino)-phenyl]-acrylic acid methyl ester (25e)

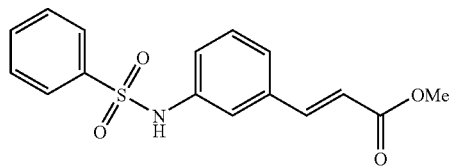

Using an analogous method, the title compound was obtained from benzenesulfonyl chloride (24e) and 3-(3-aminophenyl)acrylic acid methyl ester (23) as a white solid, yield 85%. ¹H NMR (CDCl₃, TMS), δ: 3.78 (3H, s); 6.34 (1H, d, J=16.0 Hz); 6.74 (1H, br, s); 6.98–7.83 (10H, m).

Example 149

3-[3-(Benzene-4-sulfonylamino)-phenyl]-acrylic acid (26e)

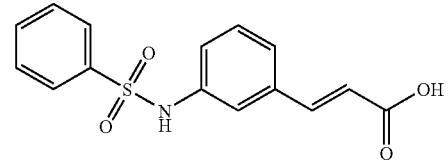

Using an analogous method, the title compound was obtained from 3-[3-(benzene-4-sulfonylamino)-phenyl]-acrylic acid methyl ester (25e) and sodium hydroxide, ca. yield of the crude product 88%.

Example 150

3-[3-(Benzene-4-sulfonylamino)-phenyl]-acryloyl chloride (27e)

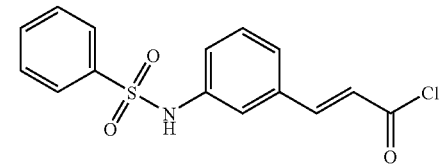

Using an analogous method, the title compound was obtained from 3-[3-(benzene-4-sulfonylamino)-phenyl]-acrylic acid (26e) and oxalyl chloride, ca. yield of the crude product 98% (yellow oil).

Example 151

3-(3-Benzenesulfonylamino-phenyl)-N-hydroxy-acrylamide (PX089344)

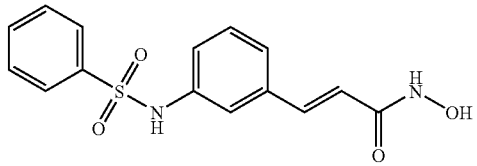

Using an analogous method, the title compound was obtained from 3-[3-(benzene-4-sulfonylamino)-phenyl]-acryloyl chloride (27e) and hydroxylamine hydrochloride, yield 86%. M.p. 172° C. $^1$H NMR (DMSO-d$_6$, HMDSO) δ: 6.35 (d, J=16.0 Hz, 1H); 6.96–7.92 (m, 10H); 9.03 (br s, 1H); 10.38 (s, 1H); 10.78 ppm (br s, 1H). HPLC analysis on Symmetry C$_{18}$ column: impurities <3%(column size 3.9× 150 mm; mobile phase acetonitrile—0.1M phosphate buffer (pH 2.5), 35:65; detector UV 220 nm; flow rate 0.8 ml/min; sample concentration 1.0 mg/ml). Anal. Calcd for C$_{15}$H$_{14}$N$_2$O$_4$S, %: C, 56.59; H, 4.43; N, 8.80. Found, %: C, 56.48; H, 4.57; N, 8.45.

Example 152

Sodium 2-(2-methoxycarbonyl-vinyl)benzenesulfonate (32)

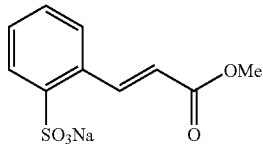

A mixture of sodium 2-formylbenzenesulfonate hydrate (31) (tech., purity 75%; 1.33 g, 4.79 mmol), potassium carbonate (1.32 g, 9.56 mmol), and trimethyl phosphonoacetate (1.05 g, 5.77 mmol) in water (2.5 ml) was vigorously stirred at ambient temperature for 1 hour. The precipitate was filtered and carefully washed with methanol. The methanol extract was evaporated to give the title compound (0.66 g, 52%) as a white solid. $^1$H NMR (DMSO-d$_6$, HMDSO), δ: 3.72 (3H, s); 6.43 (1H, d, J=16.0 Hz); 7.18–7.96 (4H, m); 8.83 (1H, d, J=16.0 Hz).

Example 153

3-(2-Chlorosulfonylphenyl)acrylic acid methyl ester (33)

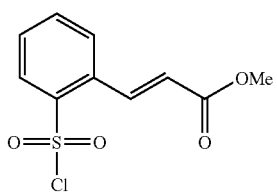

To a solution of 2-(2-methoxycarbonyl-vinyl)benzenesulfonate (32) (0.63 g, 2.38 mmol) in benzene (2 ml) thionyl chloride (1.43 g, 12.00 mmol) and three drops of dimethylformamide were added, and the resultant suspension was stirred at reflux temperature for 1.5 hours. The reaction mixture was evaporated and the residue was dissolved in benzene (5 ml). The benzene solution was filtered and the filtrate was evaporated to give the title compound (0.47 g, 71%) as an oil.

Example 154

3-(2-Phenylsulfamoyl-phenyl)-acrylic acid methyl ester (34a)

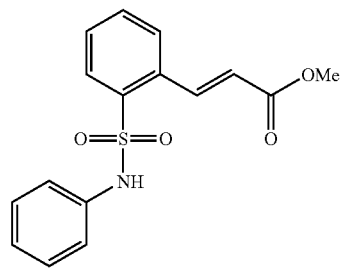

To a mixture of aniline (0.33 g, 3.53 mmol) and pyridine (1 ml) a solution of 3-(2-chlorosulfonylphenyl)acrylic acid methyl ester (33) (0.45 g, 1.72 mmol) in dichloromethane (3 ml) was added and the resultant solution was stirred at 50° C. for 1 hour. The reaction mixture was evaporated and the residue was partitioned between ethyl acetate and 10% HCl. The organic layer was washed successively with water, saturated NaCl and dried (Na$_2$SO$_4$). The solvent was removed and the residue was chromatographed on silica gel with ethyl acetate-chloroform (1:7, v/v) as eluent. The obtained product was washed with diethyl ether to give the title compound (0.33 g, 60%). $^1$H NMR (CDCl$_3$, HMDSO), δ: 3.86 (3H, s); 6.27 (1H, d, J=16.0 Hz); 6.69 (1H, br s); 6.87–7.67 (8H, m); 7.94–8.13 (1H, m); 8.49 (1H, d, J=16.0 Hz).

Example 155

3-(2-Phenylsulfamoyl-phenyl)-acrylic acid (35a)

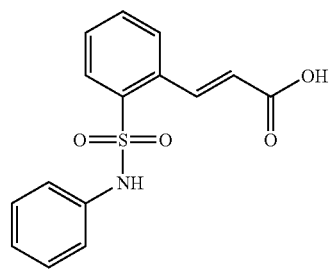

3-(2-phenylsulfamoyl-phenyl)-acrylic acid methyl ester (34a) (0.30 g, 0.94 mmol) was dissolved in methanol (4 ml), 1N NaOH solution (2.82 ml, 2.82 mmol) was added and the resultant solution was stirred at ambient temperature overnight The reaction mixture was partitioned between ethyl acetate and water. The aqueous layer was acidified with 10% HCl solution and stirred at ambient temperature for 1 hour. The precipitated solid was filtered, washed with water and dried in desiccator over P₂O₅. The title compound (0.2 g, 70%) was obtained as a white solid. ¹H NMR (DMSO-d₆, HMDSO), δ: 6.40 (1H, d, J=16.0 Hz); 6.93–7.32 (5H, m); 7.45–8.00 (5H, m); 8.47 (1H, d, J=16.0 Hz); 10.59 (1H, br s).

Example 156

3-(2-Phenylsulfamoyl-phenyl)-acryloyl chloride (36a)

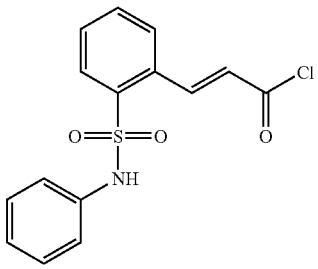

To a suspension of 3-(2-phenylsulfamoyl-phenyl)acrylic acid (35a) (0.18 g, 0.59 mmol) in dichloromethane (3.0 ml) oxalyl chloride (0.18 ml, 2.06 mmol) and one drop of dimethylformamide were added. The reaction mixture was stirred at 40° C. for one hour and concentrated under reduced pressure to give crude title compound (0.19 g, 99%).

Example 157

N-Hydroxy-3-(2-phenylsulfamoylphenyl)acrylamide (37a) (PX116242)

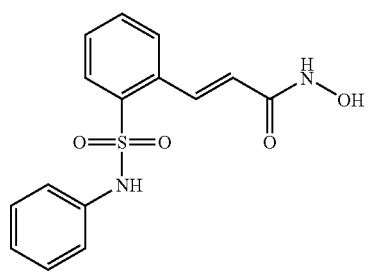

To a suspension of hydroxylamine hydrochloride (0.21 g, 3.01 mmol) in tetrahydrofuran (4.0 ml) a saturated NaHCO₃ solution (2.6 ml) was added and the resultant mixture was stirred at ambient temperature for 25 min. To the reaction mixture a 3-(2-phenylsulfamoyl-phenyl)acryloyl chloride (36a) (0.19 g, 0.59 mmol) solution in tetrahydrofuran (2.5 ml) was added and the mixture was stirred at ambient temperature for 2 hours. The reaction mixture was partitioned between ethyl acetate and 2N HCl. The organic layer was washed successively with water and saturated NaCl, and the solvent was removed. The residue was washed with diethyl ether and crystallised from acetonitrile to give the title compound (0.056 g, 30%) as white crystals, m.p. 205–206.5° C. ¹H NMR (DMSO-d₆, HMDSO), δ: 6.37 (1H, d, J=16.0 Hz); 6.99–8.04 (10H, m); 8.23 (1H, d, J=116.0 Hz); 10.55 (1H, s); 10.83 (1H, br s). HPLC analysis on Symmetry C₁₈ column: impurities 6.4% (column size 3.9× 150 mm; mobile phase acetonitrile—0.1M phosphate buffer, pH 2.5, 30:70; sample concentration 0.2 mg/ml; flow rate 1.2 ml/min; detector UV 220 nm). Anal. Calcd for $C_{15}H_{14}N_2O_4S*0.1H_2O$, %: C, 56.28; H, 8.75; N, 4.47. Found, %: C, 55.63; H, 9.07; N, 4.36.

Example 158

3-[2-(Naphthalen-1-ylsulfamoyl)-phenyl]-acrylic acid methyl ester (34b)

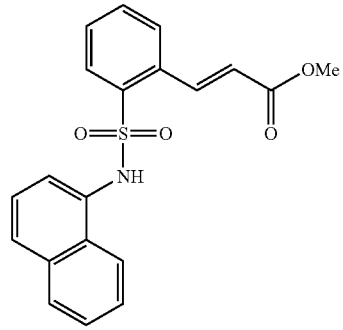

Using an analogous method, the title compound was obtained from 3-(2-chlorosulfonylphenyl)acrylic acid methyl ester (33) and 1-aminonaphthalene, yield 59%. ¹H NMR (CDCl₃, HMDSO), δ: 3.76 (3H, s); 6.22 (1H, d, J=16.0 Hz); 6.88–7.85 (11H, m); 7.94–8.12 (1H, m); 8.51 (1H, d, J=16.0 Hz).

Example 159

3-[2-(Naphthalen-1-ylsulfamoyl)-phenyl]-acrylic acid (35b)

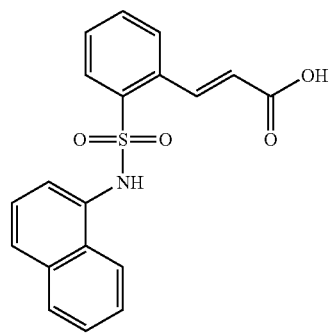

Using an analogous method, the title compound was obtained from 3-[2-(naphthalen-1-ylsulfamoyl)phenyl]-acrylic acid methyl ester (34b) and sodium hydroxide, yield 41%. ¹H NMR (DMSO-d₆, HMDSO), δ: 6.16 (1H, d, J=16.0 Hz); 7.18–7.95 (12H, m); 8.29 (1H, d, J=16.0 Hz); 10.54 (1H, br s).

Example 160

3-[2-(Naphthalen-1-ylsulfamoyl)-phenyl]-acryloyl chloride (36b)

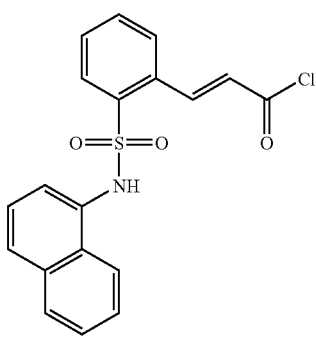

Using an analogous method, the title compound was obtained from 3-[2-(naphthalen-1-ylsulfamoyl)-phenyl]-acrylic acid (35b) and oxalyl chloride in a form of a crude product, yield ca. 98%.

Example 161

N-Hydroxy-3-[2-(naphthalen-1-ylsulfamoyl)-phenyl]-acrylamide (37b) (PX117447)

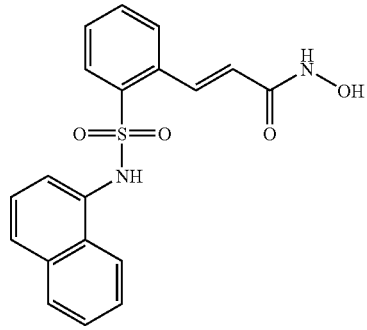

Using an analogous method, the title compound was obtained from 3-[2-(naphthalen-1-ylsulfamoyl)-phenyl]-acryloyl chloride (36b) and hydroxylamine hydrochloride, yield 38%, m.p. 186–187° C. $^1$H NMR (DMSO-$d_6$, HMDSO), δ: 6.29 (1H, d, J=15.0 Hz); 7.17–8.16 (11H, m); 8.36 (1H, d, J=15.0 Hz); 9.14 (1H, br s); 10.57 (1H, s); 10.83 (1H, s). HPLC analysis on Symmetry $C_8$ column: impurities 6.4% (column size 3.9×150 mm; mobile phase acetonitrile—0.1M phosphate buffer, pH 2.5, 35:65; sample concentration 0.5 mg/ml; flow rate 1.6 ml/min; detector UV 220 nm). Anal. Calcd for $C_{19}H_{16}N_2O_4S*0.4H_2O$, %: C, 60.76; H, 4.51; N, 7.46. Found, %: C, 60.46; H, 4.35; N, 7.69.

Example 162

3-[2-(Methyl-phenyl-sulfamoyl)-phenyl]-acrylic acid methyl ester (34c)

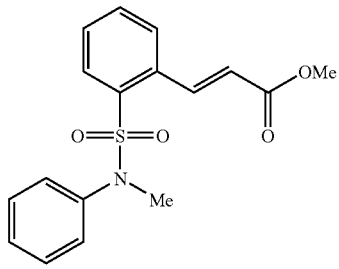

Using an analogous method, the title compound was obtained from 3-(2-chlorosulfonylphenyl)acrylic acid methyl ester (33) and N-methylaniline, yield 54%.
$^1$H NMR (DMSO-$d_6$, HMDSO), δ:3.13 (3H, s); 3.67 (3H, s); 6.29 (1H, d, J=16.0 Hz); 7.01–7.45 (5H, m); 7.52–8.09 (5H, m).

Example 163

3-[2-(Methyl-phenyl-sulfamoyl)-phenyl]-acrylic acid (35c)

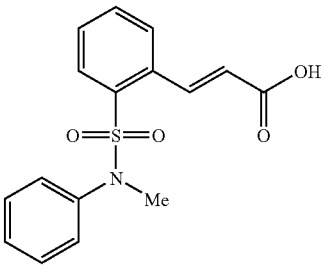

Using an analogous method, the title compound was obtained from 3-[2-(methyl-phenyl-sulfamoyl)-phenyl]-acrylic acid methyl ester (34c) and sodium hydroxide, yield 48%. $^1$H NMR (DMSO-$d_6$, HMDSO), δ: 3.17 (3H, s); 6.28 (1H, d, J=16.0 Hz); 7.06–7.42 (5H, m); 7.53–8.20 (6H, m).

Example 164

3-[2-(Methyl-phenyl-sulfamoyl)-phenyl]-acryloyl chloride (36c)

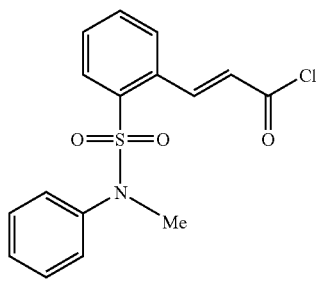

Using an analogous method, the title compound was obtained from 3-[2-(methyl-phenyl-sulfamoyl)-phenyl]-acrylic acid (35c) and oxalyl chloride in a form of the crude product, yield ca. 99%.

Example 165

N-Hydroxy-3-[2-(methyl-phenyl-sulfamoyl)-phenyl]-acrylamide (37c) (PX117448)

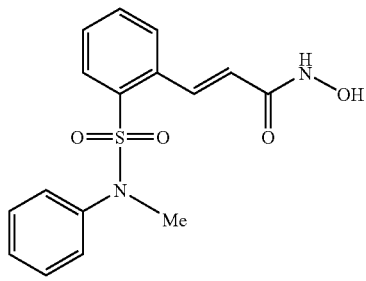

Using an analogous method, the title compound was obtained from 3-[2-(methyl-phenyl-sulfamoyl)-phenyl]-acryloyl chloride (36c) and hydroxylamine hydrochloride, yield 40%, m.p. 144.5–145.5° C. $^1$H NMR (DMSO-$d_6$, HMDSO), δ: 3.16 (3H, s); 6.32 (1H, d, J=16.0 Hz); 7.00–7.86 (9H, m); 8.09 (1H, d, J=16.0 Hz); 9.12 (1H, br s); 10.80 (1H, s). HPLC analysis on Zorbax SB $C_{18}$ column: impurities 1.0% (column size 4.6×150 mm; mobile phase methanol—0.1% $H_3PO_4$, gradient from 50:50 to 90:10; sample concentration 0.5 mg/ml; flow rate 1.5 ml/min; detector UV 230 nm). Anal. Calcd for $C_{16}H_{16}N_2O_4S*0.7H_2O$, %: C, 55.70; H, 5.08; N, 8.12. Found, %: C, 55.17; H, 4.65; N, 8.05.

Example 166

3-(4-Chlorosulfonyl-phenyl)-acrylic acid (42)

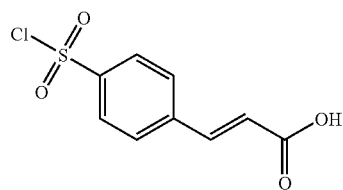

To neat chlorosulfonic acid (5.3 ml, 80 mmol) at 0–5° C. temperature slowly cinnamic acid (41) (1.47 g, 10 mmol) was added. As the reaction proceeded hydrogen chloride gas evolved. The reaction mixture was stirred successively at 0° C. for 1 hour, at ambient temperature for 2 hours and at 40–42° C. for 2 hours. The dark, viscous syrup was poured onto ice, the precipitated solid was filtered and washed with water. The title compound (0.5 g, 20%) as a white solid was obtained. $^1$H NMR (DMSO-$d_6$, HMDSO), δ 6.55 (1H, d, J=16 Hz); 7.58 (1H, d, J=16.0 Hz); 7.65 (4H, s); 8.15 (1H, br s).

Example 167

3-(4-Phenylsulfamoyl-phenyl)-acrylic acid (43a)

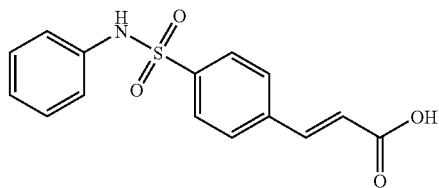

To a mixture of aniline (0.35 g, 3.75 mmol) and pyridine (1 ml) a solution of 3-(4-chlorosulfonyl-phenyl)acrylic acid (42) (0.45 g, 1.82 mmol) in dichloromethane (3 ml) was added and the resultant solution was stirred at 40° C. for 1 hour. The reaction mixture was evaporated and the residue was partitioned between ethyl acetate and 6N HCl. The organic layer was washed successively with water, saturated NaCl and dried ($Na_2SO_4$). The solvent was evaporated under reduced pressure to give the title compound (0.30 g, 54%). $^1$H NMR (DMSO-$d_6$, HMDSO), δ: 6.60 (1H, d, J=16.0 Hz); 6.93–7.43 (5H, m); 7.60 (1H, d, J=16.0 Hz); 7.79 (2H, d, J=8.0 Hz); 7.87 (2H, d, J=8.0 Hz); 10.35 (1H, s).

Example 168

3-(4-Phenylsulfamoyl-phenyl)-acryloyl chloride (44a)

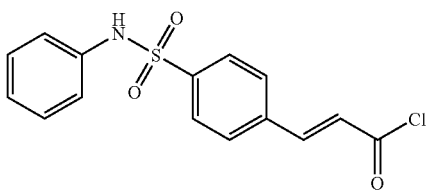

To a suspension of 3-(4-phenylsulfamoyl-phenyl)-acrylic acid (43a) (0.25 g, 0.82 mmol) in dichloromethane (4.7 ml) oxalyl chloride (0.32 ml, 3.68 mmol) and one drop of dimethylformamide were added. The reaction mixture was stirred at 40° C. for one hour and concentrated under reduced pressure to give crude title compound (0.24 g, 92%).

Example 169

N-Hydroxy-3-(4-phenylsulfamoylphenyl)-acrylamide (45a) (PX117450)

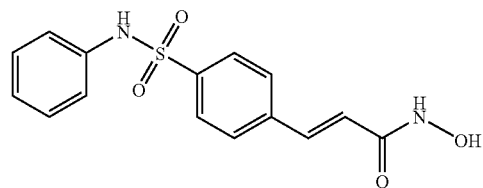

To a suspension of hydroxylamine hydrochloride (0.21 g, 3.01 mmol) in tetrahydrofuran (4.0 ml) a saturated $NaHCO_3$ solution (2.6 ml) was added and the resultant mixture was stirred at ambient temperature for 0.25 min. To the reaction mixture a 3-(4-phenylsulfamoyl-phenyl)-acryloyl chloride (44a) (0.19 g, 0.59 mmol) solution in tetrahydrofuran (2.5 ml) was added and the mixture was stirred at ambient temperature for 2 hours. The reaction mixture was partitioned between ethyl acetate and 2N HCl. The organic layer was washed successively with water and saturated NaCl, and the solvent was removed. The residue was washed with diethyl ether to give the title compound (0.074 g, 39%) as white crystals, m.p. 176–177.5° C. $^1$H NMR (DMSO-$d_6$, HMDSO), δ: 6.54 (1H, d, J=16.0 Hz); 6.96–7.32 (5H, m); 7.47 (1H, d, J=16.0 Hz); 7.76 (4H, s); 9.14 (1H, br s); 10.29 (1H, br s); 10.86 (1H, s). Anal. Calcd for $C_{15}H_{14}N_2O_4S$, %: C, 56.59; H, 4.43; N, 8.80. Found, %: 55.82, H, 4.38; N, 9.01.

Example 170

3-[4-(Naphthalen-2-ylsulfamoyl)-phenyl]-acrylic acid (43b)

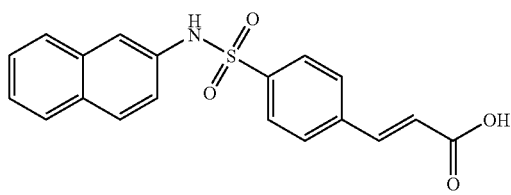

Using an analogous method, the title compound was obtained from 3-(4-chlorosulfonyl-phenyl)-acrylic acid (42) and 2-aminonaphthalene, yield 49%. $^1$H NMR (DMSO-$d_6$, HMDSO), δ:6.62 (1H, d, J=16.0 Hz); 7.19 (1H, dd, J=8.0 and 2.0 Hz); 7.34–8.14 (11H, m); 10.32 (1H, br s).

Example 171

3-[4-(Naphthalen-2-ylsulfamoyl)-phenyl]-acryloyl chloride (44b)

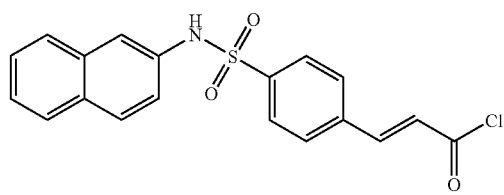

Using an analogous method, the title compound was obtained from 3-[4-(naphthalen-2-ylsulfamoyl)-phenyl]-acrylic acid (43b) and oxalyl chloride, ca. yield of the crude product 98% (yellow oil).

Example 172

N-Hydroxy-3-[4-(naphthalen-2-ylsulfamoyl)-phenyl]-acrylamide (45b) (PX117736)°

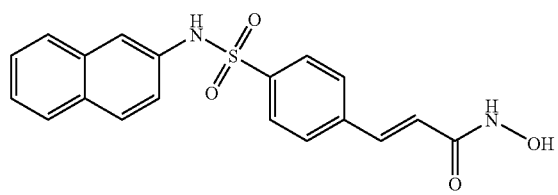

Using an analogous method, the title compound was obtained from 3-[4-(naphthalen-2-ylsulfamoyl)-phenyl]-acryloyl chloride (44b) and hydroxylamine hydrochloride, yield 25%. M.p. 198.5–199.5° C. $^1$H NMR (DMSO-$d_5$, HMDSO), δ: 6.54 (1H, d, J=16.0 Hz); 7.16 (1H, dd, J=8.0 and 2.0 Hz); 7.29–8.12 (11H, m); 9.11 (1H, br s); 10.87 (1H, s). HPLC analysis on Symmetry $C_8$ column: impurities 1.8% (column size 3.9×150 mm; mobile phase acetonitrile—0.1M phosphate buffer (pH 2.5), 35:65; detector UV 254 nm; flow rate 1.5 ml/min; sample concentration 0.5 mg/ml). Anal. Calcd for $C_{19}H_{16}N_2O_4S$*0.2$H_2O$, %: C, 61.34; H, 4.44; N, 7.53. Found, %: C, 60.96; H, 4.28; N, 7.56.

Example 173

3-[4-(Biphenyl-4-ylsulfamoyl)-phenyl]-acrylic acid (43c)

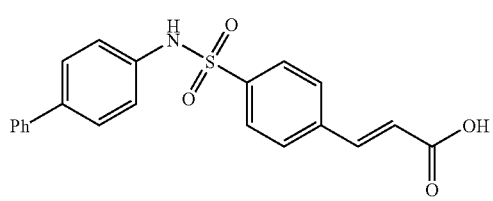

Using an analogous method, the title compound was obtained from 3-(4-chlorosulfonyl-phenyl)-acrylic acid (42) and 4-aminobiphenyl, yield 67%. $^1$H NMR (DMSO-$d_6$, HMDSO), δ: 6.62 (1H, d, J=16.0 Hz); 7.19 (2H, d, J=8.0 Hz); 7.25–7.75 (9H, m); 7.77–7.95 (4H, m); 10.46 (1H, br s).

Example 174

3-[4-(Biphenyl-4-ylsulfamoyl)-phenyl]-acryloyl chloride (44c)

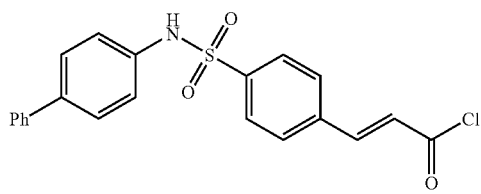

Using an analogous method, the title compound was obtained from 3-[4-(biphenyl-4-ylsulfamoyl)-phenyl]-acrylic acid (43c) and oxalyl chloride, ca. yield of the crude product 79% (yellow oil).

Example 175

N-Hydroxy-3-[4-(biphenyl-4-ylsulfamoyl)-phenyl]-acrylamide (45c) (PX117792)

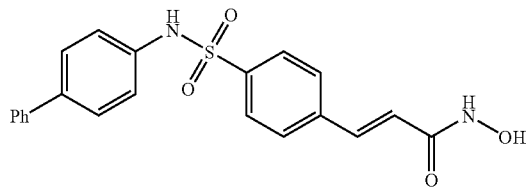

Using an analogous method, the title compound was obtained from 3-[4-(biphenyl-4-ylsulfamoyl)phenyl]-acryloyl chloride (44c) and hydroxylamine hydrochloride, yield 32%. M.p. 211–211.5° C. $^1$H NMR (DMSO-$d_6$, HMDSO), δ: 6.53 (1H, d, J=16.0 Hz); 7.19 (2H, d, J=8.0 Hz); 7.32–7.69 (8H, m); 7.72–7.92 (4H, m); 9.09 (1H, br s); 10.45 (1H, s); 10.85 (1H, br s). HPLC analysis on Zorbax SB—C18 column: impurities 3% (column size 4.6×150 mm; mobile phase acetonitrile—0.1% H$_3$PO$_4$, gradient from 50 to 100% (10 min); detector UV 254 nm; flow rate 1.0 ml/min; sample concentration 0.65 mg/ml). Anal. Calcd for C$_{21}$H$_{18}$N$_2$O$_4$S, %: C, 63.94; H, 4.60; N, 7.10. Found, %: C, 63.51; H, 4.37; N, 7.11.

Example 176

3-[4-(4-Bromo-phenylsulfamoyl)-phenyl]-acrylic acid (43d)

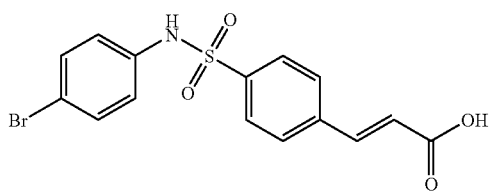

Using an analogous method, the title compound was obtained from 3-(4-chlorosulfonyl-phenyl)acrylic acid (42) and 4-bromoaniline, yield 66%. $^1$H NMR (DMSO-d$_6$, HMDSO), δ: 6.60 (1H, d, J=16.0 Hz); 7.09 (2H, d, J=8.0 Hz); 7.44 (2H, d, J=8.0 Hz); 7.60 (1H, d, J=116.0 Hz); 7.73–7.85 (4H, m); 10.49 (1H, br s).

Example 177

3-[4-(4-Bromo-phenylsulfamoyl)-phenyl]-acryloyl chloride (44d)

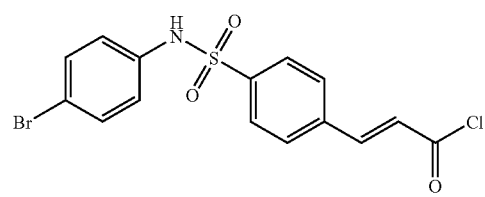

Using an analogous method, the title compound was obtained from 3-[4-(4-bromo-phenylsulfamoyl)-phenyl]-acrylic acid (43d) and oxalyl chloride, ca. yield of the crude product 91% (yellow oil).

Example 178

N-Hydroxy-3-[4-(4-bromo-phenylsulfamoyl)phenyl]-acrylamide (45d) (PX117795)

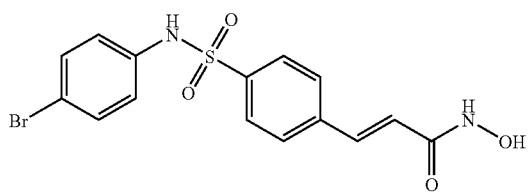

Using an analogous method, the title compound was obtained from 3-[4-(4-bromo-phenylsulfamoyl)-phenyl]-acryloyl chloride (44d) and hydroxylamine hydrochloride, yield 59%. M.p. 219–220.5° C. $^1$H NMR (DMSO-d$_6$, HMDSO), δ: 6.54 (1H, d, J=16.0 Hz); 7.05 (2H, d, J=8.0 Hz); 7.43 (2H, d, J=8.0 Hz); 7.49 (1H, d, J=16.0 Hz); 7.63–7.87 (4H, m); 9.11 (1H, br s); 10.45 (1H, s); 10.83 (1H, br s). HPLC analysis on Zorbax SB—C18 column: impurities 3% (column size 4.6×150 mm; mobile phase acetonitrile—0.1% H$_3$PO$_4$, gradient from 30 to 100% (15 min); detector UV 254 nm; flow rate 1.0 ml/min; sample concentration 0.65 mg/ml). Anal. Calcd for C$_{15}$H$_{13}$BrN$_2$O$_4$S, %: C, 45.35; H, 3.30; N, 7.05. Found, %: C, 45.44; H, 3.28; N, 7.05.

Example 179

3-[4-(4-Chloro-phenylsulfamoyl)-phenyl]-acrylic acid (43e)

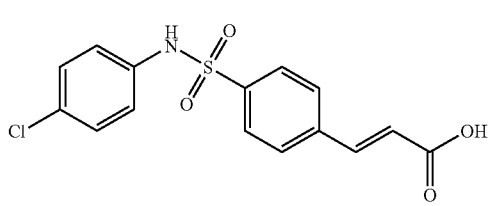

Using an analogous method, the title compound was obtained from 3-(4-chlorosulfonyl-phenyl)-acrylic acid (42) and 4-chloroaniline, yield. 83%. $^1$H NMR (DMSO-d$_6$, HMDSO), δ: 6.63 (1H, d, J=16.0 Hz); 7.09 (2H, d, J=8.0 Hz); 7.34 (2H, d, J=8.0 Hz); 7.58 (2H, d, J=8.0 Hz); 7.72 (2H, d, J=8.0 Hz); 7.84 (2H, d, J=8.0 Hz); 10.47 (1H, br s).

Example 180

3-[4-(4-Chloro-phenylsulfamoyl)-phenyl]-acryloyl chloride (44e)

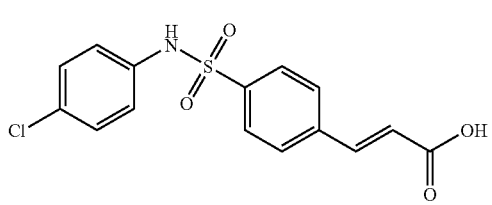

Using an analogous method, the title compound was obtained from 3-[4-(4-chloro-phenylsulfamoyl)phenyl]-acrylic acid (43e) and oxalyl chloride, ca. yield of the crude product 71% (yellow oil).

Example 181

N-Hydroxy-3-[4-(4-chloro-phenylsulfamoyl)-phenyl]-acrylamide (45e) (PX117796)

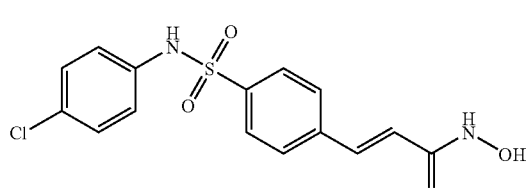

Using an analogous method, the title compound was obtained from 3-[4-(4-chloro-phenylsulfamoyl)-phenyl]- acryloyl chloride (44e) and hydroxylamine hydrochloride, yield 33%. M.p. 201–202° C. $^1$H NMR (DMSO-$d_6$, HMDSO), δ: 6.52 (1H, d, J=16.0 Hz); 7.08 (2H, d, J=8.0 Hz); 7.29 (2H, d, J=8.0 Hz); 7.45 (1H, d, J=16.0 Hz); 7.63 7.89 (5H, m); 10.43 (1H, br s); 10.83 (1H, br s). HPLC analysis on Zorbax SB—C18 column: impurities 6% (column size 4.6×150 mm; mobile phase acetonitrile—0.1% $H_3PO_4$, gradient from 30 to 100% (15 min); detector UV 254 nm; flow rate 1.0 ml/min; sample concentration 0.5 mg/ml). Anal. Calcd for $C_{15}H_{13}ClN_2O_4S$, %: C, 51.07; H, 3.71; N, 7.94. Found, %: C, 51.14; H, 3.70; N, 7.86.

Example 182

3-Bromo-N-phenyl-benzenesulfonamide (52a)

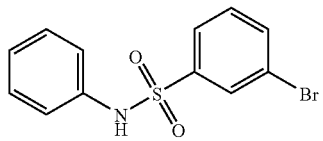

3-Bromobenzenesulfonyl chloride (51a) (1.0 g, 3.9 mmol) was added to a mixture of aniline (0.47 g, 5.1 mmol) in acetonitrile (10 ml) and sodium carbonate (1.3 g, 12.3 mmol) in water (10 ml). The mixture was stirred at ambient temperature for 1 hour and the reaction product was extracted with ethyl acetate (30 ml). The extract was dried ($Na_2SO_4$) and solvents were removed under reduced pressure to give the title compound (1.15 g, 94%) as an oil witch solidified upon standing. M.p. 98–100° C. $^1$H NMR (DMSO-$d_6$, HMDSO) δ: 6.94–7.48 (5H, m, $C_6H_5$); 7.50–7.96 (4H, m, $C_6H_4$); 10.36 (1H, s, NH).

Example 183

3-(3-Hydroxyprop-1-ynyl)-N-phenylbenzenesulfonamide (53a)

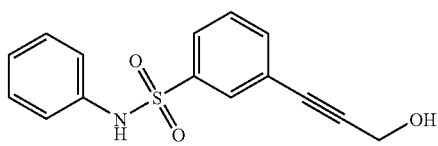

A mixture of 3-bromo-N-phenyl-benzenesulfonamide (52a) (1.0 g, 3.2 mmol), benzene (2.4 ml), tetrakis(triphenylphosphine)palladium(0) (0.4 g, 0.34 mmol), copper iodide (0.032 g, 0.16 mmol), triethylamine (2.4 ml, 17.2 mmol), and propargyl alcohol (1.0 ml, 17.2 mmol)) was refluxed under argon for 30 min. The reaction mixture was diluted with 5% HCl (50 ml) and product was extracted with ethyl acetate (50 ml). The extract was washed successively with 5% $NaHCO_3$, water and dried ($Na_2SO_4$). The solvents were removed under reduced pressure and the product was purified on silica gel with ethyl acetate-hexane (1:1, v/v) as eluent. The title compound (0.59 g, 64%) was obtained as an oil. $^1$H NMR (DMSO-$d_6$, HMDSO) δ: 4.29 (2H, d, J=6.0 Hz, $CH_2$); 5.36 (1H, t, J=6.0 Hz, OH); 6.94–7.32 (5H, m, $C_6H_5$); 7.35–7.91 (4H, m, $C_6H_4$); 10.32 (1H, s, NH).

Example 184

3-(3-Oxoprop-1-ynyl)-N-phenylbenzenesulfonamide (54a)

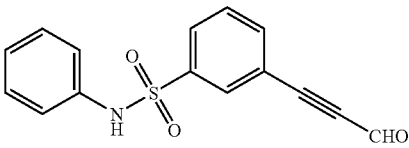

3-(3-Hydroxyprop-1-ynyl)-N-phenylbenzenesulfonamide (53a) (0.55 g, 1.9 mmol) was dissolved in a solution of Dess-Martin reagent in methylene chloride (0.157 g/ml) (8.2 ml) and the resultant mixture was stirred at ambient temperature for 30 min. The mixture was partitioned between water (50 ml) and ether (50 ml), and ether solution was washed successively with 5% $Na_2CO_3$, water, and dried ($Na_2SO_4$). The solvents were removed under reduced pressure to give the title compound (0.47 g, 72%) as an oil. The crude product 54a was used in the further step without an additional purification. $^1$H NMR (DMSO-$d_6$, HMDSO) δ: 6.96–7.41 (5H, m, $C_6H_5$); 7.54–8.07 (4H, m, $C_6H_4$); 9.45 (1H, s, CH); 10.41 (1H, s, NH).

Example 185

(E)-5-(3-Phenylsulfamoylphenyl)pent-2-en-4-ynoic acid methyl ester (55a)

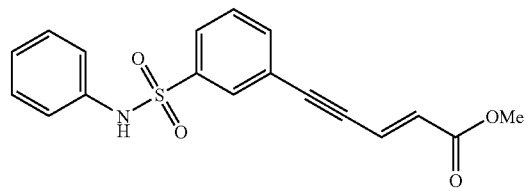

To a solution of trimethyl phosphonoacetate (0.81 g, 4.5 mmol) in dry tetrahydrofuran (20 ml) under an argon atmosphere at 15–20° C. sodium hydride (0.12 g, 5.0 mmol) was added. The mixture was stirred at ambient temperature for 1 hour, and a solution of 3-(3-oxoprop-1-ynyl)-N-phenylbenzenesulfonamide (54a) (0.44 g, 1.5 mmol) in dry tetrahydrofuran (20 ml) was added dropwise at 15–20° C. The reaction mixture was stirred at ambient temperature for 1 hour and quenched by 3% HCl (20 ml). The product was extracted with ethyl acetate (50 ml), the extract was washed with 5% $NaHCO_3$, water and dried ($Na_2SO_4$). The solvents were removed under reduced pressure and the residue was chromatographed on silica gel with ethyl acetate-hexane (1:2, v/v) as eluent to give the title compound (0.39 g, 74%) as a white solid. M.p. 134–136° C. $^1$H NMR (DMSO-$d_6$, HMDSO) δ: 3.73 (3H, s, $CH_3$); 6.49 (1H, d, J=15.5 Hz, CH); 7.03 (1H, d, J=15.5 Hz, CH); 7.01–7.38 (5H, m, $C_6H_5$); 7.41–7.89 (4H, m, $C_6H_4$); 10.34 (1H, s, NH).

Example 186

(E)-5-(3-Phenylsulfamoylphenyl)pent-2-en-4-ynoic acid (56a)

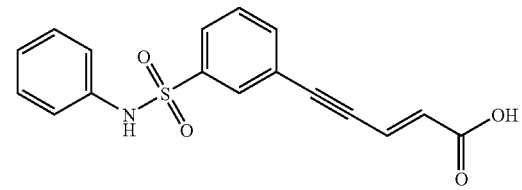

To a solution of E-5-(3-phenylsulfamoylphenyl)pent-2-en-4-ynoic acid methyl ester (55a) (0.34 g, 1 mmol) in methanol (3 ml) 1N solution of sodium hydroxide (3 ml) was added and the mixture was stirred at ambient temperature for 3 hours. Methanol was removed under reduced pressure, to the residue water (5 ml) was added and the mixture was acidified with 3% HCl. The precipitate was filtered, washed with water, and dried to give the title compound (0.31 g, 95%) as white crystals. M.p. 188–190° C. $^1$H NMR (DMSO-$d_6$, HMDSO) δ: 6.36 (1H, d, J=15.8 Hz, CH); 6.92 (1H, d, J=15.8 Hz, CH); 7.01–7.36 (5H, m, $C_6H_5$); 7.38–7.89 (4H, m, $C_6H_4$); 10.32 (1H, s, NH).

Example 187

(E)-5-(3-Phenylsulfamoylphenyl)pent-2-en-4-ynoic acid hydroxyamide (58a) (PX116238)

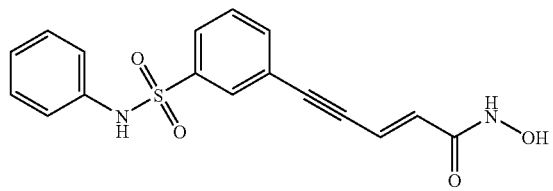

To a solution of (E)-5-(3-phenylsulfamoylphenyl)pent-2-en-4-ynoic acid (56a) (0.25 g 0.77 mmol) in methylene chloride (5 ml) oxalyl chloride (0.42 g 3.1 mmol) was added. The resultant mixture was stirred for 1 hour at ambient temperature and the solvents were removed under reduced pressure. The crude product (57a) was dissolved in acetonitrile (5 ml) and the obtained solution to a mixture of hydroxylamine hydrochloride (0.3 g, 4.3 mmol) and $NaHCO_3$ (0.3 g, 3.6 mmol) in water (8 ml) was added. The reaction mixture was stirred for 10 min. and the product was extracted with ethyl acetate (30 ml). The extract was washed with 10% $Na_2CO_3$, and the aqueous phase was acidified with 3% HCl. The precipitate was filtered and dried to give the title compound (0.12 g, (46%). M.p 88–90° C. $^1$H NMR (DMSO-$d_6$, HMDSO) δ: 6.41 (1H, d, J=115.8 Hz, CH); 6.82 (1H, d, J=15.8 Hz, CH); 6.92–7.41 (5H, m, $C_6H_5$); 7.47–8.01 (4H, m, $C_6H_4$); 8.94–11.21 (3H, br s, NH, NH, OH). Anal. Calcd for $C_{17}H_{14}N_2O_4S$*0.4$H_2O$: C, 58.58; H, 4.27; N, 8.01. Found: C, 58.12; H, 4.03; N, 7.80.

Example 188

4-Iodo-N-phenyl-benzenesulfonamide (52b)

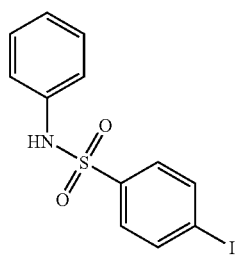

Using an analogous method, the title compound was obtained from 4-iodobenzenesulfonyl chloride (51b) and aniline, yield 86%, m.p. 135–137° C. $^1$H NMR (DMSO-$d_6$, HMDSO) δ: 6.85–7.36 (5H, m, $C_6H_5$); 7.52 (2H, d, J=8.5 Hz, $C_6H_2$); 7.89 (2H, d, J=8.5 Hz, $C_6H_2$); 10.32 (1H, s, NH).

Example 189

4-(3-Hydroxyprop-1-ynyl)-N-phenylbenzenesulfonamide (53b)

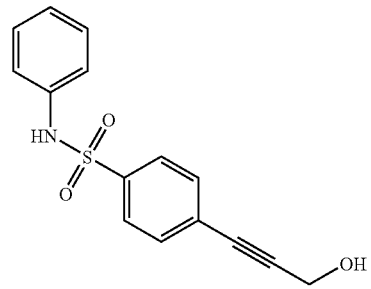

Using an analogous method, the title compound was obtained from 4-iodo-N-phenyl-benzenesulfonamide (52b) and propargyl alcohol, yield 86%, m.p. 161–163° C. $^1$H NMR (DMSO-$d_6$, HMDSO) δ: 4.29 (2H, d, J=6.0 Hz, $CH_2$); 5.38 (1H, t, J=6.0 Hz, OH); 6.92–7.38 (5H, m, $C_6H_5$); 7.54 (2H, d, J=9.0 Hz, $C_6H_2$); 7.73 (2H, d, J=9.0 Hz, $C_6H_2$); 10.29 (1H, s, NH).

Example 190

4-(3-Oxoprop-1-ynyl)-N-phenylbenzenesulfonamide (54b)

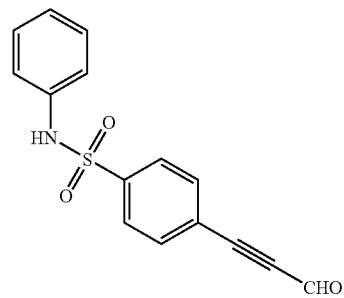

Using an analogous method, the title compound was obtained from 4-(3-hydroxyprop-1-ynyl)-N-phenylbenzenesulfonamide (53b) and Dess-Martin reagent, yield 70%, m.p. 161–163° C. $^1$H NMR (DMSO-$d_6$, HMDSO) δ: 6.92–7.41 (5H, m, $C_6H_5$); 7.83 (4H, s, $C_6H_4$); 9.43 (1H, s, CH); 10.42 (1H, s, NH).

Example 191

E-5-(4-Phenylsulfamoylphenyl)pent-2-en-4-ynoic acid methyl ester (55b)

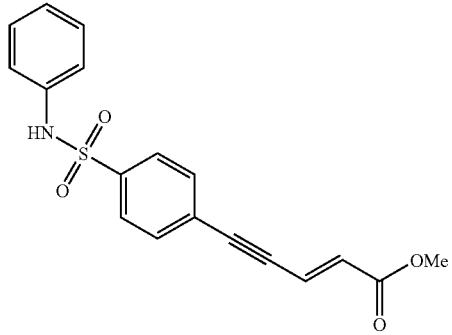

Using an analogous method, the title compound was obtained from 4-(3-oxoprop-1-ynyl)-N-phenylbenzenesulfonamide (54b) and trimethyl phosphonoacetate, yield 49%, m.p. 153–155° C. $^1$H NMR (DMSO-d$_6$, HMDSO) δ: 3.72 (3H, s, CH$_3$); 6.49 (1H, d, J=16.0 Hz, CH); 6.98 (1H, d, J=16.0 Hz, CH); 6.92–7.38 (5H, m, C$_6$H$_5$); 7.64 (2H, d, J=9.0 Hz, C$_6$H$_2$); 7.76 (2H, d, J=9.0 Hz, C$_6$H$_2$); 10.32 (1H, s, NH).

Example 192

5-(4-Phenylsulfamoylphenyl)pent-2-en-4-ynoic acid (56b)

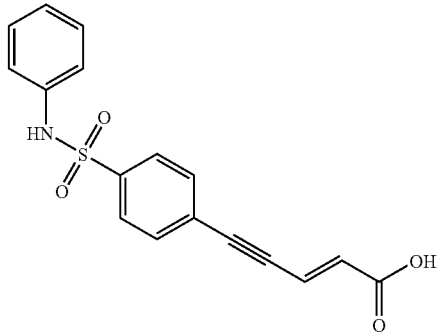

Using an analogous method, the title compound was obtained from E-5-(4-phenylsulfamoylphenyl)pent-2-en-4-ynoic Acid Methyl Ester (55b), yield 81%, m.p. 234–236° C. $^1$H NMR (DMSO-d$_6$, HMDSO) δ: 6.39 (1H, d, J=16.0 Hz, CH); 6.95 (1H, d, J=16.0 Hz, CH); 6.94–7.39 (5H, m, C$_6$H$_5$); 7.69 (2H, d, J=9.0 Hz, C$_6$H$_2$); 7.83 (2H, d, J=9.0 Hz, C$_6$H$_2$); 10.36 (1H, s, NH), 12.77 (1H, br s, OH).

Example 193

E-5-(4-Phenylsulfamoylphenyl)pent-2-en-4-ynoic acid hydroxyamide (58b) (PX117453)

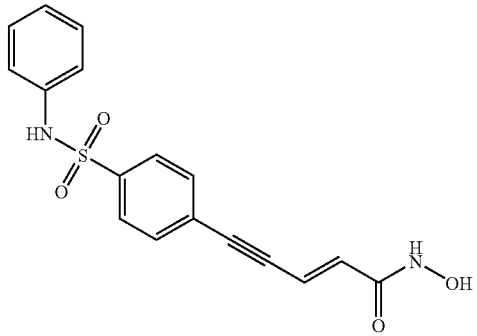

Using an analogous method, the title compound was obtained from 5-(4-phenylsulfamoylphenyl)pent-2-en-4-ynoic acid (56b) via (E)-5-[4-phenylsulfamoylphenyl]-2-penten-4-ynoyl chloride (57b), yield 59%, m.p. 161–163° C. $^1$H NMR (DMSO-d$_6$, HMDSO) δ:6.38 (1H, d, J=16.0 Hz, CH); 6.78 (1H, d, J=16.0 Hz, CH); 6.89–7.43 (5H, m, C$_6$H$_5$); 7.67 (2H, d, J=9.0 Hz, C$_6$H$_2$); 7.78 (2H, d, J=9.0 Hz, C$_6$H$_2$); 10.05 (3H, br s, NH, NH, OH). Anal. Calcd for C$_{17}$H$_{14}$N$_2$O$_4$S* 0.25H$_2$O: C, 58.86; H, 4.21; N, 8.08. Found: C, 58.36; H, 3.93; N, 7.82.

Example 194

Sodium 6-ethoxy-6-oxo-1-hexanesulfonate (62b)

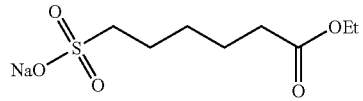

To a solution of ethyl 6bromohexanoate (61b) (2.48 g, 11.0 mmol) in ethanol (6 ml) a solution of sodium sulfite (2.16 g, 20.6 mmol) in water (9 ml) was added and the resulting mixture was refluxed for 1 hour. The reaction mixture was evaporated under reduced pressure and the obtained solid was extracted with boiling ethanol in Soxhlet extraction apparatus for 15–20 hours. The extract was evaporated and the residue was crystallised from ethanol-diethyl ether (1:10) giving the title compound (2.71 g, 99%) in a form of a white solid material. $^1$H NMR (DMSO-d$_6$, HMDSO), δ: 1.05–1.78 (6H, m); 1.17 (3H, t, J=7.2 Hz); 2.26 (4H, t, J=7.5 Hz); 4.05 (2H, q, J=7.2 Hz).

Example 195

Ethyl 6-(chlorosulfonyl)hexanoate (63b)

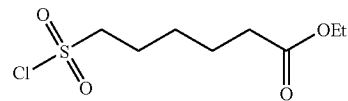

Sodium 6ethoxy-6-oxo-1-hexanesulfonate (62b) (1.68 g, 6.8 mmol) was mixed with phosphorus pentachloride and the mixture was carefully pestled in a mortar. After the reaction came to the end (the foaming of the reaction mixture ceased) the mixture was extracted with dry benzene (50 ml). The extract was evaporated under reduced pressure and the residue was dried in vacuum to give crude title compound (1.03 g, 61%) as a hygroscopic oil. The chloride (63b) was used in further reactions without additional purification.

Example 196

Ethyl 6-(anilinosulfonyl)hexanoate (64b)

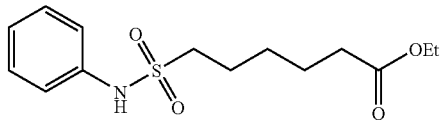

To a solution of ethyl 6-(chlorosulfonyl)hexanoate (63b) (0.5 g, 2.0 mmol) in benzene (5 ml) aniline (0.8 g, 8.5 mmol) was added and the resulting solution was stirred at ambient temperature for 24 hours. The reaction mixture was partitioned between ethyl acetate and 1N HCl. The organic layer was washed successively with water, saturated NaCl, and dried (Na$_2$SO$_4$). The solvent was evaporated and the residue was chromatographed on silica gel with petroleum ethertert-butylmethyl ether (3:2, v/v) as eluent to give the title compound (0.45 g, 75%) as an oil. ¹H NMR (DMSO-d₆, HMDSO), δ: 1.03–1.81 (6H, m); 1.15 (3H, t, J=7.1 Hz); 2.23 (2H, t, J=6.8 Hz); 3.07 (2H, t, J=7.6 Hz); 4.04 (2H, q, J=7.1 Hz); 7.00–7.47 (5H, m); 9.76 (1H, s).

Example 197

6-(Anilinosulfonyl)-N-hydroxyhexanamide (67b) (PX117234)

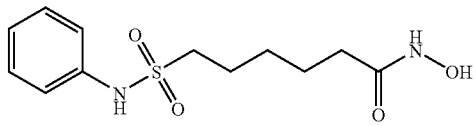

To a mixture of ethyl 6-(anilinosulfonyl)hexanoate (64b) and hydroxylamine hydrochloride (0.43 g, 6.2 mmol) in methanol (5 ml) the 3.43 N solution of sodium methylate (2.62 ml, 9.0 mmol) in methanol was added and the reaction was stirred at ambient temperature for 40 min. The reaction mixture was poured into saturated NaH₂PO₄ (15 ml) and extracted with ethyl acetate. The extract was washed successively with water, saturated NaCl, and dried (Na₂SO₄). The solvent was evaporated, the residue was washed with diethyl ether and crystallised from ethyl acetate. The title compound (0.3 g, 69%) was obtained as white crystals, m.p. 97–98° C. ¹H NMR (DMSO-d₆, HMDSO), δ: 1.02–1.78 (m, 6H, CH₂); 1.90 (br t, 2H, J=6.4 Hz, CH₂); 3.06 (t, 2H, J=7.0 Hz, CH₂); 6.94–7.60 (m, 5H, arom.); 8.66 (br s, 1H, NH); 9.76 (br s, 1H, NH); 10.36 (br s, 1H, OH). HPLC analysis on Symmetry C₈ column: impurities 3.5% (column size 3.9×150 mm; mobile phase acetonitrile—0.1M phosphate buffer (pH 2.5), 30:70; detector UV 220 nm; flow rate 1.1 ml/min; sample concentration 0.4 mg/ml). Anal. Calcd for C₁₂H₁₈N₂O₄S, %: C, 50.33; H, 6.34; N, 9.78; S, 11.20. Found, %: C, 50.10; H, 6.22; N, 9.83; S, 11.10.

Example 198

Sodium 5-ethoxy-5-oxo-1-pentanesulfonate (62a)

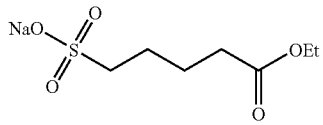

Using an analogous method, the title compound was obtained from ethyl 5-bromopentanoate (61a) and sodium sulfite in a form of white crystals, yield 98%.

¹H NMR (DMSO-d₆, HMDSO), δ: 1.17 (3H, t, J=7.0 Hz); 1.37–1.73 (4H, m); 2.12–2.56 (4H, m, partially overlapped with a signal of DMSO); 4.04 (2H, q, J=7.0 Hz).

Example 199

Ethyl 6-(chlorosulfonyl)pentanoate (63a)

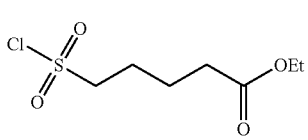

Using an analogous method, the title compound was obtained from sodium 5-ethoxy-5-oxo-1-pentanesulfonate (62a) and phosphorus pentachloride, ca. yield of the crude product 90% (hygroscopic oil).

Example 200

Ethyl 6-(anilinosulfonyl)pentanoate (64a)

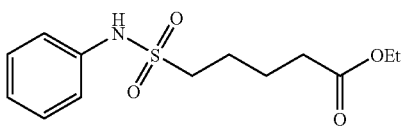

Using an analogous method, the title compound was obtained from ethyl 6-(chlorosulfonyl)pentanoate (63a) and aniline as an oil, yield 38%. ¹H NMR (DMSO-d₆, HMDSO), δ: 1.15 (3H, t, J=7.0 Hz); 1.48–1.81 (4H, m); 2.27 (2H, t, J=6.2 Hz); 3.09 (2H, t, J=6.7 Hz); 4.04 (2H, q, J=7.0 Hz); 6.98–7.48 (5H, m); 9.78 (1H, s).

Example 201

5-(Anilinosulfonyl)-N-hydroxypentanamide (67a) (PX117233)

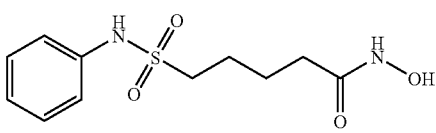

Using an analogous method, the title compound was obtained from ethyl 6-(anilinosulfonyl)pentanoate (64a) and hydroxylamine hydrochloride, yield 49%, m.p. 128–129° C. (from ethyl acetate). ¹H NMR (DMSO-d₆, HMDSO) δ: 1.37–1.78 (m, 4H, CH₂); 1.92 (t, 2H, J=5.9 Hz, CH₂); 3.07 (t, 2H, J=7.0 Hz, CH₂); 6.97–7.47 (m, 5H, C₆H₅); 8.69 (s, 1H, NH); 9.78 (s, 1H, NH); 10.33 (s, 1H, OH). HPLC analysis on Symmetry C₈ column: impurities 1.2% (column size 3.9×150 mm; mobile phase acetonitrile—0.1M phosphate buffer (pH 2.5), 25:75; detector UV 220 nm; flow rate 1.2 ml/min; sample concentration 0.5 mg/ml). Anal. Calcd for C₁₁H₁₆N₂O₄S, %: C, 48.52; H, 5.92; N, 10.29; S, 11.77. Found, %: C, 48.57; H, 5.92; N, 10.21; S, 11.65.

Example 202

Ethyl 5-[(2-naphthylamino)sulfonyl] pentanoate (64e)

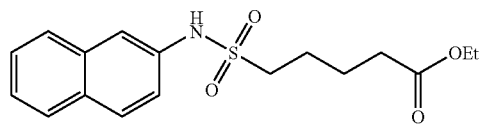

Using an analogous method, the title compound was obtained from ethyl 6-(chlorosulfonyl)pentanoate (63a) and 2-naphthylamine as brown crystals, yield 20%. ¹H NMR (DMSO-$d_6$, HMDSO), δ: 1.11 (3H, t, J=7.1 Hz); 1.35–1.88 (4H, m); 2.25 (2H, t, J=6.2 Hz); 3.18 (2H, t, J=6.7 Hz); 3.99 (2H, q, J=7.1 Hz); 7.27–7.97 (7H, m); 10.03 (1H, s).

Example 203

N-Hydroxy-5-[(2-naphthylamino)sulfonyl]pentanamide (67e) (PX117235)

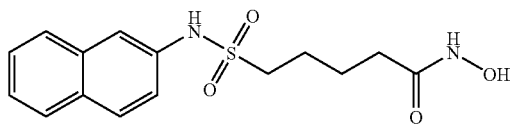

Using an analogous method, the title compound was obtained from ethyl 5-[(2-naphthylamino)sulfonyl]pentanoate (64e) and hydroxylamine hydrochloride, yield 55%, m.p. 163–164° C. (from ethyl acetate). $^1$H NMR (DMSO-$d_6$, HMDSO) δ: 1.39–1.78 (m, 4H, CH$_2$); 1.93 (t, 2H, J=6.4 Hz, CH$_2$); 3.16 (m, 2H, overlapped with a H$_2$O signal from DMSO-$d_6$, CH$_2$); 7.30–7.61 (m, 3H, arom.); 7.67 (1H, d, J=2.0 Hz, arom.); 7.76–7.99 (m, 3H, arom.); 8.67 (br s, 1H, NH); 10.00 (br s, 1H, NH); 10.31 (br s, 1H, OH). HPLC analysis on Symmetry C$_{18}$ column: impurities 1% (column size 3.9×150 mm; mobile phase acetonitrile—0.1M phosphate buffer (pH 2.5), 35:65; detector UV 230 nm; flow rate 1.1 ml/min; sample concentration 0.5 mg/ml). Anal. Calcd for C$_{15}$H$_{18}$N$_2$O$_4$S, %: C, 55.89; H, 5.63; N, 8.69; S, 9.95. Found, %: C, 55.83; H, 5.52; N, 8.68; S, 9.95.

Example 204

Sodium 7-methoxy-7-oxo-1-heptanesulfonate (62c)

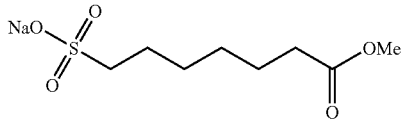

Using an analogous method, the title compound was obtained from methyl 7-bromoheptanoate (61c) and sodium sulfite as white crystals, yield 98%. $^1$H NMR (DMSO-$d_6$, HMDSO), δ: 1.05–1.76 (8H, m); 2.27 (4H, t, partially overlapped with a signal of DMSO, J=6.6 Hz); 3.58 (3H, s).

Example 205

Methyl 7-(chlorosulfonyl)heptanoate (63c)

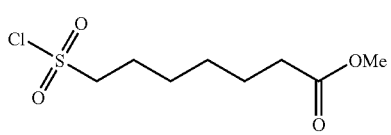

Using an analogous method, the title compound was obtained from sodium 7-methoxy-7-oxo-1-heptanesulfonate (62c) and phosphorus pentachloride, ca. yield of the crude product 73% (hygroscopic oil).

Example 206

Methyl 7-(anilinosulfonyl)heptanoate (64c)

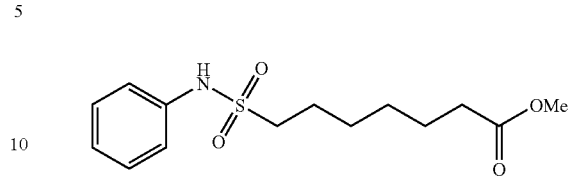

Using an analogous method, the title compound was obtained from methyl 7-(chlorosulfonyl)heptanoate (63c) and aniline as an oil, yield 53%. $^1$H NMR (DMSO-$d_6$, HMDSO), δ: 81.05–1.83 (8H, m); 2.24 (2H, t, J=6.8 Hz); 3.06 (2H, t, J=7.4 Hz); 3.57 (3H, s); 6.97–7.45 (5H, m); 9.76 (1H, s).

Example 207

5-(Anilinosulfonyl)-N-hydroxyheptanamide (67c) (PX117236)

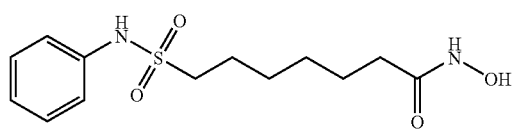

Using an analogous method, the title compound was obtained from methyl 7-(anilinosulfonyl)heptanoate (64c) and hydroxylamine hydrochloride, yield 74%, m.p. 94–95° C. (from ethyl acetate). $^1$H NMR (DMSO-$d_6$, HMDSO) δ: 1.07–1.51 (m, 6H, CH$_2$); 1.53–1.73 (m, 2H, CH$_2$); 1.89 (t, 2H, J=7.2 Hz, CH$_2$); 3.04 (t, 2H, J=7.6 Hz, CH$_2$); 7.03–7.40 (m, 5H, C$_6$H$_5$); 8.67 (s, 1H, NH); 9.78 (s, 1H, NH); 10.33 (s, 1H, OH). HPLC analysis on Symmetry C$_8$ column: impurities 3.5% (column size 3.9×150 mm; mobile phase acetonitrile—0.1M phosphate buffer (pH 2.5), 35:65; detector UV 220 nm; flow rate 0.9 ml/min; sample concentration 0.3 mg/ml). Anal. Calcd for C$_{13}$H$_{20}$N$_2$O$_4$S, %: C, 51.98; H, 6.71; N, 9.33; S, 10.67. Found, %: C, 51.83; H, 6.64; N, 9.23; S, 10.65.

Example 208

Sodium 8-methoxy-8-oxo-1-octanesulfonate (62d)

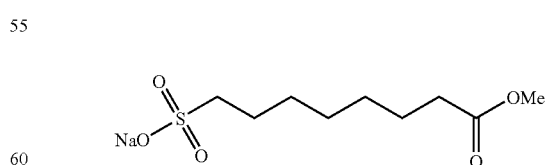

Using an analogous method, the title compound was obtained from methyl 8-bromooctanoate (61d) and sodium sulfite as white crystals, yield 98%. $^1$H NMR DMSO-$d_6$, HMDSO), δ: 1.00–1.75 (10H, m); 2.28 (4H, t, partially overlapped with signal of DMSO, J=7.8 Hz); 3.58 (3H, s).

Example 209

Methyl 8-(chlorosulfonyl)octanoate (63d)

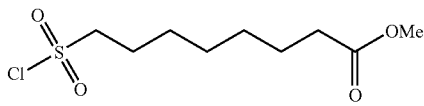

Using an analogous method, the title compound was obtained from sodium 8-methoxy-8-oxo-1-octanesulfonate (62d) and phosphorus pentachloride, ca. yield of the crude product 73% (hygroscopic oil).

Example 210

Methyl 8-(anilinosulfonyl)octanoate (64d)

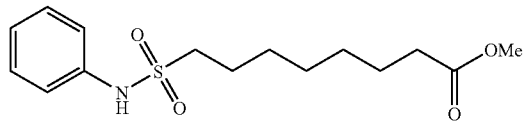

Using an analogous method, the title compound was obtained from methyl 8-(chlorosulfonyl)octanoate (63d) and aniline as an oil, yield 54%. $^1$H NMR (DMSO-$d_6$, HMDSO), δ: 1.01–1.80 (10H, m); 2.25 (2H, t, J=6.9 Hz); 3.06 (2H, t, J=7.5 Hz); 3.57 (3H, s); 6.99–7.46 (5H, m); 9.75 (1H, s).

Example 211

5-(Anilinosulfonyl)-N-hydroxyoctanamide (67d) (PX117245)

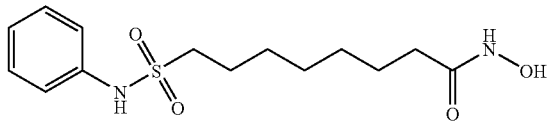

Using an analogous method, the title compound was obtained from methyl 8-(anilinosulfonyl)octanoate (64d) and hydroxylamine hydrochloride, yield 76%, m.p. 87–88° C. (from ethyl acetate). $^1$H NMR (DMSO-$d_6$, HMDSO) δ: 1.08–1.51 (m, 8H, CH$_2$); 1.52–1.73 (m, 2H, CH$_2$); 1.90 (t, 2H, J=7.2 Hz, CH$_2$); 3.05 (t, 2H, J=7.6 Hz, CH$_2$); 7.02–7.39 (m, 5H, C$_6$H$_5$); 8.66 (s, 1H, NH); 9.74 (s, 1H, NH); 10.32 (s, 1H, OH). HPLC analysis on Symmetry C$_8$ column: impurities 3% (column size 3.9×150 mm; mobile phase acetonitrile—0.1M phosphate buffer (pH 2.5), 35:65; detector UV 220 nm; flow rate 1.1 ml/min; sample concentration 0.4 mg/ml). Anal. Calcd for C$_{14}$H$_{22}$N$_2$O$_4$S, %: C, 53.48; H, 7.05; N, 8.91; S, 10.20. Found, %: C, 53.23; H, 7.05; N, 8.82; S, 10.25.

Example 212

Methyl 7-[(methylanilino)sulfonyl]heptanoate (65c)

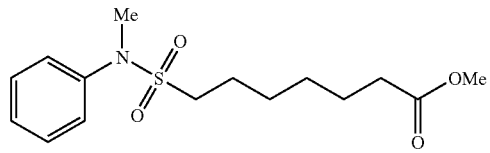

Using an analogous method, the title compound was obtained from methyl 7-(chlorosulfonyl)heptanoate (63c) and N-methylaniline as white crystals, yield 70%. $^1$H NMR (DMSO-$d_6$, HMDSO), δ: 1.10–1.77 (8H, m); 2.26 (2H, t, J=6.8 Hz); 3.11 (2H, t, J=7.4 Hz); 3.25 (3H, s); 3.57 (3H, s); 7.24–7.51 (5H, m).

Example 213

N-Hydroxy-7-[(methylanilino)sulfonyl]heptanamide (68c) (PX117260)

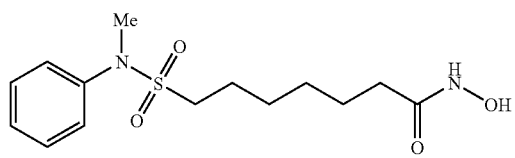

Using an analogous method, the title compound was obtained from methyl 7-(methylanilinosulfonyl)heptanoate (65c) and hydroxylamine hydrochloride, yield 59%, m.p. 69–70° C. (from ethyl acetate). $^1$H NMR (DMSO-$d_6$, HMDSO) δ: 1.11–1.70 (m, 8H, CH$_2$); 1.91 (t, 2H, J=7.2 Hz, CH$_2$); 3.09 (t, 2H, J=7.7 Hz, CH$_2$); 3.25 (s, 3H, CH$_3$); 7.21–7.45 (m, 5H, C$_6$H$_5$); 8.65 (br s, 1H, NH); 10.32 (s, 1H, OH). HPLC analysis on Symmetry Cl$_8$ column: impurities <1% (column size 3.9×150 mm; mobile phase acetonitrile—0.1M phosphate buffer (pH 2.5), 30:70; detector UV 220 nm; flow rate 1.1 ml/min; sample concentration 0.5 mg/ml). Anal. Calcd for C$_{14}$H$_2$N$_2$O$_4$S, %: C, 53.48; H, 7.05; N, 8.91; S, 10.20. Found, %: C, 53.44; H, 7.05; N, 8.86; S, 10.13.

Example 214

Ethyl 6-[(methylanilino)sulfonyl]hexanoate (65b)

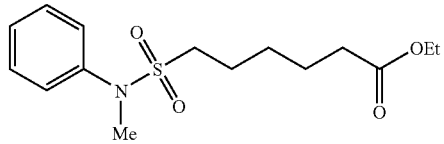

Using an analogous method, the title compound was obtained from ethyl 6-(chlorosulfonyl)hexanoate (63b) and N-methylaniline as an oil, yield 43%. $^1$H NMR (DMSO-$d_6$, HMDSO), δ: 1.10–1.77 (8H, m); 2.26 (2H, t, J=6.8 Hz); 3.11 (2H, t, J=7.4 Hz); 3.25 (3H, s); 3.57 (3H, s); 7.24–7.51 (5H, m).

Example 215

N-Hydroxy-6-[(methylanilino)sulfonyl]hexanamide (68b) (PX117410)

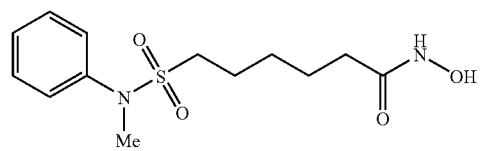

Using an analogous method, the title compound was obtained from ethyl 6-(methylanilinosulfonyl)hexanoate (65b) and hydroxylamine hydrochloride, yield 40%, m.p. 121–122° C. (from ethyl acetate). $^1$H NMR (DMSO-d$_6$, HMDSO) δ: 1.13–1.72 (m, 6H, CH$_2$); 1.91 (t, 2H, J=7.0 Hz, CH$_2$); 3.09 (t, 2H, J=7.6 Hz, CH$_2$); 3.25 (s, 3H, CH$_3$); 7.22–7.46 (m, 5H, C$_6$H$_5$); 8.68 (s, 1H, NH); 10.35 (s, 1H, OH). HPLC analysis on Zorbax SB—C$_{18}$ column: impurities ~6% (column size 4.6×150 mm; mobile phase methanol—0.1% H$_3$PO$_4$, gradient from 50:50 to 90:10; detector UV 230 nm; flow rate 1.5 ml/min; sample concentration 0.5 mg/ml). Anal. Calcd for C$_{13}$H$_{20}$N$_2$O$_4$S, %: C, 51.98; H, 6.71; N, 9.33; S, 10.67. Found, %: C, 51.76; H, 6.63; N, 9.29; S, 10.63.

Example 216

Methyl 8-[(methylanilino)sulfonyl]octanoate (65d)

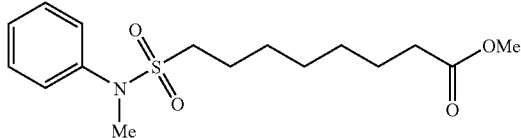

Using an analogous method, the title compound was obtained from methyl 8-(chlorosulfonyl)octanoate (63d) and N-methylaniline as an oil, yield 68%. $^1$H NMR (DMSO-d$_6$, HMDSO), δ: 1.05–1.76 (10H, m); 2.27 (2H, t, J=7.0 Hz); 3.11 (2H, t, J=7.3 Hz); 3.25 (3H, s); 3.57 (3H, s); 7.23–7.51 (5H, m).

Example 217

N-Hydroxy-8-[(methylanilino)sulfonyl]octanamide (68d) (PX117411)

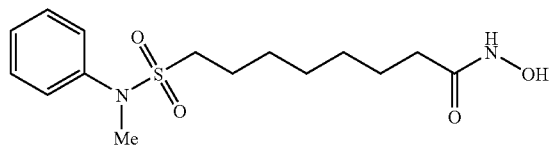

Using an analogous method, the title compound was obtained from methyl 8-(methylanilinosulfonyl)octanoate (65d) and hydroxylamine hydrochloride, yield 66%, m.p. 65.5–66.5° C. (from ethyl acetate). $^1$H NMR (DMSO-d$_6$, HMDSO) δ: 1.06–1.72 (m, 10H, CH$_2$); 1.91 (t, 2H, J=7.2 Hz, CH$_2$); 3.09 (t, 2H, J=7.6 Hz, CH$_2$); 3.25 (s, 3H, CH$_3$); 7.21–7.50 (m, 5H, C$_6$H$_5$); 8.64 (s, 1H, NH); 10.31 (s, 1H, OH). HPLC analysis on Zorbax SB—C$_{18}$ column: impurities ~6% (column size 4.6×150 mm; mobile phase methanol—0.1% H$_3$PO$_4$, gradient from 50:50 to 90:10; detector UV 230 nm; flow rate 1.5 ml/min; sample concentration 0.7 mg/ml). Anal. Calcd for C$_{15}$H$_{24}$N$_2$O$_4$S, %: C, 54.86; H, 7.37; N, 8.53; S, 9.76. Found, %: C, 54.68; H, 7.30; N, 8.55; S, 9.70.

Example 218

Ethyl 6-[(benzylanilino)sulfonyl]hexanoate (66b)

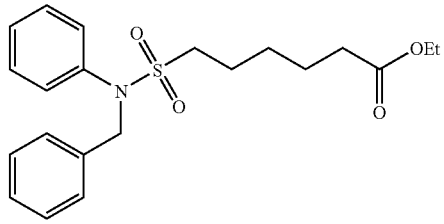

To a cold solution (ice bath) of ethyl 6-(anilinosulfonyl)hexanoate (64b) (0.86 g, 2.88 mmol) in 1,2-dimethoxyethane (5 ml) a 60% suspension of sodium hydride in mineral oil (0.12 g, 3.0 mmol) and a solution of benzylbromide (0.49 g, 2.88 mmol) in 1,2-dimethoxyethane (3 ml) were added, and the resulting solution was stirred at ambient temperature for 24 hours. The reaction mixture was poured into water and the resulting mixture was extracted with ethyl acetate. The organic layer was washed successively with water, saturated NaCl, and dried (Na$_2$SO$_4$). The solvent was evaporated and the residue was chromatographed on silica gel with petroleum ether-tert-butylmethyl ether (3:2, v/v) as eluent to give the title compound (0.56 g, 50%) as an oil. $^1$H NMR (DMSO-d$_6$, HMDSO), 8:1.16 (3H, t, J=7.0 Hz); 1.21–1.87 (6H, m); 2.27 (2H, t, J=6.6 Hz); 3.21 (2H, t, partially overlapped with a signal of H$_2$O, J=7.6 Hz); 4.05 (2H, q, J=7.0 Hz); 4.89 (2H, s); 7.14–7.58 (10H, m).

Example 219

6-[(Benzylanilino)sulfonyl]-N-hydroxyhexanamide (69b) (PX117414)

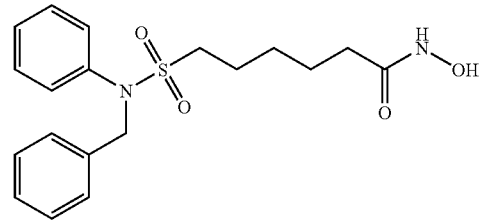

Using an analogous method, the title compound was obtained from ethyl 6-[(benzylanilino)sulfonyl]hexanoate (66b) and hydroxylamine hydrochloride, yield 93%, m.p. 129–129.5° C. (from ethyl acetate). $^1$H NMR (DMSO-d$_6$, HMDSO) δ: 1.11–1.56 (m, 4H, CH$_2$); 1.61–1.79 (m, 2H, CH$_2$); 1.93 (t, 2H, J=7.2 Hz, CH$_2$); 3.19 (t, 2H, J=7.5 Hz, CH$_2$); 4.89 (s, 2H, CH$_2$Ph); 7.16–7.41 (m, 10H, 2C$_6$H$_5$); 8.67 (s, 1H, NH); 10.36 (s, 1H, OH). HPLC analysis on Symmetry C$_{18}$ column: impurities 3% (column size 3.9× 1.50 mm; acetonitrile—0.1M phosphate buffer (pH 2.5), 40:60; detector UV 220 nm; flow rate 1.2 ml/min; sample concentration 0.5 mg/ml). Anal. Calcd for C$_{19}$H$_{24}$N$_2$O$_4$S, %: C, 60.62; H, 6.43; N, 7.44; S, 8.52. Found, %: C, 60.37; H, 6.35; N, 7.45; S, 8.46.

Example 220

Methyl 8-[(benzylanilino)sulfonyl]octanoate (66d)

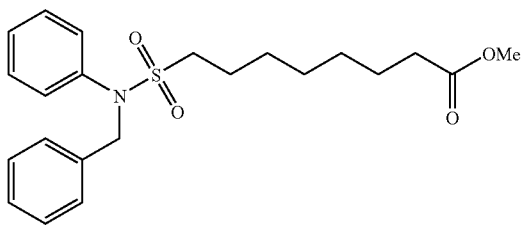

Using an analogous method, the title compound was obtained from methyl 8-(anilinosulfonyl)octanoate (64d), 60% suspension of sodium hydride in mineral oil, and benzylamine as white crystals, yield 23%. $^1$H NMR (DMSO-$d_6$, HMDSO), δ: 1.06–1.87 (10H, m); 2.28 (2H, t, J=6.8 Hz); 3.21 (2H, t, J=7.8 Hz); 3.58 (3H, s); 4.89 (2H, s); 7.14–7.45 (10H, m).

Example 221

8-[(Benzylanilino)sulfonyl]-N-hydroxyoctanamide (69d) (PX117412)

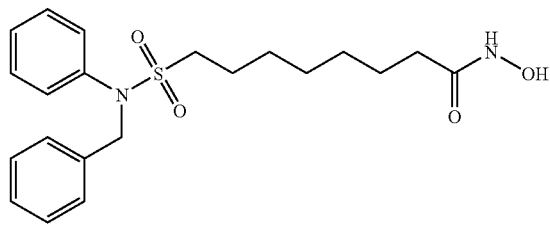

Using an analogous method, the title compound was obtained from methyl 8-[(benzylanilino)sulfonyl]octanoate (66d) and hydroxylamine hydrochloride, yield 83%, m.p. 119–119.5° C. (from ethyl acetate). $^1$H NMR (DMSO-$d_6$, HMDSO) δ: 1.11–1.57 (m, 8H, CH$_2$); 1.60–1.81 (m, 2H, CH$_2$); 1.93 (t, 2H, J=7.2 Hz, CH$_2$); 3.20 (t, 2H, J=7.5 Hz, CH$_2$); 4.89 (s, 2H, CH$_2$Ph); 7.17–7.41 (m, 10H, 2C$_6$H$_5$); 8.67 (s, 1H, NH); 10.34 (s, 1H, OH). HPLC analysis on Symmetry C$_8$ column: impurities 5.6% (column size 3.9× 150 mm; acetonitrile—0.1M phosphate buffer (pH 2.5), 50:50; detector UV 220 nm; flow rate 1.3 ml/min; sample concentration 0.5 mg/ml). Anal. Calcd for C$_{21}$H$_{28}$N$_2$O$_4$S*0.25H$_2$O, %: C, 61.67; H, 7.02; N, 6.85; S, 7.84. Found, %: C, 61.50; H, 6.87; N, 6.85; S, 7.89.

Example 222

3-(4-Nitro-phenyl)-acrylic acid methyl ester (72)

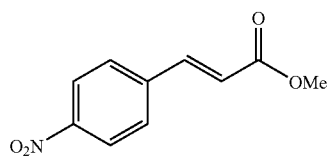

Thionyl chloride (28.8 ml, 0.4 mol) was added dropwise to methanol (450 ml) at −10° C. temperature. To the obtained solution was added 3-(4-nitrophenyl)-acrylic acid (71) (38.63 g, 0.2 mol) and the reaction mixture was stirred at 0° C. for 3 hours, at ambient temperature for 24 hours and at 40° C. for 1 hour. The resulting precipitate was filtered, washed with methanol (2×10 ml) and dried affording the title compound in a form of yellow crystals (39.55 g, 96%). $^1$H NMR (DMSO-$d_6$, HMDSO), δ: 3.69 (2H, br s); 3.77 (3H, s); 6.87 (1H, d, J=16.0 Hz); 7.67–8.39 (5H, m).

Example 223

3-(4-Amino-phenyl)-acrylic acid methyl ester (73)

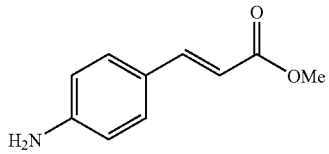

A mixture of 3-(4-nitro-phenyl)-acrylic acid methyl ester (72) (39.54 g, 0.191 mol) and SnCl$_2$.2H$_2$O (220 g, 0.98 mol) in anhydrous ethanol (300 ml) was heated at 50° C. for 1 hour and at 75° C. for 1 hour. The reaction mixture was allowed to cool to 10° C., treated with 20% NaOH solution to pH 8–9, and extracted with ethyl acetate (3×200 ml). The organic extract was washed with saturated NaCl (3×150 ml), dried (MgSO$_4$), and evaporated under reduced pressure. Recrystallization from isopropanol (180 ml) afforded pure title compound in a form of yellowish crystals (17.938 g, 53%). $^1$H NMR (DMSO-$d_6$, HMDSO), δ: 3.64 (3H, s); 5.73 (2H, s); 6.22 (1H, d, J=16.0 Hz); 6.57 (2H, d, J=8.0 Hz); 7.38 (2H, d, J=8.0 Hz); 7.50 (1H, d, J=16.0 Hz).

Example 224

3-(4-Benzenesulfonylamino-phenyl)-acrylic acid methyl ester (74)

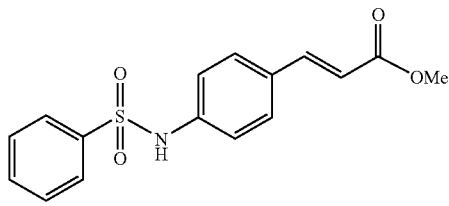

To a suspension of 3-(4-aminophenyl)-acrylic acid methyl ester (73) (1.740 g, 6.18 mmol) in methylene chloride (10 ml) benzenesulfonyl chloride (1.094 g, 6.20 mmol) and pyridine (0.563 g, 7.00 mmol) were added. The resulting suspension was stirred at 15° C. for 24 hours and filtrated. The precipitate was washed with methylene chloride (10 ml), NaHCO$_3$ solution (10 ml), and water (2×20 ml). The obtained solid was dried to give the title compound (1.962 g, 75%). $^1$H NMR (DMSO-$d_6$, HMDSO), δ: 3.71 (3H, s); 6.51 (1H, d, J=16.0 Hz); 7.57–8.11 (10H, m); 10.59 (1H, s).

Example 225

3-(4-Benzenesulfonylaminophenyl)-N-hydroxyacrylamide (75) (PX106499)

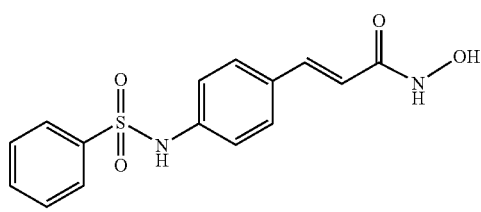

To a mixture, consisting of dioxane (25 ml), methanol (3 ml), and water (1 ml), hydroxylamine hydrochloride (0.834 g, 12 mmol) and NaOH (0.960 g, 24 mmol) followed by 3-(4-benzenesulfonylamino-phenyl)-acrylic acid methyl ester (74) (1.735 g, 4.1 mmol)) were added. The resulting mixture was vigorously stirred at ambient temperature for 24 hours and evaporated under reduced pressure. The residue was mixed with warm (50° C.) water and filtered. The aqueous solution was acidified with hydrochloric acid to pH 4 and filtered. The precipitate was washed with water (2×10 ml), ethyl acetate (10 ml), and crystallised from acetonitrile (15 ml) to give title compound as a yellow solid (0.405 g, 31%). M.p. 189–191° C. $^1$H NMR (DMSO-d$_6$, HMDSO) δ: 6.30 (d, 1H, J=15.8 Hz); 7.12 (d, 2H, J=8.6 Hz); 7.32 (d, 1H, J=15.8 Hz); 7.45 (d, 2H, J=8.4 Hz); 7.48–7.86 (6H, m); 9.01 (s, 1H); 10.56 (s, 1H); 10.72 (s, 1H). HPLC analysis on Zorbax SB—C18 column: impurities 1.8% (column size 4.6×150 mm; mobile phase acetonitrile—0.1% H$_3$PO$_4$, gradient from 30:70 to 100:0; sample concentration 1.0 mg/ml; detector UV 220 nm). Anal. Calcd for C$_{15}$H$_{14}$N$_2$O$_4$S, %: C, 56.59; H, 4.43; N, 8.80; S, 10.07. Found, %: C, 56.03; H, 4.24; N, 8.66; S, 10.02.

Example 226

3-[4-(Biphenyl-4-sulfonylamino)-phenyl]-acrylic acid (82a)

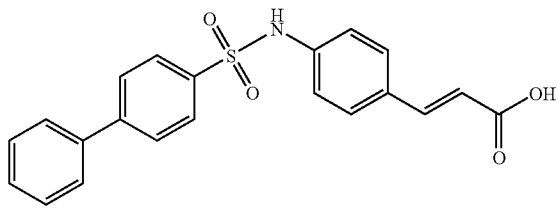

To a solution of 3-(4-aminophenyl)-acrylic acid hydrochloride (81) (0.3 g, 1.5 mmol) in dioxane (10 ml) and 0.63 M NaHCO$_3$ (9.56 ml, 6.0 mmol) biphenyl-4-sulfochloride (0.5 g, 1.78 mmol) was added and the resulting mixture was stirred at room temperature for 60 min. The reaction mixture was partitioned between ethyl acetate and 2N HCl. The organic layer was washed successively with water, saturated NaCl, and dried (Na$_2$SO$_4$). The solvent was evaporated and the residue was crystallised from acetonitrile to give the title compound (0.27 g, 47%). $^1$H NMR (DMSO-d$_6$, HMDSO), B: 6.37 (1H, d, J=16.0 Hz); 7.19 (2H, d, J=8.0 Hz); 7.36–7.80 (8H, m); 7.86 (5H, m); 10.66 (1H, br s).

Example 227

3-[4-(Biphenyl-4-sulfonylamino)-phenyl]-acryloyl chloride (83a)

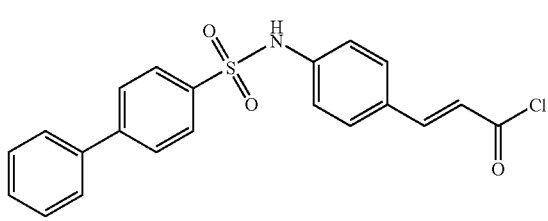

To a suspension of 3-[4-(biphenyl-4-sulfonylamino)-phenyl]-acrylic acid (82a) (0.27 g, 0.71 mmol) in dichloromethane (3 ml) oxalyl chloride (0.3 ml, 3.39 mmol) and one drop of dimethylformamide were added. The reaction mixture was stirred at 40° C. for one hour and concentrated under reduced pressure to give crude title compound (0.277 g, 98%).

Example 228

(E)-N-Hydroxy-3-[4-(4-biphenylsulfonylamino)-phenyl]-2-propenamide (84a) (PX117793)

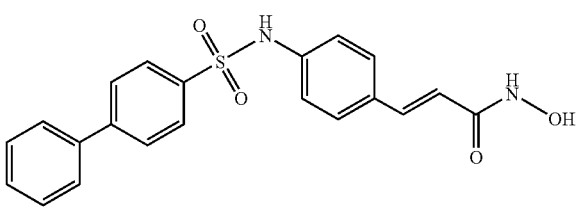

To a suspension of hydroxylamine hydrochloride (0.27 g, 3.88 mmol) in tetrahydrofuran (5 ml) saturated NaHCO$_3$ solution (3 ml) was added and the resultant mixture was stirred at ambient temperature for 10 min. To the reaction mixture a solution of crude 3-[3-(3-methoxy-phenylsulfamoyl)-phenyl]-acryloyl chloride (83a) (0.27 g, 0.68 mmol) in tetrahydrofuran (3.5 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from acetonitrile and washed with diethyl ether affording the title compound as a white solid (0.1 g, 37%). M.p. 190–191.5° C. $^1$H NMR (DMSO-d$_6$, HMDSO) δ: 6.29 (1H, d, J=16.0 Hz); 7.16 (2H, d, J=8.0 Hz); 7.24–7.78 (8H, m); 7.86 (4H, m); 8.94 (1H, br s); 10.57 (1H, s); 10.66 (1H, br s). HPLC analysis on Zorbax SB—C18 column: impurities 4% (column size 4.6×150 mm; mobile phase acetonitrile—0.1% H$_3$PO$_4$, gradient from 30 to 100%; sample concentration 0.2 mg/ml; flow rate 1.0 ml/min; detector UV 254 nm). Anal. Calcd for C$_{21}$H$_{18}$N$_2$O$_4$S, %: C, 63.94; H, 4.60; N, 7.10. Found, %: C C, 63.64; H, 4.45; N, 7.00.

Example 229

3-[4-(3,4-Dimethoxy-benzenesulfonylamino)-phenyl]-acrylic acid (82b)

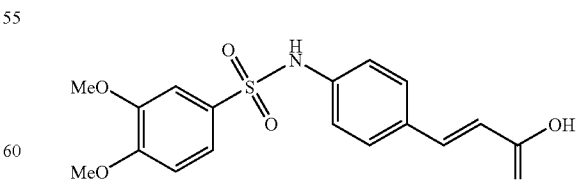

Using an analogous method, the title compound was obtained from 3-(4-aminophenyl)-acrylic acid hydrochloride (81) and 3,4-dimethoxybenzenesulfonyl chloride as a white solid, yield 56%. $^1$H NMR (DMSO-d$_6$, HMDSO), δ:

3.74 (3H, s); 3.77 (3H, s); 6.34 (1H, d, J=16.0 Hz); 6.94–7.69 (8H, m); 10.36 (1H, br s).

Example 230

3-[4-(3,4-Dimethoxy-benzenesulfonylamino)-phenyl]-acryloyl chloride (83b)

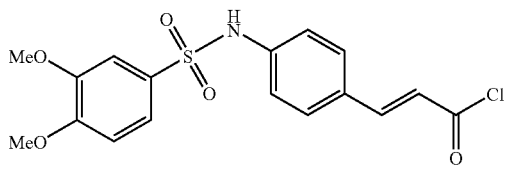

Using an analogous method, the title compound was obtained from 3-[4-(3,4-dimethoxy-benzenesulfonylamino)-phenyl]-acrylic acid (82b) and oxalyl chloride, yield of the crude product ca. 76%.

Example 231

(E)-N-Hydroxy-3-[4-(3,4-dimethoxyphenylsulfonylamino)-phenyl]-2-propenamide (84b) (PX117794)

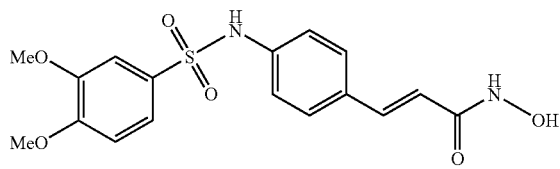

Using an analogous method, the title compound was obtained from 3-[4-(3,4-dimethoxy-benzenesulfonylamino)-phenyl]-acryloyl chloride (83b) and hydroxylamine hydrochloride, yield 35%. M.p. 178.5179° C. $^1$H NMR (DMSO-$d_6$, HMDSO), δ: 3.72 (3H, s); 3.78 (3H, s); 6.32 (1H, d, J=16.0 Hz); 7.00–7.65 (8H, m); 8.98 (1H, br s); 10.32 (1H, br s); 10.69 (1H, s). HPLC analysis on Zorbax SB—C18 column: impurities 3.5% (column size 4.6×150 mm; mobile phase acetonitrile—0,1 M phosphate buffer (pH 2.5), 25:75; sample concentration 0.5 mg/ml; flow rate 1.0 ml/min; detector UV 254 nm). Anal. Calcd for $C_{17}H_{18}N_2O_6S$, %: C, 53.96; H, 4.79; N, 7.40. Found, %: C, 53.58; H, 4.56; N, 7.62.

Example 232

6-Benzenesulfonylaminohexanoic acid methyl ester (93a)

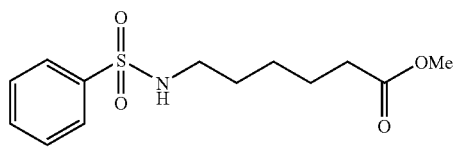

Benzenesulfonyl chloride (92a) (0.88 g, 5.0 mmol) was added to the mixture of methyl 6-aminohexanoate hydrochloride (91) (1.82 g, 10 mmol) in acetonitrile (10 ml) and sodium carbonate (2.6 g, 24.6 mmol) in water (10 ml). The mixture was stirred for 6 hours at ambient temperature, and the product was extracted with ethyl acetate (30 ml). The extract was dried ($Na_2SO_4$) and solvents were removed under reduced pressure. The product was chromatographed on silica gel with ethyl acetate-hexane (1:2) as eluent. The title compound was obtained as oil (1.28 g, 90%). $^1$H NMR δH (90 MHz, DMSO-$d_6$) δ: 0.90–1.63 (6H, m, $CH_2$); 2.21 (2H, t, J=7.0 Hz, $CH_2$); 2.71 (2H, q, J=6.0 Hz, $CH_2N$); 3.58 (3H, s, $CH_3$); 7.40–7.72 (3H, m, $C_6H_3$); 7.72–7.89 (2H, m, $C_6H_2$).

Example 233

6-Benzenesulfonylaminohexanoic acid hydroxyamide (94a) (PX106522)

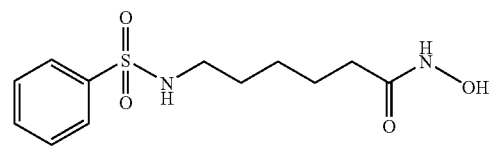

By an analogous method, the title compound was obtained from 6-benzene-sulfonylaminohexanoic acid methyl ester (93a). Yield 47%, m.p. 80–82° C. $^1$H NMR δH (90 MHz, DMSO-$d_6$) δ: 0.98–1.58 (6H, m, $CH_2$); 1.87 (2H, t, J=7.5 Hz, $CH_2$); 2.69 (2H, q, J=6.0 Hz, $CH_2N$); 7.38–7.69 (4H, m, $C_6H_3$; NH); 7.69–7.87 (2H, m, $C_6H_2$); 8.58 (1H, s, NH), 10.27 (1H, s, OH). HPLC analysis on Symmetry $C_{18}$ column: impurities <1% (column size 3.9×150 mm; mobile phase acetonitrile—0.1M phosphate buffer (pH 2.5), 25:75; detector UV 220 nm; sample concentration 1.0 mg/ml). Anal. Calcd for $C_{12}H_{18}N_2O_4S$: C, 50.33; H, 6.34; N, 9.78. Found: C, 50.48; H, 6.25; N, 9.69.

Example 234

6-(E-2-Phenylethenesulfonylamino)hexanoic acid methyl ester (93b)

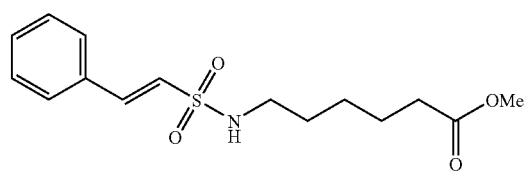

By an analogous method, the title compound was obtained from 2-phenyl-ethenesulfonyl chloride (92b) and and methyl 6-aminohexanoate hydrochloride (91) by the method of example 2, yield 56%, m.p. 47–49° C. $^1$H NMR δH (90 MHz, DMSO-$d_6$) δ: 0.98–1.66 (6H, m, $CH_2$); 1.91 (2H, t, J=6.5 Hz, $CH_2$); 2.83 (2H, t, J=6.0 Hz, $CH_2$); 3.59 (3H, s, $CH_3$); 7.14 (1H, d, J=16.0 Hz, CH); 7.33 (1H, d, J=16.0 Hz, CH); 7.33–7.89 (5H, m, $C_6H_5$).

Example 235

6-(2-Phenylethenesulfonylamino)hexanoic acid hydroxyamide (94b) (PX117429)

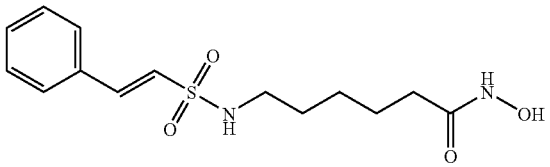

By an analogous method, the title compound was obtained from 6-(E-2-phenylethenesulfonylamino)hexanoic acid methyl ester (93b). Yield 62%, m.p. 107–109° C. $^1$H NMR δH (90 MHz, DMSO-$d_6$) δ: 1.03–1.670 (6H, m, $CH_2$); 2.25 (2H, t, J=6.6 Hz, $CH_2$); 2.86 (2H, t, J=6.5 Hz, $CH_2$); 7.13 (1H, d, J=16.0 Hz, CH); 7.36 (1H, d, J=16.0 Hz, CH); 7.36–7.87 (5H, m, $C_6H_5$); 8.38–9.43 (3H, br s, NH, NH, OH). HPLC analysis on Symmetry $C_{18}$ column: impurities <1% (column size 3.9×150 mm; mobile phase acetonitrile—0.1M phosphate buffer (pH 2.5), 30:70; detector UV 230 nm; sample concentration 0.11 mg/ml). Anal. Calcd for $C_{14}H_{20}N_2O_4S$: C, 53.83; H, 6.45; N, 8.97. Found: C, 53.30; H, 6.32; N, 8.53.

Example 236

6-(Pyridine-3-sulfonylamino)hexanoic acid methyl ester (93c)

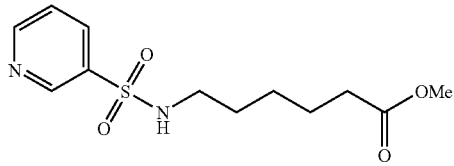

Pyridine-3-sulfonyl chloride hydrochloride (92c) (1.8 g, 5.0 mmol) was added to a solution of methyl 6-aminohexanoate hydrochloride (91) (1.82 g, 10 mmol) and triethylamine (3.03 g, 30 mmol) in acetonitrile (30 ml). The mixture was stirred for 1 hour at ambient temperature, filtered and solvents were removed under reduced pressure. The oily product was dissolved in water (15 ml) and extracted with ethyl ether (50 ml). The extract was dried ($Na_2SO_4$) and the solvents were removed under reduced pressure. The title compound (1.09 g, 76%) was obtained as oil and was used for the next step without an additional purification. $^1$H NMR δH (90 MHz, DMSO-$d_6$) δ: 0.80–1.51 (6H, m, $CH_2$); 1.83 (2H, t, J=6.5 Hz, $CH_2$); 2.76 (2H, t, J=6.5 Hz, $CH_2N$); 3.58 (3H, s, $CH_3$); 7.54 (1H, dd, J=5.0 Hz, J=8.2 Hz, $C_5HN$); 8.12 (1H, dt, J=2.0 Hz, J=8.2 Hz, $C_5HN$); 8.61 (1H, dd, J=2.0 Hz, J=5.0 Hz, $C_5HN$); 8.81 (1H, d, J=2.0 Hz, $C_5HN$).

Example 237

6-(Pyridine-3-sulfonylamino)hexanoic acid hydroxyamide oxalate (94c) (PX117432)

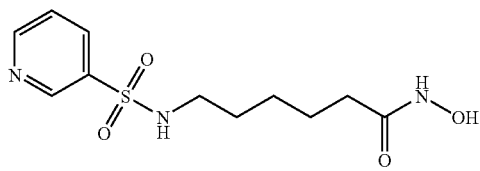

A solution of sodium methylate (12 mmol) in methanol (10 ml) was added to a solution of hydroxylamine hydrochloride (0.56 g, 8 mmol) in methanol (16 ml). The mixture was stirred for 10 min, and NaCl was filtered off. 6-(Pyridine-3-sulfonylamino)hexanoic acid methyl ester (93c) (0.58 g, 2 mmol) was added to the filtrate and the mixture was left to stand overnight at ambient temperature. The precipitate was filtered off, dissolved in water (20 ml) and oxalic acid (0.36 g, 4 mmol) was added to the solution. Water was removed under reduced pressure and the product was crystallised from methanol. The title compound (0.33 g, 44%) was obtained as white solid. M.p. 132–134° C. $^1$H NMR δH (90 MHz, DMSO-$d_6$) δ: 0.78–1.49 (6H, m, $CH_2$); 1.83 (2H, t, J=6.5 Hz, $CH_2$); 2.76 (2H, t, J=6.5 Hz, $CH_2N$); 7.54 (1H, dd, J=5.0 Hz, J=8.2 Hz, $C_5HN$); 8.12 (1H, dt, J=2.0 Hz, J=8.2 Hz, $C_5HN$); 8.61 (1H, dd, J=2.0 Hz, J=5.0 Hz, $C_5HN$); 8.81 (1H, d, J=2.0 Hz, $C_5HN$). HPLC analysis on Symmetry $C_{18}$ column: impurities <1% (column size 3.9×150 mm; mobile phase acetonitrile—0.1M phosphate buffer (pH 2.5), 5:95; detector UV 254 nm; sample concentration 1.0 mg/ml). Anal. Calcd for $C_{11}H_{17}N_3O_4S$*(COOH)$_2$: C, 41.38; H, 5.07; N, 11.13. Found: C, 41.53; H, 5.10; N, 19.83.

Example 238

3-{3-[(Benzo[1,3]dioxol-5-ylmethyl)-sulfamoyl]-phenyl}-acrylic acid methyl ester

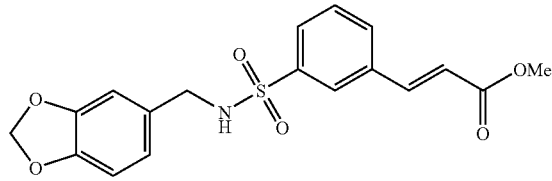

A solution of 3-(3-chlorosulfonylphenyl)acrylic acid methyl ester (0.4 g, 1.53 mmol) in dioxane (5 ml) was added to a mixture of piperonylamine (0.23 g, 1.52 mmol) in dioxane (1 ml) and $NaHCO_3$ (0.25 g, 3.06 mmol) in water (3 ml), and the resultant solution was stirred at room temperature until the completion of the reaction (control by TLC). The reaction mixture was evaporated and the residue was partitioned between ethyl acetate and 2N HCl. The organic layer was washed successively with water, saturated NaCl, and dried ($Na_2SO_4$). The solvent was removed and the residue was chromatographed on silica gel with petroleum ether-ethyl acetate (2:1, v/v) as eluent. The obtained product was washed with diethyl ether to give the title compound (0.47 g, 81%) as a white solid. $^1$H NMR (DMSO-$d_6$, HMDSO), δ: 3.72 (3H, s); 3.96 (2H, d, J=6.4 Hz); 5.94 (2H, s); 6.66–6.85 (3H, m); 6.71 (1H, d, J=16.4 Hz); 7.49–8.07 (5H, m); 8.14 (1H, br t, J=6.4 Hz).

Example 239

3-{3-[(Benzo[1,3]dioxol-5-ylmethyl)-sulfamoyl]-phenyl}-acrylic acid

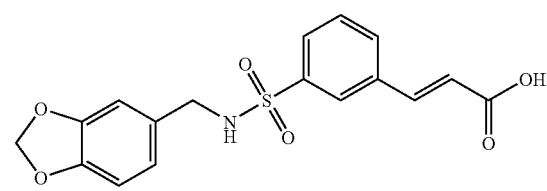

To a suspension of 3-{3-[(benzo[1,3]dioxol-5-ylmethyl)-sulfamoyl]-phenyl}-acrylic acid methyl ester (0.47 g, 1.25 mmol) in methanol (6 ml) 1N NaOH solution (3.75 ml, 3.75 mmol) was added and the resultant mixture was stirred at ambient temperature overnight. The reaction mixture was partitioned between ethyl acetate and water. The aqueous layer was acidified with 2N HCl solution and stirred for 30 min. The precipitated solid was filtered, washed with water and dried in desiccator over $P_2O_5$. The title compound was obtained as a white solid (0.39 g, 87%).

Example 240

3-{3-[(Benzo[1,3]dioxol-5-ylmethyl)-sulfamoyl]-phenyl}-acryloyl chloride

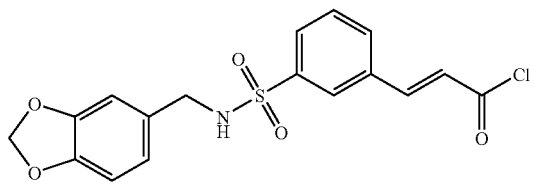

To a suspension of 3-{3-[(benzo[1,3]dioxol-5-ylmethyl)-sulfamoyl]-phenyl}-acrylic acid (0.39 g, 1.08 mmol) in dichloromethane (4 ml) oxalyl chloride (0.28 ml, 3.24 mmol) and one drop of dimethylformamide were added. The reaction mixture was stirred at 40° C. for one hour and concentrated under reduced pressure to give crude title compound (0.41 g, quant.).

Example 241

3-{3-[(Benzo[1,3]dioxol-5-ylmethyl)-sulfamoyl]-phenyl}-N-hydroxy-acrylamide (PX117226)

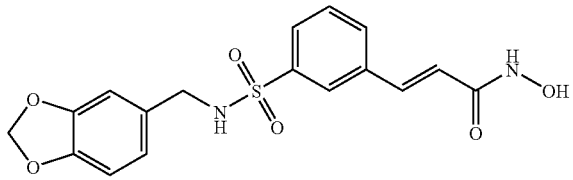

To a suspension of hydroxylamine hydrochloride (0.37 g, 5.40 mmol) in tetrahydrofuran (6 ml) a saturated $NaHCO_3$ solution (4.5 ml) was added and the resultant mixture was stirred at ambient temperature for 10 min. To the reaction mixture a solution of crude 3-{3-[(benzo[1,3]dioxol-5-ylmethyl)-sulfamoyl]-phenyl}-acryloyl chloride (0.41 g) in tetrahydrofuran (4 ml) was added and the mixture was stirred at ambient temperature for one hour. The reaction mixture was partitioned between ethyl acetate and 2N HCl. The organic layer was washed successively with water and saturated NaCl, then the solvent was removed. The residue was crystallised from ethyl acetate and washed with diethyl ether affording the title compound (0.14 g, 35%). M.p. 163° C. $^1$H NMR (DMSO-$d_6$, HMDSO) δ: 3.92 (2H, d, J=6.4 Hz); 5.92 (2H, s); 6.49 (1H, d, J=16.0 Hz); 6.67 (3H, s); 7.34–7.89 (5H, m); 8.12 (1H, t, J=6.4 Hz); 9.07 (1H, br s); 10.78 (1H, br s). HPLC analysis on Symmetry $C_8$ column: impurities 3.5% (column size 3.9×150 mm; mobile phase acetonitrile—0.1M phosphate buffer (pH 2.5), 30:70; sample concentration 0.25 mg/ml; flow rate 1.2 ml/min; detector UV 254 nm). Anal. Calcd for $C_{17}H_{16}N_2O_6S$, %: C, 54.25; H, 4.28; N, 7.44. Founds %: C, 54.19; H, 4.20; N, 7.33.

Biological Activity

Candidate compounds were assessed for their ability to inhibit deacetylase activity (biochemical assays) and to inhibit cell proliferation (cell-based antiproliferation assays), as described below.

Primary Assay: Deacetylase Activity

Briefly, this assay relies on the release of radioactive acetate from a radioactively labelled histone fragment by the action of HDAC enzyme. Test compounds, which inhibit HDAC, reduce the yield of radioactive acetate. Signal (e.g., scintillation counts) measured in the presence and absence of a test compound provide an indication of that compound's ability to inhibit HDAC activity. Decreased activity indicates increased inhibition by the test compound.

The histone fragment was an N-terminal sequence from histone H4, and it was labelled with radioactively labelled acetyl groups using tritiated acetylcoenzyme A (coA) in conjunction with an enzyme which is the histone acetyltransferase domain of the transcriptional coactivator p300. 0.33 mg of peptide H4 (the N-terminal 20 amino acids of histone H4, synthesised using conventional methods) were incubated with His6-tagged p300 histones acetyltransferase domain (amino acids 1195–1673, expressed in E. coli strain BLR(DE3)pLysS (Novagen, Cat. No. 69451-3) and 3H-acetyl coA (10 μL of 3.95 Ci/mmol; from Amersham) in a total volume of 300 μL of HAT buffer (50 mM TrisCl pH 8, 5% glycerol, 50 mM KCl, 0.1 mM ethylenediaminetetraacetic acid (EDTA), 1 mM dithiothreitol (DTT) and 1 mM 4-(2-aminoethyl)-benzenesulfonylfluoride (AEBSF)). The mixture was incubated at 30° C. for 45 min after which the His-p300 was removed using nickel-trinitriloacetic acid agarose (Qiagen, Cat No. 30210). The acetylated peptide was then separated from free acetyl coA by size exclusion chromatography on Sephadex G-15 (Sigma G-15-120), using distilled $H_2O$ as the mobile phase. After purification of the radiolabelled histone fragment, it was incubated with a source of HDAC (e.g., an extract of HeLa cells (a rich source of HDAC), recombinantly produced HDAC1 or HDAC2) and any released acetate was extracted into an organic phase and quantitatively determined using scintillation counting. By including a test compound with the source of HDAC, that compound's ability to inhibit the HDAC was determined.

HeLa Cell Extract

The HeLa cell extract was made from HeLa cells (ATCC Ref. No. CCL-2) by freeze-thawing three times in 60 mM Tris Cl pH 8.0, 450 mM NaCl, 30% glycerol. Two cell volumes of extraction buffer were used, and particulate material was centrifuged out (20800 g, 4° C., 10 min). The supernatant extract having deacetylase activity was aliquotted and frozen for storage.

Recombinantly Produced HDAC1 and HDAC2

Recombinant plasmids were prepared as follows.

Full length human HDAC1 was cloned by PCR using a λgt11 Jurkat cDNA library (Clontech-HL5012b). The amplified fragment was inserted into the EcoRI-SalI sites of pFlag-CTC vector (Sigma-E5394), in frame with the Flag tag. A second PCR was carried out in order to amplify a fragment containing the HDAC1 sequence fused to the Flag tag. The resulting fragment was subcloned into the EcoRI-SacI sites of the baculovirus transfer vector pAcHTL-C (Pharmingen-21466P).

Full length human HDAC2 was subcloned into pAcHLT-A baculovirus transfer vector (Pharmingen-21464P) by PCR amplification of the EcoRI-Sac1 fragment from a HDAC2-pFlag-CTC construct.

Recombinant protein expression and purification was performed as follows.

HDAC1 and HDAC2 recombinant baculoviruses were constructed using BaculoGold Transfection Kit (Pharmingen-554740). Transfer vectors were co-transfected into SF9 insect cells (Pharmingen-21300C). Amplification of recombinant viruses was performed according to the Pharmingen Instruction Manual. SF9 cells were maintained in serum-free SF900 medium (Gibco 10902-096).

For protein production, $2\times10^7$ cells were infected with the appropriate recombinant virus for 3 days. Cells were then harvested and spun at 3,000 rpm for 5 minutes. They were then washed twice in PBS and resuspended in 2 pellet volumes of lysis buffer (25 mM HEPES pH 7.9, 0.1 mM EDTA, 400 mM KCl, 10% glycerol, 0.1% NP-40, 1 mM AEBSF). Resuspended cells were frozen on dry ice and thawed at 37° C. 3 times and centrifuged for 10 minutes at 14,000 rpm. The supernatant was collected and incubated with 300 µl of 50% Ni-NTA agarose bead slurry (Qiagen-30210). Incubation was carried out at 4° C. for 1 hour on a rotating wheel. The slurry was then centrifuged at 500 g for 5 minutes. Beads were washed twice in 1 ml of wash buffer (25 mM HEPES pH7.9, 0.1 mM EDTA, 150 mM KCl, 10% glycerol, 0.1% NP-40, 1 mM AEBSF). Protein was eluted 3 times in 300 µl elution buffer (25 mM HEPES pH 7.9, 0.1 mM EDTA, 250 mM KCl, 10% glycerol, 0.1% NP-40, 1 mM AEBSF) containing increasing concentrations of imidazole: 0.2 M, 0.5 M and 1 M. Each elution was performed for 5 minutes at room temperature. Eluted protein was kept in 50% glycerol at −70° C.

Assay Method

A source of HDAC (e.g., 2 µL of crude HeLa extract, 5 µL of HDAC1 or HDAC2; in elution buffer, as above) was incubated with 3 µL of radioactively labelled peptide along with appropriate dilutions of candidate compounds (1.5 µL) in a total volume of 150 µL of buffer (20 mM Tris pH 7.4, 10% glycerol). The reaction was carried out at 37° C. for one hour, after which the reaction was stopped by adding 20 µL of 1 M HCl/0.4 M sodium acetate. Then, 750 µL of ethyl acetate was added, the samples vortexed and, after centrifugation (14000 rpm, 5 min), 600 µL from the upper phase were transferred to a vial containing 3 mL of scintillation liquid (UltimaGold, Packard, Cat. No. 6013329). Radioactivity was measured using a Tri-Carb 2100TR Liquid Scintillation Analyzer (Packard).

Percent activity (% activity) for each test compound was calculated as:

% activity=$\{(S^C-B)/(S°-B)\}\times 100$ wherein $S^C$ denotes signal measured in the presence of enzyme and the compound being tested, $S°$ denotes signal measured in the presence of enzyme but in the absence of the compound being tested, and B denotes the background signal measured in the absence of both enzyme and compound being tested. The IC50 corresponds to the concentration which achieves 50% activity.

IC50 data for several compounds of the present invention, as determined using this assay, are also shown in Table 1, below.

Measurement of cell viability in the presence of increasing concentration of test compound at different time points is used to assess both cytotoxicity and the effect of the compound on cell proliferation.

Secondary Assay: Cell Proliferation

Compounds with HDAC inhibition activity, as determined using the primary assay, were subsequently evaluated using secondary cell-based assays. The following cell lines were used:

HeLa—Human cervical adenocarcinoma cell line (ATCC ref. No. CCL-2).

K11-HPV E7 transformed human keratinocyte line provided by Pidder Jansen-Duerr, Institut für Biomedizinische Alternsforschung, Innsbruck, Austria.

NHEK-Ad—Primary human adult keratinocyte line (Cambrex Corp., East Rutherford, N.J., USA).

JURKAT—Human T-cell line (ATCC no. TIB-152).

Assay Method

Cells were cultured, exposed to candidate compounds, and incubated for a time, and the number of viable cells was then assessed using the Cell Proliferation Reagent WST-1 from Boehringer Mannheim (Cat. No. 1 644 807), described below.

Cells were plated in 96-well plates at $3-10\times10^3$ cells/well in 100 µL of culture medium. The following day, different concentrations of candidate compounds were added and the cells incubated at 37° C. for 48 h. Subsequently, 10 µL/well of WST-1 reagent was added and the cells reincubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multi-well spectrophotometer by measuring the absorbance of the dye solution at 450 nm wavelength (reference wavelength 690 nm).

Percent activity (% activity) in reducing the number of viable cells was calculated for each test compound as:

% activity=$\{(S^C-B)/(S°-B)\}\times 100$ wherein $S^C$ denotes signal measured in the presence of the compound being tested, $S°$ denotes signal measured in the absence of the compound being tested, and B denotes the background signal measured in blank wells containing medium only. The IC50 corresponds to the concentration which achieves 50% activity. IC50 values were calculated using the software package Prism 3.0 (GraphPad Software Inc., San Diego, Calif.), setting top value at 100 and bottom value at 0.

IC50 data for several compounds of the present invention, as determined using this assay, are also shown in Table 2, below.

Measurement of cell viability in the presence of increasing concentration of test compound at different time points is used to assess both cytotoxicity and the effect of the compound on cell proliferation.

Biological Data

IC50 (or percent activity) data for several compounds of the present invention, as determined using the assays described above are summarised in Table 1 and Table 2, below.

TABLE 1

Biochemical Assay Data

| No. | Compound Ref. | HDAC Inhibition (IC50 unless otherwise specified) HeLa | HDAC1 | HDAC2 |
|---|---|---|---|---|
|  | TSA | 5 | 15 | 17 |
|  | Oxamflatin | 38 | — | — |
| 1 | PX089342 | 125 | 50 | — |
| 2 | PX089344 | 89 | — | 172 |
| 3 | PX106499 | 35 | — | — |
| 4 | PX106522 | 1580 | — | — |
| 5 | PX117432 | 24% @ 500 | — | — |
| 6 | PX117780 | 125 | — | — |
| 7 | PX117781 | 58 | — | — |
| 8 | PX117793 | 50 | — | — |
| 9 | PX117794 | 24 | — | — |
| 10 | PX089343 | 24% @ 1 μm | — | — |
| 11 | PX105684 | 19.5 | — | 124 |
| 12 | PX105685 | 238 | — | 600 |
| 13 | PX105844 | 15 | 29 | — |
| 14 | PX106508 | 31 | 90 | — |
| 15 | PX106509 | 6 | — | — |
| 16 | PX106510 | 12 | — | — |
| 17 | PX106511 | 35 | — | — |
| 18 | PX106512 | 22 | 458 | — |
| 19 | PX116238 | 14 | — | — |
| 20 | PX116242 | 9% @ 500 | — | — |
| 21 | PX117225 | 640 | — | — |
| 22 | PX117226 | 26.3 | — | — |
| 23 | PX117227 | 50 | — | — |
| 24 | PX117228 | 7 | — | — |
| 25 | PX117233 | 21% @ 500 | — | — |
| 26 | PX117234 | 59% @ 500 | — | — |
| 27 | PX117235 | 40% @ 500 | — | — |
| 28 | PX117236 | 54% @ 500 | — | — |
| 29 | PX117245 | 16 | — | — |
| 30 | PX117250 | 192 | — | — |
| 31 | PX117260 | 35% @ 500 | — | — |
| 32 | PX117410 | 40% @ 500 | — | — |
| 33 | PX117411 | 39% @ 500 | — | — |
| 34 | PX117412 | 54% @ 500 | — | — |
| 35 | PX117414 | 46% @ 500 | — | — |
| 36 | PX117429 | 73% @ 500 | — | — |
| 37 | PX117445 | 2 | — | — |
| 38 | PX117446 | 18 | — | — |
| 39 | PX117447 | 3% @ 500 | — | — |
| 40 | PX117448 | 3% @ 500 | — | — |
| 41 | PX117450 | 20 | — | — |
| 42 | PX117453 | 45 | — | — |
| 43 | PX117710 | 125 | — | — |
| 44 | PX117712 | 14 | — | — |
| 45 | PX117713 | 138 | — | — |
| 46 | PX117715 | 10 | — | — |
| 47 | PX117734 | 8 | — | — |
| 48 | PX117735 | 6 | — | — |
| 49 | PX117736 | 6 | — | — |
| 50 | PX117773 | 67 | — | — |
| 51 | PX117774 | 396 | — | — |
| 52 | PX117775 | 16 | — | — |
| 53 | PX117778 | >400 | — | — |
| 54 | PX117779 | 250 | — | — |
| 55 | PX117782 | 38 | — | — |
| 56 | PX117787 | 67 | — | — |
| 57 | PX117788 | 36 | — | — |
| 58 | PX117789 | 30 | — | — |
| 59 | PX117790 | 175 | — | — |
| 60 | PX117791 | 250 | — | — |
| 61 | PX117792 | 48 | — | — |
| 62 | PX117795 | 13 | — | — |
| 63 | PX117796 | 19 | — | — |
| 64 | PX117798 | 50 | — | — |

TABLE 2

Cell-Based Antiproliferation Assay Data

| No. | Compound Ref. | Cell Proliferation Inhibition WST-1 (IC50 unless otherwise specified) HeLa | K11 | NHEK-AD | Jurkat |
|---|---|---|---|---|---|
|  | TSA | 0.350 | 0.38 | 0.2 | 0.042 |
|  | Oxamflatin | 1.1 | 4.56 | 3.53 | 0.260 |
|  | MS-275 | — | 9.16 | 3.1 | 0.365 |
|  | SAHA | — | 6.82 | 5.37 | 0.750 |
| 1 | PX089342 | 4.1 | — | — | — |
| 2 | PX089344 | 8.9 | — | — | — |
| 3 | PX106499 | 3.8 | — | — | — |
| 4 | PX106522 | 16.7 | — | — | — |
| 5 | PX117432 | — | — | — | — |
| 6 | PX117780 | 16.8 | 10.5 | — | 4.0 |
| 7 | PX117781 | 3.4 | 2.2 | — | 0.8 |
| 8 | PX117793 | 2.0 | 2.7 | — | 0.5 |
| 9 | PX117794 | 3.3 | 2.3 | — | 0.6 |
| 10 | PX089343 | — | — | — | — |
| 11 | PX105684 | 2.2 | 2.4 | 1.5 | 0.2 |
| 12 | PX105685 | 7.3 | — | — | — |
| 13 | PX105844 | 0.4 | — | — | — |
| 14 | PX106508 | 1.6 | 3.5 | — | 0.30 |
| 15 | PX106509 | 2.0 | 2.0 | — | 0.33 |
| 16 | PX106510 | 2.3 | 4.2 | — | 0.25 |
| 17 | PX106511 | 0.38 | 2.5 | — | 0.235 |
| 18 | PX106512 | 1.9 | 2.4 | — | 0.21 |
| 19 | PX116238 | 0.8 | — | — | — |
| 20 | PX116242 | — | — | — | — |
| 21 | PX117225 | 11.9 | 26% @ 20 μM | — | 3.3 |
| 22 | PX117226 | 0.5 | 2.8 | — | 0.10 |
| 23 | PX117227 | 1.2 | 4.7 | — | 0.36 |
| 24 | PX117228 | 0.8 | 1.4 | 1.2 | 0.15 |
| 25 | PX117233 | — | — | — | — |
| 26 | PX117234 | — | — | — | — |
| 27 | PX117235 | — | — | — | — |
| 28 | PX117236 | — | — | — | — |
| 29 | PX117245 | 0.31 | — | 0.52 | 1.1 |
| 30 | PX117250 | 7.8 | — | — | 1.0 |
| 31 | PX117260 | — | — | — | — |
| 32 | PX117410 | — | — | — | — |
| 33 | PX117411 | — | — | — | — |
| 34 | PX117412 | — | — | — | — |
| 35 | PX117414 | — | — | — | — |
| 36 | PX117429 | — | — | — | — |
| 37 | PX117445 | 1.1 | 1.2 | 0.75 | 0.13 |
| 38 | PX117446 | 6.0 | 3.7 | — | 0.43 |
| 39 | PX117447 | 77.8 | — | — | — |
| 40 | PX117448 | 88.9 | — | — | — |
| 41 | PX117450 | 1.6 | — | — | — |
| 42 | PX117453 | 5.7 | 4.2 | — | 1.1 |
| 43 | PX117710 | 5.0 | 4.0 | — | 0.42 |
| 44 | PX117712 | 1.1 | 0.65 | — | 0.13 |
| 45 | PX117713 | 5.1 | 9.2 | — | 0.62 |
| 46 | PX117715 | 1.5 | 0.93 | — | 0.29 |
| 47 | PX117734 | 2.1 | 0.88 | — | 0.079 |
| 48 | PX117735 | — | 3.1 | — | 0.074 |
| 49 | PX117736 | — | 0.80 | — | 0.12 |
| 50 | PX117773 | 3.4 | 6.2 | — | 1.2 |
| 51 | PX117774 | 6.4 | 7.0 | — | 1.0 |
| 52 | PX117775 | 2.1 | 5.3 | — | 0.53 |
| 53 | PX117778 | — | >30 | — | >10 |
| 54 | PX117779 | 9.6 | 1.4 | — | 1.1 |
| 55 | PX117782 | 2.9 | 15.6 | — | 0.35 |
| 56 | PX117787 | 2.6 | 1.2 | — | 0.50 |
| 57 | PX117788 | 2.0 | 1.7 | — | 0.29 |
| 58 | PX117789 | 1.1 | 0.8 | — | 0.3 |
| 59 | PX117790 | 12.5 | 8.0 | — | 2.1 |
| 60 | PX117791 | 3.6 | 6.7 | — | 1.3 |
| 61 | PX117792 | 1.4 | 0.4 | — | 0.43 |
| 62 | PX117795 | 3.4 | 1.5 | — | 0.51 |
| 63 | PX117796 | 2.6 | 1.2 | — | 0.56 |
| 64 | PX117798 | 0.9 | 0.35 | — | 3.6 |

Activity (1) (A) As mentioned above, in one embodiment, the compounds employ, as J, a "reverse" sulfonamide linkage (i.e., —NHSO$_2$—). Such compounds enjoy the surprising and unexpected property of superior activity as compared to their "forward" sulfonamide (i.e., —SO$_2$NH—) analogs.

(2) (B1) As mentioned above, in one embodiment, the compounds employ, as Q$^2$, a phenylene-meta-C$_{1-7}$alkylene linkage. Such compounds enjoy the surprising and unexpected property of superior activity as compared to their ortho and para analogs.

(3) (B2) As mentioned above, in one embodiment, the compounds employ, as Q$^2$, a phenylene-meta-ethylene linkage. Such compounds enjoy the surprising and unexpected property of superior activity as compared to their ortho and para analogs.

(4) (C1) As mentioned above, in one embodiment, the compounds employ, as Q$^1$, either: a covalent bond, or: an aryl leader having a backbone of at least two carbon atoms. Such compounds enjoy the surprising and unexpected property of superior activity as compared to analogs which comprise, as Q$^1$, an aryl leader having a backbone of one carbon atom.

(5) (C2) As mentioned above, in one embodiment, the compounds employ, as Q$^1$, a covalent bond. Such compounds enjoy the surprising and unexpected property of superior activity as compared to analogs which comprise, as Q$^1$, an aryl leader having a backbone of one carbon atom.

(6) (C3) As mentioned above, in one embodiment, the compounds employ, as Q$^1$, an aryl leader having a backbone of at least two carbon atoms. Such compounds enjoy the surprising and unexpected property of superior activity as compared to analogs which comprise, as Q$^1$, an aryl leader having a backbone of one carbon atom, and often as compared to analogs which comprise, as Q$^1$, a covalent bond.

(7) (A+B1) As mentioned above, in one embodiment, the compounds employ, as J, a "reverse" sulfonamide linkage (i.e., —NHSO$_2$—); and as Q$^2$; a phenylene-meta-C$_{1-7}$alkylene linkage. Such compounds enjoy the surprising and unexpected property of superior activity as compared to analogs which do not employ these groups.

(8) (A+B2) As mentioned above, in one embodiment, the compounds employ, as J, a "reverse" sulfonamide linkage (i.e., —NHSO$_2$—); and as Q$^2$; a phenylene-meta-ethylene linkage. Such compounds enjoy the surprising and unexpected property of superior activity as compared to analogs which do not employ these groups.

(9) (A+C1) As mentioned above, in one embodiment, the compounds employ, as J, a "reverse" sulfonamide linkage (i.e., —NHSO$_2$—); and as Q$^1$; either a covalent bond, or an aryl leader having a backbone of at least two carbon atoms. Such compounds enjoy the surprising and unexpected property of superior activity as compared to analogs which do not employ these groups.

(10) (A+C2) As mentioned above, in one embodiment, the compounds employ, as J, a "reverse" sulfonamide linkage (i.e., —NHSO$_2$—); and as Q$^1$; a covalent bond. Such compounds enjoy the surprising and unexpected property of superior activity as compared to analogs which do not employ these groups.

(11) (A+C3) As mentioned above, in one embodiment, the compounds employ, as J, a "reverse" sulfonamide linkage (i.e., —NHSO$_2$—); and as Q$^1$; an aryl leader having a backbone of at least two carbon atoms. Such compounds enjoy the surprising and unexpected property of superior activity as compared to analogs which do not employ these groups.

(12) (B1+C1) As mentioned above, in one embodiment, the compounds employ, as Q$^2$, a phenylene-meta-C$_{1-7}$alkylene linkage; and, as Q$^1$, either: a covalent bond, or: an aryl leader having a backbone of at least two carbon atoms. Such compounds enjoy the surprising and unexpected property of superior activity as compared to analogs which do not employ these groups.

(13) (B1+C2) As mentioned above, in one embodiment, the compounds employ, as Q$^2$, a phenylene-meta-C$_{1-7}$alkylene linkage; and, as Q$^1$, a covalent bond. Such compounds enjoy the surprising and unexpected property of superior activity as compared to analogs which do not employ these groups.

(14) (B1+C3) As mentioned above, in one embodiment, the compounds employ, as Q$^2$, a phenylene-meta-C$_{1-7}$alkylene linkage; and, as Q$^1$, an aryl leader having a backbone of at least two carbon atoms. Such compounds enjoy the surprising and unexpected property of superior activity as compared to analogs which do not employ these groups.

(15) (B2+C1) As mentioned above, in one embodiment, the compounds employ, as Q$^2$, a phenylene-meta-ethylene linkage; and, as Q$^1$, either: a covalent bond, or: an aryl leader having a backbone of at least two carbon atoms. Such compounds enjoy the surprising and unexpected property of superior activity as compared to analogs which do not employ these groups.

16) (B2+C2) As mentioned above, in one embodiment, the compounds employ, as Q$^2$, a phenylene-meta-ethylene linkage; and, as Q$^1$, a covalent bond. Such compounds enjoy the surprising and unexpected property of superior activity as compared to analogs which do not employ these groups.

17) (B2+C3) As mentioned above, in one embodiment, the compounds employ, as Q$^2$, a phenylene-meta-ethylene linkage; and, as Q$^1$, an aryl leader having a backbone of at least two carbon atoms. Such compounds enjoy the surprising and unexpected property of superior activity as compared to analogs which do not employ these groups.

(18) (A+B1+C1) As mentioned above, in one embodiment, the compounds employ, as J, a "reverse" sulfonamide linkage (i.e., —NHSO$_2$—); as Q$^2$; a phenylene-meta-C$_{1-7}$alkylene linkage; and, as Q$^1$, either: a covalent bond, or: an aryl leader having a backbone of at least two carbon atoms. Such compounds enjoy the surprising and unexpected property of superior activity as compared to analogs which do not employ these groups.

(19) (A+B1+C2) As mentioned above, in one embodiment, the compounds employ, as J, a "reverse" sulfonamide linkage (i.e., —NHSO$_2$—); as Q$^2$; a phenylene-meta-C$_{1-7}$alkylene linkage; and, as Q$^1$, a covalent bond. Such compounds enjoy the surprising and unexpected property of superior activity as compared to analogs which do not employ these groups.

(20) (A+B1+C3) As mentioned above, in one embodiment, the compounds employ, as J, a "reverse" sulfonamide linkage (i.e., —NHSO$_2$—); as Q$^2$; a phenylene-meta-C$_{1-7}$alkylene linkage; and, as Q$^1$, an aryl leader having a backbone of at least two carbon atoms. Such compounds enjoy the surprising and unexpected property of superior activity as compared to analogs which do not employ these groups.

(21) (A+B2+C1) As mentioned above, in one embodiment, the compounds employ, as J, a "reverse" sulfonamide linkage (i.e., —NHSO$_2$—); as Q$^2$; a phenylene-meta-ethylene linkage; and, as Q$^1$, either: a covalent bond, or: an aryl leader having a backbone of at least two carbon atoms. Such compounds enjoy the surprising and unexpected property of superior activity as compared to analogs which do not employ these groups.

(22) ((A+B2+C2) As mentioned above in one embodiment, the compounds employ, as J, a "reverse" sulfonamide linkage (i.e., —NHSO$_2$—); as Q$^2$; a phenylene-meta-ethylene linkage; and, as Q$^1$, a covalent bond. Such compounds enjoy the surprising and unexpected property of superior activity as compared to analogs which do not employ these groups.

(23) (A+B2+C3) As mentioned above, in one embodiment, the compounds employ, as J, a "reverse" sulfonamide linkage (i.e., —NHSO$_2$—); as Q$^2$; a phenylene-meta-ethylene linkage; and, as Q$^1$, an aryl leader having a backbone of at least two carbon atoms. Such compounds enjoy the surprising and unexpected property of superior activity as compared to analogs which do not employ these groups.

Comparative Data for Sulfonamide Direction

Comparative data for sets of compounds, where the only difference in chemical structure is the sulfonamide direction, are shown below.

Compounds which employ, as J, a "reverse" sulfonamide linkage (i.e., —NHSO$_2$—) surprisingly and unexpectedly have superior activity as compared to their "forward" sulfonamide (i.e., —SO$_2$NH—) analogs.

| Compound | Q$^1$ | J | o/m/p | HeLa IC50 |
|---|---|---|---|---|
| PX117234 | — | —NHSO$_2$— | — | 59% @ 500 nM |
| PX106522 | — | —SO$_2$NH— | — | 1.6 μM |
| PX105684 | — | —NHSO$_2$— | m | 20 nM |
| PX089344 | — | —SO$_2$NH— | m | 89 nM |
| PX106511 | —CH$_2$— | —NHSO$_2$— | m | 35 nM |
| PX089343 | —CH$_2$— | —SO$_2$NH— | m | 24% @ 1 μM |
| PX117450 | — | —NHSO$_2$— | p | 20 nM |
| PX106499 | — | —SO$_2$NH— | p | 35 nM |
| PX106508 | — | —NHSO$_2$— | m | 31 nM |
| PX089342 | — | —SO$_2$NH— | m | 125 nM |
| PX116238 | — | —NHSO$_2$— | m | 14 nM |
| Oxamflatin | — | —SO$_2$NH— | m | 38 nM |

Comparative Data for Phenylene-Alkylene Acid Leader Orientation

Comparative data for sets of compounds, where the only difference in chemical structure is the ortho/meta/para orientation of the phenylene-alkylene acid leader, are shown below.

In some embodiments, compounds which employ, as Q$^2$, a phenylene-meta-C$_{1-7}$alkylene linkage surprisingly and unexpectedly have superior activity as compared to their ortho and para analogs.

For compounds with a "forward" sulfonamide linkage, para analogs are more active than meta analogs. Surprisingly and unexpectedly, for compounds with a "reverse" sulfonamide linkage, meta analogs are as active, or more active, than para analogs. Thus, compounds which employ both, as J, a "reverse" sulfonamide linkage (i.e., —NHSO$_2$—) and, as Q$^2$, a phenylene-meta-C$_{1-7}$alkylene linkage, surprisingly and unexpectedly have superior activity as compared to their "forward" analogs.

| Compound | Q$^1$ | J | o/m/p | HeLa IC50 |
|---|---|---|---|---|
| PX117447 | — | —NHSO$_2$— | o | 3% @ 500 nM |
| PX117228 | — | —NHSO$_2$— | m | 7 nM |
| PX117448 | — | —NMeSO$_2$— | o | 3% @ 500 nM |
| PX105685 | — | —NMeSO$_2$— | m | 238 nM |

-continued

| Compound | Q¹ | J | o/m/p | HeLa IC50 |
|---|---|---|---|---|

[Structure: phenyl-J-phenyl-CH=CH-C(=O)-NH-OH]

| PX116242 | — | —NHSO₂— | o | 9% @ 500 nM |
| PX105684 | — | —NHSO₂— | m | 20 nM |
| PX117450 | — | —NHSO₂— | p | 20 nM |

[Structure: phenyl-J-phenyl-CH=CH-C(=O)-NH-OH]

| PX089344 | — | —SO₂NH— | m | 89 nM |
| PX106499 | — | —SO₂NH— | p | 35 nM |

[Structure: phenyl-J-phenyl-C≡C-CH=CH-C(=O)-NH-OH]

| PX116238 | — | —NHSO₂— | m | 14 nM |
| PX117453 | — | —NHSO₂— | p | 45 nM |

Comparative Data for Aryl Leader, Q¹

Comparative data for sets of compounds, where the only difference in chemical structure is the aryl leader, are shown below.

Compounds which employ, as Q¹, either: a covalent bond, or: an aryl leader having a backbone of at least two carbon atoms surprisingly and unexpectedly have superior activity as compared to their analogs which comprise, as Q¹, an aryl leader having a backbone of one carbon atom. The observation that, as Q¹, a one atom backbone gives substantially reduced activity as compared to a covalent bond, but that a two atom backbone give substantially improved activity as compared to a one atom backbone, is surprising and unexpected.

| Compound | Q¹ | J | o/m/p | HeLa IC50 |
|---|---|---|---|---|

[Structure: phenyl-O-Q¹-J-phenyl-CH=CH-C(=O)-NH-OH]

| PX105684 | — | —NHSO₂— | m | 19.5 nM |
| PX106511 | —CH₂— | —NHSO₂— | m | 35 nM |
| PX106512 | —CH₂CH₂— | —NHSO₂— | m | 22 nM |

-continued

| Compound | Q¹ | J | o/m/p | HeLa IC50 |
|---|---|---|---|---|

[Structure: phenyl-O-Q¹-J-phenyl-CH=CH-C(=O)-NH-OH]

| PX089344 | — | —SO₂NH— | m | 89 nM |
| PX089343 | —CH₂— | —SO₂NH— | m | 24% @ 1 µM |
| PX117446 | —CH=CH— | —SO₂NH— | m | 18 nM |

[Structure: naphthyl-O-Q¹-J-phenyl-CH=CH-C(=O)-NH-OH]

| PX117228 | — | —NHSO₂— | m | 7 nM |
| PX117225 | —CH₂— | —NHSO₂— | m | 640 nM |

REFERENCES

A number of patents and publications are cited herein in order to more fully describe and disclose the invention and the state of the art to which the invention pertains. Full citations for these references are provided herein. Each of these references is incorporated herein by reference in its entirety into the present disclosure.

Andrews et al., 2000, *Int. J. Parasitol.*, Vol. 30, No. 6, pp. 761–768.

Bernhard, D. et al., 1999, "Apoptosis induced by the histone deacetylase inhibitor sodium butyrate in human leukemic lymphoblasts," *FASEB J.*, Vol. 13, No. 14, pp. 1991–2001.

Bernstein et al., 2000, *Proc. Natl. Acad. Sci. USA*, Vol. 97; No. 25, pp. 1378–13713.

Brehm, A., et al., 1998, "Retinoblastoma protein recruits histone deacetylase to repress transcription," *Nature*, 1998, Vol. 391, pp. 597–601.

Breslow et al., 1994, "Potent inducers of terminal differentiation and methods of use thereof," U.S. Pat. No. 5,369,108 issued 29 Nov. 1994.

Breslow et al., 1995, "Novel potent inducers of terminal differentiation and methods of use thereof," published international (PCT) patent application number WO 95/31977 published 30 Nov. 1995.

Breslow et al., 1997, "Potent inducers of terminal differentiation and methods of use thereof," U.S. Pat. No. 5,700,811 issued 23 Dec. 1997.

Chang et al., 2000, *Nucleic Acids Res.*, Vol. 28, No. 20, pp. 3918–3925.

Corneil et al., 1998, published Japanese patent application, publication number JP 10114681 A2.

Dangond et al., 1998, *Biochem. Biophys. Res. Commun.*, Vol. 242, No. 3, pp. 648–652.

David, G., et al., 1998, *Oncogene*, Vol. 16(19), pp. 2549–2556.

Davie, J. R., 1998, "Covalent modifications of histones: expression from chromatic templates," *Curr. Opin. Genet. Dev.*, Vol. 8, pp. 173–178.

Delorme et al., 2001, "Inhibitors of Histone Deacetylase," published international (PCT) patent application number WO 01/38322 published 31 May 2001.

Desai et al., 1999, *Proc. AACR*, Vol. 40, abstract #2396.

Emiliani, S., et al., 1998, "Characterization of a human RPD3 ortholog, HDAC3," *Proc. Natl. Acad. Sci. USA*, Vol. 95, p. 2795–2800.

Finnin et al., 1999, *Nature*, Vol. 401, pp. 188–193.

Furukawa et al., 1998, U.S. Pat. No. 5,834,249, "Process for production of protein," 10 Nov. 1998.

Geerts et al., 1998, European patent publication no. EP 0 827 742 A1, published 11 Mar. 1998.

Glick, R. D., et al., 1999, "Hybrid polar histone deacetylase inhibitor induces apoptosis and CD95/CD95 ligand expression in human neuroblastoma," *Cancer Research*, Vol. 59, No. 17, pp. 4392–4399.

Grozinger et al., 1999, *Proc. Natl. Acad. Sci. USA, Vol. 96*; pp. 4868–4873.

Hashimoto, N., et al., 1989, "Cell proliferation inhibitors," European Patent Publication No. EP 0 301 861 A1.

Hoshikawa, Y., et al., 1994, *Exp. Cell. Res.*, Vol. 214(1), pp. 189–197.

Howe, L., et al., 1999, *Crit. Rev. Eukaryot. Gene Expr.*, Vol. 9(3–4), pp. 231–243.

Iavarone et al., 1999, *Mol. Cell Biol.*, Vol. 19, No. 1, pp. 916–922.

Jung et al., 1997, *Bioorganic & Medicinal Chemistry Letters*, Vol. 7, No. 13, pp. 1655–1658.

Jung et al., 1999, *J. Med. Chem.*, Vol. 42, pp. 4669–4679.

Kao et al., 2000, *Genes & Dev.*, Vol. 14, p. 55–66.

Kato et al., 1998, U.S. Pat. No. 5,804,601, "Aromatic hydroxamic acid compounds, their production and use," 8 Sep. 1998.

Kijima et al., 1993, *J. Biol. Chem.*, Vol. 268, pp. 22429–22435.

Kim et al., 1999, *Oncogene*, Vol. 18(15), pp. 2461–2470.

Kim et al., 2001, *Nature Medicine*, Vol. 7, No. 4, pp. 437–443.

Kim, M. S., et al., 2001 "Histone deacetylases induce angiogenesis by negative regulation of tumour suppressor genes," *Nature Medicine*, Vol 7. No. 4 pp. 437–443.

Kimura et al., 1994, *Biol. Pharm. Bull.*, Vol. 17, No. 3, pp. 399–402.

Kitamura, K., et al., 2000, *Br. J. Haematol.*, Vol. 108(4), pp. 696–702.

Kouzarides, T., 1999, "Histone acetylases and deacetylases in cell proliferation," *Curr. Olin. Genet. Dev.*, Vol. 9, No. 1, pp. 40–48.

Kuusisto et al., 2001, *Biochem. Biophys. Res. Commun.*, Vol. 280, No. 1, pp. 223–228.

Kwon et al., 1998, *Proc. Natl. Acad. Sci. USA*, Vol. 95, pp. 3356–3361.

Laherty, C. D., et al., 1997, *Cell*, Vol. 89(3), pp. 349–356.

Lea and Tuisyan, 1995, *Anticancer Res.*, Vol. 15, pp. 879–883.

Lea et al., 1999, *Int. J. Oncol.*, Vol. 2, pp. 347–352.

Lin, R. J., et al., 1998, *Nature*, Vol. 391(6669), pp. 811–814.

Massa et al., 26 May 2001, *Journal of Medicinal Chemistry*, Vol. 44, No. 13, pp. 2069–2072.

McCaffrey et al., 1997, *Blood*, Vol. 90, No. 5, pp. 2075–2083.

Mielnicki, L. M., et al., 1999, *Exp. Cell. Res.*, Vol. 249(1), pp. 161–176.

Ng, H. H. and Bird, A., 2000, *Trends Biochem. Sci.*, Vol. 25(3), pp. 121–126.

Niki et al., 1999, *Hepatology*, Vol. 29, No. 3, pp. 858–867.

Nokajima et al., 1998, *Exp. Cell Res.*, Vol. 241, pp. 126–133.

Ohtani et al., 1993, "Hydroxamic acid derivatives based on aromatic sulfonamide," published international (PCT) patent application number WO 93/12075 published 24 Jun. 1993.

Ohtani et al., 1996, "(2E)-5-[3-[(Phenylsulfonyl)amino]phenyl]-pent-2-en-4-yno-hydroxamic acid and its derivatives as novel and potent inhibitors of ras transformation," *J. Medicinal Chemistry*, Vol. 39, No. 15, pp. 2871–2873.

Onishi et al., 1996, *Science*, Vol. 274, pp. 939–940.

Parsons et al., 1998, "Hydroxamic acid compounds having anticancer and anti-parasitic properties," published international (PCT) patent application number WO 98/55449 published 10 Dec. 1998.

Pazin, M. J., et al., 1997, "What's up and down with histone deacetylaton and transcription?," *Cell*, Vol. 89, No. 3, pp. 325–328.

Richon et al, 1996, *Proc. Natl. Acad. Sci. USA*, Vol. 93, pp. 5705–5708.

Richon et al., 1998, "A class of hybrid poler inducers of transformed cell differentiation inhibits histone deacetylases," *Proc. Natl. Acad. Sci. USA*, Vol. 95, pp. 3003–3007.

Richon et al., 2001, "Novel class of cytodifferentiating agents and histone deacetylase inhibitors, and methods of use thereof," published international (PCT) patent application number WO 01/18171 published 15 Mar. 2001.

Saito et al., 1999, *Proc. Natl. Acad. Sci. USA*, Vol. 96, pp. 4592–4597.

Saunders, N. et al, 1999 "Histone deacetylase inhibitors as potential anti-skin cancer agents," *Cancer Res.*, Vol. 59, No. 2 pp. 399–404.

Sonoda, H. et al., 1996, *Oncogene*, Vol. 13, pp. 143–149.

Spencer, V. A. and Davie, J. R., 1999, *Gene*, Vol. 240(1), pp. 1–12.

Suzuki et al., 1998, Japanese patent publication number 10–182583 published 7 Jul. 1998.

Suzuki et al., 1999, "Synthesis and histone deactylase inhibitory activity of new benzamide derivatives," *J. Med. Chem.*, Vol. 42, pp. 3001–3003.

Takahashi et al., 1996, *J. Antibiot.* (Tokyo), Vol. 49, No. 5, pp. 453–457.

Takahashi, I., et al, 1996, "Selective inhibition of IL-2 gene expression by trichostatin A, a potent inhibitor of mammalian histone deacetylase," *J. Antibiot.* (Tokyo), Vol. 49, No. 5, pp. 453–457.

Tauton, J., et al., 1996, "A mammalian histone deacetylase related to the yeast transcriptional regulator Rpd3p," *Science*, Vol. 272, pp. 408–411.

Tsuji et al., 1976, *J. Antibiot.* (Tokyo), Vol. 29, No. 1, pp. 1–6.

Ueda, H., et al., 1994, *J. Antibiot.* (Tokyo), Vol. 47(3), pp. 315–323.

Van den Wyngaert et al., 2000, *FEBS*, Vol. 478, pp. 77–83.

Vigushin et al., 2001, *Clin. Cancer Res.*, Vol. 7, No. 4, pp. 971–976.

Warrell et al., 1998, *J. Natl. Cancer Inst.*, Vol. 90, pp. 1621–1625.

Wong, J., et al., 1998, *EMBO J.*, Vol. 17(2), pp. 520–534.

Yang, W. M., et al., 1996, "Transcriptional repression of YY1 is mediated by interaction with a mammalian homolog of the yeast global regulator RPD3," *Proc. Natl. Acad. Sci. USA*, Vol. 93, pp. 12845–12850.

Yang, W. M., et al., 1997, "Isolation and characterization of cDNAs corresponding to an additional member of the human histone deacetylase gene family," *J. Biol. Chem.*, Vol 272, pp. 28001–28007.

Yoshida et al., 1995, *Bioessays*, Vol. 17, pp. 423–430.

Yoshida, M. and Horinouchi, S., 1999, *Ann. N.Y. Acad. Sci.*, Vol. 886, pp. 23–36.

Yoshida, M., Beppu, T., 1988, "Reversible arrest of proliferation of rat 3Y1 fibroblasts in both G1 and G2 phases by trichostatin A," *Exp. Cell. Res.*, Vol. 177, pp. 122–131.

Yoshida, M., et al., 1990a, *J. Biol. Chem.*, Vol. 265(28), pp. 17174–17179.

Yoshida, M., et al., 1990b, *J. Antibiot.* (Tokyo), Vol. 43(9), pp. 1101–1106.

The invention claimed is:

1. A compound selected from compounds of the formula:

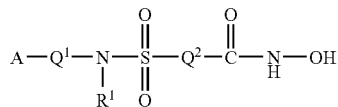

wherein:
A is an aryl group;
$Q^1$ is a covalent bond or an aryl leader group;
$R^1$ is a sulfonamido substituent; and,
$Q^2$ is an acid leader group;
and wherein:
A, is a $C_{5-20}$aryl group, and is optionally substituted;
the aryl leader group, if present, is:
a $C_{1-7}$alkylene group;
and is optionally substituted;
the sulfonamido substituent, $R^1$, is:
hydrogen,
$C_{1-7}$alkyl,
$C_{3-20}$heterocyclyl, or
$C_{5-20}$aryl;
the acid leader group, $Q^2$, is:
$C_{4-7}$alkylene
having a backbone length of from 4 to 7 carbon atoms;
and is optionally substituted;
and pharmaceutically acceptable salts, solvates, amides, esters, ethers, chemically protected forms, and prodrugs thereof.

2. A compound according to claim 1, wherein $Q^1$ is an aryl leader group.

3. A compound according to claim 1, wherein $Q^1$ is an aryl leader group and is a saturated $C_{1-7}$alkylene group and is optionally substituted.

4. A compound according to claim 1, wherein $Q^1$ is an aryl leader group and is a partially unsaturated $C_{2-7}$alkylene group and is optionally substituted.

5. A compound according to claim 1, wherein $Q^1$ is an aryl leader group and is an aliphatic $C_{1-7}$alkylene group and is optionally substituted.

6. A compound according to claim 1, wherein $Q^1$ is an aryl leader group and is a linear $C_{1-7}$alkylene group and is optionally substituted.

7. A compound according to claim 1, wherein $Q^1$ is an aryl leader group and is a saturated aliphatic $C_{1-7}$alkylene group and is optionally substituted.

8. A compound according to claim 1, wherein $Q^1$ is an aryl leader group and is a saturated linear $C_{1-7}$alkylene group and is optionally substituted.

9. A compound according to claim 1, wherein $Q^1$ is an aryl leader group and is a partially unsaturated aliphatic $C_{2-7}$alkylene group and is optionally substituted.

10. A compound according to claim 1, wherein $Q^1$ is an aryl leader group and is a partially unsaturated linear $C_{2-7}$alkylene group and is optionally substituted.

11. A compound according to claim 1, wherein $Q^1$ is an aryl leader group and has a backbone of at least 2 carbon atoms.

12. A compound according to claim 1, wherein $Q^1$ is an aryl leader group and has a backbone of at least 3 carbon atoms.

13. A compound according to claim 1, wherein $Q^1$ is an aryl leader group and has a backbone of from 2 to 7 carbon atoms.

14. A compound according to claim 7, wherein $Q^1$ is an aryl leader group and has a backbone of from 2 to 7 carbon atoms.

15. A compound according to claim 9, wherein $Q^1$ is an aryl leader group and has a backbone of from 2 to 7 carbon atoms.

16. A compound according to claim 1, wherein $Q^1$ is an aryl leader group and has a backbone of from 3 to 7 carbon atoms.

17. A compound according to claim 1, wherein $Q^1$ is an aryl leader group and has a backbone of 2 carbon atoms.

18. A compound according to claim 7, wherein $Q^1$ is an aryl leader group and has a backbone of 2 carbon atoms.

19. A compound according to claim 9, wherein $Q^1$ is an aryl leader group and has a backbone of 2 carbon atoms.

20. A compound according to claim 1, wherein $Q^1$ is an aryl leader group and has a backbone of 3 carbon atoms.

21. A compound according to claim 1, wherein $Q^1$ is an aryl leader group and has a backbone of 4 carbon atoms.

22. A compound according to claim 1, wherein $Q^1$ is an aryl leader group and has a backbone of 5 carbon atoms.

23. A compound according to claim 1, wherein $Q^1$ is an aryl leader group and is unsubstituted.

24. A compound according to claim 7, wherein $Q^1$ is an aryl leader group and is unsubstituted.

25. A compound according to claim 9, wherein $Q^1$ is an aryl leader group and is unsubstituted.

26. A compound according to claim 13, wherein $Q^1$ is an aryl leader group and is unsubstituted.

27. A compound according to claim 17, wherein $Q^1$ is an aryl leader group and is unsubstituted.

28. A compound according to claim 1, wherein $Q^1$ is an aryl leader group and is substituted.

29. A compound according to claim 1, wherein $Q^1$ is an aryl leader group and is unsubstituted or substituted with one or more groups selected from: halo, hydroxy, ether, $C_{5-20}$aryl, acyl, amido, and oxo.

30. A compound according to claim 7, wherein $Q^1$ is an aryl leader group and is unsubstituted or substituted with one or more groups selected from: halo, hydroxy, ether, $C_{5-20}$aryl, acyl, amido, and oxo.

31. A compound according to claim 9, wherein $Q^1$ is an aryl leader group and is unsubstituted or substituted with one or more groups selected from: halo, hydroxy, ether, $C_{5-20}$aryl, acyl, amido, and oxo.

32. A compound according to claim 13, wherein $Q^1$ is an aryl leader group and is unsubstituted or substituted with one or more groups selected from: halo, hydroxy, ether, $C_{5-20}$aryl, acyl, amido, and oxo.

33. A compound according to claim 17, wherein $Q^1$ is an aryl leader group and is unsubstituted or substituted with one or more groups selected from: halo, hydroxy, ether, $C_{5-20}$aryl, acyl, amido, and oxo.

34. A compound according to claim 1, wherein $Q^1$ is an aryl leader group and is unsubstituted or substituted with one or more groups selected from: —F, —Cl, —Br, —I, —OH, —OMe, —OEt, —OPr, -Ph, and =O.

35. A compound according to claim 1, wherein $Q^1$ is an aryl leader group and is selected from —CH$_2$—, —CH$_2$CH$_2$—, —CH$_2$CH$_2$CH$_2$—, —CH=CH—, —CH=CH—CH=CH—, and C$_5$cycloalkyl.

36. A compound according to claim 1, wherein $Q^1$ is an aryl leader group and is selected from —CH$_2$—, —CH$_2$CH$_2$—, —CH$_2$CH$_2$CH$_2$—, —CH=CH—, and —CH=CH—CH=CH—.

37. A compound according to claim 1, wherein $Q^1$ is an aryl leader group and is selected from —CH$_2$—, —CH$_2$CH$_2$—, and —CH=CH—.

38. A compound according to claim 1, wherein $Q^1$ is a covalent bond.

39. A compound according to claim 1, wherein the acid leader group, $Q^2$ is substituted.

40. A compound according to claim 1, wherein the acid leader group, $Q^2$ is unsubstituted.

41. A compound according to claim 1, wherein the acid leader, $Q^2$, is an unsubstituted saturated linear C$_{4-7}$alkylene group.

42. A compound according to claim 7, wherein the acid leader, $Q^2$, is an unsubstituted saturated linear C$_{4-7}$alkylene group.

43. A compound according to claim 9, wherein the acid leader, $Q^2$, is an unsubstituted saturated linear C$_{4-7}$alkylene group.

44. A compound according to claim 13, wherein the acid leader, $Q^2$, is an unsubstituted saturated linear C$_{4-7}$alkylene group.

45. A compound according to claim 14, wherein the acid leader, $Q^2$, is an unsubstituted saturated linear C$_{4-7}$alkylene group.

46. A compound according to claim 15, wherein the acid leader, $Q^2$, is an unsubstituted saturated linear C$_{4-7}$alkylene group.

47. A compound according to claim 17, wherein the acid leader, $Q^2$, is an unsubstituted saturated linear C$_{4-7}$alkylene group.

48. A compound according to claim 18, wherein the acid leader, $Q^2$, is an unsubstituted saturated linear C$_{4-7}$alkylene group.

49. A compound according to claim 19, wherein the acid leader, $Q^2$, is an unsubstituted saturated linear C$_{4-7}$alkylene group.

50. A compound according to claim 23, wherein the acid leader, $Q^2$, is an unsubstituted saturated linear C$_{4-7}$alkylene group.

51. A compound according to claim 29, wherein the acid leader, $Q^2$, is an unsubstituted saturated linear C$_{4-7}$alkylene group.

52. A compound according to claim 36, wherein the acid leader, $Q^2$, is an unsubstituted saturated linear C$_{4-7}$alkylene group.

53. A compound according to claim 37, wherein the acid leader, $Q^2$, is an unsubstituted saturated linear C$_{4-7}$alkylene group.

54. A compound according to claim 38, wherein the acid leader, $Q^2$, is an unsubstituted saturated linear C$_{4-7}$alkylene group.

55. A compound according to claim 1, wherein A is C$_{5-20}$heteroaryl or C$_{5-20}$carboaryl, and is optionally substituted.

56. A compound according to claim 1, wherein A is C$_{5-20}$aryl group derived from one of the following: benzene, pyridine, furan, indole, pyrrole, imidazole, naphthalene, quinoline, benzimidazole, benzothiofuran, fluorene, acridine, and carbazole.

57. A compound according to claim 5, wherein A is an optionally substituted phenyl group.

58. A compound according to claim 7, wherein A is an optionally substituted phenyl group.

59. A compound according to claim 9, wherein A is an optionally substituted phenyl group.

60. A compound according to claim 13, wherein A is an optionally substituted phenyl group.

61. A compound according to claim 17, wherein A is an optionally substituted phenyl group.

62. A compound according to claim 23, wherein A is an optionally substituted phenyl group.

63. A compound according to claim 29, wherein A is an optionally substituted phenyl group.

64. A compound according to claim 36, wherein A is an optionally substituted phenyl group.

65. A compound according to claim 37, wherein A is an optionally substituted phenyl group.

66. A compound according to claim 38, wherein A is an optionally substituted phenyl group.

67. A compound according to claim 1, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

68. A compound according to claim 7, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

69. A compound according to claim 9, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

70. A compound according to claim 13, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

71. A compound according to claim 17, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

72. A compound according to claim 23, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

73. A compound according to claim 29, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

74. A compound according to claim 36, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

75. A compound according to claim 37, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

76. A compound according to claim 38, wherein A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

77. A compound according to claim 1, wherein $R^1$ is hydrogen, $C_{1-7}$alkyl, or $C_{5-20}$aryl.

78. A compound according to claim 1, wherein $R^1$ is hydrogen or $C_{1-7}$alkyl.

79. A compound according to claim 1, wherein $R^1$ is —H, -Me, or -Et.

80. A compound according to claim 1, wherein $R^1$ is —H.

81. A compound selected from compounds of the formula:

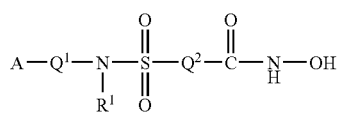

wherein:
- $Q^1$ is a covalent bond or an aliphatic $C_{1-7}$alkylene group;
- $Q^2$ is an unsubstituted saturated linear $C_{4-7}$alkylene group;
- $R^1$ is hydrogen, $C_{1-7}$alkyl, or $C_{5-20}$aryl;
- A is an optionally substituted phenyl group;
- and pharmaceutically acceptable salts, solvates, amides, esters, ethers, chemically protected forms, and prodrugs thereof.

82. A compound selected from compounds of the formula:

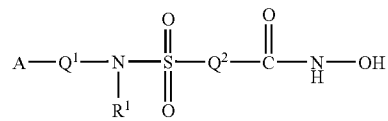

wherein:
- $Q^1$ is a covalent bond, —$CH_2$—, —$CH_2CH_2$—, or —CH=CH—;
- $Q^2$ is an unsubstituted saturated linear $C_{4-7}$alkylene group;
- $R^1$ is hydrogen, $C_{1-7}$alkyl, or $C_{5-20}$aryl;
- A is an optionally substituted phenyl group;
- and pharmaceutically acceptable salts, solvates, amides, esters, ethers, chemically protected forms, and prodrugs thereof.

83. A compound selected from compounds of the formula:

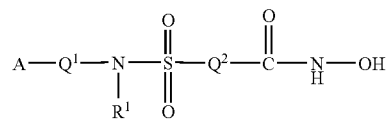

wherein:
- $Q^1$ is a covalent bond, —$CH_2$—, —$CH_2CH_2$—, or —CH=CH—;
- $Q^2$ is an unsubstituted saturated linear $C_{4-7}$alkylene group;
- $R^1$ is hydrogen, $C_{1-7}$alkyl, or $C_{5-20}$aryl;
- A is a phenyl group optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl;
- and pharmaceutically acceptable salts, solvates, amides, esters, ethers, chemically protected forms, and prodrugs thereof.

84. A compound according to claim 1, selected from compounds of the following formula and pharmaceutically acceptable salts, solvates, amides, esters, ethers, chemically protected forms, and prodrugs thereof:

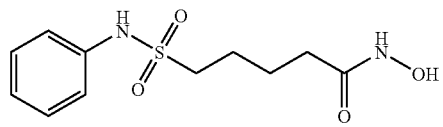

85. A compound according to claim 1, selected from compounds of the following formula and pharmaceutically acceptable salts, solvates, amides, esters, ethers, chemically protected forms, and prodrugs thereof:

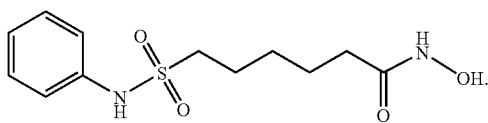

86. A compound according to claim 1, selected from compounds of the following formula and pharmaceutically acceptable salts, solvates, amides, esters, ethers, chemically protected forms, and prodrugs thereof:

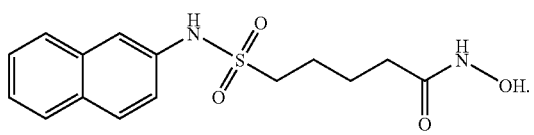

87. A compound according to claim 1, selected from compounds of the following formula and pharmaceutically acceptable salts, solvates, amides, esters, ethers, chemically protected forms, and prodrugs thereof:

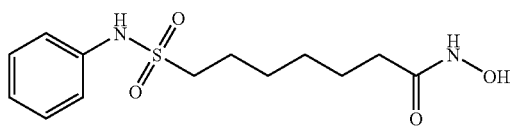

88. A compound according to claim 1, selected from compounds of the following formula and pharmaceutically acceptable salts, solvates, amides, esters, ethers, chemically protected forms, and prodrugs thereof:

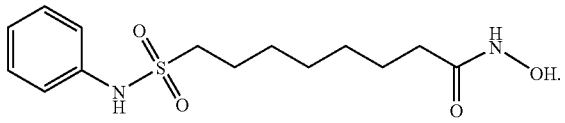

89. A compound according to claim 1, selected from compounds of the following formula and pharmaceutically acceptable salts, solvates, amides, esters, ethers, chemically protected forms, and prodrugs thereof:

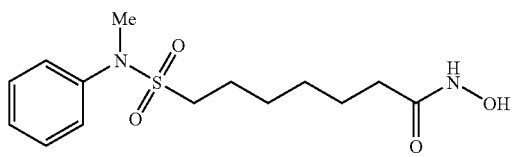

90. A compound according to claim 1, selected from compounds of the following formula and pharmaceutically acceptable salts, solvates, amides, esters, ethers, chemically protected forms, and prodrugs thereof:

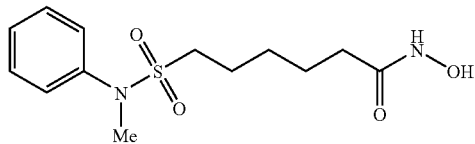

91. A compound according to claim 1, selected from compounds of the following formula and pharmaceutically acceptable salts, solvates, amides, esters, ethers, chemically protected forms, and prodrugs thereof:

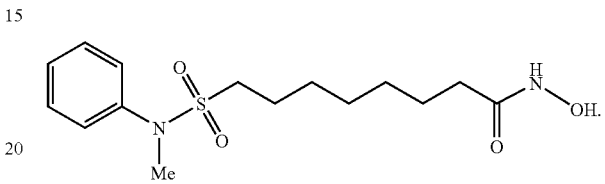

92. A compound according to claim 1, selected from compounds of the following formula and pharmaceutically acceptable salts, solvates, amides, esters, ethers, chemically protected forms, and prodrugs thereof:

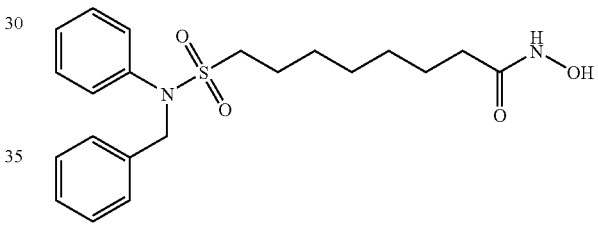

93. A compound according to claim 1, selected from compounds of the following formula and pharmaceutically acceptable salts, solvates, amides, esters, ethers, chemically protected forms, and prodrugs thereof:

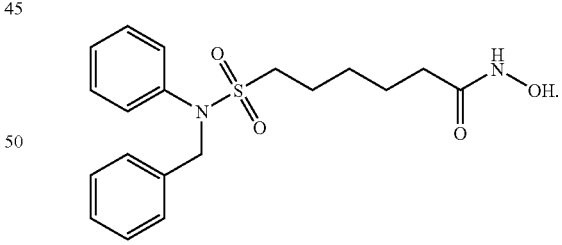

94. A composition comprising a compound according to claim 1 and a pharmaceutically acceptable carrier or diluent.

95. A method of inhibiting HDAC in a cell comprising said cell with an effective amount of a compound according to claim 1.

96. A method of treatment of a proliferative condition selected from the group consisting of malignant neoplasm, leukemia, bone disease, and atherosclerosis comprising administering to a subject suffering from said proliferative condition a therapeutically-effective amount of a compound according to claim 1.

97. A method of treatment of psoriasis comprising administering to a subject suffering from psoriasis a therapeutically-effective amount of a compound according to claim 1.

98. A method of treatment of a fibroproliferative disorder comprising administering to a subject suffering from a fibroproliferative disorder a therapeutically-effective amount of a compound according to claim 1.

99. A method of treatment of liver fibrosis comprising admistering to a subject suffering from liver fibrosis a therapeutically-effective amount of a compound according to claim 1.

100. A method of treatment of a smooth muscle proliferative disorder comprising administering to a subject suffering from a smooth muscle proliferative disorder a therapeutically-effective amount of a compound according to claim 1.

101. A method of treatment of atherosclerosis or restenosis comprising administering to a subject suffering from atherosclerosis or restenosis therapeutically-effective amount of a compound according to claim 1.

102. A method of treatment of a neurodegenerative disease or spino-cerebellar degeneration comprising administering to a subject suffering from a neurodegenerative disease or spino-cerebellar degeneration a therapeutically-effective amount of a compound according to claim 1.

103. A method of treatment of Alzheimer's disease, Parkinson's desease, Huntington's chores, or amyotropic lateral sclerosis comprising administering to a subject suffering from Alzheimer's disease, Parkinson's disease, Huntington's chorea, or amyotropic lateral sclerosis a therapeutically-effective amount of a compound according to claim 1.

104. A method of treatment of an inflammatory disease comprising administering to a subject suffering from an inflammatory disease a therapeutically-effective amount of a compound according to claim 1.

105. A method of treatment of osteoarthritis or rheumatoid arthritis comprising administering to a subject suffering from osteoarthritis or rheumatoid arthritis a therapeutically-effective amount of a compound according to claim 1.

106. A method of treatment of diabetic retinopathy comprising administering to a subject suffering from diabetic retinopathy a therapeutically-effective amount of a compound according to claim 1.

107. A method of treatment of a haematopoietic disorder comprising administering to a subject suffering from a haematopoietic disorder a therapeutically-effective amount of a compound according to claim 1.

108. A method of treatment of anaemia comprising administering to a subject suffering from anaemia a therapeutically-effective amount of a compound according to claim 1.

109. A method of treatment of sickle cell anaemia or thalassaeimia comprising administering to a subject suffering from sickle cell anaemia or thalassaeimia a therapeutically-effective amount of a compound according to claim 1.

110. A method of treatment of a fungal infection comprising admistering to a subject suffering from a fungal infection a therapeutically-effective amount of a compound according to claim 1.

111. A method of treatment of a parasitic infection comprising administering to a subject suffering from a parasitic infection a therapeutically-effective amount of a compound according to claim 1.

112. A method of treatment of malaria, trypanosomiasis, helminthiasis, or a protozoal infection comprising administering to a subject suffering from malaria, trypanosomiasis, helminthiasis, or a protozoal infection a therapeutically-effective amount of a compound according to claim 1.

113. A method of treatment of a bacterial infection comprising administering to a subject suffering from a bacterial infection a therapeutically-effective amount of a compound according to claim 1.

114. A method of treatment of a viral infection comprising administering to a subject suffering from a viral infection a therapeutically-effective amount of a compound according to claim 1.

115. A method of treatment of multiple sclerosis, autoimmune diabetes, lupus, atopic dermatitis, allergies, asthma, allergic rhinitis, or inflammatory bowel disease comprising administering to a subject suffering from multiple sclerosis, autoimmune diabetes, lupus, atopic dermatitis, allergies, asthma, allergic rhinitis, or inflammatory bowel disease a therapeutically-effective amount of a compound according to claim 1.

116. A method of treatment of lung cancer comprising administering to a subject suffering from lung cancer a therapeutically-effective amount of a compound according to claim 1.

117. A method of treatment of colon cancer comprising administering to a subject suffering from colon cancer a therapeutically-effective amount of a compound according to claim 1.

118. A method of treatment of breast cancer comprising administering to a subject suffering from breast cancer a therapeutically-effective amount of a compound according to claim 1.

119. A method of treatment of ovarian cancer comprising administering to a subject suffering from ovarian cancer a therapeutically-effective amount of a compound according to claim 1.

120. A method of treatment of prostate cancer comprising administering to a subject suffering from prostate cancer a therapeutically-effective amount of a compound according to claim 1.

121. A method of treatment of liver cancer comprising administering to a subject suffering from liver cancer a therapeutically-effective amount of a compound according to claim 1.

122. A method of treatment of pancreas cancer comprising administering to a subject suffering from pancreas cancer a therapeutically-effective amount of a compound according to claim 1.

123. A method of treatment of brain cancer comprising administering to a subject suffering from brain cancer a therapeutically-effective amount of a compound according to claim 1.

124. A method of treatment of skin cancer comprising administering to a subject suffering from skin cancer a therapeutically-effective amount of a compound according to claim 1.

* * * * *